(12) United States Patent
Witty et al.

(10) Patent No.: US 9,376,436 B2
(45) Date of Patent: *Jun. 28, 2016

(54) 2-(PYRIDIN-2YL)-1, 7-DIAZA-SPIRO [4.4] NONANE-6-ONE COMPOUND AS VOLTAGE-GATED SODIUM CHANNELS MODULATORS

(71) Applicant: CONVERGENCE PHARMACEUTICALS LIMITED, London (GB)

(72) Inventors: David R. Witty, Cambridgeshire (GB); David T. MacPherson, Cambridgeshire (GB); Gerard M. P. Giblin, Cambridgeshire (GB); Steven J. Stanway, Cambridgeshire (GB); Antonio K. K. Vong, Cambridgeshire (GB)

(73) Assignee: Convergence Pharmaceuticals Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/365,372

(22) PCT Filed: Dec. 21, 2012

(86) PCT No.: PCT/GB2012/053234
§ 371 (c)(1),
(2) Date: Nov. 12, 2014

(87) PCT Pub. No.: WO2013/093497
PCT Pub. Date: Jun. 27, 2013

(65) Prior Publication Data
US 2015/0225400 A1  Aug. 13, 2015

Related U.S. Application Data

(60) Provisional application No. 61/579,613, filed on Dec. 22, 2011.

(30) Foreign Application Priority Data

Dec. 22, 2011  (GB) .................................. 1122113.2

(51) Int. Cl.
*C07D 487/10* (2006.01)
*C07D 471/10* (2006.01)

(52) U.S. Cl.
CPC ............ *C07D 471/10* (2013.01); *C07D 487/10* (2013.01)

(58) Field of Classification Search
CPC .................................................... C07D 487/10
USPC ........................................... 546/15; 514/278
See application file for complete search history.

(56) References Cited

U.S. PATENT DOCUMENTS

| | | | |
|---|---|---|---|
| 7,655,693 B2 | 2/2010 | Alvaro et al. | |
| 7,803,833 B2 | 9/2010 | Alvaro et al. | |
| 7,855,218 B2 | 12/2010 | Alvaro et al. | |
| 8,093,268 B2 | 1/2012 | Alvaro et al. | |
| 8,143,306 B2 | 3/2012 | Alvaro et al. | |
| 8,153,623 B2 | 4/2012 | Alvaro et al. | |
| 8,153,681 B2 | 4/2012 | Alvaro et al. | |
| 8,759,542 B2 | 6/2014 | Zajac | |
| 2009/0318530 A1 | 12/2009 | Alvaro et al. | |
| 2009/0326032 A1 | 12/2009 | Alvaro et al. | |
| 2010/0105688 A1 | 4/2010 | Alvaro et al. | |
| 2010/0130583 A1 | 5/2010 | Alvaro et al. | |
| 2014/0350040 A1 | 11/2014 | Witty et al. | |
| 2015/0119404 A1 | 4/2015 | Giblin et al. | |
| 2015/0166551 A1 | 6/2015 | Giblin et al. | |

FOREIGN PATENT DOCUMENTS

| | | |
|---|---|---|
| WO | WO-2005/035535 A1 | 4/2005 |
| WO | WO-2007/042240 A1 | 4/2007 |
| WO | WO-2008/090114 A1 | 7/2008 |
| WO | WO-2008/090115 A1 | 7/2008 |

OTHER PUBLICATIONS

Guillory (in Brittain ed.), "Polymorphism in Pharmaceutical Solids.," NY: Marcel Dekker, Inc., 1999, 1-2, 125-181, 183-226.*

(Continued)

*Primary Examiner* — Patricia L Morris
(74) *Attorney, Agent, or Firm* — Honigman Miller Schwartz and Cohn LLP; Kathryn D. Doyle; Jonathan P. O'Obrien

(57) ABSTRACT

The invention relates to spiro derivatives of formula (I), to the use of said derivatives in treating diseases and conditions mediated by modulation of voltage-gated sodium channels, to compositions containing said derivatives and processes for their preparation.

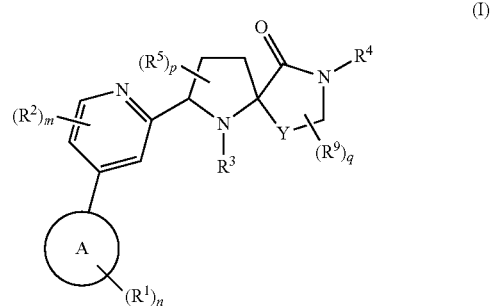

12 Claims, No Drawings

(56) References Cited

OTHER PUBLICATIONS

Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Invanisevic et al. "Use of X-ray . . . " Pharm. Sci. Encycl. p. 1-42 (2010).*
Bhattacharya excerpt fr Brittain, H. ed., Polymorphism in Pharmaceutical SolidsDrugs and the Pharmaceutical Sciences ; V. 95 New York Marcel Dekker, Inc., 1999.*
Ivanisevic, I. Pharm. Form. Qual. 2011, pp. 30-33.*
Kirk-Othmer "Crystallization" Encyclopedia of Chem. Tech. v. 8, p. 95-147 (2002).*
Seddon "Pseudopolymorph . . . " Crystal Growth & design v.4(6) p. 1087 (2004) (2 pages from internet).*
Eijkelkamp, Niels, et al., "Neurological perspectives on voltage-gated sodium channels," Brain: A Journal of Neurology, 135, pp. 2585-2612 (2012).
Large, C.H., et al., "The relationship between sodium channel inhibition and anticonvulsant activity in a model of generalised seizure in the rat," Epilepsy Res. Jul. 2009; 85(1):96-106, doi: 10.1016/j.eplepsyres.2009.02.018. Epub Mar. 28, 2009. PMID: 19329281 http://www.ncbi.nlm.nih.gov/pubmed/19329281.

* cited by examiner

2-(PYRIDIN-2YL)-1, 7-DIAZA-SPIRO [4.4] NONANE-6-ONE COMPOUND AS VOLTAGE-GATED SODIUM CHANNELS MODULATORS

FIELD OF THE INVENTION

The invention relates to spiro derivatives, to the use of said derivatives in treating diseases and conditions mediated by modulation of voltage-gated sodium channels, to compositions containing said derivatives and processes for their preparation.

BACKGROUND OF THE INVENTION

Voltage-gated sodium channels are responsible for the initial phase of the action potential, which is a wave of electrical depolarisation usually initiated at the soma of the neuron and propagated along the nerve axon to the terminals. At the terminals, the action potential triggers the influx of calcium and the release of neurotransmitter. Drugs, such as lidocaine, that block voltage-gated sodium channels are used as local anaesthetics. Other sodium channel blockers, such as lamotrigine and carbamazepine are used to treat epilepsy. In the latter case, partial inhibition of voltage-gated sodium channels reduces neuronal excitability and reduces seizure propagation. In the case of local anaesthetics, regional block of sodium channels on sensory neurons prevents the conduction of painful stimuli. A key feature of these drugs is their state-dependent mechanism of action. The drugs are thought to stabilise an inactivated conformation of the channel that is adopted rapidly after the channel opens. This inactivated state provides a refractory period before the channel returns to its resting (closed) state ready to be reactivated. As a result, state-dependent sodium channel blockers inhibit the firing of neurons at high frequency, for example in response to painful stimuli, and will help to prevent repetitive firing during periods of prolonged neuronal depolarisation that might occur, for example, during a seizure. Action potentials triggered at low frequencies, for example in the heart, will not be significantly affected by these drugs, although the safety margin differs in each case, since at high enough concentrations each of these drugs is capable of blocking the resting or open states of the channels.

The voltage-gated sodium channel family is made up of 10 subtypes, four of which are brain specific, NaV1.1, 1.2, 1.3 and 1.6. Of the other subtypes, NaV1.4 is found only in skeletal muscle, NaV1.5 is specific to cardiac muscle, and NaV1.7, 1.8, and 1.9 are found predominantly in sensory neurons. The hypothesised binding site for state-dependent sodium channel blockers is highly conserved between all the subtypes. As a result, drugs such as lidocaine, lamotrigine and carbamazepine do not distinguish between the subtypes. However, selectivity can be achieved as a result of the different frequencies at which the channels normally operate.

Drugs that block voltage-gated sodium channels in a state-dependent manner are also used in the treatment of bipolar disorder, either to reduce symptoms of mania or depression, or as mood stabilisers to prevent the emergence of mood episodes. Clinical and preclinical evidence also suggests that state-dependent sodium channel blockers may help to reduce the symptoms of schizophrenia. For example, lamotrigine has been shown to reduce symptoms of psychosis induced by ketamine in healthy human volunteers, and furthermore, studies in patients suggest that the drug can augment the antipsychotic efficacy of some atypical antipsychotic drugs, such as clozapine or olanzapine. It is hypothesised that efficacy in these psychiatric disorders may result in part from a reduction of excessive glutamate release. The reduction in glutamate release is thought to be a consequence of state-dependent sodium channel inhibition in key brain areas, such as the frontal cortex. However, interaction with voltage-gated calcium channels may also contribute to the efficacy of these drugs.

WO 2007/042240 (Glaxo Group Limited) describes a series of quaternary alpha-aminocarboxamide derivatives as modulators of voltage-gated sodium channels.

The object of the invention is to identify alternative compounds which modulate voltage-gated sodium channels.

SUMMARY OF THE INVENTION

According to a first aspect, the invention provides a compound of formula (I) or a pharmaceutically acceptable salt or solvate thereof:

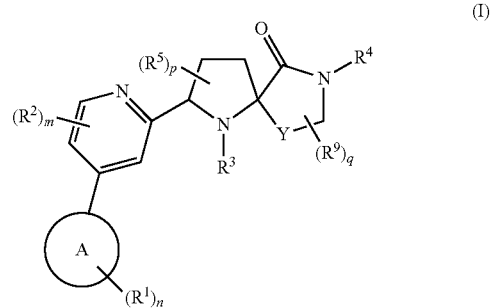

wherein:
Ring A represents a phenyl ring, a 5- or 6-membered aromatic heterocyclic ring or a 5- to 12-membered aromatic or non-aromatic bicyclic heterocyclic group;
n represents an integer selected from 0 to 4;
each $R^1$ independently represents $C_{1-6}$ alkyl, $C_{2-6}$ alkenyl, $C_{2-6}$ alkynyl, halogen, halo$C_{1-6}$ alkyl, $C_{1-6}$ alkoxy, —$CH_2$—$C_{1-6}$ alkoxy, halo$C_{1-6}$ alkoxy, —C(=O)—$C_{1-6}$ alkyl, —Z—$C_{3-8}$ cycloalkyl, —Z-phenyl, —Z-Het, —$SO_2C_{1-6}$ alkyl, —CN, —OH, —$CONR^6R^7$, —$NR^6R^7$, wherein said Het group represents a 5- or 6-membered aromatic heterocyclic ring or a 4- to 7-membered non-aromatic heterocyclic ring, wherein said $C_{3-8}$ cycloalkyl, phenyl or Het group of $R^1$ may be optionally substituted by one or more (e.g. 1, 2 or 3) $R^8$ groups and wherein n represents an integer greater than 1, said $R^1$ groups represent no more than one —Z—$C_{3-8}$ cycloalkyl or one —Z-phenyl or one —Z-Het group;
Z represents a bond or a linker selected from —O—, —$CH_2$—, —$CH_2$—O—, —$OCH(CH_3)$— or —O—$CH_2$—;
$R^6$ and $R^7$ independently represent hydrogen or $C_{1-6}$ alkyl or $R^6$ and $R^7$ together with the nitrogen atom to which they are attached join to form a 4- to 7-membered nitrogen containing non-aromatic heterocyclic ring;
$R^8$ represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN, —$NR^6R^7$ or =O;
m represents an integer selected from 0 to 3;
each $R^2$ independently represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN or —$NR^7R^8$;
$R^3$ represents hydrogen or $C_{1-6}$ alkyl;

R⁴ represents hydrogen or $C_{1-6}$ alkyl;
each R⁵ independently represents $C_{1-3}$ alkyl or fluoro;
each R⁹ independently represents $C_{1-3}$ alkyl;
Y represents —$CH_2$— or —$(CH_2)_2$—; and
p and q independently represent an integer from 0 to 3.

DETAILED DESCRIPTION OF THE INVENTION

According to one particular aspect of the invention which may be mentioned, there is provided a compound of formula (I) or a pharmaceutically acceptable salt or solvate thereof:

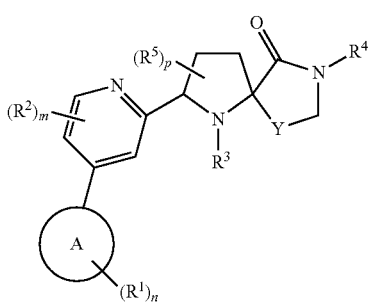

(I)

wherein:
Ring A represents a phenyl ring, a 5- or 6-membered aromatic heterocyclic ring or a 5- to 12-membered aromatic or non-aromatic bicyclic heterocyclic group;
n represents an integer selected from 0 to 4;
each R¹ independently represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —Z-phenyl, —Z-Het, —CN, —CONR⁶R⁷, —NR⁶R⁷, wherein said Het group represents a 5- or 6-membered aromatic heterocyclic ring or a 4- to 7-membered non-aromatic heterocyclic ring, wherein said phenyl or Het group of R¹ may be optionally substituted by one or more (e.g. 1, 2 or 3) R⁸ groups and wherein n represents an integer greater than 1, said R¹ groups represent no more than one —Z-phenyl or one —Z-Het group;
Z represents a bond or a linker selected from —O—, —$CH_2$—, —$CH_2$—O— or —O—$CH_2$—;
R⁶ and R⁷ independently represent hydrogen or $C_{1-6}$ alkyl or R⁶ and R⁷ together with the nitrogen atom to which they are attached join to form a 4- to 7-membered nitrogen containing non-aromatic heterocyclic ring;
R⁸ represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN or —NR⁶R⁷;
m represents an integer selected from 0 to 3;
each R² independently represents $C_{1-6}$ alkyl, $C_{2-6}$ alkenyl, $C_{2-6}$ alkynyl, halogen, halo$C_{1-6}$ alkyl, $C_{1-6}$ alkoxy, halo$C_{1-6}$ alkoxy, —CN or —NR⁷R⁸;
R³ represents hydrogen or $C_{1-6}$ alkyl;
R⁴ represents hydrogen or $C_{1-6}$ alkyl;
each R⁵ independently represents $C_{1-3}$ alkyl or fluoro;
Y represents —$CH_2$— or —$(CH_2)_2$—; and
p represents an integer from 0 to 3.

The term 'halo' or 'halogen' as used herein refers to fluorine, chlorine, bromine or iodine.

The term '$C_{1-3}$alkyl' as used herein as a group or part of a group refers to a linear or branched saturated hydrocarbon group containing from 1 to 3 carbon atoms. The term '$C_{1-6}$alkyl' as used herein as a group or part of a group refers to a linear or branched saturated hydrocarbon group containing from 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{2-6}$alkenyl' as used herein as a group or part of a group refers to a linear or branched hydrocarbon group containing from 2 to 6 carbon atoms and containing a carbon carbon double bond.

The term '$C_{2-6}$alkynyl' as used herein as a group or part of a group refers to a linear or branched hydrocarbon group having from 2 to 6 carbon atoms and containing a carbon carbon triple bond.

The term '$C_{1-6}$alkoxy' as used herein as a group or part of a group refers to an —O—$C_{1-6}$alkyl group wherein $C_{1-6}$alkyl is as defined herein. Examples of such groups include methoxy, ethoxy, propoxy, butoxy, and the like.

The term 'halo$C_{1-6}$alkyl' as used herein as a group or part of a group refers to a $C_{1-6}$alkyl group as defined herein wherein one or more than one hydrogen atom is replaced with a halogen. The term 'halo$C_{1-6}$alkyl' therefore includes monohalo$C_{1-6}$alkyl and also polyhalo$C_{1-6}$alkyl. There may be one, two, three or more hydrogen atoms replaced with a halogen, so the halo$C_{1-6}$alkyl may have one, two, three or more halogens. Examples of such groups include fluoroethyl, fluoromethyl, trifluoromethyl or trifluoroethyl and the like.

The term 'halo$C_{1-6}$alkoxy' as used herein as a group or part of a group refers to a —O—$C_{1-6}$alkyl group as defined herein wherein one or more than one hydrogen atom is replaced with a halogen. The term 'halo$C_{1-6}$alkoxy' therefore includes monohalo$C_{1-6}$alkoxy, and also polyhalo$C_{1-6}$alkoxy. There may be one, two, three or more hydrogen atoms replaced with a halogen, so the halo$C_{1-6}$alkoxy may have one, two, three or more halogens. Examples of such groups include fluoroethyloxy, difluoromethoxy or trifluoromethoxy and the like.

The term '$C_{3-8}$cycloalkyl' as used herein as a group or part of a group refers to a saturated hydrocarbon ring containing from 3 to 8 carbon atoms. Examples of such groups include cyclopropyl, cyclobutyl, cyclopentyl, cyclohexyl, cycloheptyl, cyclooctyl and the like.

The term 5- or 6-membered aromatic heterocyclic ring means a heterocyclyl group containing one or more carbon atoms, one or more hydrogen atoms and one or more heteroatoms such as nitrogen, oxygen and sulfur; the carbon and heteroatoms being interconnected to form a ring. Examples of five membered aromatic heterocyclic groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups. Examples of six membered aromatic heterocyclic groups include but are not limited to pyridine, pyrazine, pyridazine, pyrimidine and triazine.

The term 4- or 7-membered non-aromatic heterocyclic ring means a heterocyclyl group containing one or more carbon atoms, one or more hydrogen atoms and one or more heteroatoms such as nitrogen, oxygen and sulfur; the carbon and heteroatoms being interconnected to form a ring. The term "non-aromatic" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "saturated" or "fully saturated" refers to rings where there are no multiple bonds between ring atoms. Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

The term 4- to 7-membered nitrogen containing non-aromatic heterocyclic ring means a non-aromatic heterocyclyl ring as defined herein wherein the ring must contain at least one ring nitrogen atom. Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidinone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

Particular examples of 5- to 12-membered bicyclic heterocyclic groups typically comprise groups containing a five membered ring fused to another five membered ring and include but are not limited to imidazothiazole (e.g. imidazo[2,1-b]thiazole) and imidazoimidazole (e.g. imidazo[1,2-a]imidazole).

Particular examples of 5- to 12-membered bicyclic heterocyclic groups typically comprise groups containing a six membered ring fused to a five membered ring and include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of 5- to 12-membered bicyclic heterocyclic groups typically comprise groups containing two fused six membered rings and include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Particular examples of 5- to 12-membered bicyclic heterocyclic groups typically comprise groups containing an aromatic ring and a non-aromatic ring and include, tetrahydroisoquinoline, tetrahydroquinoline, dihydrobenzthiophene, dihydrobenzfuran, 2,3-dihydrobenzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, and indoline groups.

For the avoidance of doubt, unless otherwise indicated, the term "substituted" means substituted by one or more defined groups. In the case where groups may be selected from a number of alternative groups, the selected groups may be the same or different.

For the avoidance of doubt, the term "independently" means that where more than one substituent is selected from a number of possible substituents, those substituents may be the same or different.

In one embodiment, Ring A represents a phenyl ring, a 5- or 6-membered aromatic heterocyclic ring (such as thiophenyl, pyrazolyl or pyridyl) or a 5- to 12-membered aromatic or non-aromatic bicyclic heterocyclic group (such as indolyl, indazolyl, quinolinyl, dihydrobenzofuranyl or benzodioxolyl). In a further embodiment, Ring A represents a phenyl ring.

In one embodiment, n represents an integer selected from 0 to 3. In a further embodiment, n represents an integer selected from 1 to 3. In a yet further embodiment, n represents an integer selected from 1 to 2. In one embodiment, n represents 1. In an alternative embodiment, n represents 2.

In one embodiment, $R^1$ independently represents $C_{1-6}$ alkyl (such as methyl, ethyl, isopropyl or isopentyl), halogen (such as fluorine or chlorine), halo$C_{1-6}$ alkyl (such as $CF_3$), $C_{1-6}$ alkoxy (such as —O-methyl, —O—$CH_2$—$CH_3$, —O-$CD_2$-$CH_3$, —O-propyl, —O-butyl, —O—$CH(Me)_2$ or —O—$CH_2$—$CH(Me)_2$), halo$C_{1-6}$ alkoxy (such as —O—$CF_3$, —$OCHF_2$, —$OCH_2CHF_2$, —$OCH_2CH_2F$ or —$CH_2$—O—$CF_3$), —$CH_2$—$C_{1-6}$ alkoxy (such as —$CH_2$OMe or —$CH_2$OEt), —$SO_2C_{1-6}$ alkyl (such as —$SO_2$Et), —C(=O)—$C_{1-6}$ alkyl (such as —C(=O)-Et), —Z—$C_{3-8}$ cycloalkyl (such as -cyclopropyl, —O— cyclopropyl, —O-ethylcyclopropyl, or —OCH($CH_3$)-cyclopropyl) —Z-aryl (such as —O-phenyl, —O—$CH_2$-phenyl or —$CH_2$—O-phenyl), —CN, —OH, —$CONR^6R^7$ (such as —$CONH_2$), —$NR^6R^7$ (such as —$N(Me)_2$) or —Z-Het (such as -pyrrolidinyl or -pyrazolyl) wherein said phenyl, $C_{3-8}$ cycloalkyl or Het groups are optionally substituted by one or more (e.g. 1, 2 or 3) $R^8$ groups such as halogen (e.g. fluorine), $C_{1-6}$ alkyl (such as methyl or ethyl), —CN, =O or halo$C_{1-6}$ alkoxy (e.g. —O—$CF_3$).

In a further embodiment, $R^1$ independently represents $C_{1-6}$ alkyl (such as methyl, ethyl or isopropyl), halogen (such as fluorine or chlorine), halo$C_{1-6}$ alkyl (such as $CF_3$), $C_{1-6}$ alkoxy (such as —O-methyl, —O-ethyl, —O-propyl, —O-butyl, —O—$CH(Me)_2$ or —O—$CH_2$—$CH(Me)_2$), halo$C_{1-6}$ alkoxy (such as —O—$CF_3$, —$OCHF_2$ or —$CH_2$—O—$CF_3$), —Z-aryl (such as —O-phenyl, —O—$CH_2$-phenyl or —$CH_2$—O-phenyl), —CN, —$CONR^6R^7$ (such as $CONH_2$) or —$NR^6R^7$ (such as —$N(Me)_2$), wherein said phenyl groups are optionally substituted by one or more (e.g. 1, 2 or 3) $R^8$ groups such as halogen (e.g. fluorine) or halo$C_{1-6}$ alkoxy (e.g. —O—$CF_3$).

In a further embodiment, $R^1$ independently represents $C_{1-6}$ alkyl (such as methyl), halogen (such as fluorine or chlorine), halo$C_{1-6}$ alkyl (such as $CF_3$), $C_{1-6}$ alkoxy (such as —O-methyl, —O-ethyl or —O—$CH(Me)_2$), halo$C_{1-6}$ alkoxy (such as —O—$CF_3$ or —$OCHF_2$), —CN or —$CONR^6R^7$ (such as $CONH_2$).

In one embodiment, Z represents —O—, —$CH_2$—O—, —$OCH(CH_3)$— or —O—$CH_2$—. In a further embodiment, Z represents —O—, —$CH_2$—O— or —O—$CH_2$—.

In one embodiment, $R^6$ and $R^7$ independently represent hydrogen or $C_{1-6}$ alkyl. In a further embodiment, $R^6$ and $R^7$ independently represent hydrogen or methyl. In yet a further embodiment, $R^6$ and $R^7$ both represent hydrogen.

In one embodiment, $R^8$ represents halogen (e.g. fluorine or chlorine), halo$C_{1-6}$ alkoxy (e.g. —O—$CF_3$), CN or $C_{1-6}$ alkyl (e.g. methyl or ethyl) or =O. In a further embodiment, $R^8$ represents halogen (e.g. fluorine or chlorine) or halo$C_{1-6}$ alkoxy (e.g. —O—$CF_3$).

In one embodiment, m represents an integer selected from 0 to 2. In a further embodiment, m represents an integer selected from 0 to 1. In one embodiment, m represents 1. In an alternative embodiment, m represents 0.

In one embodiment, $R^2$ independently represents $C_{1-6}$ alkyl, halogen, halo$C_{1-6}$alkyl, $C_{1-6}$ alkoxy or halo$C_{1-6}$ alkoxy. In a further embodiment, $R^2$ independently represents $C_{1-6}$ alkyl (such as methyl, ethyl or isopropyl), halogen (such as fluorine) or $C_{1-6}$ alkoxy (such as —O-Me or —OC(Me)$_3$). In a yet further embodiment, $R^2$ independently represents $C_{1-6}$ alkyl (such as methyl), halogen (such as fluorine) or $C_{1-6}$ alkoxy (such as —OC(Me)$_3$). In a still yet further embodiment, $R^2$ independently represents $C_{1-6}$ alkyl (such as methyl).

In one embodiment, $R^3$ represents hydrogen, methyl or ethyl. In a further embodiment, $R^3$ represents hydrogen or methyl. In a yet further embodiment, $R^3$ represents hydrogen.

In one embodiment, $R^4$ represents hydrogen, methyl or ethyl. In a further embodiment, $R^4$ represents hydrogen or methyl. In a yet further embodiment, $R^4$ represents methyl.

When present, $R^5$ independently represents $C_1$-3 alkyl (such as methyl) or fluoro. In a further embodiment, $R^5$ represents methyl or fluoro. In a yet further embodiment, $R^5$ represents fluoro.

When present, $R^9$ represents methyl.

In one embodiment, p represents 0 to 2. In a further embodiment, p represents 0. In an alternative embodiment, p represents 1. In an alternative embodiment, p represents 2.

In one embodiment, q represents 0 to 2. In a further embodiment, q represents 0. In an alternative embodiment, q represents 1. In an alternative embodiment, q represents 2.

In one embodiment, p and q both represent 0. In an alternative embodiment, p represents 0 and q represents 1 or 2. In an alternative embodiment, q represents 0 and p represents 1 or 2.

In one embodiment, Y represents a —CH$_2$— group. In an alternative embodiment, Y represents a —(CH$_2$)$_2$— group.

In one embodiment, the compound of formula (I) is a compound of E1-E99 or an alternative pharmaceutically acceptable salt, solvate or free base preparation thereof. In a further embodiment, the compound of formula (I) is a compound of E1, E1a and E2-E260 or an alternative pharmaceutically acceptable salt, solvate or free base preparation thereof.

In one embodiment, the compound of formula (I) is other than 7-methyl-2-[4-[3-(trifluoromethoxy)phenyl]-2-pyridyl]-1,7-diazaspiro[4.4]nonan-6-one. In a further embodiment, the compound of formula (I) is other than:
(2R,5S)-7-methyl-2-[4-[3-(trifluoromethoxy)phenyl]-2-pyridyl]-1,7-diazaspiro[4.4]nonan-6-one hydrochloride (E1);
(2R,5S)-7-methyl-2-[4-[3-(trifluoromethoxy)phenyl]-2-pyridyl]-1,7-diazaspiro[4.4]nonan-6-one hemisulfate hydrate (E1a); or
(2S,5S)-7-methyl-2-[4-[3-(trifluoromethoxy)phenyl]-2-pyridyl]-1,7-diazaspiro[4.4]nonan-6-one hydrochloride (E260).

Thus, in a further embodiment, the compound of formula (I) is a compound of E2-E259 or an alternative pharmaceutically acceptable salt, solvate or free base preparation thereof.

A reference to a compound of formula (I) and sub-groups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, prodrugs, isotopes and protected forms thereof as defined in any aspect of the invention (except intermediate compounds in chemical processes) are referred to as "compounds of the invention".

Many compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-aminosalicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate salt, also known as a hemisulfate salt Where the compounds of formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention. In one embodiment, the pharmaceutically acceptable solvates of the compounds of the invention include the hydrate thereof.

Compounds of formula (I) containing an amine function may also form N-oxides. A reference herein to a compound of formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of formula (I) may exist in a number of different geometric isomeric, and tautomeric forms and references to compounds of formula (I) include all such forms. For the avoidance of doubt, where a compound can exist in one of several geometric isomeric or tautomeric forms and only one is specifically described or shown, all others are nevertheless embraced by formula (I).

In one embodiment, the invention provides compounds of formula (Ia)

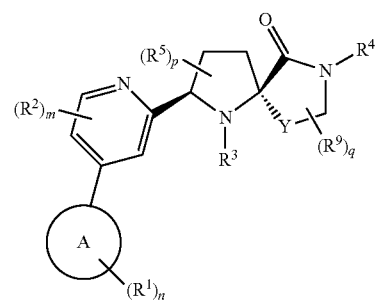

(Ia)

wherein $R^1$, $R^2$, $R^3$, $R^4$, $R^5$, $R^9$, m, n, p, q, Y and A are as defined herein for compounds of formula (I).

In one embodiment, the invention provides compounds of formula (Ib)

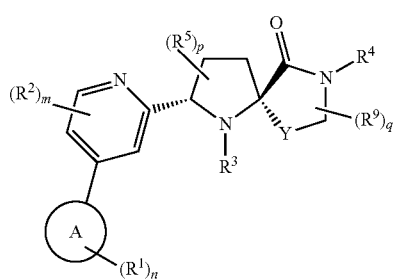

(Ib)

wherein $R^1$, $R^2$, $R^3$, $R^4$, $R^5$, $R^9$, m, n, p, q, A and Y are as defined herein for compounds of formula (I).

In one embodiment, the invention provides compounds of formula (Ic)

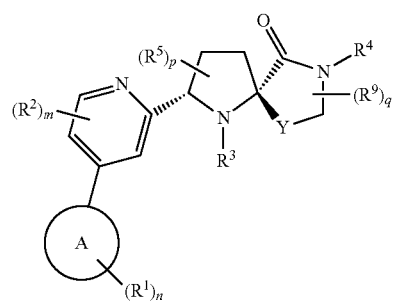

(Ic)

wherein $R^1$, $R^2$, $R^3$, $R^4$, $R^5$, $R^9$, m, n, p, q, A and Y are as defined herein for compounds of formula (I).

In one embodiment, the invention provides compounds of formula (Id)

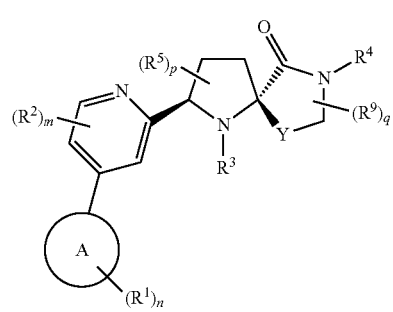

(Id)

wherein $R^1$, $R^2$, $R^3$, $R^4$, $R^5$, $R^9$, m, n, p, q, A and Y are as defined herein for compounds of formula (I).

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

According to a further aspect of the invention there is provided a process for preparing a compound of formula (I) as herein defined which comprises:
(a) reacting a compound of formula (II):

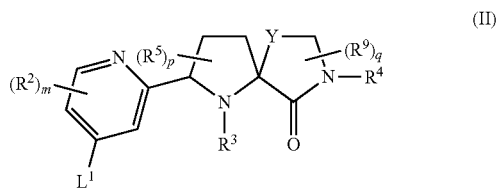

(II)

or a protected derivative thereof, wherein $R^2$, $R^3$, $R^4$, $R^5$, $R^9$, m, p, q and Y are as defined herein for compounds of formula (I) and $L^1$ represents a suitable leaving group such as a halogen atom (e.g. bromine) or an —O—SO$_2$CF$_3$ group, with a boronic acid derivative or an aryl-tin derivative of a compound of formula A-(R$^1$)$_n$, wherein A, n and R$^1$ are as defined herein for compounds of formula (I);

(b) forming a compound of formula (I) wherein $R^3$ represents hydrogen by reduction of a compound of formula (III):

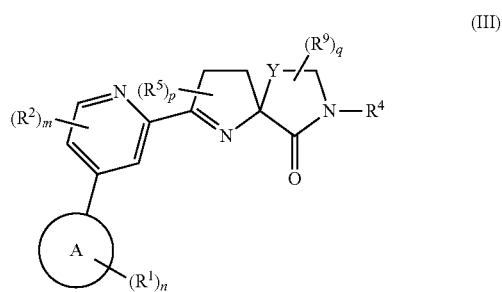

(III)

or a protected derivative thereof, wherein $R^1$, $R^2$, $R^4$, $R^5$, $R^9$, m, n, p, q, A and Y are as defined herein for compounds of formula (I);

(c) deprotection of a protected derivative of a compound of formula (I);

(d) interconversion of a compound of formula (I) or protected derivative thereof to a further compound of formula (I) or protected derivative thereof, such as the conversion of the amino group to a Boc-protected amine to facilitate purification, followed by removal of said protecting group;

(e) optional formation of a pharmaceutically acceptable salt of a compound of formula (I).

When $L^1$ represents an —O—SO$_2$CF$_3$ group, process (a) typically comprises a Suzuki coupling reaction in the presence of a suitable catalyst such as a Palladium catalyst and a suitable base such as potassium carbonate in a suitable solvent such as aqueous 1,4-dioxane.

When $L^1$ represents a halogen atom such as bromine, process (a) typically comprises a Suzuki coupling reaction in the presence of a suitable catalyst such as a palladium tetrakis triphenylphosphine and a suitable base. It is recognised that alternative aryl coupling protocols can be used in place of a Suzuki reaction, for example a Stille coupling.

Process (b) typically comprises the use of suitable reducing agents such as sodium triacetoxyborohydride, in the presence of a suitable acid (such as HCl), borane or a modified borane such as tertiarybutylamine:borane complex, or hydrogenation over a suitable catalyst such as platinum.

Compounds of formula (II) wherein $R^3$ represents hydrogen and p and q both represent 0 may be prepared in accordance with Scheme 1:

Scheme 1

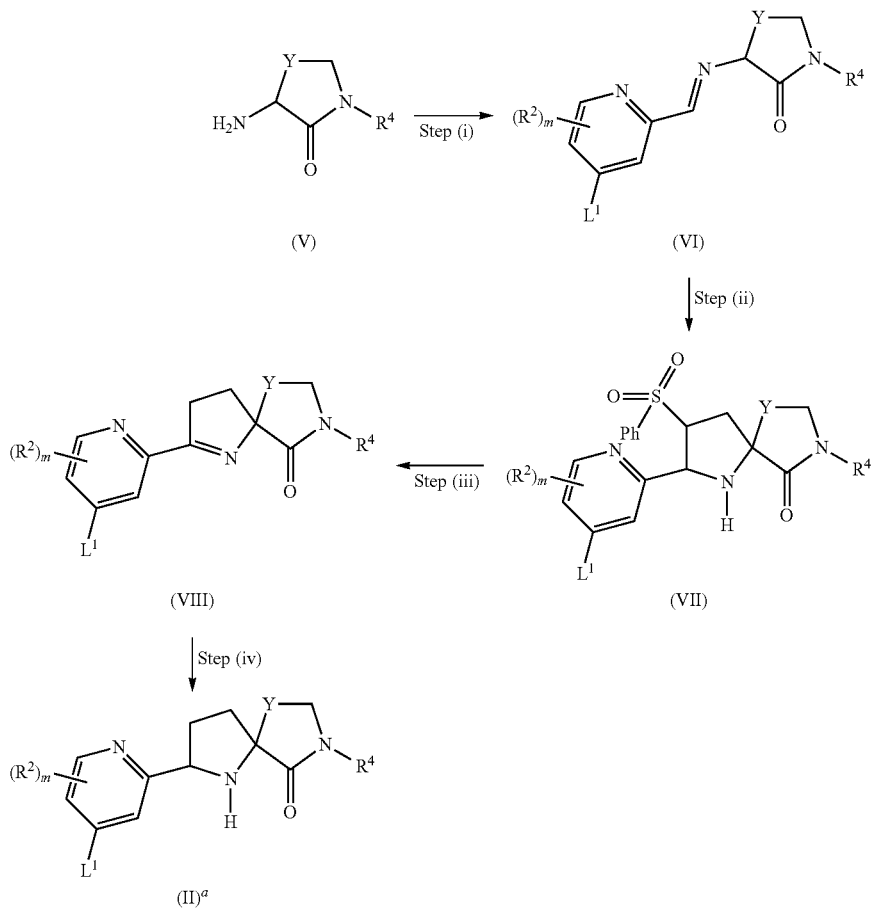

wherein $R^2$, $R^4$, m and Y are as defined herein for compounds of formula (I) and, $L^1$ represents a suitable leaving group such as a halogen atom (e.g. bromine) or an —O—$SO_2$—$CF_3$ group.

Step (i) typically comprises condensation of a compound of formula (V) with a suitable carboxyaldehyde compound in the presence of a dehydrating agent such as magnesium sulfate in a solvent such as dichloromethane.

Step (ii) typically comprises a [3+2]cycloaddition reaction with phenyl vinyl sulfone catalysed by a transition metal salt such as a silver or copper salt (e.g. silver acetate) or a lewis acid (such as calcium triflate), typically in the presence of a base and optionally a chiral phosphine ligand such as 1-(di (1-naphthenyl)phosphinyl)-2-((4S)-4-(propan-2-yl)-4,5-dihydro-1,3-oxazolyl)-ferrocene.

Step (iii) typically comprises elimination of the phenyl sulfone with a strong base such as potassium tert-butoxide.

Step (iv) typically comprises reduction of the imine using a hydride donor such as sodium borohydride or sodium triacetoxyborohydride in the presence of a suitable acid (such as HCl), borane or a modified borane (such as tertiarybutylamine:borane complex), or hydrogenation over a suitable catalyst such as platinum.

Compounds of formula (III) wherein p and q both represent 0 may be prepared in accordance with Scheme 2:

Scheme 2

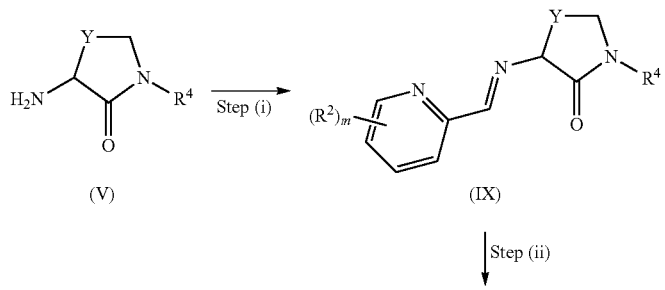

-continued

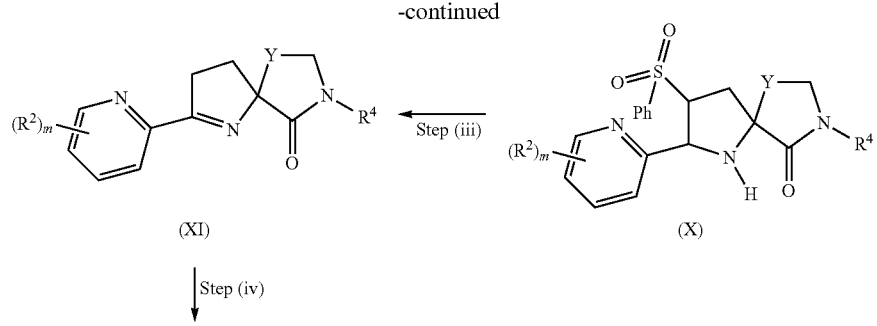

(XI)          (X)

↓ Step (iv)

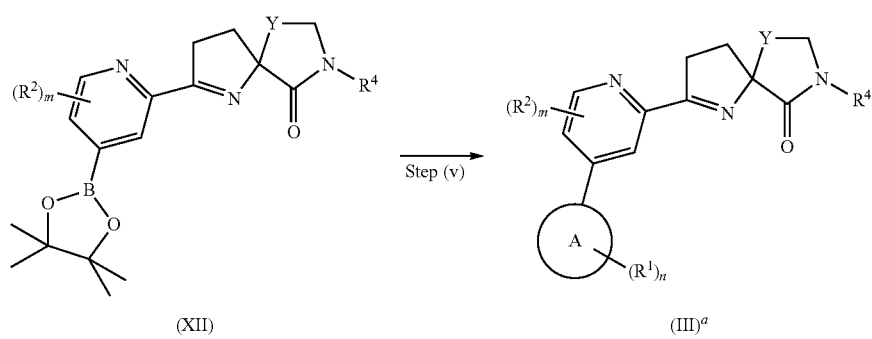

(XII)          (III)$^a$ wherein $R^1$, $R^2$, $R^4$, m, n, A and Y are as defined herein for compounds of formula (I).

Step (i) typically comprises condensation of a compound of formula (V) with a suitable carboxyaldehyde compound in the presence of a dehydrating agent such as magnesium sulfate in a solvent such as dichloromethane.

Step (ii) typically comprises a [3+2]cycloaddition reaction with phenyl vinyl sulfone catalysed by a transition metal salt such as silver or copper salt, in the presence of a base and optionally a chiral phosphine ligand.

Step (iii) typically comprises elimination of the phenyl vinyl sulfone typically with a strong base such as potassium tert-butoxide.

Step (iv) typically comprises a borylation reaction using bis(pinacolato)diboron, in the presence of an Iridium catalyst such as a (1,5-cyclooctadiene)(methoxy)iridium(I) dimer.

Step (v) typically comprises a biaryl coupling, such as Suzuki coupling, with a derivative of a compound A-$(R^1)_n$ catalysed by, for example, 1,1'-bis(diphenylphosphino)-ferrocene-palladium(II) dichloride in a solvent system comprising, for example, dichloromethane and water in the presence of a base, such as sodium carbonate.

Compounds of formula (III) wherein p and q both represent 0 may also be prepared in accordance with Scheme 3:

Scheme 3

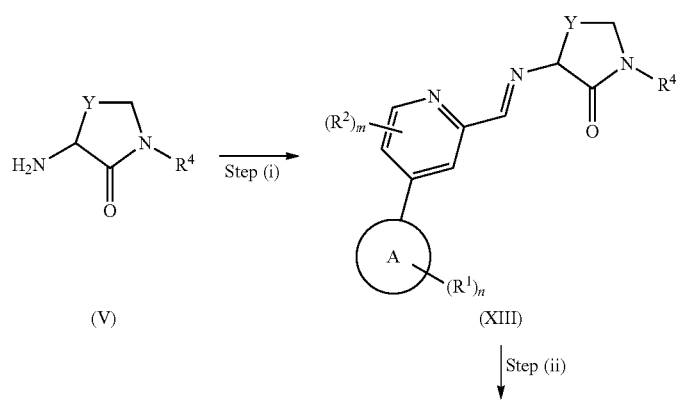

(V)          (XIII)

↓ Step (ii)

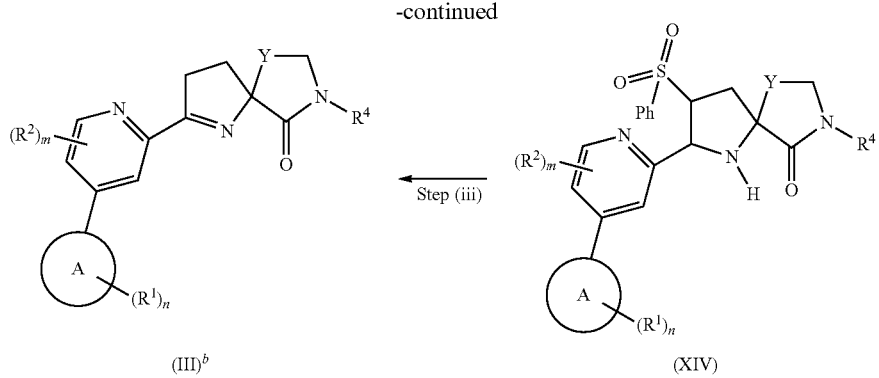

wherein R[1], R[2], R[4], m, n, A and Y are as defined herein for compounds of formula (I).

Step (i) typically comprises condensation of a compound of formula (V) with a carboxyaldehyde compound, including for example a compound of formula (XXXIV), in the presence of a dehydrating agent such as magnesium sulfate in a solvent such as dichloromethane.

Step (ii) typically comprises a [3+2]cycloaddition reaction with phenyl vinyl sulfone catalysed by a transition metal salt such as a silver or copper salt, in the presence of a base and optionally a chiral phosphine ligand.

Step (iii) typically comprises elimination of the phenyl vinyl sulfone typically with a strong base such as potassium tert-butoxide.

Alternatively, compounds of formula (III) wherein p and q both represent 0 may also be prepared in accordance with Scheme 4:

Scheme 4

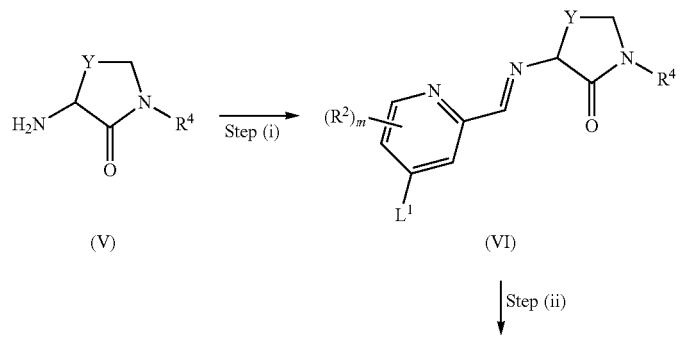

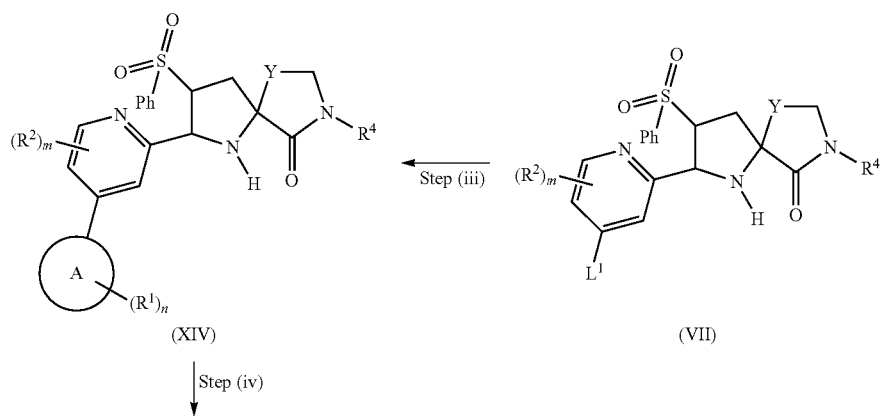

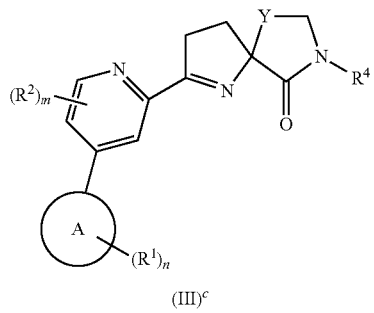

(III)<sup>c</sup> wherein $R^1$, $R^2$, $R^4$, m, n, A and Y are as defined herein for compounds of formula (I) and $L^1$ represents a suitable leaving group, such as bromine.

Step (i) typically comprises condensation of a compound of formula (V) with a suitable carboxaldehyde compound in the presence of a dehydrating agent such as magnesium sulfate in a solvent such as dichloromethane.

Step (ii) typically comprises a [3+2]cycloaddition reaction with phenyl vinyl sulfone catalysed by a transition metal salt such as silver or copper salt, in the presence of a base and optionally a chiral phosphine ligand.

Step (iii) typically comprises biaryl coupling such as a Suzuki coupling with a boronic acid derivative of a compound of formula A-$(R^1)_n$ catalysed by, for example, bis(triphenylphosphine)palladium(II) chloride in a solvent system comprising for example dimethoxyethane and water and in the presence of a base such as sodium carbonate.

Step (iv) typically comprises elimination of the phenyl vinyl sulfone with a strong base such as potassium tert-butoxide.

Alternatively, a compound of formula (III) wherein p and q both represent 0, can be prepared by following Scheme 1, except for carrying out Suzuki coupling before reduction at Step (iv), as depicted in Scheme 5:

Scheme 5

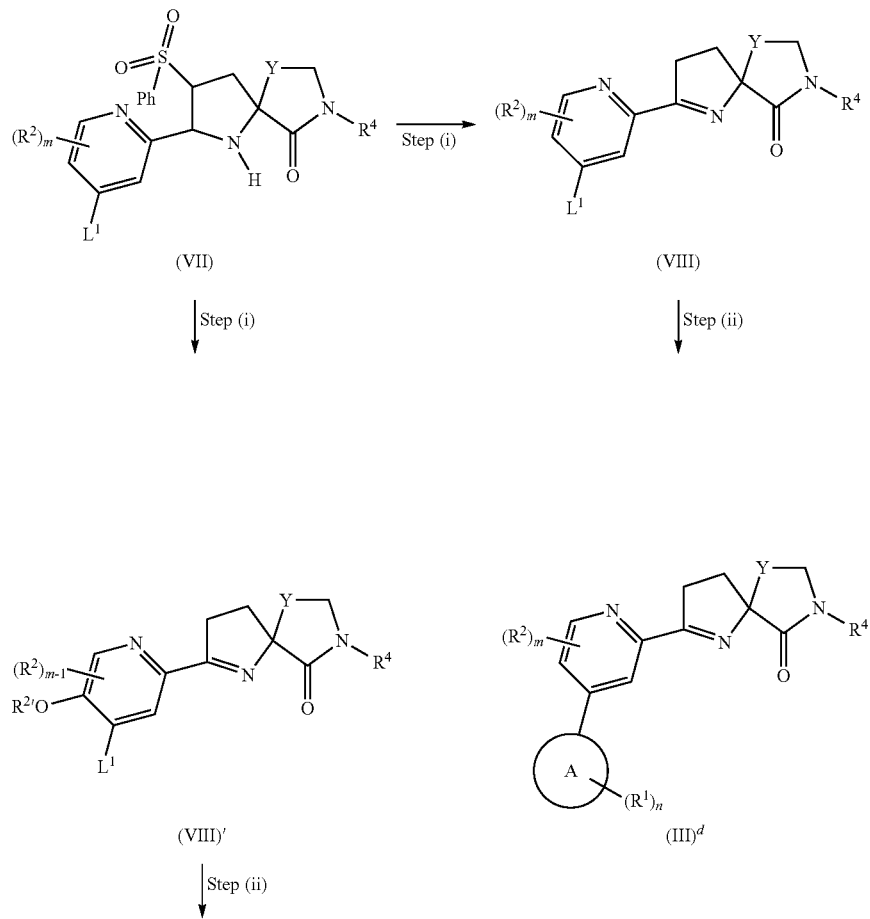

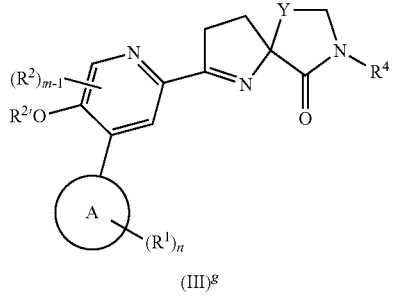

(III)$^g$ wherein $R^1$, $R^2$, $R^4$, m, n, A and Y are as defined herein for compounds of formula (I) and, $L^1$ represents a suitable leaving group such as a halogen atom (e.g. bromine) or an —O—SO$_2$—CF$_3$ group.

Step (i) typically comprises elimination of the phenyl vinyl sulfone with a strong base such as potassium tert-butoxide, or sodium methoxide. In the case where an $R^2$ group is at the 5-position of the pyridine ring and is a leaving group (such as F or Cl), this group may, in the course of the reaction (or as a separate subsequent reaction), be displaced by an alkoxide group (such as tBuO or MeO) to give a compound of formula (VIII)'.

Step (ii) typically comprises biaryl coupling such as a Suzuki coupling with a boronic acid derivative of a compound of formula A-(R$^1$)$_n$ catalysed by, for example, bis(triphenylphosphine)palladium(II) chloride in a solvent system comprising for example dimethoxyethane and water and in the presence of a base such as sodium carbonate.

The compounds of formula (V) may be prepared in accordance with known methodology or, for example compounds of formula (V) wherein Y represents —CH$_2$—, $R^4$ represents H, p represents 2 and $R^5$ represents methyl may be prepared in accordance with Scheme 6:

Scheme 6

Step (i) typically comprises a Horner-Wadsworth-Emmons condensation reaction of an optionally substituted carbamate protected alpha aminocarboxaldehyde with an optionally substituted methyl 2-(tert-butoxycarbonylamino) acetate in the presence of a catalyst such as 1,8-diazabicyclo (5.4.0)undec-7-ene.

Step (ii) typically comprises a continuous hydrogenation reaction performed in a flow system, for example by using a hydrogenation reactor such as an H-cube, and passing a flow of substrate through a packed catalyst cartridge.

Step (iii) typically comprises deprotection of the amine group with a strong acid such as HCl in a solvent such as dioxane.

Examples of suitable carboxaldehyde compounds referred to hereinbefore may be prepared in accordance with Scheme 7:

Scheme 7

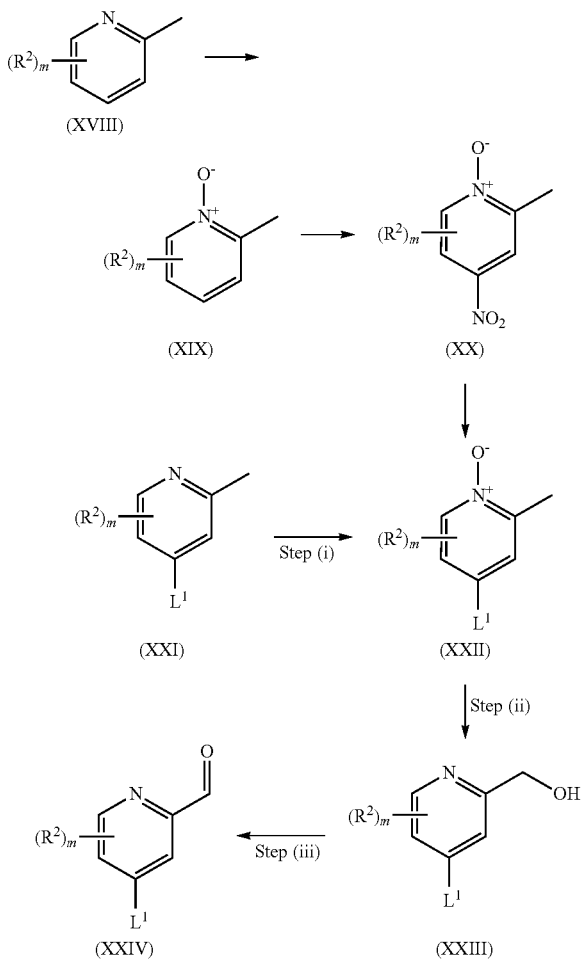

wherein $R^2$ and m are as defined herein for compounds of formula (I) and $L^1$ represents a suitable leaving group, such as bromine.

Step (i) typically comprises nucleophilic substitution of a nitro oxide-pyridine such as 2,3-dimethyl-4-nitro-1-oxido-pyridin-1-ium by using an acyl halide in the presence of an acid, such as acetyl bromide in acetic acid.

Step (ii) typically comprises addition of a hydroxyl group in a Boekelheide rearrangement using an acid anhydride such as trifluoroacetic anhydride in the presence of a solvent such as dichloromethane.

Step (iii) typically comprises oxidation of the alcohol group, for example a Swern oxidation using an acyl chloride such as oxalyl chloride in the presence of a solvent such as dimethyl sulfoxide.

Carboxaldehyde compounds of formula (XXXIV) suitable for reacting with compounds of formula (V) in Scheme 3 may also be prepared according to Scheme 8:

Scheme 8

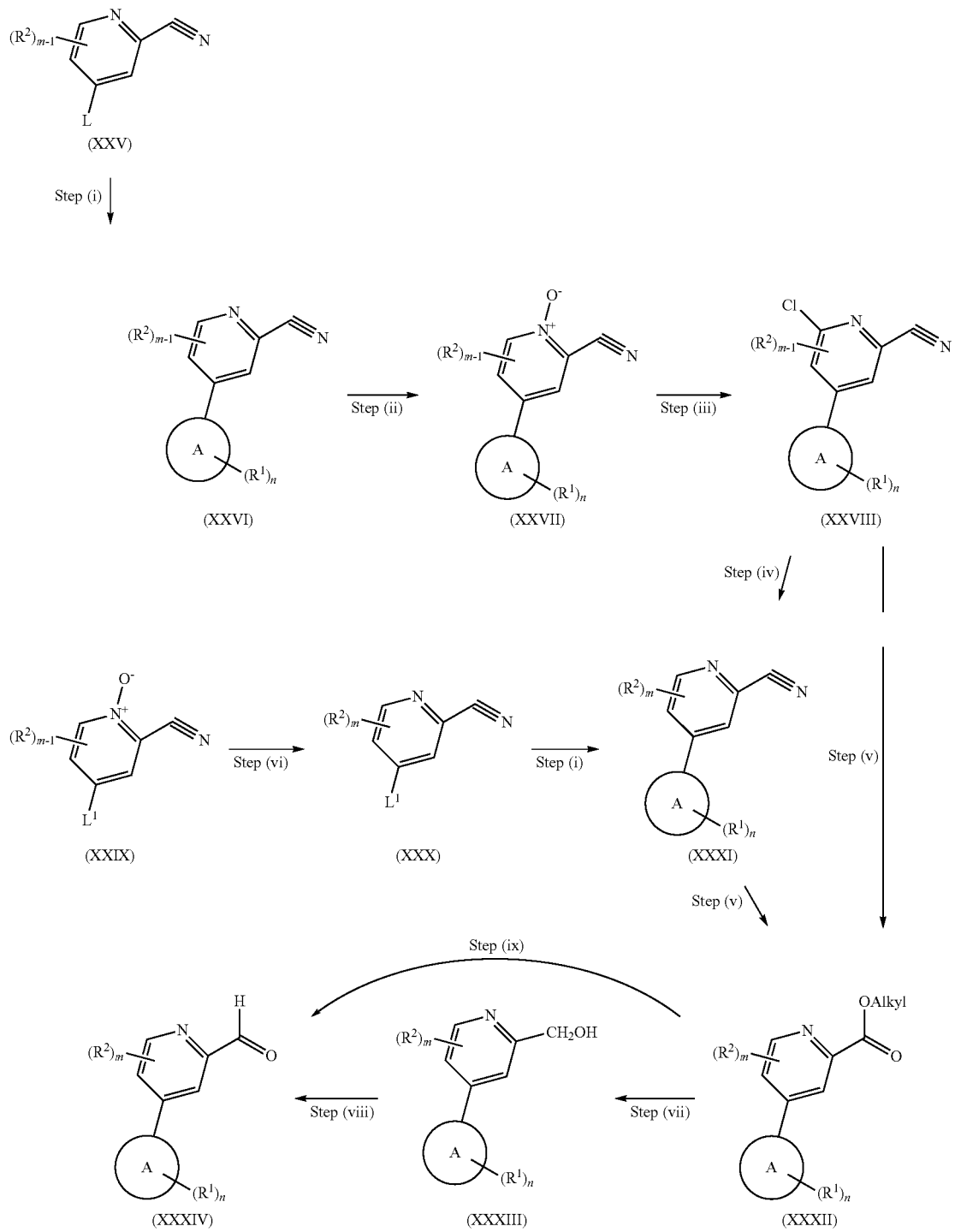

wherein A, $R^1$, $R^2$ and m are as defined herein for compounds of formula (I) and $L^1$ represents a suitable leaving group, such as chlorine or bromine.

Step (i) typically comprises a Suzuki coupling of a 2-cyanopyridine (such as 4-chloropyridine-2-carbonitrile with an aromatic boronic acid (such as 5-ethoxy-2-fluorophenylboronic acid) in the presence of a suitable transition metal catalyst (such as $PdCl_2(PPh_3)_2$) in the presence of a base (such as sodium carbonate) and in a suitable solvent such as DME.

Step (ii) comprises an oxidation to an N-oxide using for example metachloroperbenzoic acid, in a suitable solvent such as dichloromethane.

Step (iii) typically comprises treatment with an agent such as phosphorus oxychloride.

Step (iv) involves the nucleophilic aromatic substitution of the chloride with a carbon nucleophile such as Grignard agent in a suitable solvent such as THF in the presence of a catalyst such as $Fe(acac)_3$ Step (v) involves the treatment with an alcohol (such as methanol or ethanol) in the presence of a strong base such as sodium methoxide or sodium hydroxide to cause solvolysis of the nitrile to an ester and effect nucleophilic displacement of any chloride $R_2$ group.

Step (vi) involves the reaction of a pyridine oxide with cyanating dehydrating agent such as diethoxyphosphorylformonitrile in the presence of a base such as triethylamine in a suitable solvent such as acetonitrile. Alternatively the same transformation may be achieved by treatment with an alkylating agent such as dimethyl sulphate in a suitable solvent such as acetonitrile followed by a source of cyanide ion such as potassium cyanide.

Step (vii) comprises the reduction of an ester to an alcohol using a hydride reducing agent such as sodium borohydride in a suitable solvent such as ethanol.

Step (viii) comprises oxidation of the alcohol group to an aldehyde which may be achieved using Swern conditions (such as oxalyl chloride and DMSO in the presence of triethylamine), or alternatively by using a Dess-Martin Periodinane reaction or an oxidant such as manganese dioxide.

Step (ix) comprises the partial reduction of the ester to an aldehyde using a hindered hydride reducing agent such as diisobutyl aluminium hydride in a solvent such as toluene.

Arylboronic acids and esters of formula (XXXVI) suitable for coupling in a Suzuki reaction, such as the reaction with a compound of formula (II) to form a compound of formula (I), may be formed as indicated in Scheme 9:

Scheme 9

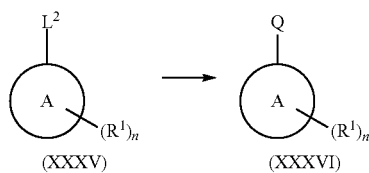

wherein A, $R^1$, and n are as defined herein for compounds of formula (I) and $L^2$ represents a suitable leaving group, such as iodine, bromine, chloride or trifluoromethanesulfonate and Q represents a boronic acid, a cyclic pinacolborate ester or a dialkyl borate ester.

The transformation of Scheme 9 may be achieved by the reaction of a compound of formula (XXXV) with a diboralane species such as bis(pinocolato)diboron in the presence of a suitable catalyst such as $Pd(dppf)Cl_2.CH_2Cl_2$ and a mild base such as potassium acetate in a suitable solvent such as DMF. Alternatively, for the case where $L^2$ is chlorine, bromine or iodine, this material can be treated with butyl lithium at low temperature in a suitable solvent such as diethyl ether or THF, and quenched with a trialkylborate such as trimethyl borate or triisopropyl borate.

Compounds of formula (XXXV) may be prepared by the method shown in Scheme 10:

Scheme 10

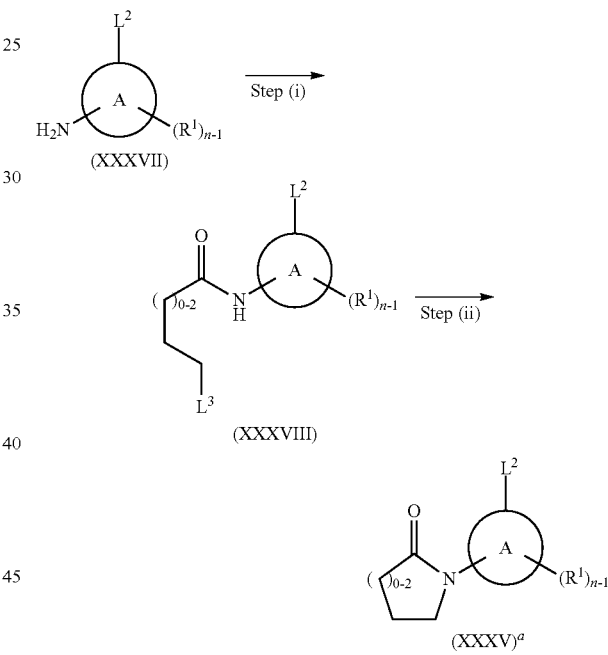

wherein A, $R^1$, and n are as defined herein for compounds of formula (I) and $L^2$ represents a suitable leaving group, such as iodine, bromine, chloride or trifluoromethanesulfonate and $L^3$ represents a suitable leaving group such as halide or mesylate.

Step (i) comprises the amidation of an amino substituted aryl group with a suitable alkyl acid chloride (for example 4-chlorobutanoyl chloride) in the presence of a base such as triethylamine and in a solvent such as dichloromethane, or by reacting the pyridine with the corresponding acid and an amide coupling agent.

Step (ii) comprises a cyclisation which may be carried out by treatment with a strong base such as sodium hydride in a suitable solvent such as THF.

Compounds of formula (XXXV) may also be prepared by the method shown in Scheme 11:

Scheme 11

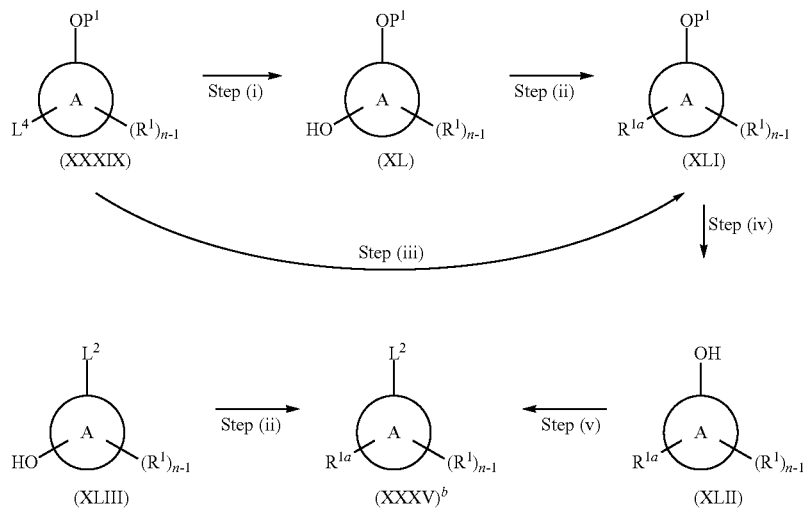

wherein $R^1$, A and n are as defined herein for compounds of formula (I), $R^{1a}$ represents an alkoxy or O-linked haloalkyl group, or an N or C-linked aromatic group and, $L^2$ represents a suitable leaving group such as a halogen atom (e.g. bromine) or an —O—SO$_2$—CF$_3$ group, $L^4$ represents a halogen (such as bromine or iodine) and $P^1$ represents a protecting group (such as benzyl).

Step (i) comprises the reaction of a suitable bromoaryl compound with a source of hydroxide (such as potassium hydroxide) in the presense of a suitable transition metal catalyst (for example a palladium alkylphosphine complex) in a suitable solvent such as water.

Step (ii) comprises the alkylation of a phenol with an alkylation agent (such as iodoethane) in the presence of a base such as cesium carbonate in a solvent such as DMF.

Step (iii) comprises either (a) a coupling to an NH heterocycle (3-methyl-1H-pyrazole) by heating with copper iodide in the presence of a suitable ligand (such as 1,2-diaminocyclohexane) and in a suitable solvent such as 1,4-dioxane together with an appropriate base (such as potassium phosphate); or (b) a coupling to an aryl boronic acid or ester (such as 1-methyl-4-(4,4,5,5-tetramethyl-1,3,2-dioxaborolan-2-yl)-1 h-pyrazole) in the presence of a palladium catalyst (such as bis(triphenylphosphine)palladium (II) dichloride) and a base (such as sodium carbonate) in a suitable solvent system such as acetonitrile-water.

Step (iv) comprises the removal of a protecting group for example by hydrogenation over a palladium metal catalyst in an alcohol solvent.

Step (v) comprises the conversion of an aromatic alcohol to a leaving group such as a trifluoromethane sulfonic acid ester which may be achieved by treatment with trifluoromethanesulfonic anhydride in the presence of a suitable base such as pyridine and in an appropriate solvent such as dichloromethane.

Compounds of formula (XXXV) may also be prepared by the method shown in Scheme 12:

Scheme 12

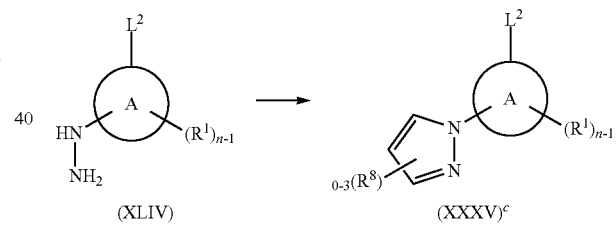

wherein $R^1$, A, $R^8$ and n are as defined herein for compounds of formula (I) and, $L^2$ represents a suitable leaving group such as a halogen atom (e.g. bromine).

The transformation may be achieved by the condensation of an aryl hydrazine of formula (XLIV) with a beta-dicarbonyl species (or protected variant thereof such as 4,4-dimethoxybutan-2-one) in a suitable solvent such as ethanol.

An alternative route to compounds of formula (III) wherein p and q both represent 0 is shown in Scheme 13:

Scheme 13

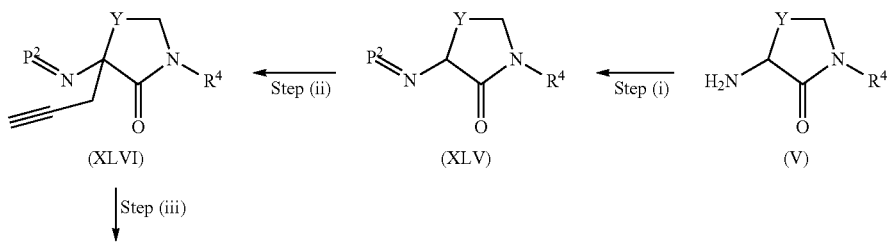

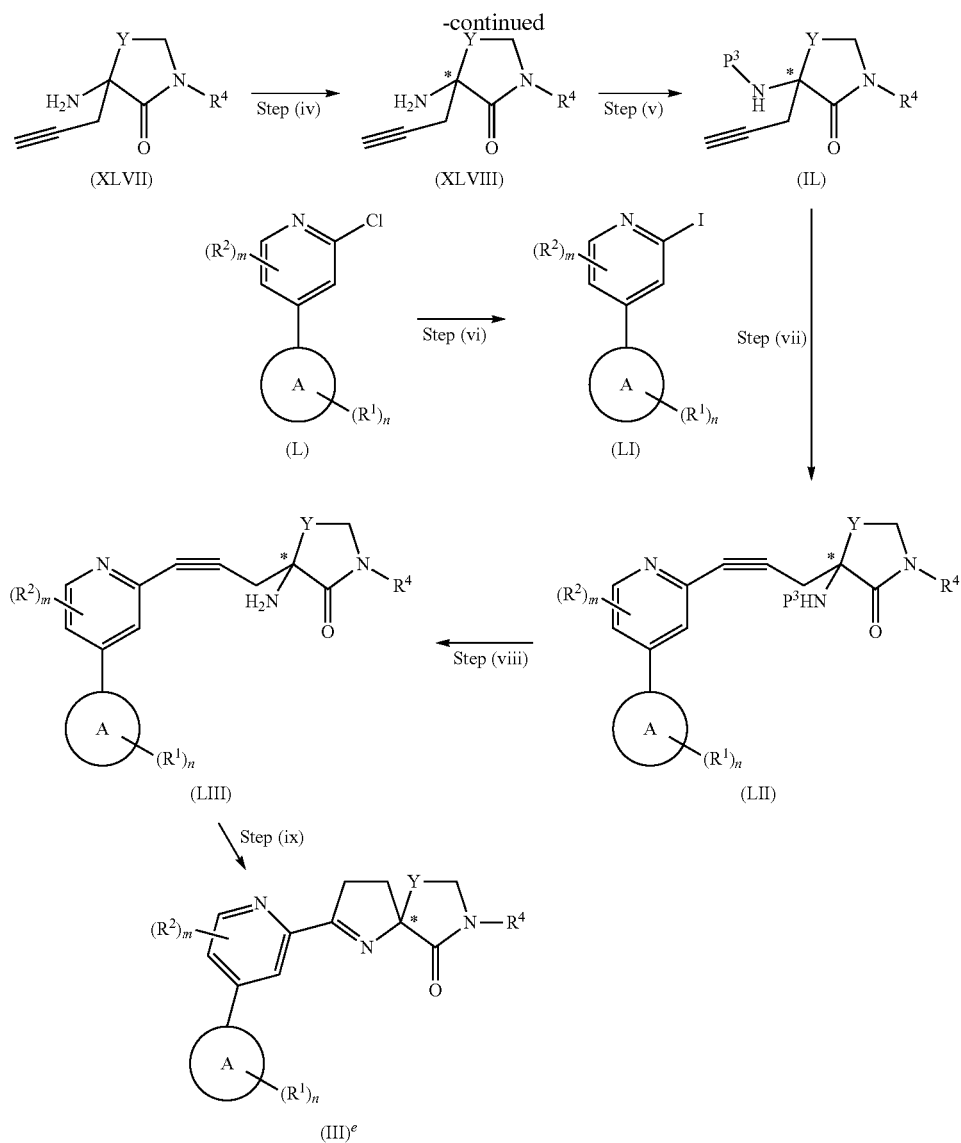

wherein $R^1$, $R^2$, $R^4$, n, m, Y and A, are as defined herein for compounds of formula (I) and both $P^2$ and $P^3$ represents nitrogen protecting groups.

Step (i) comprises the N-protection of the amino group of amide (V) by for example reaction with an imine such as benzophenone imine in a suitable solvent such as DCE.

Step (ii) comprises reaction with a propargylating agent such as propargyl bromide in the presence of a base such as potassium tert-butoxide in a suitable solvent such as THF.

Step (iii) comprises the removal of the N-protecting group which may typically be achieved by treatment with a mild acid (such as citric acid) in a suitable solvent such as THF.

Step (iv) comprises a chiral resolution step in which the amine (XLVII) is formed into a chiral salt by fractional crystallisation of a co-solution with a chiral acid (for example (2S)-2-(6-methoxy-2-naphthyl)propanoic acid or (+)-mandelic acid) from an appropriate solvent (for example acetonitrile, THF or IPA), followed by liberation of the resolved amine by treatment with a base such as a basic ion exchange resin.

Step (v) comprises protection of the amino nitrogen, which can be achieved, for example by introducing a Boc group by treatment of the amine with Boc anhydride.

Step (vi) comprises the conversion of a substituted 2-chloropyridine to a 2-iodopyridine which may typically be achieved by treatment with concentrated aqueous HI solution or by using sodium iodide in acetyl chloride.

Step (vii) comprises a Sonogashira coupling which typically uses a copper catalyst such as copper iodide, a palladium catalyst (for example $PdCl_2(Ph_3P)_2$) and frequently includes an amine base such as diethylamine or diisopropylamine, in a suitable solvent such as THF, DCE, acetonitrile or tert-butyl methyl ether.

Step (viii) is an acid catalysed deprotection step which is typically achieved by treatment with trifluoroacetic acid, formic acid or sulphuric acid in a suitable solvent such as dichloromethane, 1,4-dioxane, THF or water.

Step (ix) is typically achieved by treatment with a silver or gold salt such as silver triflate in a solvent such as acetonitrile.

Compounds of formula (III) where q represents 0, p represents 1 or 2 and $R^5$ represents fluorine may be prepared as shown in Scheme 14:

Scheme 14

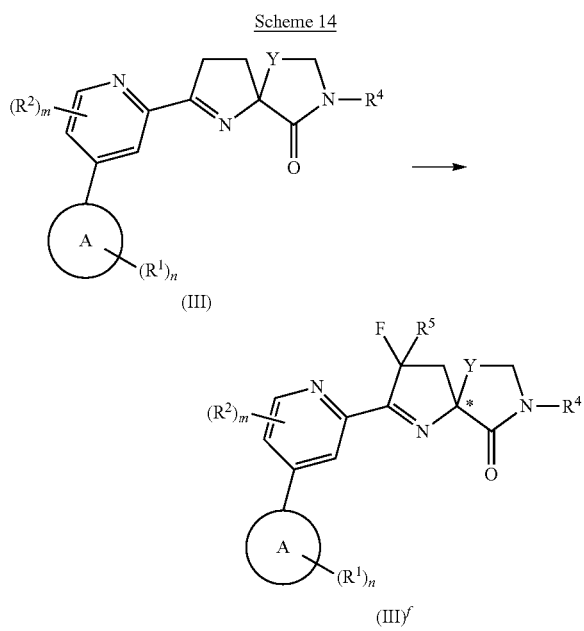

(III)

(III)′ wherein $R^1$, $R^2$, $R^4$, m, n, A and Y are as defined herein for compounds of formula (I).

The transformation may be achieved by an electrophilic fluorinating agent for example 1-chloromethyl-4-fluoro-1,4-diazoniabicyclo[2.2.2]octane bis(tetrafluoroborate), together with an acid catalyst such as trifluoroacetic acid in a suitable solvent such as acetonitrile.

It will be appreciated by those skilled in organic synthesis that two or more chemical steps in the schemes above may be run sequentially without isolation of intermediate materials.

A wide range of well known functional group interconversions for process (e) are known by a person skilled in the art for converting a precursor compound to a compound of formula (I) and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described in Schemes 1-14 are followed or preceded by one or more reactions known to the skilled of the art and are performed in an appropriate order to achieve the requisite substitutions on $R^1$, $R^2$, $R^3$ and $R^4$, defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of esters groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
Sonogashira alkyne-iodoaromatic coupling,
N-oxidation,
salification.

One particular interconversion which may be mentioned includes alkylation of compounds of formula (I) wherein $R^4$ represents hydrogen to a compound of formula (I) wherein $R^4$ represents $C_{1-6}$ alkyl. Such an interconversion reaction typically comprises a suitable base such as sodium hydride to deprotonate the amide followed by treatment with an alkylating agent such as methyl iodide in a solvent such as DMF.

Another particular interconversion which may be mentioned is where a compound of formula (I) with an $R^1$ alkoxy group has that group converted to a hydroxyl group (for example by treatment with boron tribromide), This group in turn may be alkylated (for example with an alkyl alcohol under Mitsunobu conditions).

One further particular interconversion which may be mentioned includes alkylation of compounds of formula (I) wherein $R^3$ represents hydrogen to a compound of formula (I) wherein $R^3$ represents $C_{1-6}$ alkyl. Such an interconversion reaction typically comprises reductive amination with an aldehyde in the presence of a suitable mild hydride donor agent such as sodium acetoxyborohydride, or reaction with an alkylating agent such as ethyl iodide in the presence of a base such as potassium carbonate.

It is recognised that the sequence of reactions involving aryl coupling and reduction may be varied. It is also recognised that a wide range of palladium based catalysts are suitable for conducting aryl coupling reactions.

It may also be recognised that isomer separation may occur at any suitable stage in the synthetic sequence. It should be stressed that such chiral separation forms a key aspect of the invention and that such separation may be conducted in accordance with the methodology described herein or may be conducted in accordance with known methodology. It is also recognised that it may be beneficial to temporarily form a protected derivative of an intermediate in the synthesis, for example, a Boc-protected amine, or SEM-protected amide, in order to facilitate chromatographic separation, chiral resolution or to give improved solubility or yields in particular steps.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. Alternatively an aldehyde or ketone may be masked as a germinal dihalide, for example as a difluoride. In both cases, the aldehyde or ketone group is readily regenerated by hydrolysis using an excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$C$_6$H$_4$C$_6$H$_5$, —NH-Boc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulphonyl)ethyl carbamate (—NH-Psec).

Other protecting groups for amines, such as cyclic amines and heterocyclic N—H groups, include toluenesulphonyl (tosyl) and methanesulphonyl (mesyl) groups, benzyl groups such as a para-methoxybenzyl (PMB) group and tetrahydropyranyl (THP) groups.

Additionally amines may be protected as imines, including substituted benzylimines and benzhydrylimines.

A carboxylic acid group may be protected as an ester for example, as: an $C_{1-7}$alkyl ester (e.g., a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$alkyl ester; or a $C_{5-20}$ aryl-$C_{1-7}$ alkyl ester (e.g., a benzyl ester; a nitrobenzyl ester; para-methoxybenzyl ester.

As discussed hereinabove, it is believed that compounds of the invention may be useful for the treatment of diseases and conditions mediated by modulation of voltage-gated sodium channels.

In one embodiment, the compounds will be state-dependent sodium channel inhibitors.

In another embodiment, the compounds will be subtype selective NaV1.7 sodium channel state-dependent inhibitors.

In another embodiment, the compounds will be state-dependent sodium channel inhibitors which have a suitable developability profile on oral administration, for example in terms of exposure (Cmax) and/or bioavailability.

In one embodiment, the compounds will be sodium channel inhibitors.

In another embodiment, the compounds will be subtype selective NaV1.7 sodium channel inhibitors.

In another embodiment, the compounds will be sodium channel inhibitors which have a suitable developability profile on oral administration, for example in terms of exposure (Cmax) and/or bioavailability.

According to a further aspect of the invention, there is provided compounds of the invention for use as a medicament, preferably a human medicament.

According to a further aspect the invention provides the use of compounds of the invention in the manufacture of a medicament for treating or preventing a disease or condition mediated by modulation of voltage-gated sodium channels.

In one particular embodiment, compounds of the invention may be useful as analgesics. For example they may be useful in the treatment of chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention may be useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention may also be useful in the amelioration of inflammatory disorders, for example in the treatment of skin conditions (e.g. sunburn, burns, eczema, dermatitis, psoriasis); ophthalmic diseases; lung disorders (e.g. asthma, bronchitis, emphysema, allergic rhinitis, non-allergic rhinitis, cough, respiratory distress syndrome, pigeon fancier's disease, farmer's lung, chronic obstructive pulmonary disease, (COPD); gastrointestinal tract disorders (e.g. Crohn's disease, ulcerative colitis, coeliac disease, regional ileitis, irritable bowel syndrome, inflammatory bowel disease, gastroesophageal reflux disease); other conditions with an inflammatory component such as migraine, multiple sclerosis and myocardial ischemia.

In one embodiment, the compounds of the invention are useful in the treatment of neuropathic pain or inflammatory pain as described herein.

Without wishing to be bound by theory, other diseases or conditions that may be mediated by modulation of voltage-gated sodium channels are selected from the list consisting of [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

ii) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

iii) Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

iv) Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

v) Enhancement of cognition including the treatment of cognition impairment in other diseases such as schizophrenia, bipolar disorder, depression, other psychiatric disorders and psychotic conditions associated with cognitive impairment, e.g. Alzheimer's disease:
vi) Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:
vii) Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):
viii) Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).
ix) Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):
x) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9): and
xi) Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).
xii) Impulse control disorder" including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

In another embodiment, diseases or conditions that may be mediated by modulation of voltage gated sodium channels are depression or mood disorders In another embodiment, diseases or conditions that may be mediated by modulation of voltage gated sodium channels are substance related disorders.

In a further embodiment, diseases or conditions that may be mediated by modulation of voltage gated sodium channels are Bipolar Disorders (including Bipolar I Disorder, Bipolar II Disorder (i.e. Recurrent Major Depressive Episodes with Hypomanic Episodes) (296.89), Cyclothymic Disorder (301.13) or Bipolar Disorder Not Otherwise Specified (296.80)).

In a still further embodiment, diseases or conditions that may be mediated by modulation of voltage gated sodium channels are Nicotine-Related Disorders such as Nicotine Dependence (305.1), Nicotine Withdrawal (292.0) or Nicotine-Related Disorder Not Otherwise Specified (292.9).

Compounds of the invention may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Compounds of the invention may also be useful in the treatment of bladder hyperrelexia following bladder inflammation.

Compounds of the invention may also be useful in the treatment of neurodegenerative diseases and neurodegeneration such as dementia, particularly degenerative dementia (including senile dementia, Alzheimer's disease, Pick's disease, Huntington's chorea, Parkinson's disease and Creutzfeldt-Jakob disease, motor neuron disease); The compounds may also be useful for the treatment of amyotrophic lateral sclerosis (ALS) and neuroinflamation.

Compounds of the invention may also be useful in neuroprotection and in the treatment of neurodegeneration following stroke, cardiac arrest, pulmonary bypass, traumatic brain injury, spinal cord injury or the like.

Compounds of the invention may also be useful in the treatment of tinnitus, and as local anaesthetics.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

When used in the treatment or prophylaxis of pain, the compound of formula (I) or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for example COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO 99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilising antiepileptic drugs; cholinesterase inhibitors such as galantamine; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQ/Kv7 channel openers, such as retigabine; additional COX-2 inhibitors are disclosed in U.S. Pat. No. 5,474,995, U.S. Pat. No. 5,633,272, U.S. Pat. No. 5,466,823, U.S. Pat. No. 6,310,099 and U.S. Pat. No. 6,291,523; and in WO 96/25405, WO 97/38986, WO 98/03484, WO 97/14691, WO 99/12930, WO 00/26216, WO 00/52008, WO 00/38311, WO 01/58881 and WO 02/18374.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example lofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstral agents for example pyridoxine and progesterones.

The compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstral agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

It will be appreciated that references herein to "treatment" extend to prophylaxis, prevention of recurrence and suppression or amelioration of symptoms (whether mild, moderate or severe) as well as the treatment of established conditions.

The compound of the invention may be administered as the raw chemical but the active ingredient is preferably presented as a pharmaceutical formulation.

According to a further aspect, the invention provides a pharmaceutical composition comprising a compound of the invention, in association with one or more pharmaceutically acceptable carrier(s), diluents(s) and/or excipient(s). The carrier, diluent and/or excipient must be "acceptable" in the sense of being compatible with the other ingredients of the composition and not deleterious to the recipient thereof.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter-sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit will for example contain from 5-1000 mg of the active ingredient. The dosage as employed for adult human treatment may range from 10 to 3000 mg per day depending on the route and frequency of administration. For oral administration a typical dose may be in the range of 50 to 1500 mg per day, for example 120 to 1000 mg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The embodiments described for the first aspect similarly apply to these further aspects. The diseases and conditions described above extend, where appropriate, to these further aspects:
  i) A compound of the invention for use in treating or preventing a disease or condition mediated by modulation of voltage-gated sodium channels.
  ii) A method of treatment or prevention of a disease or condition mediated by modulation of voltage-gated sodium channels in a mammal comprising administering an effective amount of a compound of the invention.
  iii) Use of a compound of the invention in the manufacture of a medicament to treat or prevent a disease or condition mediated by modulation of voltage-gated sodium channels.
  iv) Use of a compound of the invention to treat or prevent a disease or condition mediated by modulation of voltage-gated sodium channels.

Examples

The invention is illustrated by the Examples described below.

In the procedures that follow, after each starting material, reference to a Description or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

The absolute configuration of the stereocentres within the spiro fused compounds prepared from achiral starting materials and resolved by use of chiral chromatography have been assigned using a combination of optical rotation and NMR spectroscopy (for determining the relative stereochemistry of adjacent stereocentres) and relating these to chiral intermediates and final compounds which have had their absolute configurations determined by single crystal X-ray crystallography. For example, the absolute stereochemistry of E50 and E96 were determined by X-ray crystallography. E50 and E96 were derived from imine intermediates D31S and D43R respectively thus defining the stereochemistry of the single stereocentre in these intermediates as S in D31S and R in D43R, with the carbonyl attached to the chiral centre by a solid wedged bond (note the Cahn-Ingold-Prelog priority changes for the groups attached to the chiral centre in D31S and D43R). The optical rotations for these intermediates were positive and analogous imine intermediates with a positive optical rotation were also assigned the stereochemistry represented by the carbonyl with a solid wedge bond (S for the 5,6-spiro system and R for 5,5-spiro system). The relative stereochemistry of the aryl bearing stereocentre was determined by comparison of the $^1$H NMR spectrum for both isomers and relating these to the NMR spectra of E50 and E96 and intermediates in their synthesis. The chemical shift of the benzylic proton in isomers with the aryl group cis to the carbonyl group as in E50 and E96 was generally upfield (by 0.1-0.4 ppm) when compared to isomers with the aryl group trans to the carbonyl group.

Compounds are named using ACD/Name PRO 6.02 chemical naming software (Advanced Chemistry Development Inc., Toronto, Ontario, M5H2L3, Canada), or using Lexichem's automatic chemical naming software (OpenEye Scientific Software Inc. Santa Fe, N. Mex., USA).

Proton Magnetic Resonance (NMR) spectra are typically recorded on a Bruker instruments at 300, 400 or 500 MHz. Chemical shifts are reported in ppm (δ) using the residual solvent line as internal standard. Splitting patterns are designed as s, singlet; d, doublet; t, triplet; q, quartet; m, multiplet; br, broad. The NMR spectra were recorded at a temperature ranging from 25 to 90° C. When more than one conformer was detected the chemical shifts for the most abundant one is reported.

LC-MS Data (LC-MS) is typically generated on an Waters ZQ Mass Spectrometer, operating in switched ES+ and ES− ionization modes coupled to an Agilent 1100 Series HPLC system with in line Aglient 1100 UV-DAD and Sedere SEDEX 75 ELSD Detection. Instrument control and data acquisition is mediated through the Waters MassLynx-OpenLynx software suite. Separation was performed on a Waters SunFire C18 (30×4.6 mm, 3.5 μm) column Flow Rate: 3.0 mL/min. column temperature 30° C. Injection Volume: 5.0 μL. Mobile phase [A]: 3:97:0.05 (v/v/v) Acetonitrile: Water: Formic Acid. Mobile Phase [B]: 97:3:0.05 (v/v/v) Acetonitrile: Water: Formic Acid. Gradient: 97% [A]3% [B] for 0.1 min. Ramp to 3% [A]97% [B] at 4.0 min. Hold at 97% [B] to 5 min. Return to 97% [A] at 6 min. Detector parameters: UV-DAD: Range 190 to 450 nm, Interval 2 nm, Threshold 0.1 mAU. ELSD: Temperature 40° C., Range 8. Mass Spectrometer: ES+: Mass Range 125 to 625 in 0.50 sec. Interscan delay 0.25 sec. Capillary 4.0 kV. ES−: Mass Range 125 to 625 in 0.50 sec. Interscan delay 0.25 sec. Capillary 3.0 kV.

In the mass spectra only one peak in the molecular ion cluster is usually reported.

For reactions involving microwave irradiation, a Biotage Initiator was used.

Chiral chromatography was typically performed using a ChiralPak™ AD-H or ChirakPak IA column from Daicel® using heptane/ethanol or heptane/ethanol/methanol mixtures as eluent. Analytical chiral HPLC was carried out either on an Agilent 1100 series HPLC system or on a Gilson HPLC system using a 250×4.6 mm column and a flow rate of 1 ml/min. Preparative chiral HPLC was carried out using a Gilson preparative HPLC system on a 250×19 mm semi-preparative column with a flow rate of 18 ml/min.

Flash silica gel chromatography was carried out on silica gel 230-400 mesh (supplied by Merck AG Darmstadt, Germany) or over pre-packed Biotage silica or NH silica cartridges.

Optical rotations were measured using an Optical Activity Ltd AA-10 automatic polarimeter (Cambridge, UK) using a cell of 10 cm path length and in chloroform solution unless otherwise indicated.

SCX cartridges are ion exchange solid phase extraction columns supplied by Varian. The eluent used with SCX cartridges is methanol followed by 0.2-2.0M ammonia solution in methanol.

In most preparations, purification was performed using Biotage automatic flash chromatography (SP4 or Isolera) systems.

The following abbreviations are used herein:
Boc tertButyloxycarbonyl
CBz Benzyloxycarbonyl
Dppf 1,1'-Bis(diphenylphosphino)ferrocene
DBU 1,8-Diazabicyclo (5.4.0)undec-7-ene
DCE 1,2-dichloroethane
DCM Dichloromethane
DIBAL Diisobutylaluminium hydride
DME Dimethoxyethane
DMF Dimethylformamide
DMSO Dimethylsulfoxide
EtOAc Ethyl Acetate
Et$_2$O Ether
Fe(acac)$_3$ Iron (III) tri(acetoacetate)
HCl Hydrochloric Acid
HPLC High-performance liquid chromatography
K$_2$CO$_3$ Potassium carbonate
LC-MS Liquid chromatography-Mass spectrometry
mCPBA Metachloroperbenzoic acid
MeCN Acetonitrile
MeOH Methanol
MgSO$_4$ Magnesium sulfate
Na$_2$CO$_3$ Sodium carbonate
NaOH Sodium hydroxide
NMP N-methylpyrrolidinone
PdCl$_2$(Ph$_3$P)$_2$ Bis(triphenylphosphine)palladium(II) chloride
SEM trimethylsilylethyloxymethyl
SiO$_2$ Silica gel
tBME Tertiary butyl methyl ether
TFAA Trifluoroacetic anhydride
THF Tetrahydrofuran Description 1

3-[(E)-(4-Bromo-2-pyridyl)methyleneamino]-1-methyl-pyrrolidin-2-one (D1)

To a stirred solution of 4-bromopyridine-2-carbaldehyde (2232.1 mg, 12 mmol) in anhydrous DCM (60 mL) under nitrogen at room temperature, was added racemic 3-amino-1-methyl-pyrrolidin-2-one (1506.8 mg, 13.2 mmol) [CAS: 2483-65-0] and magnesium sulfate (4500 mg, 37.4 mmol). The resulting mixture was left to stir at room temperature overnight. It was filtered and the filtrate washed with half saturated brine. The organic layer was dried (Na$_2$SO$_4$) and evaporated to give 3-[(E)-(4-bromo-2-pyridyl)methyleneamino]-1-methyl-pyrrolidin-2-one (D1) (3.15 g, 11.2 mmol, 93% yield), as a cream solid;

300 MHz $^1$H NMR $\delta_H$ (CDCl$_3$) 2.30-2.41 (1H, m), 2.41-2.55 (1H, m), 2.94 (3H, s), 2.46 (1H, dt), 3.60 (1H, ddd), 4.20 (1H, t), 7.50 (1H, d), 7.21 (1H, s), 8.48 (1H, s), 8.49 (1H, d).

Description 2

3-(Benzenesulfonyl)-2-(4-bromo-2-pyridyl)-7-methyl-1,7-diazaspiro[4.4]nonan-6-one (D2)

A mixture of 3-[(E)-(4-bromo-2-pyridyl)methyleneamino]-1-methyl-pyrrolidin-2-one (which may be prepared as described in Description 1) (564.3 mg, 2 mmol) and phenyl vinyl sulfone (339.8 mg, 2.02 mmol) in THF (10 mL) was treated with silver acetate (333.99 mg, 2 mmol). The mixture was stirred at room temp for 2 hours, filtered through Celite and concentrated to give the title compound as a brown gum; M/Z: 450, 452 (M+H$^+$)

Description 3

(5R)-2-(4-Bromo-pyridin-2-yl)-7-methyl-1,7-diaza-spiro[4.4]non-1-en-6-one (D3R) and (5S)-2-(4-Bromo-pyridin-2-yl)-7-methyl-1,7-diaza-spiro[4.4]non-1-en-6-one (D3S)

Method A

A mixture of 3-(benzenesulfonyl)-2-(4-bromo-2-pyridyl)-7-methyl-1,7-diazaspiro[4.4]nonan-6-one (which may be prepared as described in Description 2) (900.7 mg, 2 mmol) in THF (10 mL) under nitrogen at 0° C. was treated with potassium tert-butoxide in THF (2.94 mL, 5 mmol) portionwise over 10 minutes. The mixture was stirred at 0° C. for 1 hour and then acetic acid (0.29 mL, 5 mmol) was added and the mixture was filtered through Celite and then concentrated. Chromatography of the crude material on a Si—NH column (0-80% ethyl acetate in isohexane) gave 329 mg of a racemic mix of the title compounds as cream solid.

300 MHz $^1$H NMR $\delta_H$ (CDCl$_3$) 1.89-1.96 (1H, m), 2.13-2.23 (1H, m), 2.44 (1H, ddd), 2.58 (1H, ddd), 2.97 (3H, s), 3.20-3.44 (3H, m), 3.66-3.74 (1H, m), 7.70 (1H, d), 8.85 (1H, s), 8.97 (1H, d).

This was separated into two enantiomers by chiral chromatography using a ChiralPak AD-H column eluting with 15% ethanol in heptanes. The optical rotation of the isomers is based on analysis of separately purified samples;

Fast isomer: (R)-2-(4-Bromo-pyridin-2-yl)-7-methyl-1,7-diaza-spiro[4.4]non-1-en-6-one (D3R);
Optical rotation $\alpha[^D/_{22}]$=+86.9 (c=1, CHCl$_3$).
Slow isomer: (S)-2-(4-Bromo-pyridin-2-yl)-7-methyl-1,7-diaza-spiro[4.4]non-1-en-6-one (D3S);
Optical rotation $\alpha[^D/_{22}]$=+85.8 (c=1, CHCl$_3$)

Method B

To a stirred solution of 3-[(E)-(4-bromo-2-pyridyl)methyleneamino]-1-methyl-pyrrolidin-2-one (which may be prepared as described in Description 1) (8.1 g, 28.709 mmol) in anhydrous THF (80 mL) under nitrogen at room temperature, was added phenyl vinyl sulfone (4.926 g, 29.283 mmol) and silver acetate (0.53 g, 3.18 mmol) The resulting mixture was left to stir at room temperature for 1.5 hours. The reaction mixture was filtered through Celite and the filtrate was stirred under nitrogen in an ice bath and treated with potassium t-butoxide (33.78 mL of 1.7 M solution in THF, 57.42 mmol) over 5 minutes. After completion of the addition, the mixture was stirred at room temperature for 1 hour, acetic acid (3.29 mL, 57.42 mmol) was added and the mixture was stirred for 5 minutes and then filtered through Celite and concentrated. Chromatography (Biotage Si—NH column, 10-100% ethyl acetate in isohexane) followed by trituration of the isolated product with ether and drying under vacuum gave the title compounds as an off-white solid 5.74 g (racemic). Purification as in Method A gave the separate enantiomers.

Description 4

(2R,5S)-2-(4-Bromo-2-pyridyl)-7-methyl-1,7-diazaspiro[4.4]nonan-6-one (D4R) and (2S,5S)-2-(4-Bromo-2-pyridyl)-7-methyl-1,7-diazaspiro[4.4]nonan-6-one (D4S)

To a stirred solution of (5S)-2-(4-bromo-pyridin-2-yl)-7-methyl-1,7-diaza-spiro[4.4]non-1-en-6-one (which may be prepared as described in Description 3)(1.08 g 3.5 mmol) in anhydrous DCM (18 mL) under nitrogen at room temperature, was added conc HCl (0.37 mL, 3.68 mmol) and after 5 minutes sodium triacetoxyborohydride (2226.21 mg, 10.5 mmol). The resulting mixture was left to stir at room temperature for 1 hour. Saturated $Na_2CO_3$ solution was added (approximately 3 mL) and the mixture was stirred for 10 minutes. The solvents were evaporated and DCM was added and the solution was dried with $Na_2SO_4$ and filtered and evaporated to give a yellow oil (approximately 1.1 g) which was purified by flash chromatography on KP-NH silica (0-100% ethyl acetate in isohexane) to give 614 mg of predominantly trans isomer (D4R) and 379 mg of an approximately 6:1 mixture of the cis isomer (D4S) and trans isomer. The trans isomer was further purified by preparative chiral HPLC. Characterisation based on separately purified isomers gave trans isomer (2R,5S)-2-(4-bromo-2-pyridyl)-7-methyl-1,7-diazaspiro[4.4]nonan-6-one (D4R);

300 MHz $^1$H NMR $\delta_H$ (CDCl$_3$) 1.82-1.95 (2H, m), 2.00-2.24 (3H, m), 2.5 (1H, br s), 2.47-2.59 (1H, m), 2.90 (3H, s), 3.26-3.37 (2H, m), 4.68 (1H, t), 7.32 (1H, d), 7.75 (1H, s), 8.34 (1H, d).

Cis isomer (2S,5S)-2-(4-bromo-2-pyridyl)-7-methyl-1,7-diazaspiro[4.4]nonan-6-one (D4S);

300 MHz $^1$H NMR $\delta_H$ (CDCl$_3$) 1.76-1.87 (1H, m), 1.99-2.20 (4H, m), 2.29-2.40 (1H, m), 2.8 (1H, br s), 2.90 (3H, s), 2.28-3.41 (2H, m), 4.38 (1H, t), 7.33 (1H, d), 7.75 (1H, s), 8.38 (1H, d).

Description 5

4-Bromo-1-hydroxy-2,3-dimethyl-pyridin-1-ium acetate (D5)

To a stirred solution of acetyl bromide (67.45 mL, 912.28 mmol) in acetic acid (140 mL) was added 2,3-dimethyl-4-nitro-1-oxido-pyridin-1-ium [TCl](15.34 g, 91.23 mmol) portionwise under nitrogen. The reaction was then warmed to 80° C. for 3 hours. The reaction was cooled and poured into a beaker of ice, and then basified with $K_2CO_3$ [caution]. The aqueous was then extracted with EtOAc (600 mL) and the organics were washed with brine (100 mL), dried over MgSO$_4$, filtered and concentrated in vacuo. This gave 4-bromo-1-hydroxy-2,3-dimethyl-pyridin-1-ium acetate (D5)(18.12 g, 65.677 mmol, 72% yield);

300 MHz $^1$H NMR $\delta_H$ (CDCl$_3$) 2.02 (3H, s), 2.45 (3H, s), 2.63 (3H, s), 7.40 (1H, d), 8.17 (1H, d), 11.5 (1H br s).

Description 6

(4-Bromo-3-methyl-2-pyridyl)methanol (D6)

To a stirred solution of 4-bromo-1-hydroxy-2,3-dimethyl-pyridin-1-ium acetate (which may be prepared as described in Description 5) (18120 mg, 69.13 mmol) in DCM (100 mL) was added trifluoroacetic anhydride (23.89 mL, 171.9 mmol) dropwise and the reaction was stirred at room temperature for 8 hours, then additional trifluoroacetic anhydride (23.89 mL, 171.9 mmol) was introduced. After 1 day, the reaction mixture was concentrated in vacuo to remove excess TFAA & DCM. The residue was then diluted with MeOH (200 mL) and a solution of saturated aqueous $K_2CO_3$ (approximately 100 mL) was added with caution [exotherms]. The resultant suspension was stirred for 3 hours and then concentrated in vacuo. The residue was then partitioned between DCM (200 mL) and water (200 mL). The organics were separated and dried over MgSO$_4$, filtered and concentrated in vacuo. The residue was dissolved in DCM (100 mL) and trifluoroacetic anhydride (23.89 mL, 171.9 mmol) was added dropwise and the reaction was stirred at room temperature for 16 hours. The reaction mixture was concentrated in vacuo, and the residue, diluted with MeOH (200 mL) and a solution of saturated aqueous $K_2CO_3$ (approximately 100 mL) was added with caution, and the resulting suspension was stirred for 3 hours. The reaction mixture was then concentrated in vacuo, and the residue was partitioned between DCM (200 mL) and water (200 mL). The organics were separated and dried over MgSO$_4$, filtered and concentrated in vacuo. The residue was purified over silica (100 g SNAP), using the Isolera instrument, eluting with EtOAc: isohexane 0%-50%. Fractions containing desired product were combined and concentrated in vacuo to give (4-bromo-3-methyl-2-pyridyl)methanol (D6) (7055 mg, 34.917 mmol, 50.5% yield) as a yellow solid;

300 MHz $^1$H NMR $\delta_H$ (CDCl$_3$) 2.29 (3H, s), 4.73 (3H, s), 7.48 (1H, d), 8.23 (1H, d).

Description 7

4-Bromo-3-methyl-pyridine-2-carbaldehyde (D7)

To a stirred and cooled (−78° C.) solution of oxalyl chloride (2.82 mL, 33.37 mmol) in DCM (70 mL) under nitrogen was added dropwise a solution of dimethyl sulfoxide (5.17 mL, 72.81 mmol) in DCM (10 mL). Stirring was continued for 10 minutes. A solution of (4-bromo-3-methyl-2-pyridyl)methanol (which may be prepared as described in Description 6) (6130 mg, 30.34 mmol) in DCM (35 mL) was then added dropwise over 20 minutes. The reaction was then allowed to stir for 1 hour. Triethylamine (18.98 mL, 136.53 mmol) was then added dropwise and the reaction was allowed to warm to room temperature over 1.5 hours. The reaction was then quenched by addition of water (approximately 100 mL). The organics were separated and washed with additional water (150 mL). The organics were dried using a hydrophobic frit and concentrated in vacuo to give 4-bromo-3-methyl-pyridine-2-carbaldehyde (D7) (5.709 g, 28.541 mmol, 94.1% yield) as a brown oil which crystallised on standing.

300 MHz $^1$H NMR $\delta_H$ (CDCl$_3$) 2.78 (3H, s), 7.72 (1H, d), 8.46 (1H, d), 10.15 (1H, s).

Description 8

7-(Benzenesulfonyl)-8-(4-bromo-3-methyl-2-pyridyl)-3-methyl-3,9-diazaspiro[4.4]nonan-4-one (D8)

To a stirred solution of 3-amino-1-methyl-pyrrolidin-2-one (3258.49 mg, 28.55 mmol) in methanol (8 mL) was added 4-bromo-3-methyl-pyridine-2-carbaldehyde (which may be prepared as described in Description 7) (5710 mg, 28.55 mmol), phenyl vinyl sulfone (4801.68 mg, 28.55 mmol), and calcium triflate (482.74 mg, 1.43 mmol). The reaction was stirred for 5 minutes. Triethylamine (3.97 mL, 28.55 mmol) was then added [caution—slight exotherm observed], and the reaction was stirred for 15 minutes. A large amount of solid was observed to precipitate out of the reaction, this was sonicated and stirred for a further 15 minutes. The solid was then filtered off, and washed with additional methanol (approximately 10 mL). The pale cream solid was then washed with diethyl ether (10 mL), and air dried for 10 minutes to give a colourless solid, then dissolved in MeOH (8 mL), and treated with phenyl vinyl sulfone (4801.68 mg, 28.55 mmol), calcium triflate (482.74 mg, 1.43 mmol) and lastly triethylamine (3.97 mL, 28.55 mmol). The reaction mixture was then stirred at room temperature for 16 hours. The solid was filtered off, and washed with $Et_2O$ (10 mL). The solid was then air dried for 15 minutes on the sinter to afford 7-(benzene-sulfonyl)-8-(4-bromo-3-methyl-2-pyridyl)-3-methyl-3,9-diazaspiro[4.4]nonan-4-one (D8) (3520 mg, 7.58 mmol, 26.5% yield);
M/Z: 464, 466 (M+H$^+$)

Description 9

(5R)-2-(4-Bromo-3-methyl-2-pyridyl)-7-methyl-1,7-diazaspiro[4.4]non-1-en-6-one (D9R) and (5S)-2-(4-Bromo-3-methyl-2-pyridyl)-7-methyl-1,7-diazaspiro[4.4]non-1-en-6-one (D9S)

To an ice cooled solution of 7-(benzenesulfonyl)-8-(4-bromo-3-methyl-2-pyridyl)-3-methyl-3,9-diazaspiro[4.4]nonan-4-one (which may be prepared as described in Description 8) (3500 mg, 7.54 mmol) in THF (5 mL) was added potassium tert-butoxide (1691 mg, 15.07 mmol) and the reaction was stirred for 1 hour. Additional KO$^t$Bu (1.7 g, 15.1 mmol) was added and the reaction was stirred at 00° C. for 1 hour, and allowed to warm to room temperature overnight. The reaction was quenched by addition of acetic acid (3.45 mL, 60.3 mmol), concentrated in vacuo and loaded onto a silica column (100 g SNAP). Elution using EtOAc gave 2-(4-bromo-3-methyl-2-pyridyl)-7-methyl-1,7-diazaspiro[4.4]non-1-en-6-one (1410 mg, 4.3762 mmol, 58.063% yield) as a pale yellow crystalline solid;
300 MHz $^1$H NMR $\delta_H$ (CDCl$_3$) 1.87-1.96 (1H, m), 2.11-2.22 (1H, m), 2.40-2.57 (2H, m), 2.12 (3H, s), 2.96 (3H, s), 3.25-3.33 (2H, m), 3.36-3.45 (1H, m), 3.08-3.18 (1H, m), 7.53 (1H, d), 8.25 (1H, d).

This material was dissolved in ethanol: heptane (50%, 18 mL), and separated using chiral HPLC (ChiralPak AD-H). Fractions containing faster running peak were combined and concentrated in vacuo to give a colourless oil which crystallised on standing (5S)-2-(4-bromo-3-methyl-2-pyridyl)-7-methyl-1,7-diazaspiro[4.4]non-1-en-6-one (D9S) (435 mg, 1.3501 mmol);
Optical rotation α[$^D/_{22}$]=−112 (c=1, CHCl$_3$).
Fractions containing the slower peak were combined and concentrated in vacuo to give a colourless oil which crystallised on standing (5R)-2-(4-bromo-3-methyl-2-pyridyl)-7-methyl-1,7-diazaspiro[4.4]non-1-en-6-one (D9R), (458 mg, 1.4215 mmol);
Optical rotation α[$^D/_{22}$]=+116 (c=1, CHCl$_3$).

Description 10

(5R)-2-(4-Bromo-3-methyl-2-pyridyl)-7-methyl-1,7-diazaspiro[4.4]-nonan-6-one (D10)

To a stirred solution of (5R)-2-(4-bromo-3-methyl-2-pyridyl)-7-methyl-1,7-diazaspiro[4.4]non-1-en-6-one (which may be prepared as described in Description 9) (510 mg, 1.58 mmol) in DCM (10 mL) under nitrogen at 00° C. was added concentrated hydrochloric acid (0.14 mL, 1.58 mmol) followed by sodium triacetoxyborohydride (1341.89 mg, 6.33 mmol). The reaction was then allowed to stir while gradually warming to room temperature over 4 hours. The reaction was quenched by addition of aqueous NaOH (2 M, 10 mL), and the reaction was diluted with DCM (10 mL). The layers were separated, and the organic layer was dried using a hydrophobic frit. The organics were then concentrated in vacuo to give the desired products as a colourless oil: (5R)-2-(4-bromo-3-methyl-2-pyridyl)-7-methyl-1,7-diazaspiro[4.4]nonan-6-one; (D10) (403 mg, 0.6215 mmol, 39.3% yield) as a mixture of diastereomers at the 2-position;
M/Z: 324, 326 (M+H$^+$).

Description 11

(5S)-3-(4-Bromo-3-methyl-2-pyridyl)-8-methyl-4,8-diazaspiro[4.4]-nonan-9-one (D11)

Applying the method of Description 10 but using (5S)-2-(4-bromo-3-methyl-2-pyridyl)-7-methyl-1,7-diazaspiro[4.4]non-1-en-6-one (which may be prepared as described in Description 9) (431 mg, 1.3 mmol) in place of its enantiomer and other components scaled in molar ratio, a mixture of desired product epimers were obtained as a colourless oil: (5S)-3-(4-bromo-3-methyl-2-pyridyl)-8-methyl-4,8-diazaspiro[4.4]nonan-9-one (D11) (421 mg, 0.649 mmol, 48.5% yield);
M/Z: 324, 326 (M+H$^+$).

Description 12

7-(Benzenesulfonyl)-8-(4-bromo-6-methyl-2-pyridyl)-3-methyl-3,9-diazaspiro[4.4]nonan-4-one (D12)

3-Amino-1-methyl-pyrrolidin-2-one (2.66 g, 23.32 mmol) in THF (5 mL) was added to a solution of 4-bromo-6-methyl-pyridine-2-carbaldehyde [CAS: 448906-71-6](4.24 g, 21.2 mmol) and magnesium sulfate (3.57 g, 29.68 mmol) in THF (50 mL) under N$_2$ at room temperature and the reaction was stirred for 30 minutes. To this mixture was added vinylsulfonylbenzene (4.28 g, 25.44 mmol), followed by silver acetate (3.89 g, 23.32 mmol) and the reaction was stirred for 5 minutes. DBU (3.49 mL, 23.32 mmol) was added and stirring was continued for 1 hour. The reaction was diluted with DCM, filtered, washed with further DCM and the combined organic phases evaporated to afford a black semi-solid. This was suspended in EtOAc and water was added. The remaining solid was filtered off and washed with additional EtOAc and combined with the organics phase. The layers were separated and the organic phase dried (Na$_2$SO$_4$) and the solvent evaporated to afford a black oil.

This was purified using a Biotage SP4, on silica (100 g SNAP cartridge), eluting with 100% EtOAc to afford partially purified material which was further purified by trituration with methanol. The mother liquors were passed through an SCX column, eluting successively with methanol and 0.5 M ammonia in methanol, then purifying the base eluted material by crystallisation from methanol. The combined solids comprised 7-(benzenesulfonyl)-8-(4-bromo-6-methyl-2-pyridyl)-3-methyl-3,9-diazaspiro[4.4]-nonan-4-one (D12) (1.36 g, 2.93 mmol, 14% yield);

300 MHz $^1$H NMR $\delta_H$ (CDCl$_3$) 2.21-2.32 (1H, m), 2.39-2.66 (3H, m), 2.42 (3H, s), 2.93 (3H, s), 2.10 (1H, d), 3.33-3.53 (2H, m), 4.24-4.33 (1H, m), 4.38-4.45 (1H, m), 6.97 (1H, s), 7.12 (1H, s), 7.45 (2H, t), 7.58 (1H, t), 7.27 (2H, d).

Description 13

2-(4-Bromo-6-methyl-2-pyridyl)-7-methyl-1,7-diazaspiro[4.4]non-1-en-6-one (D13)

To a solution of 7-(benzenesulfonyl)-8-(4-bromo-6-methyl-2-pyridyl)-3-methyl-3,9-diazaspiro[4.4]nonan-4-one (which may be prepared as described in Description 12) in THF (20 mL) at 00° C. was added 1.7 M potassium tert-butoxide in THF (2.69 mL, 4.58 mmol) dropwise over 5 minutes. The reaction mixture was stirred at 00° C. for 1.5 hours. The reaction was quenched by the addition of acetic acid (0.26 mL, 4.58 mmol) and then the mixture was filtered, washed with dichloromethane and the filtrate concentrated at reduced pressure to give a brown gum. The product was purified by silica gel chromatography eluting with 40-100% ethyl acetate in iso-hexane to give racemic 2-(4-bromo-6-methyl-2-pyridyl)-7-methyl-1,7-diazaspiro[4.4]non-1-en-6-one a pale yellow solid (D13) (314 mg);

300 MHz $^1$H NMR $\delta_H$ (CDCl$_3$) 1.83-1.94 (1H, m), 2.10-2.21 (1H, m), 2.39-2.60 (2H, m), 2.57 (3H, s), 2.95 (3H, s), 3.19-3.41 (3H, m), 3.62-3.71 (1H, m), 7.38 (1H, s), 8.13 (1H, s).

Descriptions 14 and 15

2-[2-Methyl-6-[(5S)-7-methyl-6-oxo-1,7-diazaspiro[4.4]non-1-en-2-yl]-4-pyridyl]-4-(trifluoromethyl)benzonitrile (D14S), 2-[2-Methyl-6-[(5R)-7-methyl-6-oxo-1,7-diazaspiro[4.4]non-1-en-2-yl]-4-pyridyl]-4-(trifluoromethyl)benzonitrile (D14R), 2-[2-Methyl-6-[(5R)-7-methyl-6-oxo-1,7-diazaspiro[4.4]non-1-en-2-yl]-4-pyridyl]-4-(trifluoromethyl)benzamide (D15S) and 2-[2-Methyl-6-[(5R)-7-methyl-6-oxo-1,7-diazaspiro[4.4]non-1-en-2-yl]-4-pyridyl]-4-(trifluoromethyl)benzamide (D15R)

To a solution of 2-(4-bromo-6-methyl-2-pyridyl)-7-methyl-1,7-diazaspiro[4.4]non-1-en-6-one (which may be prepared as described in Description 13) (180 mg, 0.5600 mmol) in 1,2-dimethoxyethane (3 mL) and water (1 mL) was added 2-(4,4,5,5-tetramethyl-1,3,2-dioxaborolan-2-yl)-4-(trifluoromethyl)benzonitrile (182.56 mg, 0.6100 mmol) and sodium carbonate (177.65 mg, 1.68 mmol). The reaction mixture was degassed with nitrogen and then treated with bis(triphenylphosphine)palladium (II) dichloride (19.61 mg, 0.0300 mmol). The reaction was heated in the microwave at 120° C. for 15 minutes. The reaction mixture was diluted with dichloromethane and water. After separation of the layers, the aqueous phase was re-extracted with dichloromethane and the combined organic phases passed through a hydrophobic frit. The solvent was evaporated and the residue purified by silica gel chromatography to afford 2-[2-methyl-6-(7-methyl-6-oxo-1,7-diazaspiro[4.4]non-1-en-2-yl)-4-pyridyl]-4-(trifluoromethyl)-benzonitrile (D14) as a colourless solid (74 mg);

M/Z: 413 (M+H$^+$).

Further elution of the column with 0-20% methanol in ethyl acetate gave (2-[2-methyl-6-(7-methyl-6-oxo-1,7-diazaspiro[4.4]non-1-en-2-yl)-4-pyridyl]-4-(trifluoromethyl) benzamide (D15) as a colourless solid (107 mg);

M/Z: 431 (M+H$^+$).

A second batch of D14 (190 mg, 0.4600 mmol) was dissolved in 20% ethanol in heptane (26 mL) and passed through an Chiralpak AD-H preparative column eluting with 10% EtOH/heptanes.

The first isomer to elute 2-[2-methyl-6-[(5R)-7-methyl-6-oxo-1,7-diazaspiro[4.4]-non-1-en-2-yl]-4-pyridyl]-4-(trifluoromethyl)benzonitrile (D14R) was isolated as a colourless solid (55 mg);

Optical rotation $\alpha[^D/_{22}]$=+48.9 (c=0.715, CHCl$_3$).

The second isomer to elute 2-[2-methyl-6-[(5S)-7-methyl-6-oxo-1,7-diazaspiro[4.4]non-1-en-2-yl]-4-pyridyl]-4-(trifluoromethyl)benzonitrile (D14S) was isolated as a colourless solid (57 mg);

Optical rotation $\alpha[^D/_{22}]$=−47.3 (c=0.55, CHCl$_3$).

A second batch of D15 (325 mg, 0.76 mmol) was dissolved in 20% ethanol in heptane (21 mL) and passed through an AD-H chiral preparative column eluting with 20% EtOH/heptane.

The first isomer to elute 2-[2-methyl-6-[(5R)-7-methyl-6-oxo-1,7-diazaspiro[4.4]non-1-en-2-yl]-4-pyridyl]-4-(trifluoromethyl)benzamide (D15R) was isolated as a colourless solid (120 mg);

Optical rotation $\alpha[^D/_{22}]$=+73.6 (c=0.72, CHCl$_3$).

The second isomer to elute 2-[2-methyl-6-[(5S)-7-methyl-6-oxo-1,7-diazaspiro[4.4]non-1-en-2-yl]-4-pyridyl]-4-(trifluoromethyl)benzamide (D15S) was isolated as a pale yellow solid (126 mg);

Optical rotation $\alpha[^D/_{22}]$=−70.2 (c=0.755, CHCl$_3$).

Description 16

3-(Benzenesulfonyl)-7-methyl-2-[6-methyl-4-[4-(trifluoromethyl)phenyl]-2-pyridyl]-1,7-diazaspiro[4.4]nonan-6-one (D16)

PdCl$_2$(Ph$_3$P)$_2$ (128.4 mg, 0.1800 mmol) was added to a degassed mixture of 4-trifluoromethylphenyl-boronic acid (365.03 mg, 1.92 mmol), sodium carbonate (582.01 mg, 5.49 mmol) and 7-(benzene-sulfonyl)-8-(4-bromo-6-methyl-2-pyridyl)-3-methyl-3,9-diazaspiro[4.4]nonan-4-one (which may be prepared as described in Description 12) (850 mg, 1.83 mmol) in DME (12 mL) and water (4 mL) under N$_2$ in a microwave vial and the reaction was heated in the microwave at 120° C. for 1 hour. The mixture was diluted with water/EtOAc, filtered, and the phases separated. The organic layer was dried (Na$_2$SO$_4$) and the solvent evaporated to afford a light brown solid. This was purified using a Biotage SP4, 25 g SNAP cartridge, eluting with 0 to 10% MeOH/EtOAc to afford the 3-(benzenesulfonyl)-7-methyl-2-[6-methyl-4-[4-(trifluoromethyl)-phenyl]-2-pyridyl]-1,7-diazaspiro[4.4]nonan-6-one (D16) (1 g, 1.8883 mmol) as an off-white solid (with traces of impurities);

300 MHz $^1$H NMR $\delta_H$ (CDCl$_3$) 2.24-2.38 (1H, m), 2.40-2.51 (2H, m), 2.52 (3H, s), 2.58-2.68 (1H, m), 2.92 (3H, s), 3.23 (1H, br d), 3.34-3.50 (2H, m), 4.36 (1H, m), 4.63 (1H, m), 7.18 (2H, s), 7.34-7.46 (3H, m), 7.65-7.83 (6H, m).

Description 17

(5S)-8-Methyl-3-[6-methyl-4-[4-(trifluoromethyl)phenyl]-2-pyridyl]-4,8-diazaspiro[4.4]non-3-en-9-one (D17S) and (5R)-8-Methyl-3-[6-methyl-4-[4-(trifluoromethyl)phenyl]-2-pyridyl]-4,8-diazaspiro[4.4]non-3-en-9-one (D17R)

Potassium tert-butoxide (2.22 mL, 3.78 mmol) was added dropwise to a solution of 3-(benzene-sulfonyl)-7-methyl-2-[6-methyl-4-[4-(trifluoromethyl)phenyl]-2-pyridyl]-1,7-diazaspiro[4.4]nonan-6-one (which may be prepared as described in Description 16) (1 g, 1.89 mmol) in THF (20 mL) at 00° C. under $N_2$ and the reaction was stirred at 0° C. for 1 hour. Acetic acid (0.22 mL, 3.78 mmol) was added and the reaction was stirred for 5 minutes. The solid was filtered off and the solvent was evaporated to afford a crude oil. This was purified using a Biotage SP4, 25 g SNAP cartridge, eluting with 0 to 10% MeOH in EtOAc to afford 7-methyl-2-[6-methyl-4-[4-(trifluoromethyl)phenyl]-2-pyridyl]-1,7-diazaspiro[4.4]non-1-en-6-one (641 mg, 1.4892 mmol, 78.9% yield) as a pale yellow oil;

300 MHz $^1$H NMR $\delta_H$ (CDCl$_3$) 1.89-1.98 (1H, m), 2.11-2.24 (1H, m), 2.42-2.62 (2H, m), 2.66 (3H, s), 2.96 (3H, s), 2.29-3.49 (3H, m), 3.33-3.32 (1H, m), 7.41 (1H, s), 7.70-7.84 (4H, m), 8.18 (1H, s);

A separate batch of this material (766 mg dissolved in 10 mL 30% EtOH/Heptane) was purified by chiral HPLC using an Chiralpak AD-H preparative column eluting with 10% EtOH/heptane. Fractions containing the first isomer to elute were concentrated to give a colourless foam (D17S) (234 mg);

Optical rotation $\alpha[^D/_{22}]$=–80.0 (c=1, CHCl$_3$).

Fractions containing the slower eluting isomer were concentrated to give a colourless solid (D17R) (130 mg) with a 9% impurity, but not the other isomer;

Optical rotation $\alpha[^D/_{22}]$=+81.5 (c=1, CHCl$_3$).

Description 18

(2S)-2-[4-(2-Fluoro-phenyl)-pyridin-2-yl]-7-methyl-1,7-diaza-spiro[4.4]non-1-en-6-one (D18)

To a Smith microwave tube charged with a stirred solution of (5S)-2-(4-bromo-pyridin-2-yl)-7-methyl-1,7-diaza-spiro[4.4]non-1-en-6-one (which may be prepared as described in Description 3) (460 mg, 1.4927 mmol) in anhydrous MeCN (3 mL) at room temperature, was added 2-fluorophenylboronic acid (250.63 mg, 1.7912 mmol), sodium carbonate (348.06 mg, 3.28 mmol), bis(triphenylphosphine)palladium (II) dichloride (52.39 mg, 0.0700 mmol) and water (1 mL). The tube was sealed and flushed with nitrogen. The reaction mixture was heated by microwave at 1500° C. for 30 minutes. The reaction mixture was evaporated to give a crude brown residue. This was purified by silica gel chromatography (25 g SiO$_2$) eluting with ethyl acetate in iso-hexane (10-100%). Evaporation of desired fractions gave (2S)-2-[4-(2-fluoro-phenyl)-pyridin-2-yl]-7-methyl-1,7-diaza-spiro[4.4]non-1-en-6-one (D18) (465 mg, 1.438 mmol, 96.3% yield) as a thick amber oil;

Optical rotation $\alpha[^D/_{22}]$=–76 (c=1, CHCl$_3$)

Description 19

(5S)-2-(4-Bromo-2-pyridyl)-1,7-diazaspiro[4.4]non-1-en-6-one (D19S) and (5R)-2-(4-Bromo-2-pyridyl)-1,7-diazaspiro[4.4]non-1-en-6-one (D19R)

To a suspension of 3-aminopyrrolidin-2-one (2.83 g, 28.22 mmol) in methanol (100 mL) was added 4-bromopicolinaldehyde (5 g, 26.88 mmol) and 4 A molecular sieves (20 g, 26.88 mmol). The reaction mixture was stirred for 16 hours at room temperature and then filtered through a pad of Celite. The filtrate was concentrated to give 3-[(E)-(4-bromo-2-pyridyl)methyleneamino]pyrrolidin-2-one as a brown gum (3.09 g, 11.53 mmol). This was dissolved in THF (120 mL) and treated with phenyl vinyl sulfone (1.94 g, 11.53 mmol), silver acetate (1.92 g, 0.59 mL, 11.53 mmol) and DBU (1.72 mL, 11.53 mmol). The reaction mixture was stirred for 3 hours at room temperature and then filtered through a pad of Celite and washed with dichloromethane. The filtrate was concentrated at reduced pressure to give a brown foam (9.53 g). This was dissolved in THF (120 mL) at 0° C. and treated with 1.7 M potassium tert-butoxide in THF (51.93 mL, 88.28 mmol) dropwise over 5 minutes. The reaction mixture was stirred at 0° C. for 1.5 hours. The reaction was quenched by the addition of acetic acid (5.04 mL, 88.28 mmol) and then filtered, washed with dichloromethane and the filtrate concentrated at reduced pressure to give a brown gum. The product was purified by silica gel chromatography eluting with 0-10% methanol in ethyl acetate to give 2-(4-bromo-2-pyridyl)-1,7-diazaspiro[4.4]non-1-en-6-one as an orange solid (830 mg);

M/Z: 294, 296 (M+H$^+$).

A separate preparation of this racemic material was resolved by chiral chromatography using a Chiralpak AD-H preparative column eluting with 30% EtOH/heptane. The first eluted isomer (5R)-2-(4-bromo-2-pyridyl)-1,7-diazaspiro[4.4]non-1-en-6-one (D19R) was isolated as a pale yellow solid (599 mg);

Optical rotation $\alpha[^D/_{22}]$=+8.5 (c=1.15, CHCl$_3$). The slower isomer (5S)-2-(4-bromo-2-pyridyl)-1,7-diazaspiro[4.4]non-1-en-6-one (D19S) was isolated as a pale yellow solid (661 mg);

Optical rotation $\alpha[^D/_{22}]$=–107.8 (c=1.15, CHCl$_3$)

Description 20

(5S)-2-[4-[4-(Trifluoromethyl)phenyl]-2-pyridyl]-1,7-diazaspiro[4.4]non-1-en-6-one (D20)

To a solution of (5S)-2-(4-bromo-2-pyridyl)-1,7-diazaspiro[4.4]non-1-en-6-one (which may be prepared as described in Description 19) (200 mg, 0.6800 mmol) in 1,2-dimethoxyethane (3 mL) and water (1 mL) was added [4-(trifluoromethyl)phenyl]-boronic acid (142.05 mg, 0.7500 mmol) and sodium carbonate (216.2 mg, 2.04 mmol). The reaction mixture was degassed with nitrogen and then treated with bis(triphenylphosphine)palladium (II) dichloride (23.86 mg, 0.0300 mmol). The reaction mixture was heated in the microwave at 120° C. for 50 minutes then cooled and diluted with dichloromethane and water. After separation of the layers, the aqueous phase was re-extracted with dichloromethane and the combined organic phases passed through a hydrophobic frit. The solvent was evaporated and the residue purified by silica gel chromatography eluting with 0-20% methanol in ethyl acetate to give (5S)-2-[4-[4-(trifluoromethyl)-phenyl]-2-pyridyl]-1,7-diazaspiro[4.4]non-1-en-6-one (D20) as a pale yellow solid (181 mg);

300 MHz $^1$H NMR $\delta_H$ (CDCl$_3$) 1.92-2.09 (1H, m), 2.24-2.33 (1H, m), 2.54-2.65 (2H, m), 3.35-3.50 (3H, m), 3.67-3.74 (1H, m), 6.11 (1H, s), 7.58 (1H, d), 7.80 (4H, abq), 8.43 (1H, s), 8.76 (1H, d).

Description 21

4-Bromo-5-methyl-pyridine-2-carbaldehyde (D21)

A solution of dimethyl sulfoxide (0.85 mL, 12.02 mmol) in DCM (10 mL) was added dropwise over 5 minutes to a solution of oxalyl chloride (0.47 mL, 5.51 mmol) in DCM (20 mL) at −78° C. under an atmosphere of N$_2$ (gas evolved). Stirring was continued for 10 minutes. To this solution was added (4-bromo-5-methyl-2-pyridyl)methanol [CAS: 820224-83-7](1.01 g, 5.01 mmol) in DCM (2 mL) dropwise over a period of 10 minutes. Stirring was then continued for a further 10 minutes. Triethylamine (3.13 mL, 22.54 mmol) was added dropwise and stirring continued for 5 minutes, before allowing the reaction to warm to room temperature. Water was added and the phases were separated by passing over a hydrophobic frit. The organic phase was evaporated to yield a dark brown solid which was dried under vacuum overnight (795 mg). This was purified by column chromatography on silica gel (0-100% EtOAc in isohexane) to yield 4-bromo-5-methyl-pyridine-2-carbaldehyde (D21) (619 mg, 3.0945 mmol, 61.8% yield) as an orange crystalline solid;

300 MHz $^1$H NMR $\delta_H$ (CDCl$_3$) 2.49 (3H, s), 8.14 (1H, s), 8.59 (1H, s), 10.03 (1H, s).

Description 22

3-[(E)-(4-Bromo-5-methyl-2-pyridyl)methyleneamino]-1-methyl-pyrrolidin-2-one (D22)

To a solution of 4-bromo-5-methyl-pyridine-2-carbaldehyde (which may be prepared as described in Description 21) (200 mg, 1 mmol) and 3-amino-1-methyl-pyrrolidin-2-one (125.55 mg, 1 mmol) in dry DCM (2 mL) was added magnesium sulphate (299.96 mg, 2.5 mmol) and the mixture was stirred at room temperature overnight.

Reaction mixture filtered and the filtrate washed with brine, passed over a hydrophobic frit and evaporated to a cream solid, 3-[(E)-(4-bromo-5-methyl-2-pyridyl)methyleneamino]-1-methyl-pyrrolidin-2-one (D22)(257 mg, 0.8678 mmol, 86.8% yield);

300 MHz $^1$H NMR $\delta_H$ (CDCl$_3$) 2.28-2.57 (2H, m), 2.41 (3H, s), 2.94 (3H, s), 3.40-3.48 (1H, m), 3.57-3.55 (1H, m), 4.17 (1H, t), 8.22 (1H, s), 8.43 (1H, s), 8.46 (1H, s).

Description 23

(5S)-2-(4-Bromo-5-methyl-2-pyridyl)-7-methyl-1,7-diazaspiro[4.4]non-1-en-6-one (23S) and (5R)-2-(4-Bromo-5-methyl-2-pyridyl)-7-methyl-1,7-diazaspiro[4.4]-non-1-en-6-one (23R)

To a suspension of 3-[(E)-(4-bromo-5-methyl-2-pyridyl)methyleneamino]-1-methyl-pyrrolidin-2-one (which may be prepared as described in Description 22) (4631 mg, 16.41 mmol) in MeCN (50 mL) was added methanol (5 mL) to give a solution. To this was added vinylsulfonylbenzene (3036.64 mg, 18.05 mmol), silver acetate (4.1 g, 1.26 mL, 24.62 mmol) and finally DBU (2.7 mL, 18.05 mmol). The mixture was stirred in the absence of light overnight. The reaction mixture was filtered over kieselguhr and the filtrate evaporated to yield a dark brown gum (7621.4 mg). This was dissolved in THF (75 mL) and to this was added potassium tert-butoxide in THF (28.96 mL, 49.24 mmol). The mixture was stirred at room temperature over 30 minutes then quenched by addition of acetic acid (2.82 mL, 49.24 mmol). The mixture was filtered over kieselguhr. The filtrate was evaporated to a brown syrup (11.742 g). This was purified using column chromatography (EtOAc with 1% concentrated aqueous ammonia) to yield the racemate as a brown foaming solid, 1.749 g;

300 MHz $^1$H NMR $\delta_H$ (CDCl$_3$) 1.83-1.95 (1H, m), 2.12-2.22 (1H, m), 2.39-2.50 (1H, m), 2.43 (3H, s), 2.51-2.61 (1H, m), 2.96 (3H, s), 3.18-3.40 (3H, m), 3.62-3.73 (1H, m), 8.82 (1H, s), 8.44 (1H, s).

The enantiomers were separated by chiral prep-HPLC using an Chiralpak IA column (30:70 EtOH:heptane) to yield a fast eluting enantiomer (5R)-2-(4-bromo-5-methyl-2-pyridyl)-7-methyl-1,7-diazaspiro[4.4]-non-1-en-6-one (D23R) (539 mg);

Optical rotation $\alpha[^D/_{22}]$=+81 (c=1, CHCl$_3$).

Slow eluting enantiomer: (5S)-2-(4-bromo-5-methyl-2-pyridyl)-7-methyl-1,7-diazaspiro[4.4]non-1-en-6-one (D23S) (560 mg);

Optical rotation $\alpha[^D/_{22}]$=−77 (c=1, CHCl$_3$).

Description 24

2-(Benzyloxycarbonylamino)-2-methyl-propanoic acid (D24)

To a solution of 2-amino-2-methyl-propanoic acid (10 g, 96.97 mmol) in water (75 mL) was added triethylamine (13.48 mL, 96.97 mmol) followed by the dropwise addition of a solution of benzyl (2,5-dioxopyrrolidin-1-yl) carbonate (24.17 g, 96.97 mmol) in MeCN (30 mL). The pH was monitored during the addition and afterwards was adjusted with triethylamine (1.5 mL) from pH 7 to 8. The mixture was stirred at room temperature overnight. The reaction mixture was concentrated by removal of MeCN. To the aqueous was added saturated aqueous sodium bicarbonate (2 mL) which gave a suspension. This was filtered and the solid kept to one side. The filtrate was extracted with ether (three times). The aqueous phase was acidified to pH 3 with approximately 1 M aqueous potassium bisulphate and then extracted into EtOAc (three times). The combined EtOAc extracts were dried over magnesium sulphate, filtered and evaporated to yield 2-(benzyloxycarbonylamino)-2-methyl-propanoic acid (D24) as a waxy white solid, 18.001 g;

300 MHz $^1$H NMR $\delta_H$ (CDCl$_3$) 1.60 (6H, s), 5.1 (2H, s), 5.4 (1H, br s), 8.9 (1H, br s), 7.35-7.42 (5H, m).

Description 25

Ethyl 2-(benzyloxycarbonylamino)-2-methyl-propanoate (D25)

To a solution of 2-(benzyloxycarbonylamino)-2-methyl-propanoic acid (which may be prepared as described in Description 24) (5000 mg, 21.08 mmol) in toluene (50 mL) was added ethanol (5 mL) and p-toluenesulfonic acid (400.89 mg, 2.11 mmol). The solution was stirred at 80° C. overnight. The reaction mixture was evaporated and the residues dissolved in EtOAc and washed with saturated aqueous sodium bicarbonate. The aqueous phase was back extracted into EtOAc. The combined organics were dried over magnesium sulphate, filtered and evaporated to yield the title compound as a light yellow oil (4.667 g);

300 MHz $^1$H NMR $\delta_H$ (CDCl$_3$) 1.27 (3H, q), 1.60 (6H, s), 4.19 (2H, t), 5.11 (2H, s), 5.4 (1H, br s), 7.38 (5H, s).

Description 26

Benzyl N-(1,1-dimethyl-2-oxo-ethyl)carbamate (D26)

To a solution of ethyl 2-(benzyloxycarbonylamino)-2-methyl-propanoate (which may be prepared as described in Description 25) (4667 mg, 17.59 mmol) in toluene (100 mL) cooled to −78° C. was added diisobutyl aluminium hydride (1 M in toluene) (61.57 mL, 61.57 mmol) as a thin stream over approximately 2 minutes. The mixture was stirred at −78° C. over 30 minutes then allowed to warm to 00° C. and stirred over 1.5 hours. The reaction mixture was quenched by addition of a saturated solution of Rochelle's salt. The quenched mixture was stirred over 1 hour, then extracted into ether (3 times). The combined ethereal extracts were dried over magnesium sulphate, filtered and evaporated to a clear oil. The oil was dissolved in DCM (60 mL) and 4 A molecular sieves (4 g) and pyridinium dichromate (16544.34 mg, 43.98 mmol) were added and the mixture stirred at room temperature overnight. The reaction mixture was filtered over kieselguhr and the filtrate evaporated to a dark brown oil. Purification by silica gel column chromatography (20% EtOAc in isohexane) yielded benzyl N-(1,1-dimethyl-2-oxo-ethyl)carbamate (D26) (1840 mg, 8.3164 mmol, 47.3% yield) as a clear oil;

300 MHz $^1$H NMR $\delta_H$ (CDCl$_3$) 1.40 (6H, s), 5.11 (2H, s), 5.3 (1H, br s), 7.35-7.45 (5H, m), 9.43 (1H, s).

Description 27

Methyl 4-(benzyloxycarbonylamino)-2-(tert-butoxycarbonylamino)-4-methyl-pent-2-enoate (D27)

To a solution of benzyl N-(1,1-dimethyl-2-oxo-ethyl)carbamate (which may be prepared as described in Description 26) (1740 mg, 7.86 mmol) in DCM (70 mL) was added methyl 2-(tert-butoxycarbonylamino)-2-dimethoxyphosphoryl-acetate (4675.23 mg, 15.73 mmol) and DBU (2.35 mL, 15.73 mmol). The solution was stirred at room temperature overnight. The reaction mixture was quenched with saturated aqueous ammonium chloride and extracted into DCM. The combined extracts were passed over a hydrophobic frit to yield a pale yellow oil (4.843 g). Purification by silica gel column chromatography (0-100% EtOAc in iso-hexane) yielded methyl 4-(benzyloxy-carbonylamino)-2-(tert-butoxycarbonylamino)-4-methyl-pent-2-enoate (D27) (2499 mg, 6.3677 mmol, 81% yield) as a clear oil;

300 MHz $^1$H NMR $\delta_H$ (CDCl$_3$) 1.44 (9H, s), 1.56 (6H, s), 3.78 (3H, s), 5.07 (3H, s), 6.70 (1H, br s), 6.60 (1H, br s), 7.37 (5H, br s).

Description 28 tert-Butyl N-(5,5-dimethyl-2-oxo-pyrrolidin-3-yl)carbamate (D28)

A solution of methyl 4-(benzyloxycarbonylamino)-2-(tert-butoxycarbonylamino)-4-methyl-pent-2-enoate (which may be prepared as described in Description 27) (2499 mg, 6.37 mmol) in methanol (125 mL) was passed over a 10% Pd/C cartridge on an H-Cube under full hydrogen flow at 25° C. The methanol solution evaporated to give tert-butyl N-(5,5-dimethyl-2-oxo-pyrrolidin-3-yl)carbamate (D28) (1307 mg, 5.7252 mmol, 89.9% yield);

300 MHz $^1$H NMR $\delta_H$ (CDCl$_3$) 1.29, 1.33, (6H, 2s), 1.45 (9H, s), 1.67-1.82 (2H, m), 2.60 (1H, br t), 4.35 (1H, br s), 6.1 (1H, br s).

Description 29

3-Amino-5,5-dimethyl-pyrrolidin-2-one hydrochloride (D29)

To a solution of tert-butyl N-(5,5-dimethyl-2-oxo-pyrrolidin-3-yl)carbamate (which may be prepared as described in Description 28) (1307 mg, 5.73 mmol) in DCM (5 mL) was added 4 M HCl in dioxane (2.86 mL, 11.45 mmol). The solution (which immediately started to evolve gas) was stirred at room temperature over 1 hour. The reaction mixture heavily precipitated. It was diluted with ether (approximately 50 mL) and the solid filtered under vacuum, washed with ether and dried in the vacuum oven to afford 3-amino-5,5-dimethyl-pyrrolidin-2-one hydrochloride (917 mg, 5.5701 mmol, 97.3% yield) as a white solid;

300 MHz $^1$H NMR $\delta_H$ (DMSO) 1.20, 1.25 (6H, 2s), 1.82 (1H, t), 2.28 (1H, dd), 4.07 (1H, br s), 8.5 (4H, br s).

Description 30

(5R)-2-(4-Bromo-2-pyridyl)-8,8-dimethyl-1,7-diazaspiro[4.4]non-1-en-6-one (D30R) and (5S)-2-(4-Bromo-2-pyridyl)-8,8-dimethyl-1,7-diazaspiro[4.4]non-1-en-6-one (D30S)

To a suspension of 3-amino-5,5-dimethyl-pyrrolidin-2-one hydrochloride (which may be prepared as described in Description 29) (817 mg, 4.96 mmol) in DCM (40 mL) was added triethylamine (1.38 mL, 9.93 mmol) giving a solution. To this was added magnesium sulphate (2986.02 mg, 24.81 mmol) and 4-bromopyridine-2-carbaldehyde (923.1 mg, 4.96 mmol) and the mixture was stirred at room temperature overnight. The reaction mixture was filtered and the filtrate was washed with water, passed over a hydrophobic frit and evaporated to a yellow solid. This was dissolved in MeCN (40 mL) and to this was added vinylsulfonylbenzene (834.92 mg, 4.96 mmol), silver acetate (8.28 g, 0.25 mL, 4.96 mmol) and DBU (0.74 mL, 4.96 mmol). The mixture was stirred in the absence of light for 3 hours. The reaction mixture was filtered over kieselguhr and the filtrate evaporated to a brown gum. This was dissolved in THF (16 mL) and to this solution was added 1.7 M potassium tert-butoxide in THF (8.76 mL, 14.89 mmol). The mixture was stirred at room temperature for 1 hour. The reaction mixture was quenched by addition of acetic acid (1.42 mL, 24.82 mmol), the mixture was filtered and the filtrate evaporated. Purification by silica gel column chromatography (EtOAc) yielded a brown solid which was dried under vacuum (369 mg). Separately prepared samples of this material were separated by chiral prep-HPLC Chiralpak AD-H column (30:70 EtOH:heptane) to give faster eluting isomer (5R)-2-(4-bromo-2-pyridyl)-8,8-dimethyl-1,7-diazaspiro[4.4]non-1-en-6-one (D30R);

Optical rotation $\alpha[^D/_{22}]$=+122 (c=1, CHCl$_3$).

The slower eluting isomer, (5S)-2-(4-bromo-2-pyridyl)-8,8-dimethyl-1,7-diazaspiro[4.4]non-1-en-6-one (D30S);

Optical rotation $\alpha[^D/_{22}]$=−119 (c=1, CHCl$_3$).

Description 31

(5R)-3-[4-[4-(Trifluoromethyl)phenyl]-2-pyridyl]-4,
9-diazaspiro[4.5]dec-3-en-10-one (D31R) and (5S)-
3-[4-[4-(Trifluoromethyl)phenyl]-2-pyridyl]-4,9-
diazaspiro-[4.5]dec-3-en-10-one (D31S)

A partially soluble suspension of 3-aminopiperidin-2-one (1.77 g, 15.51 mmol) in DCM (50 mL) was treated with magnesium sulphate (5.58 g, 46.52 mmol) followed by a solution of 4-[4-(trifluoromethyl)phenyl]pyridine-2-carbaldehyde [Waterstone](3.76 g, 14.97 mmol) in DCM (50 mL). The mixture was stirred overnight, filtered and the filtrate evaporated to yield an orange foam (5.27 g). This was dissolved in MeCN (150 mL) and to this solution was added phenyl vinyl sulfone (4.24 g, 25.19 mmol), silver acetate (3.80 g, 1165.63 mL, 22.76 mmol) and DBU (2.27 mL, 15.17 mmol). The mixture was stirred in the absence of light over hours then filtered over kieselguhr and the filtrate evaporated to a very dark brown gum, which was subjected to column chromatography on silica gel (eluting with 0-20% MeOH in DCM) to yield a dark brown solid (2.606 g). To a solution of this material in THF (25 mL) cooled to 00° C. was added potassium tert-butoxide in THF (8.92 mL, 15.16 mmol) dropwise over 5 minutes. The mixture was stirred at 0° C. for 30 minutes then stirred at room temperature for 3 hours. A further portion of potassium tert-butoxide was added (2.97 mL, 1 equivalent) and the mixture stirred for 2 hours. The reaction mixture was quenched with acetic acid (2 mL) and evaporated. The residue was partitioned between water and ethyl acetate and basified with saturated aqueous sodium bicarbonate. The phases were separated and the aqueous phase was extracted with ethyl acetate. The combined extracts were dried over magnesium sulphate, filtered and evaporated to yield a brown solid (1.649 g). This was purified by silica gel column chromatography (0-5% MeOH in DCM) to yield a tan solid (512 mg);

300 MHz $^1$H NMR $\delta_H$ (CDCl$_3$) 1.84-1.98 (3H, m), 1.15-1.35, (2H, m), 2.75 (1H, dddd), 3.27-3.57 (4H, m), 5.84 (1H, s), 7.55 (1H, d), 7.74, 7.82 (4H, 2d), 8.44 (1H, s), 8.74 (1H, d).

The enantiomers separated by chiral prep-HPLC (30:70 EtOH:Heptane) to yield a fast isomer (5S)-3-[4-[4-(trifluoromethyl)phenyl]-2-pyridyl]-4,9-diazaspiro[4.5]dec-3-en-10-one (D31S) (199 mg, 0.533 mmol, 10.5% yield);
Optical rotation $\alpha[^D/_{22}]$=+98 (c=1, CHCl$_3$).
Slow isomer (5R)-3-[4-[4-(trifluoromethyl)phenyl]-2-pyridyl]-4,9-diazaspiro[4.5]dec-3-en-10-one (D31R) (199 mg, 0.533 mmol, 10.5% yield);
Optical rotation $\alpha[^D/_{22}]$=−98 (c=1, CHCl$_3$).

Description 32

(5R)-7-Methyl-2-(6-methyl-2-pyridyl)-1,7-diaza-
spiro[4.4]non-1-en-6-one (D32R) and (5S)-7-Me-
thyl-2-(6-methyl-2-pyridyl)-1,7-diazaspiro[4.4]non-
1-en-6-one (D32S)

To a solution of 3-amino-1-methyl-pyrrolidin-2-one (9.52 g, 83.38 mmol) in THF (40 mL) was added magnesium sulfate (10035.85 mg, 83.38 mmol) and 6-methylpyridine-2-carbaldehyde (10.1 g, 83.38 mmol) and the reaction was stirred for 16 hours. The reaction was filtered and concentrated in vacuo. To this was added THF (40 mL), and phenyl vinyl sulfone (14024.51 mg, 83.38 mmol) was subsequently added. Silver acetate (139.16 mg, 0.8300 mmol) was then added and the reaction was placed in an ice bath. The reaction was then stirred for 6 hours while allowing to warm to room temperature. The reaction mixture was concentrated in vacuo, methanol added and evaporated again, dissolved in dry THF (120 mL), cooled in an ice bath, and potassium tert-butoxide (16.3 g, 145.26 mmol) was added portionwise. The reaction was quenched by addition of acetic acid (9.55 mL, 166.75 mmol). The reaction was subsequently concentrated in vacuo, dissolved in DCM (500 mL) and then filtered, and the filtrate was concentrated in vacuo. The solid material was recrystallised from acetone. Filtrate and mother liquors were purified by silica column chromatography eluting with a gradient of MeOH in EtOAc. Fractions containing product were combined and crystallised from hot acetone. A total of 13.1 g, (85% yield) of racemic 8-methyl-3-(6-methyl-2-pyridyl)-4,8-diazaspiro[4.4]non-3-en-9-one was obtained;

M/Z: 244 (M+H$^+$).

A portion of the racemic material (3.0 g) was dissolved in 60 mL, 50% (EtOH:MeOH 1:1):50% heptane (50 mg/mL) [required some heating and sonication] and separated using chiral HPLC using 20% (1:1 EtOH:MeOH): 80% heptanes on a chiralpak AD column. This gave the first eluting product (5S)-7-methyl-2-(6-methyl-2-pyridyl)-1,7-diazaspiro[4.4]-non-1-en-6-one (D32S) (1284 mg, 5.2774 mmol, 42.3% yield);
Optical rotation $\alpha[^D/_{22}]$=−136 (c=1, CHCl$_3$).

The second eluting peak was isolated (5R)-7-methyl-2-(6-methyl-2-pyridyl)-1,7-diazaspiro[4.4]non-1-en-6-one (D32R) (1254 mg, 5.1541 mmol, 41.4% yield);
Optical rotation $\alpha[^D/_{22}]$=+128 (c=1, CHCl$_3$).

Description 33

(5R)-2-[4-(4-Fluorophenyl)-6-methyl-2-pyridyl]-7-
methyl-1,7-diazaspiro[4.4]non-1-en-6-one (D33R)

To a microwave vial was added (5R)-7-methyl-2-(6-methyl-2-pyridyl)-1,7-diazaspiro[4.4]non-1-en-6-one (which may be prepared as described in Description 32) (100 mg, 0.4100 mmol), 4,4'-di-tert-butyl-2,2'-bipyridyl (11.03 mg, 0.0400 mmol), bis(pinocolato)-diboron (156.55 mg, 0.6200 mmol), and (1,5-cyclooctadiene)(methoxy)iridium(I) dimer (13.62 mg, 0.0200 mmol). The microwave vial was sealed and evacuated and filled with nitrogen three times. 1,2-dimethoxyethane (2 mL) was then added and the reaction was heated in the microwave at 120° C. for 10 minutes. The vessel was cooled and a solution of sodium carbonate (217.81 mg, 2.06 mmol) in water (1 mL) was added, followed by 1-bromo-4-fluorobenzene (0.06 mL, 0.5100 mmol), and finally 1,1'-bis(diphenylphosphino)ferrocene-palladium(II)dichloride-dichloromethane complex (16.82 mg, 0.0200 mmol). The reaction was then resealed, and heated in a microwave at 130° C. for 10 minutes. The cooled reaction mixture was partitioned between EtOAc (15 mL) and water (10 mL). The organics were separated, washed with brine, dried over MgSO$_4$, filtered and concentrated in vacuo. The residue was loaded onto silica (10 g SNAP column), and this was eluted with MeOH:EtOAc, 0% to 16%. Fractions containing desired product were combined and concentrated in vacuo to give (5R)-2-[4-(4-fluorophenyl)-6-methyl-2-pyridyl]-7-methyl-1,7-diazaspiro[4.4]non-1-en-6-one (D33R) (65 mg, 0.1927 mmol, 46.9% yield) as a colourless oil;

300 MHz $^1$H NMR $\delta_H$ (CDCl$_3$) 1.87-1.96 (1H, m), 2.13-2.23 (1H, m), 2.40-2.61 (2H, m), 2.63 (3H, s), 2.96 (3H, s), 3.30-3.47 (3H, m), 3.62-3.71 (1H, m), 7.15 (2H, t), 7.37 (1H, s), 7.68 (2H, dd), 8.12 (1H, s).

Description 34

5-Fluoro-2-methyl-4-nitro-1-oxido-pyridin-1-ium (D34)

To a nitrating mixture of concentrated sulphuric acid (20 mL) and concentrated nitric acid (10 mL) cooled to 0° C. was added a solution of 5-fluoro-2-methyl-1-oxido-pyridin-1-ium [CAS: 45673-79-8](5303 mg, 41.72 mmol) in sulphuric acid (5 mL). The solution was allowed to warm to room temperature and stirred for 30 minutes then heated to 110° C. and stirred for 5 hours. The reaction mixture was cooled and poured onto ice. The aqueous solution was made basic with solid sodium carbonate, giving a precipitate. The mixture was stood at room temperature overnight. The mixture was filtered and the solids kept to one side. The filtrate was extracted into DCM (3 times), and the combined extracts were dried over magnesium sulphate, filtered and evaporated to yield a yellow solid (1.183 g). The solids originally filtered off were stirred with DCM (approximately 300 mL) and then filtered. The filtrate was dried over magnesium sulphate, filtered and evaporated to yield a yellow solid (3.76 g). The combined solids comprised 5-fluoro-2-methyl-4-nitro-1-oxido-pyridin-1-ium (D34) (4.943 g, 28.72 mmol, 68.8% yield);

300 MHz $^1$H NMR $\delta_H$ (CDCl$_3$) 2.51 (3H, s), 8.06 (1H, d), 8.32 (1H, d).

Descriptions 35 and 36

(5R)-2-(4-Bromo-5-fluoro-2-pyridyl)-7-methyl-1,7-diazaspiro[4.4]non-1-en-6-one (D35R), (5S)-2-(4-Bromo-5-fluoro-2-pyridyl)-7-methyl-1,7-diazaspiro[4.4]non-1-en-6-one (D35S) and 2-(4-Bromo-5-tert-butoxy-2-pyridyl)-7-methyl-1,7-diazaspiro[4.4]non-1-en-6-one (D36)

The aldehyde 4-bromo-5-fluoro-pyridine-2-carbaldehyde was prepared by sequentially applying the methods of Description 5, 6 and 7 but using 5-fluoro-2-methyl-4-nitro-1-oxido-pyridin-1-ium (which may itself be prepared using the description in Description 34) in place of 2,3-dimethyl-4-nitro-1-oxido-pyridin-1-ium. To a solution of this aldehyde (2889 mg, 14.16 mmol) in DCM (50 mL) was added 3-amino-1-methyl-pyrrolidin-2-one (1778.22 mg, 15.58 mmol) and magnesium sulphate (8521.13 mg, 70.81 mmol). The mixture was stirred at room temperature overnight. The reaction mixture was filtered and the filtrate washed with brine, dried over magnesium sulphate, filtered and evaporated to yield 3-[(E)-(4-bromo-5-fluoro-2-pyridyl)methyleneamino]-1-methyl-pyrrolidin-2-one (3997 mg, 13.318 mmol, 94.0% yield) as a white solid. To a suspension of this material (3997 mg, 13.32 mmol) in MeCN (70 mL) was added THF (100 mL). To the solution was added vinylsulfonyl-benzene (2240.22 mg, 13.32 mmol), silver acetate (2.22 g, 13.32 mmol) and finally DBU (1.99 mL, 13.32 mmol). The mixture was stirred at room temperature for 3 days. The reaction mixture was filtered over Celite and the filtrate evaporated. The residues were dissolved in THF (70 mL) and 1.7 M potassium tert-butoxide in THF (23.5 mL, 39.95 mmol) was added and the mixture stirred at room temperature for 4 hours. The reaction mixture was quenched by addition of acetic acid (3.81 mL, 66.59 mmol). The resulting precipitate was filtered over Celite, the filtrate evaporated and the residue treated to flash chromatography (0-10% MeOH in EtOAc) to yield a brown oil (1.894 g). This was subjected to chiral preparative chromatography using (10:10:80 MeOH:EtOH:heptane). Four peaks were observed at 7.39 min 23%, 8.01 min 26%, 9.50 min 25%, 12.49 min 25%. The first two peaks co-eluted at scale and were combined to give 2-(4-bromo-5-tert-butoxy-2-pyridyl)-7-methyl-1,7-diazaspiro[4.4]non-1-en-6-one (D36);

300 MHz $^1$H NMR $\delta_H$ (CDCl$_3$) 1.49 (9H, s), 1.89 (1H, ddd), 2.12-2.21 (1H, m), 2.44 (1H, ddd), 2.50-2.59 (1H, m), 2.95 (3H, s), 3.15-3.43 (3H, m), 3.63-3.71 (1H, m), 8.38, 3.49 (2H, 2×s).

Peak 3: (5S)-2-(4-bromo-5-fluoro-2-pyridyl)-7-methyl-1,7-diazaspiro[4.4]non-1-en-6-one (D35S), identical by NMR to Peak 4;

Optical rotation α[$^D$/$_{22}$]=−80 (c=1, CHCl$_3$).

Peak 4: (5R)-2-(4-bromo-5-fluoro-2-pyridyl)-7-methyl-1,7-diazaspiro[4.4]non-1-en-6-one (D35R), 300 MHz $^1$H NMR $\delta_H$ (CDCl$_3$) 1.87-1.97 (1H, m), 2.12-2.22 (1H, m), 2.44 (1H, ddd), 2.51-2.61 (1H, m), 2.97 (3H, s), 3.17-3.44 (3H, m), 3.62-3.71 (1H, m), 8.44 (1H, d), 8.45 (1H, s);

Optical rotation α[$^D$/$_{22}$]=+73 (c=1, CHCl$_3$)

Description 37

(5S)-2-[5-tert-Butoxy-4-[4-(trifluoromethyl)phenyl]-2-pyridyl]-7-methyl-1,7-diazaspiro[4.4]non-1-en-6-one (D37S) and (5R)-2-[5-tert-Butoxy-4-[4-(trifluoromethyl)phenyl]-2-pyridyl]-7-methyl-1,7-diazaspiro[4.4]non-1-en-6-one (D37R)

To a solution of 2-(4-bromo-5-tert-butoxy-2-pyridyl)-7-methyl-1,7-diazaspiro[4.4]non-1-en-6-one (which may be prepared as described in Description 36) (605 mg, 1.59 mmol) in 1,2-dimethoxyethane (16 mL) was added water (4 mL), [4-(trifluoromethyl)phenyl]boronic acid (332.38 mg, 1.75 mmol) and sodium carbonate (505.87 mg, 4.77 mmol). The mixture was degassed with a stream of nitrogen and bis(triphenylphosphine)-palladium (II) dichloride (55.83 mg, 0.0800 mmol) was added. The mixture was heated to 120° C. over 15 minutes in a microwave. The reaction mixture was diluted with DCM and a little water and the phases separated with a hydrophobic frit. The organic filtrate was evaporated to yield a brown gum, (798 mg). Column chromatography (0-10% MeOH in EtOAc) yielded 2-[5-tert-butoxy-4-[4-(trifluoro-methyl)-phenyl]-2-pyridyl]-7-methyl-1,7-diazaspiro[4.4]non-1-en-6-one (263 mg, 0.5904 mmol, 37.1% yield) as a yellow foam;

300 MHz $^1$H NMR $\delta_H$ (CDCl$_3$) 1.2 (9H, s), 1.93 (1H, ddd), 2.12-2.23 (1H, m), 2.45 (1H, ddd), 2.57 (1H, ddd), 2.95 (3H, s), 3.23-3.48 (3H, m), 3.62-3.69 (1H, m), 7.69, 7.77 (4H, 2×d), 8.17, 8.52 (2H, 2×s).

The isomers were separated by chiral preparative HPLC to give faster running isomer: (5R)-2-[5-tert-butoxy-4-[4-(trifluoromethyl)phenyl]-2-pyridyl]-7-methyl-1,7-diazaspiro[4.4]non-1-en-6-one (D37R);

Optical rotation α[$^D$/$_{22}$]=+78 (c=1, CHCl$_3$).

Slower isomer: (5S)-2-[5-tert-butoxy-4-[4-(trifluoromethyl)phenyl]-2-pyridyl]-7-methyl-1,7-diazaspiro[4.4]non-1-en-6-one (D37S);

Optical rotation α[$^D$/$_{22}$]=−65 (c=1, CHCl$_3$).

NMR showed an impurity is present in (D37S) but the material was used in the next step.

Description 38

2-[5-(Difluoromethoxy)-2-fluoro-phenyl]-4,4,5,5-tetramethyl-1,3,2-dioxaborolane (D38)

To a solution of 2-bromo-4-(difluoromethoxy)-1-fluorobenzene [CAS: 1261475-23-3](730 mg, 3.0289 mmol) in anhydrous DMSO (5 mL) in a dry Smith microwave vessel was added bis(pinacolato)diboron (922.99 mg, 3.6347 mmol), potassium acetate (743.16 mg, 7.5723 mmol) and 1,1'-bis(diphenylphosphino)ferrocene-palladium(II)dichloride (221.62 mg, 0.3029 mmol). The reaction vessel was sealed and purged with nitrogen. The reaction mixture was heated at 100° C. for 18 hours. The reaction mixture was allowed to warm to room temperature and partitioned between ethyl acetate and water. The organic layer was washed with brine, dried (sodium sulfate) and filtered. The filtrate was evaporated and the resulting crude oily residue was purified by silica gel chromatography (50 g silica) eluting with ethyl acetate in iso-hexane (0-10%). Evaporation of desired fractions gave 2-[5-(difluoromethoxy)-2-fluoro-phenyl]-4,4,5,5-tetramethyl-1,3,2-dioxaborolane (D38) (400 mg, 1.3886 mmol, 45.8% yield) as oil. The material was used without further purification.

Description 39

Benzyl N-(2-oxopyrrolidin-3-yl)carbamate (D39)

To a solution of 3-aminopyrrolidin-2-one (2.70 g, 27 mmol) in water (36 mL) at ambient temperature was added triethylamine (4.12 mL, 29.7 mmol, 1.1 equivalent) followed by the dropwise addition over 15 minutes of a solution of N-(benzyloxycarbonyloxy)succinimide (7.4 g, 29.7 mmol, 1.1 equivalent) in MeCN (20 mL). The mixture was stirred at room temperature for 22 hours. The mixture was evaporated and the residue was partitioned between 0.5 M aqueous NaOH (500 mL) and DCM (600 mL). The aqueous fraction was further extracted with DCM (2×250 mL) and the combined organic extracts were back-washed with water (300 mL), dried (MgSO$_4$) and evaporated to a cream solid which was filtered, dried and evaporated then triturated with ether (50 mL) for 0.5 hours, before being dried at room temperature for 2 hours to give benzyl N-(2-oxopyrrolidin-3-yl)carbamate (D39) 4.4 g (70%);
M/Z: 235 (M+H$^+$)

Description 40

Benzyl N-[2-oxo-1-(2-trimethylsilylethoxymethyl) pyrrolidin-3-yl]carbamate (D40)

To a stirred solution of benzyl N-(2-oxopyrrolidin-3-yl) carbamate (which may be prepared as described in Description 39) (0.5 g, 2.13 mmol) in dry DMF (6 mL) was added in 3 equal portions a 60% dispersion of NaH in oil (90 mg, 2.25 mmol) over 5 minutes under N$_2$. After stirring for 55 minutes, 2-(chloromethoxy)ethyl-trimethyl-silane (0.42 mL, 2.35 mmol) was added dropwise over 12 minutes. The solution was stirred under N$_2$ at ambient temp for 19 hours. The reaction was quenched by addition of saturated aqueous NH$_4$Cl solution (2 mL). The mixture was evaporated and re-evaporated from toluene (3×100 mL). The residue was partitioned between DCM (30 mL) and water (30 mL). The organic phase was dried (MgSO$_4$) and evaporated to an oily solid. The material was purified by silica column chromatography: it was dissolved in toluene (6 mL) and the solution was applied to a 50 g cartridge which was then eluted on a Biotage SP4 system with a gradient of EtOAc/iso-hexane (30-100%). Relevant fractions were pooled and evaporated to give benzyl N-[2-oxo-1-(2-trimethylsilylethoxymethyl)pyrrolidin-3-yl] carbamate (D40) as a colourless oil, dried under vacuum for 2 hours at room temperature to afford 170 mg;

300 MHz $^1$H NMR $\delta_H$ (CDCl$_3$) 0.02 (9H, s), 0.9-1.9 (2H, t), 1.92 (1H, quint), 2.65-2.78 (1H, m), 3.39-3.56 (4H, m), 4.24-4.33 (1H, m), 4.70-4.85 (2H, m), 5.14 (2H, s), 5.35 (1H, br s), 7.37 (5H, br s).

Description 41

3-Amino-1-(2-trimethylsilylethoxymethyl)pyrrolidin-2-one (D41)

A suspension of 10% Pd/C paste (1 g, 0.4400 mmol), benzyl N-[2-oxo-1-(2-trimethylsilylethoxy-methyl)-pyrrolidin-3-yl]carbamate (which may be prepared as described in Description 40) (7.2 g, 19.8 mmol) and ammonium formate (3.7 g, 58.6 mmol) in methanol (400 mL) was heated at a block temperature of 55° C. under N$_2$ for 2 hours. The reaction was cooled to ambient temperature and filtered through Celite under N$_2$ and washed with MeOH (2×25 mL). The filtrate was evaporated to a colourless oil. The oil was partitioned between DCM (75 mL) and water (75 mL). The latter was re-extracted with DCM (5×50 mL) then DCM/MeOH (9:1) (2×50 mL) and the combined organic extracts were dried (Na$_2$SO$_4$) and evaporated to a colourless oil, which was dried at room temperature under vacuum for 14 hours to give 3-amino-1-(2-trimethylsilylethoxymethyl)pyrrolidin-2-one (D41) 2.7 g (11.7 mmol=59% yield);
300 MHz $^1$H NMR $\delta_H$ (CDCl$_3$) 0.01 (9H, s), 0.92 (2H, t), 1.75 (1H, quint), 2.0 (2H, br s), 2.40-2.52 (1H, m), 3.33-3.65 (5H, m), 4.68, 4.78 (2H, 2×d).

Description 42

2-(4-Bromo-6-methyl-2-pyridyl)-7-(2-trimethylsilylethoxymethyl)-1,7-diazaspiro[4.4]non-1-en-6-one (D42), (5R)-2-(4-Bromo-6-methyl-2-pyridyl)-7-(2-trimethylsilylethoxymethyl)-1,7-diazaspiro[4.4]non-1-en-6-one (D42R) and (5S)-2-(4-Bromo-6-methyl-2-pyridyl)-7-(2-tri methylsilylethoxymethyl)-1,7-diazaspiro[4.4]non-1-en-6-one (D42S)

Method A

3 Å Molecular sieves (25 g, 14.5 mmol) were weighed into a 250 mL RB flask with a stirrer bar. The flask was heated for 10 minutes under vacuum with a hot air gun to dry the sieves. When the flask was cool, a solution of 3-amino-1-(2-trimethylsilylethoxymethyl)pyrrolidin-2-one (which may be prepared as described in Description 41) (3.34 g, 14.5 mmol) in dry DCM (60 mL) was added under N$_2$ and 4-bromo-6-methyl-pyridine-2-carbaldehyde [CAS: 448906-71-6](2.9 g, 14.5 mmol) was added to the flask. The mixture was gently stirred under N$_2$ at ambient temperature for 16 hours. The reaction was filtered under suction to remove the sieves and they were washed with dry DCM (4×25 mL). The filtrate was evaporated to a brown oil which was dried at room temperature under vacuum for 1 hour. The residue was dissolved in dry THF (60 mL) and to this stirred solution, under N$_2$, was added vinylsulfonylbenzene (2.44 g, 14.5 mmol) then silver acetate (2.42 g, 0.74 mL, 14.5 mmol). The mixture was wrapped in foil and stirred at ambient temperature for 3 minutes. After a further 3 minutes DBU (2.17 mL, 14.5 mmol) was added dropwise over 3 minutes and the mixture left to stir for 3 hours under N$_2$ at ambient temperature. The reaction was filtered under suction through Celite and washed through with THF (100 mL). The filtrate was evaporated to a dark oil, dried at room temperature under vacuum for 2 hours then stored in fridge for 3 days. The material was dissolved in dry THF (60 mL) under N$_2$ and the solution cooled in an ice bath. To this stirred solution was added, over 7 minutes, 1.7 M potassium tert-butoxide in THF (26 mL, 44.2 mmol) and the mixture was stirred in the ice bath for 1.5 hours. Acetic acid (2.49 mL, 44.2 mmol) was then added over 1 minute, the ice bath was removed and the stirred solution was warmed to ambient temperature over 20 minutes. The mixture was then filtered under suction through Celite, washed with THF (3×35 mL) until the washings were colourless. The filtrate and washings were evaporated to a dark oil which was dried at room temperature under vacuum for 2 hours. This material was purified by Silica column chromatography by dissolving the oil in DCM (25 mL) and diluting with iso-hexane (25 mL). The solution was divided into 2 equal volumes and each solution was applied to a 100 g cartridge which was then eluted on a Biotage SP4 system with a gradient of EtOAc/iso-hexane (30-80%). Relevant (early) fractions were pooled and evaporated to an orange solid which was dried at room temperature under vacuum overnight to give 2-(4-bromo-6-methyl-2-pyridyl)-7-(2-trimethylsilylethoxymethyl)-1,7-diazaspiro[4.4]non-1-en-6-one (D42) (3.15 g);

300 MHz $^1$H NMR $\delta_H$ (CDCl$_3$) 0.02 (9H, s), 0.97 (2H, t), 1.77-1.97 (1H, m), 2.11-2.22 (1H, m), 2.38-2.60 (2H, m), 2.57 (3H, s), 3.20-3.40 (2H, m), 3.46-3.64 (3H, m), 3.69-3.78 (1H, m), 4.82 (2H, s), 7.38, 8.12 (2H, 2s).

Method B Sodium hydride (60% dispersion in oil, 26.03 mg, 0.6500 mmol) was added in two portions to a stirred solution of (5R)-2-(4-bromo-2-pyridyl)-1,7-diazaspiro[4.4]non-1-en-6-one (which may be prepared as described in Description 19) (174.mg, 0.5900 mmol) in dry THF (8 mL) at ambient temperature under nitrogen. After stirring for 45 mins, 2-(chloromethoxy)-ethyl-trimethyl-silane (0.12 mL, 0.6500 mmol) was added dropwise over 2 minutes. The reaction mixture was stirred over the weekend. The reaction mixture was quenched by the addition of saturated ammonium chloride solution (20 ml) and the product extracted with dichloromethane twice. The combined organic extracts were passed through a hydrophobic frit and the solvent evaporated at reduced pressure. The product was purified by silica gel chromatography eluting with 0-100% ethyl acetate in iso-hexane to give a colourless solid (199 mg) (5R)-2-(4-bromo-6-methyl-2-pyridyl)-7-(2-trimethylsilylethoxymethyl)-1,7-diazaspiro[4.4]non-1-en-6-one (D42R) (199 mg);

NMR: consistent with (D42);

M/Z: 424, 426 (M+H$^+$).

In a similar manner, (5S)-2-(4-bromo-2-pyridyl)-1,7-diazaspiro[4.4]non-1-en-6-one (which may be prepared as described in Description 19) was converted to the S isomer, (5S)-2-(4-bromo-6-methyl-2-pyridyl)-7-(2-trimethylsilylethoxymethyl)-1,7-diazaspiro[4.4]non-1-en-6-one (D42S);

M/Z: 424, 426 (M+H$^+$).

Description 43

(5R)-2-[6-Methyl-4-[4-(trifluoromethyl)phenyl]-2-pyridyl]-7-(2-trimethylsilylethoxymethyl)-1,7-diazaspiro[4.4]non-1-en-6-one (D43R) and (5S)-2-[6-Methyl-4-[4-(trifluoromethyl)phenyl]-2-pyridyl]-7-(2-trimethylsilylethoxymethyl)-1,7-diazaspiro[4.4]non-1-en-6-one (D43S)

[4-(Trifluoromethyl)phenyl]boronic acid (364 mg, 1.92 mmol) and sodium carbonate (581 mg, 5.48 mmol) were added to a solution of 2-(4-bromo-6-methyl-2-pyridyl)-7-(2-trimethylsilylethoxymethyl)-1,7-diazaspiro[4.4]non-1-en-6-one (which may be prepared as described in Description 42) (800 mg, 1.8 mmol) in monoglyme (16 mL) and water (4.8 mL) under N$_2$ at ambient temperature. The mixture was degassed by bubbling N$_2$ through it for 10 minutes. Bis(triphenylphosphine)palladium (II) dichloride (64 mg, 0.091 mmol) was then added and the stirred mixture was refluxed under N$_2$ for 2.25 hours. The solution was cooled and diluted with DCM (50 mL) and washed with water (50 mL), dried (MgSO$_4$) and evaporated to an oil which was dried at room temperature under vacuum overnight. The residue was dissolved in DCM (4 mL) and the solution applied to a 25 g silica gel chromatography cartridge which was then eluted on a Biotage SP4 system with a gradient of EtOAc-isohexane (0-100%). Relevant fractions were pooled and evaporated to an orange oil 800 mg (1.59 mmol=88%);

300 MHz $^1$H NMR $\delta_H$ (CDCl$_3$) 0.00 (9H, s), 0.97 (2H, t), 1.91-2.02 (1H, m), 2.12-2.23 (1H, m), 2.42-2.59 (2H, m), 2.68 (3H, s), 3.35-3.43 (2H, m), 3.48-3.62 (3H, m), 3.69-3.77 (1H, m), 4.78, 4.88 (2H, 2×d), 7.41 (1H, s), 7.70-7.80 (4H, m), 8.18 (1H, s).

A separately prepared sample was separated by preparative chiral chromatography: 1.26 g was dissolved in EtOH (10 mL) and heptane (10 mL) was added. The solution was taken in 0.75 mL aliquots and applied to an AD-H chiralPak 20 mm×250 mm, 5 μm column running at 18 mL/min eluting with MeOH/EtOH/heptane. The faster running isomer was identified as (5S)-2-[6-methyl-4-[4-(trifluoromethyl)phenyl]-2-pyridyl]-7-(2-trimethylsilylethoxymethyl)-1,7-diazaspiro[4.4]non-1-en-6-one (D43S) (447 mg);

Optical rotation α[$^D/_{22}$]=−40.0 (c=1, CHCl$_3$).

The slower running isomer was identified as (5R)-2-[6-methyl-4-[4-(trifluoromethyl)phenyl]-2-pyridyl]-7-(2-trimethylsilylethoxymethyl)-1,7-diazaspiro[4.4]non-1-en-6-one (D43R) (470 mg); Optical rotation α[$^D/_{22}$]=+45.0 (c=1, CHCl$_3$).

Descriptions 44 and 45

(2S,5S)-2-[6-Methyl-4-[4-(trifluoromethyl)phenyl]-2-pyridyl]-7-(2-trimethylsilylethoxymethyl)-1,7-diazaspiro[4.4]nonan-6-one (D44) and (2R,5S)-2-[6-Methyl-4-[4-(trifluoromethyl)phenyl]-2-pyridyl]-7-(2-trimethylsi ylethoxymethyl)-1,7-diazaspiro[4.4]nonan-6-one (D45)

Concentrated hydrochloric acid (0.08 mL, 0.96 mmol) was added to an ice-cooled, stirred solution of (5S)-2-[6-methyl-4-[4-(trifluoromethyl)phenyl]-2-pyridyl]-7-(2-trimethylsilylethoxy-methyl)-1,7-diazaspiro[4.4]non-1-en-6-one (438 mg, 0.87 mmol) (which may be prepared as described in Description 43) in dry DCM (12 mL) under N$_2$. After leaving for 3-5 minutes, sodium triacetoxyborohydride (737.29 mg, 3.48 mmol) was added portionwise over 3 minutes. After stirring for 20 minutes, the ice bath was removed and the mixture was stirred at ambient temperature for 1.75 hours. To the reaction mixture was then added saturated aqueous NaHCO$_3$ (15 mL) and after stirring for 15 minutes the layers were separated and the aqueous phase further extracted with DCM (15 mL). The combined organic extracts were dried (MgSO$_4$) and evaporated to a light brown oil. This was purified by silica gel column chromatography: the oil was dissolved in EtOAc/iso-hexane (1:1)(4 mL) and the solution was applied to a 25 g cartridge which was then eluted on a Biotage SP4 system in 2 phases; firstly with EtOAc-MeOH/DCM 1:4 to afford faster running isomer (2R,5S)-2-[6-methyl-4-[4-(trifluoromethyl)phenyl]-2-pyridyl]-7-(2-trimethylsilylethoxymethyl)-1,7-diazaspiro[4.4]nonan-6-one (D45) (155 mg);

300 MHz $^1$H NMR $\delta_H$ (CDCl$_3$) 0.03 (9H, s), 0.42-0.48 (2H, m), 1.88-2.28 (5H, m), 2.51-2.59 (1H, m), 2.63 (3H, s), 2.9 (1H, br s), 3.34-3.57 (4H, m), 4.69, 4.77 (2H, 2×d), 4.64 (1H, t), 7.29 (1H, s), 7.55 (1H, s), 7.74 (4H, s), and then the slower running component (2S,5S)-2-[6-methyl-4-[4-(trifluoromethyl)phenyl]-2-pyridyl]-7-(2-trimethylsilylethoxymethyl)-1,7-diazaspiro[4.4]nonan-6-one (D44) (214 mg);

300 MHz $^1$H NMR $\delta_H$ (CDCl$_3$) 0.01 (9H, s), 0.43-0.47 (2H, m), 1.85-1.93 (1H, m), 2.03-2.21 (4H, m), 2.43-2.43 (1H, m), 2.62 (3H, s), 3.0 (1H, br s), 3.37-3.48 (4H, m), 4.48 (1H, t), 4.74, 4.87 (2H, 2×s), 7.29 (1H, s), 7.70-7.80 (5H, m).

Description 46

3-Amino-1-(2-trimethylsilylethoxymethyl)piperidin-2-one (D46)

A suspension of benzyl N-(2-oxo-3-piperidyl)carbamate [CAS: 38150-56-0](25 g, 100.69 mmol) in dry THF (1000 mL) under N$_2$ was cooled in an ice bath and then 6 equal portions of 60% sodium hydride in oil dispersion (4.23 g, 105.73 mmol) were added over 10 mins under N$_2$. After stirring for 0.5 h, dry DMF (50 mL) was added to the cooled suspension and again after a further 0.5 h. To this stirred mixture was added, via dropping funnel, a solution of 2-(trimethylsilyl)ethoxymethyl chloride (18.71 mL, 105.73 mmol) in dry THF (200 mL) over 1.75 h. The resulting solution was stirred for 16 h then water (6 ml) was added and the mixture was evaporated to an oily residue. The residue was re-evaporated with toluene (500 ml) and then dissolved in DCM (500 ml) and washed with water (500 ml). The latter was re-extracted with DCM (2×200 ml) and the combined organic extracts were back-washed with water (200 ml), dried (Na$_2$SO$_4$) and evaporated to an oil, which was dried at RT for two hours under vacuum. This material was stirred with MeOH (50 ml) and an insoluble white solid was removed by filtration. The filtrate was concentrated to an oil, 37 g (approximately a 50% mixture of Benzyl N-[2-oxo-1-(2-trimethylsilylethoxymethyl)-3-piperidyl]carbamate and starting material. This was dissolved in methanol (500 mL) and mixed with 10% Pd/C paste (15 g, 97.74 mmol), and ammonium formate (17.62 g, 279.42 mmol). The suspension was heated at a block temperature of 55° C. under N$_2$ for 1.5 h. TLC showed complete (TLC systems as above). After this time the reaction was cooled and fitlered under suction through celite, which was washed with MeOH/H$_2$O (3:1) (4×25 ml). The filtrate was evaporated and re-evaporated with MeOH to give an oily solid. To the mixture was added DCM (50 ml) to give a suspension. The suspension was filtered under suction to remove a white solid. The filtrate (made back up to 50 ml volume with DCM) was purified by SiO$_2$ column chromatography by applying to a 340 g cartridge which was then eluted on a Biotage SP4 system with a gradient of MeOH/DCM (0-40%). Relevant fractions were pooled and evaporated to an almost colourless oil. This was dissolved in DCM (50 ml) and the solution washed with water (50 ml). The latter was extracted successively with DCM (4×25 ml), DCM-MeOH (9:1) (4×25 ml). The combined organic extracts were dried (MgSO$_4$) and evaporated to a colourless viscous oil, then dried at RT under vacuum for 16 hours to afford 3-amino-1-(2-trimethylsilylethoxymethyl)piperidin-2-one (D46) (2.0 g).

300 MHz $^1$H NMR $\delta_H$ (CDCl$_3$) 0.2 (9H, s), 0.88-0.97 (2H, m), 1.70-2.19 (6H, m), 2.38-2.55 (2H, m), 3.36-3.60 (4H, m), 4.67, 5.00 (2H, 2×d), 3.75 (1H, dd), 6.0 (2H, br).

Description 47

(5S)-2-(4-Bromo-2-pyridyl)-7-(2-trimethylsilylethoxymethyl)-1,7-diazaspiro[4.4]non-1-en-6-one (D47S) and (5R)-2-(4-Bromo-2-pyridyl)-7-(2-trimethylsilylethoxymethyl)-1,7-diazaspiro[4.4]non-1-en-6-one (D47R)

3 A Molecular sieves (24 g, 13.9 mmol) were weighed into a 250 ml RB flask with stirrer bar. The flask was heated for 10 mins under vacuum with a hot air gun to dry the sieves. When the flask was cool, a solution of 3-amino-1-(2-trimethylsilylethoxymethyl)piperidin-2-one (which may be prepared as described in Description 46) (4.0 g, 13.9 mmol) in dry DCM (60 mL) was added under N$_2$ and 4-bromopyridine-2-carbaldehyde (2.59 g, 13.9 mmol) was then added to the flask. The mixture was gently stirred under N$_2$ at ambient temp for 16 h. The reaction was filtered through celite under suction to remove the sieves and they were washed with DCM (4×25 ml). The filtrate was evaporated to a brown oil, dried under vacuum at RT for 1 h. This material was dissolved in dry THF (60 mL) and to this stirred solution under N$_2$ was added vinylsulfonylbenzene (2.34 g, 13.9 mmol) then silver acetate (2.3 g, 0.71 mL, 13.9 mmol). The mixture was wrapped in foil to protect from light and stirred at ambient temp for 3 mins. DBU (2.08 mL, 13.9 mmol) was added dropwise over 3 mins and the mixture left to stir for 3.75 h. The mixture was filtered through celite and washed through with more THF (4×20 ml). The filtrate was concentrated to a viscous oil, left at 4° C. for 16 h. This was dissolved in dry THF (60 mL) under N$_2$ and the solution cooled in an ice bath. To this stirred solution was added, over 5 min, 1.7M potassium t-butoxide in THF (24.53 mL, 41.7 mmol). The mixture was continuously stirred in an ice bath for 1.5 h then acetic acid (2.39 mL, 41.7 mmol) was added over 2 mins, the ice bath was removed and the stirred solution was warmed to ambient temperature over 20 mins. The mixture was then filtered under suction through celite, washed with THF (3×35 ml) until the washings were colourless. The filtrate and washings were evaporated to an dark oil, which was dried at RT under vacuum for 2 hours. This material was dissolved in DCM (50 ml) and the solution divided into 2 equal parts and each was purified by SiO$_2$ column chromatography as follows: 25 ml of the solution was applied to a 100 g cartridge which was then eluted on a Biotage SP4 system with a gradient of EtOAc/iso-hexane (20-100%). Relevant fractions were pooled and evaporated to a dark yellow oil which was dried at RT under vacuum for 2 h to give racemate (D47) (2.2 g);

300 MHz $^1$H NMR $\delta_H$ (CDCl$_3$) 0.03 (9H, s), 0.9-0.99 (2H, m), 1.78-2.00 (2H, m), 2.13-2.22 (1H, m), 2.27-2.39 (1H, m), 2.57-2.67 (1H, m), 3.19-3.44 (2H, m), 3.51-3.61 (4H, m), 4.79, 5.0 (2H, 2×d), 7.50 (1H, dd), 8.38 (1H, d), 8.45 (1H, d).

The isomers were separated by chiral preparative chromatography using AD-H chiralPak 4.6 mm×250 mm, 5 um running @1 ml/min EtOH/heptane (1:9). Solvent:EtOH/heptane (1:9)

Rt=6.0 and 9.3 mins

Faster eluting isomer (D47S) 591 mg;

Optical rotation $\alpha[^D/_{20}]=+44.0$ (c=1, CHCl$_3$); M/Z: 438, 440 (M+H+).

Slower elutinq isomer (D47R) 579 mg;

Optical rotation $\alpha[^D/_{20}]=-37.0$ (c=1, CHCl$_3$); M/Z: 438, 440 (M+H+).

Description 48

(S)-2-[4-(5-Ethoxy-2-fluoro-phenyl)-pyridin-2-yl]-7-(2-trimethylsilanyl-ethoxymethyl)-1,7-diaza-spiro[4.5]dec-1-en-6-one (D48)

5-Ethoxy-2-fluorophenylboronic acid (129.98 mg, 0.7100 mmol) and sodium carbonate (213.96 mg, 2.02 mmol) were added to a solution of (5S)-2-(4-bromo-2-pyridyl)-7-(2-trimethylsilylethoxymethyl)-1,7-diazaspiro[4.4]non-1-en-6-one (which may be prepared as described in Description 47) (295 mg, 0.6700 mmol) in monoglyme (6 mL) and water (1.8 mL) under $N_2$ at ambient temp. The mixture was degassed by bubbling $N_2$ through it for 10 mins. Bis(triphenylphosphine)palladium (II) dichloride (23.62 mg, 0.0300 mmol) was then added and the stirred mixture was refluxed under $N_2$ for 2.25 h. The reaction was cooled, diluted with DCM (40 ml) and the solution washed with water (40 ml), dried ($MgSO_4$) and evaporated to a dark brown oil, which was dried at RT under vacuum for 2 hours. This was purified by $SiO_2$ column chromatography: the oil was dissolved in DCM (3 ml) and the solution was applied to a 10 g cartridge which was then eluted on a Biotage SP4 system with a gradient of EtOAc/iso-hexane (20-100%). Relevant fractions were pooled and evaporated to a light brown oil, dried at RT under vacuum for 16 hours to afford (S)-2-[4-(5-ethoxy-2-fluoro-phenyl)-pyridin-2-yl]-7-(2-trimethylsilanyl-ethoxymethyl)-1,7-diaza-spiro[4.5]dec-1-en-6-one (D48) 274 mg;

300 MHz $^1$H NMR $\delta_H$ (CDCl$_3$) 0.01 (9H, S), 0.96 (2H, dt), 1.44 (3H, t), 1.79-1.99 (3H, m), 2.15-2.40 (2H, m), 2.56-2.58 (1H, m), 3.26-3.50 (2H, m), 3.52-3.62 (4H, m), 4.06 (2H, dd), 4.74-5.05 (2H, 2×d), 6.88-6.93 (1H, m), 7.02 (1H, dd), 7.09 (1H, t), 7.52-7.55 (1H, m), 8.32 (1J, s), 8.70 (1H, d).

Descriptions 49 and 50

(2S,5S)-2-[4-(5-Ethoxy-2-fluoro-phenyl)-pyridin-2-yl]-7-(2-trimethylsilanyl-ethoxymethyl)-1,7-diaza-spiro[4.5]decan-6-one (D49) and (2R,5S)-2-[4-(5-Ethoxy-2-fluoro-phenyl)-pyridin-2-yl]-7-(2-trimethylsilanyl-ethoxymethyl)-1,7-diaza-spiro[4.5]decan-6-one (D50)

Concentrated hydrochloric acid (0.05 mL, 0.5800 mmol) was added to an ice-cooled, stirred solution of (S)-2-[4-(5-ethoxy-2-fluoro-phenyl)-pyridin-2-yl]-7-(2-trimethylsilanyl-ethoxymethyl)-1,7-diaza-spiro[4.5]dec-1-en-6-one (which may be prepared as described in Description 48) (263 mg, 0.5300 mmol) in dry DCM (5 mL) under $N_2$. After 2 minutes sodium triacetoxyborohydride (448.mg, 2.11 mmol) was added in 2 equal portions and the cold mixture stirred for 25 mins after which the cooling bath was removed and stirring continued at ambient temp for 1.5 h. The mixture was then poured into sat. aq. NaHCO$_3$ (30 ml) with DCM (20 ml), shaken, separated and the aqueous further extracted with DCM (15 ml). The combined organic extracts were dried (MgSO$_4$) and evaporated to a light yellow oil, which was dried under vacuum. It was purified by SiO$_2$ column chromatography: the oil was dissolved in DCM (5 ml) and the solution was applied to a 25 g cartridge which was then eluted on a Biotage SP4 system with a gradient of Solvent A/EtOAc (0-100%), where Solvent A=MeOH/EtOAc/1M NH$_3$-MeOH (6:94:3). Relevant fractions were pooled to provide 2 pure diastereomeric components as almost colourless oils; (2S,5S)-2-[4-(5-Ethoxy-2-fluoro-phenyl)-pyridin-2-yl]-7-(2-trimethylsilanyl-ethoxymethyl)-1,7-diaza-spiro[4.5]decan-6-one (D49) 83 mg;

300 MHz $^1$H NMR $\delta_H$(CDCl$_3$): 0.03 (9H, s), 0.97 (2H, dt), 1.45 (3H, t), 1.89-2.09 (6H, m), 2.20-2.30 (1H, m), 2.45-2.55 (1H, m), 3.0 (1H, br.s), 3.35-3.50 (2H, m), 3.58 (2H, dd), 4.07 (2H, abq), 4.72-4.81 (2H, m), 5.0 (1H, d), 6.86-6.95 (1H, m), 6.97-6.99 (1H, m), 7.10 (1H, t), 7.32-7.34 (1H, m), 7.70 (1H, s), 8.60 (1H, d).

(2R,5S)-2-[4-(5-Ethoxy-2-fluoro-phenyl)-pyridin-2-yl]-7-(2-trimethylsilanyl-ethoxymethyl)-1,7-diaza-spiro[4.5]decan-6-one (D50) 121 mg;

300 MHz $^1$H NMR $\delta_H$(CDCl$_3$): 0.02 (9H, s), 0.95 (2H, dd), 1.45 (3H, t), 1.72-2.11 (7H, m), 2.28-2.38 (2H, m), 3.39-3.51 (2H, m), 3.58 (2H, dd), 4.05 (2H, abq), 4.31-4.38 (1H, m), 4.79-5.01 (2H, 2×d), 6.88-6.93 (1H, m), 6.98 (1H, dd), 7.08 (1H, t), 7.33-7.37 (1H, m), 7.55 (1H, s), 8.65 (1H, d).

Description 51

4-(5-Ethoxy-2-fluoro-phenyl)-5,6-dimethyl-pyridine-2-carbonitrile (D51)

(5-Ethoxy-2-fluoro-phenyl)boronic acid (1.71 g, 9.3 mmol) was added to a solution of 4-bromo-5,6-dimethyl-pyridine-2-carbonitrile (which may be prepared as described in Description 144) (1.96 g, 9.3 mmol) in monoglyme (50 mL). To this was added a hot solution of sodium carbonate (2.96 g, 27.9 mmol) in water (15 mL) under $N_2$ at ambient temp. Bis(triphenylphosphine)palladium (II) dichloride (326.38 mg, 0.4700 mmol) was then added and the whole stirred mixture was degassed by bubbling $N_2$ through it for 10 mins. The vigorously stirred mixture was then heated at reflux for 2 h. The solution was cooled and diluted with DCM (100 ml) and washed with water (75 ml), dried (Na$_2$SO$_4$) and evaporated to a black solid. This was dissolved in DCM (15 ml) and the solution applied to a 100 g SiO$_2$ chromatography cartridge which was then eluted on a Biotage SP4 system with a gradient of EtOAc-isohexane (0-30%). Relevant fractions were pooled and evaporated to a colourless solid which was dried at RT for 3 h under vacuum to give 4-(5-ethoxy-2-fluoro-phenyl)-5,6-dimethyl-pyridine-2-carbonitrile (D51) (1.87 g):

300 MHz $^1$H NMR $\delta_H$(CDCl$_3$) 1.45 (3H, t), 2.23, (3H, s), 2.64 (3H, s), 4.04 (2H, q), 6.70 (1H, dd), 6.96 (1H, dt), 7.11 (1H, t), 7.44 (1H, s).

Description 52

Methyl 4-(5-ethoxy-2-fluoro-phenyl)-5,6-dimethyl-pyridine-2-carboxylate (D52)

4M HCl in 1,4-dioxan (20 mL, 80 mmol) was added to a suspension of 4-(5-ethoxy-2-fluoro-phenyl)-5,6-dimethyl-pyridine-2-carbonitrile (which may be prepared as described in Description 51) (1.87 g, 6.92 mmol) in methanol (20 mL) at ambient temperature. The stirred, yellow solution was refluxed under $N_2$ for 9 h. The reaction was concentrated to one third the volume then poured into sat. aq. NaHCO$_3$ (100 ml). The mixture was extracted with EtOAc (3×50 ml). The combined organic extracts were dried (Na$_2$SO$_4$) and evaporated to a colourless oil which solidified. This was purified by SiO$_2$ column chromatography: the oil was dissolved in DCM (15 ml) and the solution was applied to a 100 g cartridge which was then eluted on a Biotage SP4 system with a gradient of EtOAc/iso-hexane (0-80%) to afford methyl 4-(5-ethoxy-2-fluoro-phenyl)-5,6-dimethyl-pyridine-2-carboxylate (D52);

300 MHz $^1$H NMR $\delta_H$ (CDCl$_3$): 1.44 (3H, t), 2.22 (3H, s), 2.69 (3H, s), 4.01 (3H, s), 4.05 (2H, q), 6.75 (1H, dd), 6.93 (1H, dt), 7.09 (1H, t), 7.90 (1H, s).

Description 53

4-(5-Ethoxy-2-fluoro-phenyl)-5,6-dimethyl-pyridine-2-carbaldehyde (D53)

1M DIBAL in toluene (8.7 mL, 8.7 mmol) was added dropwise over 12 minutes to a stirred solution of methyl 4-(5-ethoxy-2-fluoro-phenyl)-5,6-dimethyl-pyridine-2-carboxylate (which may be prepared as described in Description 52) (1.32 g, 4.35 mmol) in dry THF (25 mL) at −75° C. The reaction was stirred at this temp for 2.5 h then EtOH (0.2 ml) was added to quench. After 1 minute the reaction was poured into saturated Rochelle salt solution (200 ml). The mixture was extracted with EtOAc (100 ml) then DCM (2×100 ml). The combined organic extracts were dried (Na$_2$SO$_4$), filtered and evaporated to a white solid, which was dried at RT under vacuum for 16 h to afford 4-(5-ethoxy-2-fluoro-phenyl)-5,6-dimethyl-pyridine-2-carbaldehyde (D53) (1.17 g);
300 MHz $^1$H NMR $\delta_H$ (CDCl$_3$): 1.44 (3H, t), 2.25 (3H, s), 2.69 (3H, s), 4.03 (2H, q), 6.74*1H, dd), 6.95 (1H, dt), 7.09 (1H, t), 7.72 (1H, s), 10.08 (1H, s).

Description 54

(5R)-2-[4-(5-Ethoxy-2-fluoro-phenyl)-5,6-dimethyl-2-pyridyl]-7-methyl-1,7-diazaspiro[4.4]non-1-en-6-one (D54R) and (5S)-2-[4-(5-Ethoxy-2-fluoro-phenyl)-5,6-dimethyl-2-pyridyl]-7-methyl-1,7-diazaspiro[4.4]non-1-en-6-one (D54S)

4 A molecular sieves (7.0 g, 4.21 mmol) were weighed into a 100 ml RB flask with stirrer bar.
The flask was heated for 10 mins under vacuum with a hot air gun to dry the sieves. When the flask was cool, a solution of 4-(5-ethoxy-2-fluoro-phenyl)-5,6-dimethyl-pyridine-2-carbaldehyde (which may be prepared as described in Description 53) (1.15 g, 4.21 mmol) in dry DCM (25 mL) was added under N$_2$ and 3-amino-1-methyl-pyrrolidin-2-one (480.32 mg, 4.21 mmol) was then added to the flask. The mixture was gently stirred under N$_2$ at ambient temp for 23 h. The reaction was filtered through celite under suction to remove the sieves which were washed with DCM (3×25 ml). The filtrate was evaporated to a tan solid. This was dissolved in dry THF (35 mL) and to this stirred solution under N$_2$ was added vinylsulfonylbenzene (707.79 mg, 4.21 mmol) then silver acetate (702.32 mg, 4.21 mmol). The mixture was wrapped in foil to protect from light and stirred at ambient temp for 3 mins. then DBU (0.63 mL, 4.21 mmol) was added dropwise over 3 mins and the mixture left to stir for 3 h. The mixture was filtered through celite and washed through with more THF (3×15 ml). The filtrate was concentrated to a viscous oil, which was redissolved in THF (35 mL) under N$_2$ and the solution cooled in an ice bath. To this stirred solution was added over 5 min 1.7M potassium tert-butoxide in THF (7.43 mL, 12.62 mmol) and the mixture was stirred in the ice bath for 2 h then acetic acid (0.72 mL, 12.62 mmol) was added over 2 mins, the ice bath was removed and the stirred solution was warmed to ambient temp over 20 minutes. The mixture was then filtered under suction through celite, washed with THF (3×35 ml) until the washings were colourless. The filtrate and washings were evaporated to a dark oil. This was purified by SiO$_2$ column chromatography: the oil was dissolved in DCM (20 ml) and the solution was applied to a 100 g SNAP cartridge which was then eluted on a Biotage SP4 system with a gradient of Solvent A/EtOAc (0-25%) where Solvent A=MeOH/EtOAc 1:4. Relevant fractions (impure) were pooled and evaporated to a yellow foam. This was dissolved in dry THF (30 ml) cooled in an ice bath and under N2 was added 1.7M potassium t-butoxide (3 ml) over 5 mins. The solution was stirred at this temperature for 2 h then AcOH (0.3 ml) was added and the mixture warmed to ambient temp. Water (50 ml) and DCM (50 ml) were added, shaken and separated. The aqueous phase was further extracted with DCM (2×20 ml) and the combined organic extracts were dried (Na$_2$SO$_4$) and evaporated to a foam: 2-[4-(5-ethoxy-2-fluoro-phenyl)-5,6-dimethyl-2-pyridyl]-7-methyl-1,7-diazaspiro[4.4]non-1-en-6-one as a racemic mixture;
300 MHz $^1$H NMR $\delta_H$ (CDCl$_3$) 1.42 (3H, t), 1.83-1.94 (1H, m), 2.08-2.20 (1H, m), 2.18 (3H, s), 2.44 (1H, ddd), 2.54 (1H, ddd), 2.61 (3H, s), 2.93 (3H, s), 3.24-3.46 (3H, m). 3.58-3.67 (1H, m), 4.03 (2H, q), 6.75 (1H, dd), 6.89 (1H, dt), 7.04 (1H, t), 7.82 (1H, s).
This was separated into enantiomers using chiral preparative chromatography: Column: IA chiralPak 20 mm×250 mm, 5 µm running @18 ml/min; Solvent:EtOH/heptane (1:9) Rt=(5R)-2-[4-(5-ethoxy-2-fluoro-phenyl)-5,6-dimethyl-2-pyridyl]-7-methyl-1,7-diazaspiro[4.4]non-1-en-6-one (D54R) Retention time=11.8 minutes
Optical rotation $\alpha[^D/_{20}]$=+93 (c=1, CHCl$_3$); M/Z: 396 (M+H$^+$)
(5S)-2-[4-(5-ethoxy-2-fluoro-phenyl)-5,6-dimethyl-2-pyridyl]-7-methyl-1,7-diazaspiro[4.4]non-1-en-6-one (D54S) Retention time=16.1 minutes
Optical rotation $\alpha[^D/_{20}]$=−86 (c=1, CHCl$_3$); M/Z: 396 (M+H$^+$)

Description 55

(5R)-2-[4-(5-Ethoxy-2-fluoro-phenyl)-2-pyridyl]-7-methyl-1,7-diazaspiro[4.4]non-1-en-6-one (D55)

To a solution of (5R)-2-(4-bromo-pyridin-2-yl)-7-methyl-1,7-diazaspiro[4.4]non-1-en-6-one (which may be prepared as described in Description 3) (0.1670 g, 0.5419 mmol) in MeCN (2 mL) and water (0.3000 mL) in a Smith microwave vessel was added (5-ethoxy-2-fluoro-phenyl)boronic acid (0.1097 g, 0.5961 mmol), bis(triphenylphosphine)palladium (II) dichloride (0.0114 g, 0.0163 mmol) and sodium carbonate (0.1149 g, 1.0838 mmol). The reaction vessel was sealed and purged with nitrogen. The reaction mixture was heated by microwave at 100° C. for 40 min. The reaction mixture was treated with water and was extracted with DCM twice and the organic layers were collected by passing down a PhaseSep cartridge. Evaporation of solvents gave an amber oil, which was further purified by silica gel chromatography to give the desired product (5R)-2-[4-(5-ethoxy-2-fluoro-phenyl)-2-pyridyl]-7-methyl-1,7-diazaspiro[4.4]non-1-en-6-one (0.2000 g, 0.5443 mmol) (D55) as an amber oil;
300 MHz $^1$H NMR $\delta_H$ (CDCl$_3$) 1.44 (3H, t), 1.94 (1H, ddd), 2.12-2.22 (1H, m), 2.40-2.64 (2H, m), 2.96 (3H, m), 3.26-3.50 (3H, m), 3.68 (1H, q), 4.06 (1H, q), 6.90 (1H, dt), 7.02 (1H, dd), 7.09 (1H, t), 7.52-7.56 (1H, m), 8.29 (1H, s).

Description 56

(5R)-2-(4-Bromo-5-methoxy-2-pyridyl)-7-methyl-1,7-diazaspiro[4.4]non-1-en-6-one (D56)

To a solution of (5R)-2-(4-bromo-5-fluoro-2-pyridyl)-7-methyl-1,7-diazaspiro[4.4]non-1-en-6-one (which may be prepared as described in Description 35) (50 mg, 0.1500 mmol) in THF (2 mL) was added 30% wt. sodium methoxide in methanol (27.6 mg, 0.1500 mmol). The solution was stirred for 10 mins. A further 2 portions of 30% wt. sodium methoxide in methanol (27.6 mg, 0.1500 mmol) were added and the mixture stirred at room temperature for a further 10 mins. A further portion of 30% wt. sodium methoxide in methanol (27.6 mg, 0.1500 mmol) was added and the mixture stirred for 10 mins. The mixture was concentrated and the residues partitioned between water and DCM. The layers were separated with a hydrophobic frit and the organic filtrate evaporated to give (5R)-2-(4-bromo-5-methoxy-2-pyridyl)-7-methyl-1,7-diazaspiro[4.4]non-1-en-6-one (D56) as a cream solid (47 mg);

300 MHz $^1$H NMR $\delta_H$ (CDCl$_3$) 1.89 (1H, ddd), 2-11-2-21 (1H, m), 2.43 (1H, ddd), 2.55 (1H, ddd), 2.96 (3H, s), 3.15-3.43 (3H, m), 3.63-3.71 (1H, m), 4.05 (3H, s) 8.23 (1H, s), 8.38 (1H, s).

Description 57

N-(3-Bromo-4-fluoro-phenyl)-4-chloro-butanamide (D57)

A solution of 4-chlorobutanoyl chloride (4.12 mL, 36.84 mmol) in DCM (50 mL) was added over 15 mins to an ice-cooled solution of 3-bromo-4-fluoro-aniline (7 g, 36.84 mmol) and triethylamine (5.12 mL, 36.84 mmol) in DCM (100 mL) under N$_2$. After addition was complete the cooling bath was removed and the solution stirred at ambient temp for 4 h. The reaction solution was washed with water (2×150 ml) dried (MgSO$_4$) and concentrated to a white solid, which was dried at RT under vacuum overnight to give N-(3-bromo-4-fluoro-phenyl)-4-chloro-butanamide (D57) (9.04 g);

300 MHz $^1$H NMR $\delta_H$ (CDCl$_3$) 2.22 (2H, quin), 2.58 (2H, t), 3.68 (2H, t), 7.09 (1H, t), 7.18 (1H, br.s), 7.38 (1H, m), 7.86 (1H, m).

Description 58

N-(3-Bromo-4-fluoro-phenyl)pyrrolidin-2-one (D58)

60% Sodium hydride in oil dispersion (1.2 g, 29.88 mmol) was added portionwise over 5 mins to an ice-cooled, stirred solution of N-(3-bromo-4-fluoro-phenyl)-4-chloro-butanamide (which may be prepared as described in Description 57) (8 g, 27.16 mmol) in dry THF (150 mL) under N$_2$. After cooling for a further 5 mins the cooling bath was removed and the mixture stirred at ambient temp for 2 hours. The reaction mixture was then treated with AcOH (1 ml) by dropwise addition. The mixture was evaporated and the residue partitioned between DCM (150 ml) and water (150 ml). The latter was re-extracted with DCM (50 ml) and the combined organic extracts dried (MgSO$_4$) and evaporated to a white solid. The solid was dissolved in refluxing Et$_2$O (65 ml) and the solution diluted with iso-hexane (240 ml) and left to stand for 1 hour. The crystalline solid was filtered and dried. The filtrate was concentrated to approx 50 ml volume and a 2nd crop of crystals was collected and dried. The combined mass gave N-(3-bromo-4-fluoro-phenyl)pyrrolidin-2-one (D58) (6.03 g);

300 MHz $^1$H NMR $\delta_H$ (CDCl$_3$) 2.20 (2H, quin), 2.62 (2H, t), 3.85 (2H, t), 7.13 (1H, t), 7.59 (1H, m), 7.86 (1H, m).

Description 59

1-[4-Fluoro-3-(4,4,5,5-tetramethyl-1,3,2-dioxaborolan-2-yl)phenyl]pyrrolidin-2-one (D59)

A stirred mixture of N-(3-bromo-4-fluoro-phenyl)pyrrolidin-2-one (which may be prepared as described in Description 58) (6 g, 23.25 mmol), 4,4,5,5-tetramethyl-1,3,2-dioxaborolan-2-yl)-1,3,2-dioxaborolane (6.49 g, 25.57 mmol), potassium acetate (4.56 g, 46.5 mmol) and Pd(dppf)Cl$_2$ complex with DCM (569.52 mg, 0.7000 mmol) in 1,4-Dioxane (250 mL) was degassed by bubbling N$_2$ through for 10 mins. The stirred mixture was then heated at block temp 100° C. under N$_2$ for 24 h. The reaction mixture was cooled to ambient temperature and evaporated. The residue was dissolved in DCM (200 ml) and filtered under suction through celite. The filtrate was washed with water (200 ml), dried (MgSO$_4$) and evaporated to a black solid. This was purified by SiO$_2$ column chromatography: it was dissolved in DCM (25 ml) and the solution was applied to a 100 g cartridge which was then eluted on a Biotage SP4 system with a gradient of EtOAc/iso-hexane (0-80%). Relevant fractions were pooled and evaporated to a pink solid. The solid was stirred with Et$_2$O (30 ml) for 0.5 h then filtered and dried to give 1-[4-fluoro-3-(4,4,5,5-tetramethyl-1,3,2-dioxaborolan-2-yl)phenyl]pyrrolidin-2-one (D59) (5.57 g);

300 MHz $^1$H NMR $\delta_H$ (CDCl$_3$) 2.18 (2H, quin), 2.61 (2H, t), 3.89 (2H, t), 7.06 (1H, t), 7.67 (1H, m), 7.92 (1H, m).

Description 60

1-Benzyloxy-5-ethoxy-2,3-difluoro-benzene (D60)

To a solution of potassium hydroxide (2246.7 mg, 40.12 mmol) in 1,4-dioxane (5 mL) and Water (5 mL) was added 2-di-tert-butylphosphino-2',4',6'-triisopropylbiphenyl (212.63 mg, 0.5015 mmol). The reaction mixture was degassed with nitrogen and then treated with tris(dibenzylideneacetone)dipalladium-[0](183.54 mg, 0.2006 mmol) and 1-benzyloxy-5-bromo-2,3-difluoro-benzene [CAS: 1035155-54-4](3 g, 10.03 mmol) the reaction was then heated at 90° C. for 16 hours. The reaction was diluted with aq. KOH solution (2M, 150 mL) and EtOAc (150 mL). The aqueous was separated, and acidified to pH 1 with aq. HCl (2M). The organics were then extracted into EtOAc (150 mL). The organics were separated, washed with brine (150 mL), dried over MgSO$_4$, filtered and concentrated in vacuo to give crude 3-benzyloxy-4,5-difluoro-phenol ~60% pure);

300 MHz $^1$H NMR $\delta_H$ (CDCl$_3$) 5.12 (2H, s), 6.22-6.32 (2H, m), 7.32-7.68 (5H, m), 11 (1H, br.s). To this crude material (702 mg, 2.97 mmol) in DMF (7.43 mL) was added cesium carbonate (1161.98 mg, 3.57 mmol) followed by iodoethane (0.36 mL, 4.46 mmol). The mixture was stirred and sonicated for 2 hrs (approx 1 hr of each). The DMF was removed on the rotary evaporator and 2M HCl/ethyl acetate were added. The layers were separated and the organic layer was washed with water and then brine and dried (Na$_2$SO$_4$) and concentrated. Chromatography (0-10% ethyl acetate in isohexane) gave 1-benzyloxy-5-ethoxy-2,3-difluoro-benzene (D60) as an impure gum (546 mg);

300 MHz $^1$H NMR $\delta_H$ (CDCl$_3$) 1.39 (3H, t), 3.94 (2H, q), 5.12 (2H, s), 6.27-6.39 (2H, m), 7.32-7.49 (5H, m).

Description 61

5-Ethoxy-2,3-difluoro-phenol (D61)

A solution of 1-benzyloxy-5-ethoxy-2,3-difluoro-benzene (which may be prepared as described in Description 60) (546 mg, 2.07 mmol) in methanol (10 mL) was passed through a 10% Pd—C H-cube cartridge at 1 ml/min. The solution was passed through the H-cube a second time. Chromatography on silica (elution with DCM) gave 5-ethoxy-2,3-difluoro-phenol (D61) (270 mg);

300 MHz $^1$H NMR $\delta_H$ (CDCl$_3$) 1.39 (3H, t), 3.96 (2H, q), 5.17 (1H, d), 6.25-6.36 (2H, m).

Description 62

(5-Ethoxy-2,3-difluoro-phenyl)trifluoromethane-sulfonate (D62)

A solution of 5-ethoxy-2,3-difluoro-phenol (which may be prepared as described in Description 61) (270 mg, 1.55 mmol) in DCM (6 mL) was cooled to 0° C. and treated with pyridine (0.62 mL, 7.75 mmol) followed by trifluoromethane-sulfonic anhydride (0.31 mL, 1.86 mmol). The mixture was stirred for 10 mins at 0° C. and then allowed to warm to room temperature. After 30 minutes, DCM (50 ml) and 10% aq. citric acid (25 ml) were added and the product was extracted into DCM. The aqueous layer was re-extracted with DCM and the combined organic layers were dried (Na$_2$SO$_4$) and evaporated. Chromatography (0-100% DCM in isohexane) gave (5-ethoxy-2,3-difluoro-phenyl)trifluoromethanesulfonate (D62) as a clear oil (430 mg);

300 MHz $^1$H NMR $\delta_H$ (CDCl$_3$) 1.44 (3H, t), 4.00 (2H, q), 6.65 (1H, quin), 6.77 (1H, ddd).

Description 63

2-(5-Ethoxy-2,3-difluoro-phenyl)-4,4,5,5-tetramethyl-1,3,2-dioxaborolane (D63)

A solution of (5-ethoxy-2,3-difluoro-phenyl)trifluoromethanesulfonate (which may be prepared as described in Description 62) (430.01 mg, 1.4 mmol) in 1,4-dioxane (6 mL) was treated with bis(pinacolato)diboron (534.91 mg, 2.11 mmol) followed by potassium acetate (0.4082 g, 4.21 mmol). The mixture was degasssed by vacuum and nitrogen fill 4 times, and N$_2$ was bubbled through the mixture. [1,1'-Bis(diphenylphosphino)ferrocene]-dichloropalladium(II) (102.75 mg, 0.1400 mmol) was added and the mixture was refluxed under nitrogen. After 2 h, the brown mixture was cooled and then the dioxan was removed by evaporation. ethyl acetate and water (100 ml of each) were added and the product was extracted into ethyl acetate. The organic layer was dried (Na$_2$SO$_4$) and concentrated. Chromatography using 0-100% ethyl acetate in isohexane and then recolumning using 0-25% ethyl acetate in isohexane to give 2-(5-ethoxy-2,3-difluoro-phenyl)-4,4,5,5-tetramethyl-1,3,2-dioxaborolane (D63) (142 mg);

300 MHz $^1$H NMR $\delta_H$ (CDCl$_3$) 1.37 (12H, s), 1.39 (3H, t), 4.01 (2H, q), 6.70 (1H, ddd), 6.96 (1H, m).

Description 64

2-Bromo-4-ethoxy-1-methyl-benzene (D64)

To a stirred solution of 3-bromo-4-methyl-phenol (1.2 g, 6.42 mmol) in anhydrous DMF (12 mL), was added iodoethane (1.55 mL, 19.25 mmol) and potassium carbonate (1.06 g, 7.7 mmol). The resulting mixture was left to stir at 80° C. for 18 h. It was allowed to cool to room temperature, poured into brine and extracted with ethyl acetate. The combined organic layers were dried over sodium sulphate and filtered. The filtrate was evaporated and the crude residue was purified by silica gel chromatography (25 g SiO$_2$) eluting with iso-hexane. Evaporation of desired fractions gave 2-bromo-4-ethoxy-1-methyl-benzene (D64) (0.7500 g, 3.4869 mmol, 54.3% yield) as colourless oil;

300 MHz $^1$H NMR $\delta_H$ (CDCl$_3$) 1.41 (3H, t), 2.34 (3H, s), 4.00 (2H, q), 6.78 (1H, dd), 7.11 (1H, d), 7.12 (1H, d).

Description 65

2-(5-Ethoxy-2-methyl-phenyl)-4,4,5,5-tetramethyl-1,3,2-dioxaborolane (D65)

To a solution of 2-bromo-4-ethoxy-1-methyl-benzene (which may be prepared as described in Description 64), (400 mg, 1.86 mmol) in dry DMF (6 mL) in a microwave vial was added potassium acetate (0.5495 g, 5.58 mmol), 4,4,5,5-tetramethyl-2-(4,4,5,5-tetramethyl-1,3,2-dioxaborolan-2-yl)-1,3,2-dioxaborolane (708.37 mg, 2.79 mmol), and Pd(dppf)Cl$_2$.CH$_2$Cl$_2$ (151.87 mg, 0.1900 mmol). The reaction was degassed by means of a stream of nitrogen bubbling into the solution for 15 mins. The reaction was then heated to 120° C. for 40 minutes by microwave. The cooled reaction mixture was partitioned between EtOAc (20 mL) and water (80 mL), and the organics were separated, washed with brine (30 mL), dried over MgSO$_4$, filtered and concentrated in vacuo. The residue was loaded onto silica (25 g, SNAP cartridge), which was eluted with a gradient from 0% to 30% EtOAc:isohexane. Fractions containing desired product were combined and concentrated in vacuo to give 2-(5-ethoxy-2-methyl-phenyl)-4,4,5,5-tetramethyl-1,3,2-dioxaborolane (D65) (274 mg, 0.9407 mmol, 50.6% yield) as green oil;

300 MHz $^1$H NMR $\delta_H$ (CDCl$_3$) 1.35 (12H, s), 1.41 (3H, t), 2.47 (3H, s), 4.05 (2H, q), 6.88 (1H, dd), 7.09 (1H, d), 7.32 (1H, d).

Descriptions 66 and 67

1-(3-Benzyloxy-4-fluoro-phenyl)-3-methyl-pyrazole (D66) and 1-(3-Benzyloxy-4-fluoro-phenyl)-5-methyl-pyrazole (D67)

To a microwave vial containing 2-benzyloxy-4-bromo-1-fluoro-benzene [CAS: 1036724-54-5](1500 mg, 5.34 mmol) and 3-methyl-1H-pyrazole (525.68 mg, 6.4 mmol) in 1,4-dioxane (10 mL) was added copper (I) iodide (101.62 mg, 0.5300 mmol), potassium phosphate (2265.26 mg, 10.67 mmol), and (1S,2S)-(+)-1,2-diaminocyclohexane (60.93 mg, 0.5300 mmol). The vial was sealed and heated in a microwave at 200° C. for 2 h 30 minutes. The reaction was diluted with water (50 mL) and EtOAc (30 mL), and the organics were separated, washed with brine (20 mL), dried over MgSO$_4$, filtered and concentrated in vacuo. The residue was purified by column chromatography over silica (50 g, SNAP cartidge), eluting with a gradient of EtOAc:isohexane from 0% to 30%. Fractions containing the first eluting product were combined and concentrated in vacuo to give 1-(3-benzyloxy-4-fluoro-phenyl)-3-methyl-pyrazole (D66) (385 mg, 1.2274 mmol, 23% yield) as a colourless oil which crystallised on standing;

300 MHz $^1$H NMR $\delta_H$ (CDCl$_3$) 2.39 (s, 3H), 5.22 (s, 2H), 6.25 (d, 1H), 7.07-7.18 (m, 2H), 7.34-7.51 (m, 6H), 7.72 (d, 1H).

Fractions containing the second eluting product were combined and concentrated in vacuo to give 1-(3-benzyloxy-4-fluoro-phenyl)-5-methyl-pyrazole (D67) (102 mg, 0.1807 mmol, 3.4% yield) as a colourless oil;

300 MHz $^1$H NMR $\delta_H$ (CDCl$_3$) 2.26 (s, 3H), 5.18 (s, 2H), 6.19 (s, 1H), 6.98 (1H, m), 7.08-7.49 (7H, m), 7.57 (1H, d).

Description 68

2-Fluoro-5-(3-methylpyrazol-1-yl)phenol (D68)

A solution of 1-(3-benzyloxy-4-fluoro-phenyl)-3-methyl-pyrazole (which may be prepared as described in Description 66) (470 mg, 1.66 mmol) in methanol (20 mL) was hydrogenated using an H-Cube with 10% Pd/C (30 mm cartridge) at 50° C. and 1 mL/min flow rate. The eluent was concentrated in vacuo to give 2-fluoro-5-(3-methylpyrazol-1-yl)phenol (D68) (288 mg, 1.4236 mmol, 85.5% yield) as a colourless oil;

$^1$H NMR (300 MHz, MeOD) $\delta$: 2.33 (s, 3H), 6.29 (d, 1H), 7.05-7.18 (m, 2H), 7.25 (dd, 1H), 7.79 (d, 1H).

Description 69

[2-Fluoro-5-(3-methylpyrazol-1-yl)phenyl]trifluoromethanesulfonate (D69)

To an ice cooled solution of trifluoromethanesulfonic anhydride (0.29 mL, 1.72 mmol) in DCM (10 mL) was added 2-fluoro-5-(3-methylpyrazol-1-yl)phenol (which may be prepared as described in Description 68) (288 mg, 1.5 mmol) followed by pyridine (0.6 mL, 7.49 mmol). The reaction was stirred at 00° C. for 10 minutes, then allowed to warm to room temperature over 1 hour, then the reaction was stirred overnight at room temperature. Additional trifluoromethanesulfonic anhydride (0.29 mL, 1.72 mmol) was added and the reaction was stirred at room temperature for 1 hour. The reaction was diluted with DCM (30 mL) and subsequently poured into an aqueous solution of citric acid (10% w/w, 50 mL), and the layers were separated. The aqueous was then re-extracted with DCM (30 mL). The combined organics were dried through a phase separator, and concentrated in vacuo. The residue was loaded onto a silica column (10 g, SNAP cartidge), which was eluted with a gradient of EtOAc:isohexane, 0% to 30%. Fractions containing desired product were combined and concentrated in vacuo, to give [2-fluoro-5-(3-methylpyrazol-1-yl)phenyl]trifluoromethanesulfonate (D69) (308 mg, 0.9024 mmol, 60.2% yield);

$^1$H NMR (300 MHz, CDCl$_3$) $\delta$: 2.38 (s, 3H), 6.30 (d, 1H), 7.34 (t, 1H), 7.61-7.66 (m, 1H), 7.73 (dd, 1H), 7.78 (d, 1H)

Description 70

1-[4-Fluoro-3-(4,4,5,5-tetramethyl-1,3,2-dioxaborolan-2-yl)phenyl]-3-methyl-pyrazole (D70)

[2-Fluoro-5-(3-methylpyrazol-1-yl)phenyl]trifluoromethanesulfonate (which may be prepared as described in Description 69) (308 mg, 0.9500 mmol) was treated to conditions analogous to those of Description 65 and gave 1-[4-fluoro-3-(4,4,5,5-tetramethyl-1,3,2-dioxaborolan-2-yl)phenyl]-3-methyl-pyrazole (D70) (286 mg, 0.8519 mmol, 89.7% yield) as a colourless oil;

$^1$H NMR (300 MHz, CDCl$_3$) $\delta$: 1.39 (s, 12H), 2.39 (s, 3H), 6.24 (d, 1H), 7.12 (t, 1H), 7.74-7.80 (m, 1H), 7.81 (d, 1H), 7.93 (dd, 1H)

Description 71

1-(3-Benzyloxy-4-fluoro-phenyl)pyrazole (D71)

To a microwave vial containing 2-benzyloxy-4-bromo-1-fluoro-benzene [CAS: 1036724-54-5] (1500 mg, 5.34 mmol) and (1S,2S)-(+)-1,2-diaminocyclohexane (121.86 mg, 1.07 mmol) in 1,4-dioxane (10 mL) was added copper (I) iodide (203.24 mg, 1.07 mmol), potassium phosphate (2265.3 mg, 10.67 mmol), and 1H-pyrazole (363.26 mg, 5.34 mmol). The vial was sealed and heated in a microwave at 200° C. for 1 hour. The reaction mixture was diluted with water (50 mL) and EtOAc (30 mL), and the organics were separated, washed with brine (20 mL), dried over MgSO$_4$, filtered and concentrated in vacuo. The residue was purified by column chromatography over silica (25 g, SNAP cartridge), eluting with a gradient of EtOAc:isohexane from 0% to 30%. Fractions containing desired product were combined and concentrated in vacuo to give 1-(3-benzyloxy-4-fluoro-phenyl)pyrazole (D71) (649.1 mg, 2.2984 mmol, 43.1% yield) as a pale orange oil;

$^1$H NMR (300 MHz, CDCl$_3$) $\delta$: 5.23 (s, 2H), 6.48 (t, 1H), 7.12-7.21 (m, 2H), 7.34-7.53 (m, 6H), 7.73 (d, 1H), 7.84 (d, 1H).

Description 72

2-Fluoro-5-pyrazol-1-yl-phenol (D72)

A solution of 1-(3-benzyloxy-4-fluoro-phenyl)pyrazole (which may be prepared as described in Description 71) (649.1 mg, 2.42 mmol) in methanol (20 mL) was hydrogenated through an H-Cube 10% Pd/C (70 mm cartridge) at 50° C. at a flow rate of 1 ml/minute. The eluent was collected and concentrated in vacuo to give 2-fluoro-5-pyrazol-1-yl-phenol (D72) (352.5 mg, 1.8796 mmol, 77.7% yield) as a colourless oil;

$^1$H NMR (300 MHz, MeOD) $\delta$: 6.50-6.52 (m, 1H), 7.13-7.20 (m, 2H), 7.30-7.33 (m, 1H), 7.69 (d, 1H), 8.11-8.12 (d, 1H).

Description 73

(2-Fluoro-5-pyrazol-1-yl-phenyl)trifluoromethanesulfonate (D73)

2-Fluoro-5-pyrazol-1-yl-phenol (which may be prepared as described in Description 72) (352.5 mg, 1.98 mmol) was treated with conditions analogous to those of Description 69 and gave (2-fluoro-5-pyrazol-1-yl-phenyl)trifluoromethanesulfonate (D73) (551.4 mg, 1.6886 mmol, 85.3% yield);

$^1$H NMR (300 MHz, CDCl$_3$) b: 6.53 (t, 1H), 7.38 (t, 1H), 7.69 (ddd, 1H), 7.76 (d, 1H), 7.79 (dd, 1H), 7.91 (d, 1H)

Description 74

1-[4-Fluoro-3-(4,4,5,5-tetramethyl-1,3,2-dioxaborolan-2-yl)-phenyl]-pyrazole (D74)

(2-Fluoro-5-pyrazol-1-yl-phenyl)trifluoromethanesulfonate (which may be prepared as described in Description 73) (551.4 mg, 1.78 mmol) was treated to conditions analogous to those of Descrption 65 and gave 1-[4-fluoro-3-(4,4, 5,5-tetramethyl-1,3,2-dioxaborolan-2-yl)phenyl]pyrazole (D74) (391.4 mg, 1.2905 mmol, 72.6% yield) as a colourless oil;

$^1$H NMR (300 MHz, CDCl$_3$) δ: 1.39 (s, 12H), 6.48 (t, 1H), 7.15 (t, 1H), 7.73 (d, 1H), 7.81 (ddd, 1H), 7.93 (d, 1H), 8.00 (dd, 1H).

Description 75

2-[5-(Cyclopropoxy)-2-fluoro-phenyl]-4,4,5,5-tetramethyl-1,3,2-dioxaborolane (D75)

2-Bromo-4-(cyclopropoxy)-1-fluoro-benzene [CAS: 1243469-64-8](0.2000 g, 0.8656 mmol) was treated to conditions analogous to Description 59 and gave 2-[5-(cyclopropoxy)-2-fluoro-phenyl]-4,4,5,5-tetramethyl-1,3,2-dioxaborolane (D75) (260 mg, 0.9348 mmol) as an impure colourless oil. The material used without further attempt to purify;

300 MHz $^1$H NMR δ$_H$ (CDCl$_3$) 0.78 (2H, m) 1.25 (t, 2H), 1.38 (s, 12H), 4.13 (1H, q), 6.95 (t, 1H), 7.08 (1H, m), 3.37 (1H, t).

Description 76

2-[2-Fluoro-5-(methoxymethyl)phenyl]-4,4,5,5-tetramethyl-1,3,2-dioxaborolane (D76)

2-Bromo-1-fluoro-4-(methoxymethyl)benzene [CAS: 887268-22-6](400 mg, 1.83 mmol) was treated with conditions analogous to those of Description 65 and gave 2-[2-fluoro-5-(methoxymethyl)phenyl]-4,4,5,5-tetramethyl-1,3,2-dioxaborolane (D76) (260.7 mg, 0.5878 mmol, 32.2% yield) as a colourless oil;

$^1$H NMR (300 MHz, CDCl$_3$) δ: 1.38 (s, 12H), 3.39 (s, 3H), 4.43 (s, 2H), 7.03 (t, 1H), 7.41-7.47 (m, 1H), 7.71 (dd, 1H).

Description 77

2-[5-(Ethoxymethyl)-2-fluoro-phenyl]-4,4,5,5-tetramethyl-1,3,2-dioxaborolane hydrochloride (D77)

2-Bromo-4-(ethoxymethyl)-1-fluoro-benzene [CAS: 1250530-52-9](390 mg, 1.67 mmol) was treated with conditions analogous to those of Description 65 and gave 2-[5-(ethoxymethyl)-2-fluoro-phenyl]-4,4,5,5-tetramethyl-1,3,2-dioxaborolane (D77) (103.1 mg, 0.3680 mmol, 21.995% yield) as a colourless oil;

$^1$H NMR (300 MHz, CDCl$_3$) δ: 1.25 (t, 3H), 1.37 (s, 12H), 3.53 (q, 2H), 4.46 (s, 2H), 7.02 (t, 1H), 7.41-7.47 (m, 1H), 7.70 (dd, 1H).

Description 78

4-(3-Benzyloxy-4-fluoro-phenyl)-1-methyl-pyrazole (D78)

To a solution of 2-benzyloxy-4-bromo-1-fluoro-benzene [CAS: 1036724-54-5](1250 mg, 4.45 mmol) in MeCN (40 mL) and water (10 mL) was added 1-methyl-4-(4,4,5,5-tetramethyl-1,3,2-dioxaborolan-2-yl)-1 h-pyrazole (925.18 mg, 4.45 mmol), sodium carbonate (1414.18 mg, 13.34 mmol) and bis(triphenylphosphine)palladium (II) dichloride (157.92 mg, 0.2200 mmol). The reaction was then heated at 100° C. for 4 hours. The reaction mixture was poured into EtOAc (100 mL) and aq NaOH (0.5M, 200 mL). The organics were separated, and washed with brine (75 mL), dried over MgSO$_4$, filtered and concentrated in vacuo. The residue was then purified over silica (25 g, SNAP cartridge), eluting with between 0% and 40% EtOAc in isohexane. Fractions containing the desired product were combined and concentrated in vacuo to give 4-(3-benzyloxy-4-fluoro-phenyl)-1-methyl-pyrazole (D78) (760 mg, 2.5575 mmol, 57.6% yield) as a colourless oil;

$^1$H NMR (300 MHz, CDCl$_3$) δ: 3.95 (s, 3H), 5.20 (s, 2H), 6.98-7.13 (m, 3H), 7.33-7.53 (m, 6H), 7.67 (s, 1H).

Description 79

2-Fluoro-5-(1-methylpyrazol-4-yl)phenol (D79)

A solution of 4-(3-benzyloxy-4-fluoro-phenyl)-1-methyl-pyrazole (which may be prepared as described in Description 78) (760 mg, 2.69 mmol) in methanol (15 mL) was hydrogenated through a H-Cube using a 10% Pd/C (70 mm cartridge) at 50° C. with a Flow rate of 1 mL/min. The eluent was concentrated in vacuo and gave 2-fluoro-5-(1-methylpyrazol-4-yl)phenol (419.2 mg, 2.0721 mmol, 77% yield) (D79) as a colourless solid;

$^1$H NMR (300 MHz, MeOD) δ: 3.92 (s, 3H), 6.94-7.10 (m, 3H), 7.72 (s, 1H), 7.86 (s, 1H).

Description 80

[2-Fluoro-5-(1-methylpyrazol-4-yl)phenyl]trifluoromethanesulfonate (D80)

2-Fluoro-5-(1-methylpyrazol-4-yl)phenol (which may be prepared as described in Description 79) (419.2 mg, 2.18 mmol) was treated with conditions analogous to those of Description 69 and gave [2-fluoro-5-(1-methylpyrazol-4-yl)phenyl]trifluoromethanesulfonate (D80) (656 mg, 1.922 mmol, 88.1% yield);

$^1$H NMR (300 MHz, CDCl$_3$) δ: 3.98 (s, 3H), 7.23-7.29 (t, 1H), 7.39 (dd, 1H), 7.42-7.47 (m, 1H), 7.61 (s, 1H), 7.72 (s, 1H).

Description 81

4-[4-Fluoro-3-(4,4,5,5-tetramethyl-1,3,2-dioxaborolan-2-yl)phenyl]-1-methyl-pyrazole (D81)

[2-Fluoro-5-(1-methylpyrazol-4-yl)phenyl]trifluoromethanesulfonate (which may be prepared as described in Description 80) (656 mg, 2.02 mmol) was treated with conditions analogous to those of Description 65 and gave 4-[4-fluoro-3-(4,4,5,5-tetramethyl-1,3,2-dioxaborolan-2-yl)phenyl]-1-methyl-pyrazole (D81) (515.4 mg, 1.6205 mmol, 80.1% yield) as a colourless oil;

$^1$H NMR (300 MHz, CDCl$_3$) δ: 1.40 (s, 12H), 3.96 (s, 3H), 7.05 (t, 1H), 7.54 (m, 1H), 7.63 (s, 1H), 7.76 (s, 1H), 7.82 (dd, 1H).

Description 82

5-(3-Benzyloxy-4-fluoro-phenyl)-1-methyl-pyrazole (D82)

To a solution of 1-methyl-1H-pyrazole-5-boronic acid pinacol ester (1058.42 mg, 5.09 mmol) in MeCN (40 mL) and water (10 mL) was added 2-benzyloxy-4-bromo-1-fluoro-benzene [CAS: 1036724-54-5](1300 mg, 4.62 mmol), sodium carbonate (1470.8 mg, 13.88 mmol) and bis(triphenylphosphine)palladium (II) dichloride (164.24 mg, 0.2300 mmol). The reaction was then heated at 100° C. for 4 hours. The cooled reaction mixture was poured into EtOAc (70 mL) and water (100 mL). The organics were separated, and washed with brine (75 mL), dried over $MgSO_4$, filtered and concentrated in vacuo. The residue was then purified over silica (25 g, SNAP cartridge), eluting with EtOAc in isohexane from 0% to 40%. Fractions containing desired product were combined and concentrated in vacuo to give 5-(3-benzyloxy-4-fluoro-phenyl)-1-methyl-pyrazole (D82) (1026.5 mg, 3.4543 mmol, 74.7% yield) as a colourless oil;

$^1$H NMR (300 MHz, $CDCl_3$) δ: 3.75 (s, 3H), 5.21 (s, 2H), 6.25 (m, 1H), 6.94-7.02 (m, 2H), 7.19 (dd, 1H), 7.33-7.51 (m, 6H).

Description 83

2-Fluoro-5-(2-methylpyrazol-3-yl)phenol (D83)

A solution of 5-(3-benzyloxy-4-fluoro-phenyl)-1-methyl-pyrazole (which may be prepared as described in Description 82) (1026.5 mg, 3.64 mmol) in methanol (20 mL) was hydrogenated with an H-Cube using a 10% Pd/C (70 mm cartridge) at 50° C. and a flow rate of 1 mL/min. The eluent was concentrated in vacuo to give 2-fluoro-5-(2-methylpyrazol-3-yl) phenol (D83) (677.1 mg, 3.3469 mmol, 92.0% yield) as a colourless solid;

$^1$H NMR (300 MHz, MeOD) δ: 3.86 (s, 3H), 6.33 (d, 1H), 6.89-6.94 (m, 1H), 7.03 (dd, 1H), 7.18 (dd, 1H), 7.49 (d, 1H)

Description 84

[2-Fluoro-5-(2-methylpyrazol-3-yl)phenyl]trifluoromethanesulfonate (D84)

2-Fluoro-5-(2-methylpyrazol-3-yl)phenol (which may be prepared as described in Description 83) (677.1 mg, 3.52 mmol) was treated with conditions analogous to those of Description 69 and gave [2-fluoro-5-(2-methylpyrazol-3-yl) phenyl]trifluoromethanesulfonate (D84) (1044.2 mg, 3.0593 mmol, 86.8% yield);

$^1$H NMR (300 MHz, $CDCl_3$) δ: 3.91 (s, 3H), 6.35 (d, 1H), 7.36-7.47 (m, 3H), 7.55 (d, 1H).

Description 85

5-[4-Fluoro-3-(4,4,5,5-tetramethyl-1,3,2-dioxaborolan-2-yl)phenyl]-1-methyl-pyrazole (D85)

[2-Fluoro-5-(2-methylpyrazol-3-yl)phenyl]trifluoromethanesulfonate (which may be prepared as described in Description 84) (1044 mg, 3.22 mmol) was treated with conditions analogous to those of Description 65 and gave 5-[4-fluoro-3-(4,4,5,5-tetramethyl-1,3,2-dioxaborolan-2-yl)phenyl]-1-methyl-pyrazole (D85) (486.1 mg, 1.3675 mmol, 42.5% yield);

$^1$H NMR (300 MHz, $CDCl_3$) δ: 1.39 (s, 12H), 3.88 (s, 3H), 6.31 (d, 1H), 7.14 (t, 1H), 7.46-7.53 (m, 2H), 7.80 (dd, 1H).

Descriptions 86 and 87

1-(3-Bromo-4-fluoro-phenyl)-3-methyl-pyrazole (D86) and 1-(3-Bromo-4-fluoro-phenyl)-5-methylpyrazole (D87)

To a solution of (3-bromo-4-fluoro-anilino)ammonium chloride [CAS: 1166990-89-1](5412 mg, 22.41 mmol) in ethanol (30 mL) was added 4,4-dimethoxybutan-2-one (3.12 mL, 23.53 mmol), and the reaction was heated to reflux for 4 hours. The reaction mixture was concentrated in vacuo, and the residue was loaded onto silica (50 g, SNAP cartridge), eluting with EtOAc in isohexane from 0% to 25%. Fractions containing the faster running desired product were combined and concentrated in vacuo to give one of the isomers 1-(3-bromo-4-fluoro-phenyl)-3-methyl-pyrazole (D86) (1249 mg, 4.65 mmol, 20.8% yield) (1.26 g);

$^1$H NMR (300 MHz, $CDCl_3$) δ: 2.38 (s, 3H), 6.27 (d, 1H), 7.19 (t, 1H), 7.54-7.59 (m, 1H), 7.75 (d, 1H), 7.92 (dd, 1H).

The second component was concentrated in vacuo to give 1-(3-bromo-4-fluoro-phenyl)-5-methyl-pyrazole (D87) (197 mg, 0.5406 mmol, 2.4% yield);

$^1$H NMR (300 MHz, $CDCl_3$) δ: 2.37 (s, 3H), 6.22 (app bs, 1H), 7.24 (t, 1H), 7.38-7.43 (m, 1H), 7.58 (d, 1H), 7.72 (dd, 1H).

Description 88

1-[4-Fluoro-3-(4,4,5,5-tetramethyl-1,3,2-dioxaborolan-2-yl)phenyl]-5-methyl-pyrazole (D88)

1-(3-Bromo-4-fluoro-phenyl)-5-methyl-pyrazole (which may be prepared as described in Description 87) (197 mg, 0.7700 mmol) was treated with conditions analogous to those of Description 65 and gave 1-[4-fluoro-3-(4,4,5,5-tetramethyl-1,3,2-dioxaborolan-2-yl)phenyl]-5-methyl-pyrazole (D88) (54 mg, 0.1251 mmol, 16.2% yield) >70% pure;

M/Z: 303.2 $[M+H]^+$ in ES+.

Description 89

2-(4-Fluoro-3-isobutoxy-phenyl)-4,4,5,5-tetramethyl-1,3,2-dioxaborolane (D89)

A solution of 4-bromo-1-fluoro-2-isobutoxy-benzene [CAS: 1309933-68-3](250 mg, 1.01 mmol) was treated with conditions analogous to those of Description 65 and gave the title compound (D89) as a pale yellow oil (105 mg).

$^1$H NMR (300 MHz, $CDCl_3$) δ: 1.06 (6H, d), 1.37 (12H, s), 2.15 (1H, m), 3.85 (2H, d), 7.08 (1H, dd), 7.35-7.40 (2H, m).

Descriptions 90, 91, 92, 93

(2S,5R)-2-(4-Bromo-6-methyl-2-pyridyl)-7-methyl-1,7-diazaspiro[4.4]nonan-6-one (D90); (2R,5S)-2-(4-Bromo-6-methyl-2-pyridyl)-7-methyl-1,7-diazaspiro [4.4]nonan-6-one (D91); (2R,5R)-2-(4-Bromo-6-methyl-2-pyridyl)-7-methyl-1,7-diazaspiro[4.4] nonan-6-one (D92); (2S,5S)-2-(4-Bromo-6-methyl-2-pyridyl)-7-methyl-1,7-diazaspiro[4.4]nonan-6-one (D93)

To a stirred solution of 2-(4-bromo-6-methyl-2-pyridyl)-7-methyl-1,7-diazaspiro[4.4]non-1-en-6-one (which may be prepared as described in Description 13) (1641 mg, 5.09 mmol) in DCM (20 mL) under nitrogen at room temperature was added concentrated hydrochloric acid (0.44 mL, 5.09 mmol) followed by sodium triacetoxyborohydride (4321.08 mg, 20.39 mmol). The reaction was then allowed to stir at room temperature for 3 hours. The reaction was quenched by addition of saturated aqueous $Na_2CO_3$ (50 mL). The organic phase was separated using a hydrophobic frit, and subsequently concentrated in vacuo. The residue was loaded onto silica (350 g) using DCM (2 mL), and the column (Column A) was eluted with a gradient of (80:20:2 EtOAc:MeOH:0.880 NH3):EtOAc from 0%->60%. Fractions containing the faster running diastereomers were combined and concentrated in vacuo to give a racemic mixture of (2S,5R)-2-(4-bromo-6-methyl-2-pyridyl)-7-methyl-1,7-diazaspiro[4.4]nonan-6-one and (2R,5S)-2-(4-bromo-6-methyl-2-pyridyl)-7-methyl-1,7-diazaspiro[4.4]nonan-6-one (551 mg);
$^1$H NMR (300 MHz, CDCl$_3$) δ: 1.77-1.90 (m. 2H), 1.98-2.22 (m, 3H), 2.47-2.56 (m, 4H), 2.91 (s, 3H), 3.24-3.38 (m, 2H), 4.64 (t, 1H), 7.18 (s, 1H), 7.55 (s, 1H).

A racemic mixture of these (2S,5R) and (2R,5S) isomers (1239 mg) was dissolved in ethanol (6 mL) and heptane (6 mL), and the resulting solution was passed down a ChiralPak AD-H preperative column, (Column B) eluting with 50% EtOH:Heptane. Fractions containing the faster running peak were combined and concentrated in vacuo to give (2R,5S)-2-(4-bromo-6-methyl-2-pyridyl)-7-methyl-1,7-diazaspiro[4.4]nonan-6-one (D91) (439.2 mg, 1.3546 mmol);
Optical rotation α[$^D/_{22}$]=+20.5 (c=1.075, CHCl$_3$).
Fractions containing the slower running isomer from Column B were combined and concentrated in vacuo to give (2S, 5R)-2-(4-bromo-6-methyl-2-pyridyl)-7-methyl-1,7-diazaspiro[4.4]nonan-6-one (D90) (398.1 mg, 1.2279 mmol);
Optical rotation α[$^D/_{22}$]=−20.0 (c=1.0, CHCl$_3$).
Fractions containing the less polar isomer from the original normal phase chromatography column (Column A) were combined and concentrated in vacuo to give a racemic mixture of (2R,5R)-2-(4-bromo-6-methyl-2-pyridyl)-7-methyl-1,7-diazaspiro[4.4]nonan-6-one (D92) and (2S,5S)-2-(4-bromo-6-methyl-2-pyridyl)-7-methyl-1,7-diazaspiro[4.4]nonan-6-one (D93) (330.2 mg, 0.5092 mmol);
$^1$H NMR (300 MHz, CDCl$_3$) δ: 1.75-1.84 (m, 1H), 1.94-2.21 (m, 4H), 2.25-2.38 (m, 1H), 2.51 (s, 3H), 2.93 (s, 3H), 3.27-3.42 (m, 2H), 4.32 (t, 1H), 7.21 (s, 1H), 7.61 (s, 1H).

Description 94

(5-Ethoxy-2-fluoro-4-methyl-phenyl)boronic acid (D94)

In dried glassware, 2.5M n-BuLi in hexanes (18.01 mL, 45.02 mmol) was added over 15 minutes to a stirred solution of 1-ethoxy-4-fluoro-5-iodo-2-methyl-benzene [CAS: 918813-06-6](9.7 g, 34.63 mmol) in dry THF (100 mL) at −78° C. under N$_2$. After stirring for 30 mins, trimethyl borate (7.72 mL, 69.27 mmol) was added over 10 mins. The mixture was stirred for 3.25 h at −78° C. then quenched by slow addition of 1M HCl (115 ml). The mixture was warmed to ambient temperature, diluted with water (115 ml) and extracted with EtOAc (2×100 ml). The combined organic extracts were washed with saturated sodium metabisulfite soln (250 ml), brine (100 ml) and dried (MgSO$_4$). The almost colourless solution was evaporated to a cream solid, dried rt/vac/1 h (wt=6.2 g). This solid was stirred with Et$_2$O/iso-hexane (1:1) (40 ml) and filtered under suction and washed with the mixture then iso-hexane, dried rt/vac/overnight to give (5-ethoxy-2-fluoro-4-methyl-phenyl)boronic acid (D94) (4.0 g);
$^1$H NMR (300 MHz, d6-acetone) δ: 1.39 (3H, t), 2.20 (3H, s), 4.06 (2H, q), 6.88 (1H, d), 7.01 (2H, d), 7.21 (1H, d).

Description 95

5-Fluoro-2,3-dihydrobenzofuran-6-ol (D95)

To a stirred solution of 5-fluoro-6-hydroxy-benzofuran-3-one (551 mg, 3.28 mmol) in ethanol (10 mL) was added hydrazine hydrate (3.75 mL, 76.93 mmol), and the reaction was heated to reflux for 30 minutes. The reaction was subsequently concentrated in vacuo. The residue was then dissolved in ethylene glycol (10 mL), and then treated with potassium hydroxide (551.64 mg, 9.83 mmol). The reaction was then heated to 1500° C. for 3 hours. The reaction was poured into 2M aq. HCl (100 mL), and extracted with EtOAc (100 mL). The organic phase was washed with brine, dried over MgSO$_4$, filtered and concentrated in vacuo. The residue was suspended in DCM (50 mL), and the reaction was filtered. The filtrate was concentrated in vacuo and loaded onto a silica column (25 g, SNAP cartridge), which was eluted with EtOAc:isohexane 0% to 50%. Fractions containing desired product were combined and concentrated in vacuo to give 5-fluoro-2,3-dihydrobenzofuran-6-ol (D95) (190.4 mg, 1.2352 mmol, 37.7% yield) as a colourless oil which crystallised on standing;
$^1$H NMR (300 MHz, CDCl$_3$) δ: 3.15 (t, 2H), 4.58 (t, 2H), 4.95 (d, 1H), 6.47 (d, 1H), 6.92 (d, 1H).

Description 96

(5-Fluoro-2,3-dihydrobenzofuran-6-yl)trifluoromethanesulfonate (D96)

To an ice cooled solution of 5-fluoro-2,3-dihydrobenzofuran-6-ol (which may be prepared as described in Description 95) (90 mg, 0.5800 mmol) in DCM (4 mL) was added pyridine (0.24 mL, 2.92 mmol) followed by trifluoromethanesulfonic anhydride (0.11 mL, 0.6700 mmol). The reaction was stirred at 0° C. for 10 minutes, then allowed to warm to room temperature over 1 hour. The reaction was diluted with DCM (30 mL) and subsequently poured into an aqueous solution of citric acid (10% w/w, 50 mL), and the layers were separated. The aqueous was then re-extracted with DCM (30 mL). The combined organics were dried through a phase separator, and concentrated in vacuo. The residue was loaded onto a silica column (25 g, SNAP cartridge), which was eluted with an increasing gradient of EtOAc in isohexane, 0% to 25%. Fractions containing desired product were combined and concentrated in vacuo, to give (5-fluoro-2,3-dihydrobenzofuran-6-yl)trifluoromethanesulfonate (D96) (130.6 mg, 0.4335 mmol, 74.2% yield) as a pale golden oil;
$^1$H NMR (300 MHz, CDCl$_3$) δ: 3.26 (t, 2H), 4.66 (t, 2H), 6.73 (d, 1H), 7.09 (d, 1H).

Description 97

2-(5-Fluoro-2,3-dihydrobenzofuran-6-yl)-4,4,5,5-tetramethyl-1,3,2-dioxaborolane (D97)

To a solution of (5-fluoro-2,3-dihydrobenzofuran-6-yl)trifluoromethanesulfonate (which may be prepared as described in Description 96) (130.6 mg, 0.4600 mmol) in dry DMF (4 mL) was added potassium acetate (141.3 mg, 1.37 mmol) and 4,4,5,5-tetramethyl-2-(4,4,5,5-tetramethyl-1,3,2-dioxaborolan-2-yl)-1,3,2-dioxaborolane (150.64 mg, 0.5900 mmol). The reaction was degassed by evacuation of the flask and refilling with nitrogen 6 times. To the reaction was then added Pd(dppf)Cl$_2$.CH$_2$Cl$_2$ (55.9 mg, 0.0700 mmol) and the reaction was heated at 90° C. for 16 hours. The reaction was partitioned between EtOAc (90 mL) and water (90 mL), and the organics were separated, washed with brine (50 mL), dried over MgSO$_4$, filtered and concentrated in vacuo. The residue was then loaded onto silica (25 g, SNAP cartridge), which was eluted with a gradient of EtOAc:isohexane from 0% to 80%. Fractions containing desired product were combined and concentrated in vacuo to give 2-(5-fluoro-2,3-dihydrobenzofuran-6-yl)-4,4,5,5-tetramethyl-1,3,2-dioxaborolane (D97) (15.2 mg, 0.0576 mmol, 12.6% yield) as a colourless oil;
$^1$H NMR (300 MHz, CDCl$_3$) δ: 1.36 (s, 12H), 3.21 (t, 2H), 4.57 (t, 2H), 6.89 (d, 1H), 7.06 (d, 1H).

Descriptions 98 and 99 tert-Butyl (2R,5R)-2-(4-bromo-3-methyl-2-pyridyl)-7-methyl-6-oxo-1,7-diazaspiro[4.4]nonane-1-carboxylate (D98) and tert-Butyl (2S,5R)-2-(4-bromo-3-methyl-2-pyridyl)-7-methyl-6-oxo-1,7-diazaspiro[4.4]nonane-1-carboxylate (D99)

To a solution of (5R)-2-(4-bromo-3-methyl-2-pyridyl)-7-methyl-1,7-diazaspiro[4.4]nonan-6-one (which may be prepared as described in Description 10) (554.4 mg, 0.8500 mmol) in DCM (2 mL) was added and tert-butoxycarbonyl tert-butyl carbonate (373.2 mg, 1.71 mmol) the reaction was then stirred at room temperature for 3 days. The reaction was concentrated in vacuo and the residue was purified by silica gel chromatography, eluting with EtOAc in isohexane from 0% to 100%. A slower running material was isolated tert-butyl (2R,5R)-2-(4-bromo-3-methyl-2-pyridyl)-7-methyl-6-oxo-1,7-diazaspiro[4.4]nonane-1-carboxylate (D98) (225.1 mg, 0.5305 mmol, 62% yield) as a colourless oil; M/Z: 423.8, 425.9 [M+H]$^+$.

The remaining fractions were combined and concentrated in vacuo then purified using silica gel eluting with 20% acetone in EtOAc. Fractions containing pure top spot were combined and concentrated in vacuo to give tert-butyl (2S,5R)-2-(4-bromo-3-methyl-2-pyridyl)-7-methyl-6-oxo-1,7-diazaspiro[4.4]nonane-1-carboxylate (D99) (42 mg, 0.0990 mmol, 11.6% yield) as a colourless oil;
M/Z: 423.8, 425.9 [M+H]$^+$.

Description 100 tert-Butyl (2R,5R)-2-[4-(5-ethoxy-2-fluoro-phenyl)-3-methyl-2-pyridyl]-7-methyl-6-oxo-1,7-diazaspiro[4.4]nonane-1-carboxylate (D100)

To a microwave vial containing a solution of (5-ethoxy-2-fluoro-phenyl)boronic acid (121.99 mg, 0.6600 mmol) in MeCN (3 mL) and water (0.6000 mL) was added tert-butyl (2R,5R)-2-(4-bromo-3-methyl-2-pyridyl)-7-methyl-6-oxo-1,7-diazaspiro[4.4]nonane-1-carboxylate (which may be prepared as described in Description 98) (225.1 mg, 0.5300 mmol), sodium carbonate (112.41 mg, 1.06 mmol) and bis(triphenyl-phosphine)palladium (II) dichloride (18.39 mg, 0.0300 mmol). The microwave vial was sealed and heated at 140° C. for 20 minutes. The reaction was concentrated in vacuo, and the residue was purified on silica (25 g, SNAP cartridge), eluting with EtOAc in isohexane from 0% to 100%. Fractions containing desired product were combined and concentrated in vacuo to give tert-butyl (2R,5R)-2-[4-(5-ethoxy-2-fluoro-phenyl)-3-methyl-2-pyridyl]-7-methyl-6-oxo-1,7-diazaspiro[4.4]nonane-1-carboxylate (D100) (74.2 mg, 0.1534 mmol, 28.9% yield) as a colourless oil;
M/Z: 484.1 [M+H]$^+$ in ES+.

Description 101

3-(Benzhydrylidene-amino)-1-methyl-pyrrolidin-2-one (D101)

Benzophenone imine (200.04 g, 1103.8 mmol) was added dropwise over 20 minutes to a stirred solution of 2-aminopyrrolidinone (120 g, 1051.2 mmol) in DCE (1000 mL) at ambient temp under nitrogen in a 2 L flask fitted with a magnetic stirrer bar. The reagent was washed in with further DCE (100 mL). The stirred solution was heated at reflux on a heat-on block at a block temp of 95° C. for 7 h, using a N$_2$ bubbler with exhaled gas passing through a safety trap then into 2 L of water via an upturned funnel (for scrubbing NH$_3$ gas, estimated to be approx 23 L). The reaction was left to stand at ambient temp overnight under N$_2$. The mixture was evaporated to a thick, off-white oil. To this was added Et$_2$O (700 ml) and to this stirred solution, as it began to crystallize, was added iso-hexane (700 ml) over 2 minutes. The mixture was stirred for 1 h then filtered under suction and washed with Et$_2$O/iso-hexane (1:1) (500 ml). The white solid was dried at 35° C. under vacuum for 3 h to afford 3-(benzhydrylidene-amino)-1-methyl-pyrrolidin-2-one (D101) (259.4 g, 88.6%);
300 MHz NMR δ$_H$ (CDCl$_3$) 2.15-2.49 (2H, m), 2.90 (3H, s), 3.26-3.34 (1H, abq), 3.52 (1H, dt), 4.23 (1H, t), 7.30-7.49 (8H, m), 7.63-7.67 (2H, m).

Description 102

3-(Benzhydrylidene-amino)-1-methyl-3-prop-2-ynyl-pyrrolidin-2-one (D102)

Potassium tert-butoxide 1.7M in THF (602.08 mL, 1023.5 mmol) was added dropwise over a period of 2.5 h to a stirred solution of 3-(benzhydrylidene-amino)-1-methyl-pyrrolidin-2-one (259 g, 930.48 mmol) (which may be prepared as described in Description 101) and 80% solution of propargyl bromide in toluene (124.37 mL, 1116.6 mmol) in 3 A-molecular-sieve-dried reagent grade THF (1900 mL) at −65° C. under nitrogen, in a 5 L flask equipped with an overhead stirrer. After the addition was complete, the mixture was stirred at −65° C. for a further 1 h. The cooling bath was removed and a saturated solution of NaHCO$_3$ (140 ml) was added over 1 minute (at −60° C.). After a further 5 mins more sat NaHCO$_3$ solution (1.4 L) was added followed by Et$_2$O (1.4 L). The mixture was stirred for 1 h then transferred to a separating funnel and water (1.4 L) was added to dissolve all solids. The layers were separated and the aqueous further extracted with Et$_2$O (2×1 L). The combined organic extracts were re-washed with sat. brine (700 ml), diluted with water (700 ml). The organic layer was dried (MgSO$_4$) and evaporated to a volume of approx. 500-600 ml whereupon crystallization started to occur. To this stirred mixture was then added iso-hexane (1.6 L). After standing for 15 mins the cream solid was filtered under suction and washed with iso-hexane (500 ml) and dried at 50° C. under vacuum for 5 h. This afforded 3-(benzhydrylidene-amino)-1-methyl-3-prop-2-ynyl-pyrrolidin-2-one (D102) (274 g, 93%). This was pure by NMR but contains some additional water;
300 MHz NMR δ$_H$ (CDCl$_3$) 1.95 (1H, t), 2.14-2.24 (1H, m), 2.44 (3H, s), 2.45-2.64 (2H, m), 2.94 (2H, t), 3.11 (1H, dt), 7.23-7.48 (8H, m), 7.55-7.59 (2H, m).

Description 103

(3S)-3-Amino-1-methyl-3-prop-2-ynyl-pyrrolidin-2-one (D103S) and (3R)-3-Amino-1-methyl-3-prop-2-ynyl-pyrrolidin-2-one (D103R)

Method A:
To a stirred solution of 3-(benzhydrylideneamino)-1-methyl-3-prop-2-ynyl-pyrrolidin-2-one (274 g, 865.99 mmol) (which may be prepared as described in Description 102) in a 5 L flask equipped with an overhead stirrer, in THF (2.7 L)

was added citric acid monohydrate (363.96 g, 1732 mmol) in one portion. The solution was stirred at room temperature for 18 h, giving a thick white precipitate with some sticky solid adhering to the sides of the flask. This sticky solid was loosened with a spatula, then diethyl ether (1.3 L) was added and rapid stirring was continued for a further 1 h. The solid was then filtered under suction and washed efficiently with $Et_2O$ (2×1 L) and dried at 500° C. under vacuum for hours. This produced 268 g of material. This was recrystallized from hot MeOH (1.9 L); hot solution was filtered under suction to give a clear pale yellow solution. The solution was left to stand for 1 h and $Et_2O$ (3 L) was added with stirring. After standing for a further 1 h, the mixture was filtered and washed with MeOH:$Et_2O$ (1:2) (1 L) and the solid pressed dry and further dried at 50° C. under vacuum for 6 hours to afford 312 g of the citrate salt, contaminated with methanol. In a separate container, Ambersep 900 (OH) ion exchange resin (2.31 kg, 2722 7 mmol) was stirred for 5 minutes with MeOH (2 L) to pre-wash the resin. The suspended resin was filtered under suction and the moist pre-washed resin was added to a stirred suspension of the previously prepared citrate salt in methanol (3 L) in a 10 L vessel equipped with an overhead stirrer. The mixture was stirred for a total of 1.5 h at ambient temp then filtered under suction. The filtered resin was washed with MeOH (2×1.5 L). The filtrate and washings were evaporated in vacuo to an oil which was redissolved in DCM (1.5 L) and dried ($Na_2SO_4$), filtered, evaporated to a pale yellow oil, which was dried at RT overnight to give 3-amino-1-methyl-3-prop-2-ynyl-pyrrolidin-2-one (D103) (106.9 g, 79.9%);

300 MHz NMR $\delta_H$ (CDCl$_3$) 1.65 (3H, br.s), 1.94-2.05 (2H, m), 2.31-2.39 (1H, m), 2.41-2.55 (2H, m), 2.89 (3H, Me), 3.33-3.39 (2H, m).

A portion of this material (1.75 g, 11.5 mmol) was separated on chiral HPLC using a semi-prep AD-H column, eluting with 20% EtOH/heptane at 18 ml/min. Peaks were identifed at nm:

(3S)-3-amino-1-methyl-3-prop-2-ynyl-pyrrolidin-2-one (D103S) 549 mg retention time=13.7 mins (37.5%); Optical rotation $\alpha[^D/_{22}]=-81.0$ (c=0.975, CHCl$_3$);

(3R)-3-amino-1-methyl-3-prop-2-ynyl-pyrrolidin-2-one (D103R) 407 mg retention time=17.9 mins (36.4%); Optical rotation $\alpha[^D/_{22}]=+78.8$ (c=0.965, CHCl$_3$).

Method B: (3S)-3-Amino-1-methyl-3-prop-2-ynyl-pyrrolidin-2-one (D103S)

A controlled lab reactor with heated/cooled jacket and an overhead paddle-stirrer was charged with IPA (2250 mL) and (2S)-2-(6-methoxy-2-naphthyl)propanoic acid (84.72 g, 367.92 mmol) was added. The suspension was stirred and warmed to 75° C. giving a solution. A solution of 3-amino-1-methyl-3-prop-2-ynyl-pyrrolidin-2-one (which may be prepared as described in Description 103 Method A) (55.99 g, 367.92 mmol) in IPA (1100 mL) was then added dropwise over 1.5 hours. The reaction mixture was stirred at 75° C. for hr then cooled to 55° C. over 1 hr. The reaction was seeded with pure (S) isomer salt at every 1 degree drop in temperature until the seed remained out of solution (ca. 71° C.). The reaction mixture crystallised and was stirred at 55° C. for 1 hr. The mixture was then cooled to 40° C. over approximately 20 minutes and filtered under suction into a pre-warmed filter funnel over a fast filter paper. The vessel was rinsed out with IPA (600 mL) pre-warmed to 40° C. and this was used to wash the collected solids. The solids were dried under suction until no more solvent came out and then were dried in a vacuum oven at 50° C. to give a white solid, 59.37 g (3S)-1-methyl-2-oxo-3-prop-2-ynyl-pyrrolidin-3-yl]ammonium (2S)-2-(6-methoxy-2-naphthyl)propanoate. A portion of this material was removed and dissolved in methanol, passed down an SCX column, washed with methanol and then eluted with 0.5M ammonia in methanol. The ammonia elute was evaporated to a pale yellow gum, which was analysed by chiral HPLC (20:80 EtOH:heptane, IA column) showing S-isomer 99.5% and R-isomer 0.5%. Ambersep 900-OH (500 g, 155.24 mmol) was stirred in methanol (1000 mL) for 5 minutes, then filtered and dried under suction until no more liquid came out. The washed resin was added to a stirred suspension of S-isomer salt (59.37 g, 155.24 mmol) in methanol (1000 mL). The mixture was stirred for 1 hr, then filtered. The resin was resuspended in methanol (1000 mL) and stirred for an hour and then filtered. The combined filtrates were evaporated to give a slightly cloudy yellow oil. The oil was dissolved in dichloromethane (ca. 200 mL) and dried over magnesium sulphate, filtered and evaporated to give a clear yellow oil (3S)-3-amino-1-methyl-3-prop-2-ynyl-pyrrolidin-2-one (D103S) (22.729 g). This material was identical spectroscopically to that prepared by chiral chromatography in Method A.

Method C:

(3R)-3-Amino-1-methyl-3-prop-2-ynyl-pyrrolidin-2-one (D103R)

Enriched recrystallisation mother liquors containing, for example, a 91:9 ratio of (3R)-3-amino-1-methyl-3-prop-2-ynyl-pyrrolidin-2-one naproxen salt and its (3S) enantiomer, (27 g) (which may be obtained from the fractional crystalisation procedure described in Method B) were evaporated and dissolved in acetonitrile at 30±5° C. The reaction mass was heated to 70±5° C. and stirred for 10 minutes then slowly cooled to 40±2° C. A seed of the R-amine-naproxen salt was introduced and the reaction mixture maintained at 40±2° C. for 1 hr. The reaction mass was cooled to 30±5° C. and filtered. Th isolated salt was washed with acetonitrile and dried under vacuum at 47.5±2.5° C. for 6±1 hours to give 18.2 g of the salt with a 99.8% enantiomeric excess of the R isomer. The material was then converted to the free base form as described for the S-enantiomer in Method B to give the title compound (D103R). This material was identical spectroscopically to that prepared by chiral chromatography in Method A.

Description 104 tert-Butyl N-[(3S)-1-methyl-2-oxo-3-prop-2-ynyl-pyrrolidin-3-yl]carbamate (D104)

To a solution of (3S)-3-amino-1-methyl-3-prop-2-ynyl-pyrrolidin-2-one (which may be prepared as described in Description 103) (72.66 g, 477.4 mmol) in DCM (1000 mL) was added a solution of $Boc_2O$ (125.03 g, 572.88 mmol) in DCM (700 mL) in one portion. The reaction was then stirred at 40° C. (bath temp. not internal temp.) over 5 hrs, then at room temperature over the weekend. The reaction was concentrated in vacuo, and the residue was suspended in a mixture of $Et_2O$ and isohexane (1:1, 250 mL) and stirred for 30 minutes. The suspension was filtered, and the solid was washed with a mixture of $Et_2O$ and isohexane (1:1, 250 mL), followed by isohexane (3×250 mL). The solid was then dried in a vacuum oven for 2 hours (40° C.) to give a white solid, tert-butyl N-[(3S)-1-methyl-2-oxo-3-prop-2-ynyl-pyrrolidin-3-yl]carbamate (D104) (99.25 g);

300 MHz NMR $\delta_H$ (CDCl$_3$) 1.43 (9H, s), 2.01 (1H, app.t), 2.45-2.59 (3H, m), 2.78, 2.82 (1H, 2×br.s), 2.81 (3H, s), 3.35-3.45 (2H, m), 5.23 (1H, br.s).

A second crop was isolated from the filtrate to give a further batch, 5.535 g of similar purity.

Description 105

2-Iodo-4-[3-(trifluoromethoxy)phenyl]pyridine (D105)

Acetyl chloride (4.45 mL, 62.6 mmol) was added to a solution of 2-chloro-4-[3-(trifluoromethoxy)phenyl]-pyridine [CAS 1261856-64-7] (11.42 g, 41.73 mmol) and sodium iodide (31.28 g, 208.67 mmol) in MeCN (200 mL) under $N_2$, and the resulting suspension was heated at 80° C. for 18 hrs. Additional sodium iodide was added (20 mol %) and stirring was continued for 3 hrs. The reaction was cooled and the mixture was treated with aqueous sodium carbonate. After 5 minutes, solid sodium metabisulphite was added until decolourisation achieved. Water was added to redissolve a precipitate which had formed. The mixture was diluted with EtOAc and the layers separated. The aqueous layer was washed with EtOAc (2x), the combined organics were dried ($MgSO_4$) and the solvent evaporated to afford the crude 2-iodo-4-[3-(trifluoromethoxy)phenyl]pyridine (D105) (16.3 g) as a amber oil containing about ~5% of reduced 2-H material and ~8% of unreacted chloride starting material;

300 MHz NMR $\delta_H$ ($CDCl_3$) 7.35 (1H, t) 7.42-7.28 (2H, m), 7.52-7.58 (2H, m), 7.95 (1H, s), 8.46 (1H, d).

Description 106 tert-Butyl N-[(3S)-1-methyl-2-oxo-3-[3-[4-[3-(trifluoromethoxy)phenyl]-2-pyridyl]prop-2-ynyl]pyrrolidin-3-yl]carbamate (D106)

Copper Iodide (104.92 mg, 0.5500 mmol), followed by $PdCl_2(Ph_3P)_2$ (193.34 mg, 0.2800 mmol) was added portionwise to a solution of the tert-butyl N-[(3S)-1-methyl-2-oxo-3-prop-2-ynyl-pyrrolidin-3-yl]carbamate (2.78 g, 11.02 mmol) (which may be prepared as described in Description 104), 2-iodo-4-[3-(trifluoromethoxy)-phenyl]pyridine (6.03 g, 16.53 mmol) (which may be prepared as described in Description 105) and $Et_2NH$ (5.7 mL, 55.09 mmol) in THF (60 mL) under $N_2$ and the reaction was stirred at 20° C. for 18 hrs. Additional $PdCl_2(Ph_3P)_2$ (1.25 mol %) and CuI (2.5 mol %) catalyst was added. The reaction was left to stir for 3 days. The solvent was evaporated and the residue was suspended in EtOAc and washed with water/sat. aq. $NaHCO_3$. The organics were collected, dried ($Na_2SO_4$) and the solvent evaporated to afford a brown oil. This was purified using a Biotage SP4, with 100 g SNAP cartridge, eluting with 0 to 100% EtOAc in i-hexane. Clean fractions were collected and the solvent evaporated to afford a yellow oil. The remaining fractions were collected and re-columned using a SP4, 100 g SNAP cartridge, 0 to 10% MeOH/EtOAc and the product was collected and combined with the clean material from the first column to afford the tert-butyl N-[(3S)-1-methyl-2-oxo-3-[3-[4-[3-(trifluoromethoxy)phenyl]-2-pyridyl]prop-2-ynyl]pyrrolidin-3-yl]carbamate (D106) (5.38 g, 10.991 mmol, 99.8% yield) as a yellow oil containing some $Ph_3P$ residues;

300 MHz NMR $\delta_H$ ($CDCl_3$) 1.45 (9H, s), 2-49-2.72 (2H, m), 2.82 (1H, d), 2.95 (3H, s), 3.11 (1H, d), 3.42 (1H, t), 3.57 (1H, q), 5.31 (1H, br.s), 7.34 (1H, d), 7.43 (1H, d), 7.48 (1H, s), 7.54-7.61 (3H, m), 8.64 (1H, d).

Description 107

(3S)-3-Amino-1-methyl-3-[3-[4-[3-(trifluoromethoxy)phenyl]-2-pyridyl]prop-2-ynyl]pyrrolidin-2-one (D107)

Method A: Trifluoroacetic acid (10 mL, 134.63 mmol) was added to a solution of the tert-butyl N-[(3S)-1-methyl-2-oxo-3-[3-[4-[3-(trifluoromethoxy)phenyl]-2-pyridyl]prop-2-ynyl]pyrrolidin-3-yl]carbamate (which may be prepared as described in Description 106) (5.38 g, 10.99 mmol) in DCM (50 mL) at 20° C. and the reaction was stirred until complete. Solid $K_2CO_3$ was added to quench the TFA present and the mixture was diluted with water. The phases were separated and the aqueous layer was washed with dichloromethane (x2). The combined organic layers were dried ($MgSO_4$) and the solvent was evaporated to give the (3S)-3-amino-1-methyl-3-[3-[4-[3-(trifluoromethoxy)phenyl]-2-pyridyl]prop-2-ynyl]pyrrolidin-2-one (D107) (4.78 g, 12.276 mmol, 111.7% yield) as an amber oil containing some $Ph_3PO$;

300 MHz $^1$H NMR $\delta_H$ ($CDCl_3$) 1.82 (2H, br.s), 2.08 (1H, dt), 2.48 (1H, ddd), 2.78 (2H, abq), 2.93 (3H, s), 3.38-3.47 (2H, m), 7.34 (1H, d), 7.43 (1H, dd), 7.47 (1H, s), 7.51-7.62 (3H, m), 8.66 (1H, d).

Method B: A solution of tert-butyl N-[(3S)-1-methyl-2-oxo-3-[3-[4-[3-(trifluoromethoxy)phenyl]-2-pyridyl]prop-2-ynyl]pyrrolidin-3-yl]carbamate (8.91 g, 18.19 mmol) (which may be prepared as described in Description 106) in 1,4-dioxane (70 mL) was cooled in an ice bath and treated dropwise with conc. $H_2SO_4$ (7.4 mL, 93.22 mmol). The mixture was allowed to reach room temperature and after 45 mins, the mixture was again cooled in an ice bath and treated cautiously with satd. aq. $Na_2CO_3$ solution (~150 ml). The mixture was diluted with ethyl acetate (200 ml) and the product was extracted into ethyl acetate (2x150 ml). The combined organic extracts were dried ($Na_2SO_4$) and concentrated to give the title compound (D107) as an orange oil (6.88 g, 97%) consistent spectroscopically with that prepared by Method A.

Description 108

(5S)-7-Methyl-2-[4-[3-(trifluoromethoxy)phenyl]-2-pyridyl]-1,7-diazaspiro[4.4]non-1-en-6-one (D108)

Silver trifluoromethanesulphonate (564.86 mg, 2.2 mmol) was added to a solution of (3S)-3-amino-1-methyl-3-[3-[4-[3-(trifluoromethoxy)phenyl]-2-pyridyl]prop-2-ynyl]pyrrolidin-2-one (which may be prepared as described in Description 107) (4.28 g, 10.99 mmol) in MeCN (60 mL) at 40° C. and the reaction was stirred for 18 hours. Additional AgOTf (10 mol %) was added and stirring was continued for 24 hrs. The solvent was evaporated and the residue was suspended in EtOAc. The organic phase was washed with water, dried ($Na_2SO_4$) and the solvent evaporated to afford a light brown oil. This was purified using an Isolera, with a (50+100)g SNAP cartridge, eluting with 0 to 100% (mixture of 1% of 2M $NH_3$ in MeOH; 9% MeOH; 90% EtOAc) in EtOAc affording the (5S)-7-methyl-2-[4-[3-(trifluoromethoxy)phenyl]-2-pyridyl]-1,7-diazaspiro[4.4]non-1-en-6-one (D108) (3.17 g, 8.1414 mmol, 74.1% yield) as a light brown solid;

300 MHz $^1$H NMR $\delta_H$ ($CDCl_3$) 1.95 (1H, ddd), 2.19 (1H, dt), 2.46 (1H, ddd), 2.59 (1H, ddd), 2.97 (3H, s), 3.26-3.49

(3H, m), 6.68 (1H, dt), 7.32 (1H, d), 7.50-7.56 (3H, m), 7.64 (1H, d), 8.36 (1H, s), 8.74 (1H, d).

Description 109 and Description 110 tert-Butyl (2R,5S)-7-methyl-6-oxo-2-[4-[3-(trifluoromethoxy)phenyl]-2-pyridyl]-1,7-diazaspiro[4.4]nonane-1-carboxylate (D109) and tert-Butyl (2S,5S)-7-methyl-6-oxo-2-[4-[3-(trifluoromethoxy)phenyl]-2-pyridyl]-1,7-diazaspiro[4.4]nonane-1-carboxylate (D110)

Concentrated aqueous hydrochloric acid (698.76 µL, 8.14 mmol) was added to a solution of (5S)-7-methyl-2-[4-[3-(trifluoromethoxy)phenyl]-2-pyridyl]-1,7-diazaspiro[4.4]non-1-en-6-one (which may be prepared as described in Description 108) (3.17 g, 8.14 mmol) in DCM (60 mL) at 0° C. Finally, sodium triacetoxyborohydride (5.18 g, 24.42 mmol) was added in a single portion and the resulting mixture was stirred for 18 hours. The reaction was quenched by the addition of sat. aq. $Na_2CO_3$ and stirring was continued for 5 mins. The phases were separated, the organic layer was dried ($Na_2SO_4$) and the solvent was evaporated to afford an amber oil (3.24 g), a 2.3:1 mixture of 2S and 2R isomers of (5R)-7-methyl-6-oxo-2-[4-[3-(trifluoromethoxy)phenyl]-2-pyridyl]-1,7-diazaspiro[4.4]nonane (3.18 g, 8.12 mmol). This was dissolved in DCE (60 mL) and $Boc_2O$ (2.4 g, 11.01 mmol) was added and the reaction was stirred at 40° C. for 3 days. The solvent was evaporated to afford a brown oil. This was purified using Biotage SP4, with a 100 g SNAP cartridge, eluting with EtOAc followed by 0 to 10% MeOH in EtOAc. The first to elute isomer tert-butyl (2S,5S)-7-methyl-6-oxo-2-[4-[3-(trifluoromethoxy)phenyl]-2-pyridyl]-1,7-diazaspiro[4.4]nonane-1-carboxylate (D110) was isolated (1.03 g, 2.0956 mmol, 25.8% yield) and showed rotamers in the NMR spectrum;
300 MHz $^1$H NMR $\delta_H$ (CDCl$_3$) 1.18 1.45 (9H, 2×s), 1.72-1.82 (1H, m), 1.98-2.24 (3H, m), 2.35-2.78 (2H, m), 2.94, 2.98 (3H, 2×s), 3.25-3.55 (2H, m), 5.11, 5.20 (1H, 2×d), 7.22-7.31 (1H, m), 7.35-7.42 (1H, m), 7.50-7.61 (1H, m), 7.66-7.70 (1H, m), 7.79, 7.91 (1H, 2×d), 8.59-8.63 (1H, m), 8.66, 8.87 (1H, 2×s).

The slower isomer tert-butyl (2R,5S)-7-methyl-6-oxo-2-[4-[3-(trifluoromethoxy)phenyl]-2-pyridyl]-1,7-diazaspiro[4.4]nonane-1-carboxylate (D109) (2.85 g, 5.7986 mmol, 71.4% yield) also showed rotamers in the NMR spectrum;
300 MHz $^1$H NMR $\delta_H$ (CDCl$_3$) 1.18, 1.41 (9H, 2×s), 1.95-2.29 (4H, m), 2-54-2.69 (1H, m), 2-79-3.03 (1H, m), 2.91, 2.95 (3H×s), 3.29-3.60 (2H, m), 5.16, 5.32 (1H, 2×dd), 7.29-7.58 (6H, m), 8.62-8.67 (1H, m).

Description 111

4-(5-Ethoxy-2-fluoro-phenyl)pyridine-2-carbonitrile (D111)

A mixture of 4-chloropyridine-2-carbonitrile (4.1 g, 29.56 mmol) and (5-ethoxy-2-fluoro-phenyl)boronic acid (5982.6 mg, 32.52 mmol) in monoglyme (150 mL) was treated with sodium carbonate (29.56 mL, 59.13 mmol) and then $PdCl_2(PPh_3)_2$ (1037.5 mg, 1.48 mmol) and the mixture was refluxed under argon. After 2 hrs the DME was evaporated and ethyl acetate (200 ml) and water were added and the product was extracted into ethyl acetate (3 times). The extracts were dried ($Na_2SO_4$) and concentrated. Chromatography on silica gel (0-50% ethyl acetate in isohexane, using a SNAP340 cartidge on a Biotage SP4) gave 4-(5-ethoxy-2-fluoro-phenyl)pyridine-2-carbonitrile (D111) (6.12 g) as an off white solid;
300 MHz $^1$H NMR $\delta_H$ (CDCl$_3$) 1.47 (3H, t), 4.08 (2H, q), 6.95-7.02 (2H, m), 7.16 (1H, t), 7.72 (1H, d), 7.91 (1H, s), 8.79 (1H, d).

Description 112

4-(5-Ethoxy-2-fluoro-phenyl)-1-oxido-pyridin-1-ium-2-carbonitrile (D112)

A solution of 4-(5-ethoxy-2-fluoro-phenyl)pyridine-2-carbonitrile (which may be prepared as described in Description 111) (6.19 g, 25.55 mmol) in DCM (200 mL) was treated with mCPBA (7.56 g, 30.66 mmol) and then was reluxed under nitrogen for 3 days. The mixture was diluted with 5% sodium metabisulfite (100 ml) and DCM (200 ml) and shaken vigourously. The organic layer was then washed with sat $NaHCO_3$ solution (200 ml) and then dried ($Na_2SO_4$) and concentrated. Purification by flash chromatography gave 4-(5-ethoxy-2-fluoro-phenyl)-1-oxido-pyridin-1-ium-2-carbonitrile (D112) (5.102 g);
M/Z: 259 (M+H$^+$).

Description 113

6-Chloro-4-(5-ethoxy-2-fluoro-phenyl)pyridine-2-carbonitrile (D113)

A mixture of 4-(5-ethoxy-2-fluoro-phenyl)-1-oxido-pyridin-1-ium-2-carbonitrile (which may be prepared as described in Description 112) (5.1 g, 19.75 mmol) in phosphorus oxychloride (50 mL) was heated to reflux under nitrogen for 2 hrs. The $POCl_3$ was evaporated and toluene was added and then evaporated. Ethyl acetate and satd. aq. $NaHCO_3$ were added and the product was extracted into ethyl acetate (3×200 ml). The extracts were dried ($Na_2SO_4$) and concentrated. Chromatography (silica gel, ethyl acetate/isohexane) on this crude material gave 6-chloro-4-(5-ethoxy-2-fluoro-phenyl)pyridine-2-carbonitrile (D113) as a white solid;
300 MHz $^1$H NMR $\delta_H$ (CDCl$_3$) 1.46 (3H, t), 4.08 (2H, q), 6.95 (1H, dd), 7.01 (1H, dt), 7.18 (1H, t), 7.75 (1H, s), 7.84 (1H, s).

Description 114

4-(5-Ethoxy-2-fluoro-phenyl)-6-isopropyl-pyridine-2-carbonitrile (D114)

A mixture of 6-chloro-4-(5-ethoxy-2-fluoro-phenyl)pyridine-2-carbonitrile (which may be prepared as described in Description 113) (1.5 g, 5.42 mmol) NMP (2.61 mL, 27.07 mmol) and Fe(acac)$_3$ (95.73 mg, 0.2700 mmol) in THF (27.106 mL) was stirred at 0° C. and treated with 2M isopropyl magnesium chloride in THF (7.59 mmol) and the mixture was stirred at 0° C. for 30 mins. The mixture was diluted with ether (200 ml) and quenched with brine. The product was extracted into ether (3x) and the extracts were dried ($Na_2SO_4$) and evaporated. The product was purified by flash chromatography (0-100% DCM in isohexane) to give 4-(5-ethoxy-2-fluoro-phenyl)-6-isopropyl-pyridine-2-carbonitrile (D114) as a white solid;
300 MHz $^1$H NMR $\delta_H$ (CDCl$_3$) 1.38 (6H, d), 1.46 (3H, t), 3.18 (1H, sept), 4.08 (2H, q), 6.92-6.99 (2H, m), 7.15 (1H, t), 7.56 (1H, s), 7.71 (1H, s).

Description 115

Methyl 4-(5-ethoxy-2-fluoro-phenyl)-6-isopropyl-pyridine-2-carboxylate (D115)

A mixture of 4-(5-ethoxy-2-fluoro-phenyl)-6-isopropyl-pyridine-2-carbonitrile (which may be prepared as described in Description 114) (1.09 g, 3.8 mmol) in 4M HCl in dioxan (12 mL, 48 mmol) and methanol (12 mL) was heated to reflux under nitrogen overnight. The solvents were evaporated and ethyl acetate (150 ml) and NaHCO$_3$ solution (150 ml) were added. The product was extracted into ethyl acetate (3 x) and the extracts were dried (Na$_2$SO$_4$) and concentrated. Chromatography (0-10% diethyl ether in DCM) gave methyl 4-(5-ethoxy-2-fluoro-phenyl)-6-isopropyl-pyridine-2-carboxylate (D115) (730.8 mg);

300 MHz $^1$H NMR $\delta_H$ (CDCl$_3$) 1.39 (6H, d), 1.46 (3H, t), 3.30 (1H, sept), 4.03 (3H, s), 4.08 (2H, q), 6.94 (1H, dt), 7.01 (1H, dd), 7.13 (1H, t), 7.58 (1H, s), 8.14 (1H, s).

Description 116

4-(5-Ethoxy-2-fluoro-phenyl)-6-isopropyl-pyridine-2-carbaldehyde (D116)

A solution of methyl 4-(5-ethoxy-2-fluoro-phenyl)-6-isopropyl-pyridine-2-carboxylate (which may be prepared as described in Description 115) (0.72 g, 2.27 mmol) in THF (20 mL) was cooled to −78° C. under nitrogen and was treated dropwise with 1M DIBAL in toluene (4.54 mL, 4.54 mmol) over 10 minutes. The mixture was stirred at −78° C. for 2 hrs. The mixture was quenched with satd. aq. NH$_4$Cl solution (5 ml) and the mixture was allowed to reach room temperature and stirred for 30 mins. Celite was added to the mixture and the mixture was stirred for 10 minutes and then filtered through Celite and concentrated to give 4-(5-ethoxy-2-fluoro-phenyl)-6-isopropyl-pyridine-2-carbaldehyde (D116) (0.57 g);

300 MHz $^1$H NMR $\delta_H$ (CDCl$_3$) 1.41 (6H, d), 1.46 (3H, t), 3.24 (1H, sept.), 4.08 (2H, q), 6.94 (1H, dt), 7.00 (1H, dd), 7.13 (1H, t), 7.60 (1H, s), 8.97 (1H, s), 10.13 (1H, s).

Description 117

(5R)-2-[4-(5-Ethoxy-2-fluoro-phenyl)-6-isopropyl-2-pyridyl]-7-methyl-1,7-diazaspiro[4.4]non-1-en-6-one (D117R) and (5S)-2-[4-(5-Ethoxy-2-fluoro-phenyl)-6-isopropyl-2-pyridyl]-7-methyl-1,7-diazaspiro[4.4]non-1-en-6-one (D117S)

A solution of 4-(5-ethoxy-2-fluoro-phenyl)-6-isopropyl-pyridine-2-carbaldehyde (which may be prepared as described in Description 116) (570 mg, 1.98 mmol) in DCM (10 mL) was treated with 3-amino-1-methyl-pyrrolidin-2-one (226.45 mg, 1.98 mmol) and magnesium sulphate (1193.7 mg, 9.92 mmol). The mixture was stirred overnight and then filtered and concentrated to give 3-[(E)-[4-(5-ethoxy-2-fluoro-phenyl)-6-isopropyl-2-pyridyl]methyleneamino]-1-methyl-pyrrolidin-2-one as an oil. To a stirred solution of this material (759.25 mg, 1.98 mmol) in anhydrous THF (10 mL) under nitrogen at room temperature, was added phenyl vinyl sulfone (0.34 g, 2.02 mmol) and silver acetate (0.04 g, 0.01 mL, 0.2200 mmol). The resulting mixture was left to stir at room temperature for 2 h. The reaction mixture was filtered through Celite and the celite was washed with THF (approx. 20 mL). The filtrate was stirred under nitrogen in an ice bath and treated with potassium t-butoxide (2.33 mL, 3.96 mmol) over 5 minutes. After completion of the addition, the mixture was stirred at room temperature for 1 hr. Acetic acid (0.23 mL, 3.96 mmol) was added and the mixture was stirred for 5 minutes and then filtered through Celite and concentrated. The material was purified by chromatography using a Biotage Si—NH column, and eluting with 10-100% ethyl acetate in isohexane to give racemic 2-[4-(5-ethoxy-2-fluoro-phenyl)-6-isopropyl-2-pyridyl]-7-methyl-1,7-diazaspiro[4.4]non-1-en-6-one as a yellow gum (734.8 mg);

300 MHz $^1$H NMR $\delta_H$ (CDCl$_3$) 1.35 (6H, d), 1.44 (3H, t), 1.89 (1H, ddd), 2.16 (1H, app.quin.), 2.44 (1H, ddd), (2.54 (1H, m), 2.95 (3H, s), 3.12 (1H app.sept.), 3.28-3.51 (3H, m), 3.65 (1H, q), 4.06 (2H, q), 6.88 (1H, dt), 7.00 (1H, dd), 7.09 (1H, t), 7.38 (1H, s), 8.10 (1H, s).

Purification by preperative chiral HPLC (ChiralPak IA column, 10% ethanol in heptane, gave a fast isomer: (5R)-2-[4-(5-ethoxy-2-fluoro-phenyl)-6-isopropyl-2-pyridyl]-7-methyl-1,7-diazaspiro[4.4]non-1-en-6-one (D117R) as a yellow oil (281.6 mg);

Optical rotation $\alpha[^D/_{22}]$=+75.9 (c=0.975, CHCl$_3$).

The slower to elute isomer: (5S)-2-[4-(5-ethoxy-2-fluoro-phenyl)-6-isopropyl-2-pyridyl]-7-methyl-1,7-diazaspiro[4.4]non-1-en-6-one (D117S) was a yellow oil (284.5 mg);

Optical rotation $\alpha[^D/_{22}]$=−76.8 (c=0.755, CHCl$_3$).

Description 118

(5S)-7-Methyl-2-[4-[4-(trifluoromethyl)phenyl]-2-pyridyl]-1,7-diazaspiro[4.4]non-1-en-6-one (D118)

To a solution of (5S)-2-(4-bromo-2-pyridyl)-7-methyl-1,7-diazaspiro[4.4]non-1-en-6-one (which may be prepared as described in Description 3) (640 mg, 2.0768 mmol) in MeCN (8 mL) and water (1 mL) in a Smith microwave vessel was added [4-(trifluoromethyl)-phenyl]boronic acid (394.44 mg, 2.0768 mmol), bis(triphenylphosphine)palladium (II) dichloride (60 mg, 0.0855 mmol) and sodium carbonate (484.26 mg, 4.5689 mmol). The reaction vessel was sealed and purged with nitrogen. The reaction mixture was heated by microwave at 120° C. for 25 min. The reaction mixture was treated with water and was extracted with DCM twice and the organic layers were collected by passing down a PhaseSep cartridge, and evaporated. The crude residue was purified by silica gel chromatography (50 g, SiO$_2$) eluting with ethyl acetate in iso-hexane (10-100%). Evaporation of desired fractions gave (5S)-7-methyl-2-[4-[4-(trifluoromethyl)phenyl]-2-pyridyl]-1,7-diazaspiro[4.4]non-1-en-6-one (D118) (695 mg, 1.8614 mmol, 89.6% yield);

300 MHz $^1$H NMR $\delta_H$ (CDCl$_3$) 1.58 (3H, s), 1.95 (1H, ddd), 2.20 (1H, m), 2.46 (1H, ddd), 2.58 (1H, m), 2.98 (3H, s), 3.27-3.50 (3H, m), 3.68 (1H, dd), 7.58 (1H, dd), 7.75, 7.81 (4H, abq), 8.40 (1H, d), 8.75 (1H, d).

Description 119

(5R)-3-Fluoro-7-methyl-2-[4-[4-(trifluoromethyl)phenyl]-2-pyridyl]-1,7-diazaspiro[4.4]non-1-en-6-one (D119a), epimer (D119b)

Anhydrous MeCN (5 mL) was added to a dry vial charged with (5S)-7-methyl-2-[4-[4-(trifluoromethyl)phenyl]-2-pyridyl]-1,7-diazaspiro[4.4]non-1-en-6-one (which may be prepared as described in Description 118) (339.99 mg, 0.9100 mmol). Selectfluor (1500 mg, 4.23 mmol) was added to the solution followed by trifluoroacetic acid (0.04 mL, 0.5300 mmol). The vial was sealed under nitrogen and was heated to 90° C. for 24 h. The reaction mixture was allowed to cool to room temperature whence it was poured onto 0.5M sodium hydroxide. The mixture was left to stir for 10 min and extracted with ether. The combined organic layer was dried (sodium sulfate), filtered and the filtrate was evaporated to give an amber oil. The crude residue was purified by silica gel chromatography (10 g $SiO_2$) eluting with ethyl acetate in iso-hexane (10-100%). Evaporation of desired fractions gave (5R)-3-fluoro-7-methyl-2-[4-[4-(trifluoromethyl)phenyl]-2-pyridyl]-1,7-diazaspiro[4.4]non-1-en-6-one, as an amber oil, a 2:1 mixture of epimers. The isomers were separated by chiral semi-prep hplc using a ChiralPak AD-H column eluting with ethanol/n-heptane (20%:80%) to obtain a faster running epimer (D119a) (28 mg);

300 MHz $^1$H NMR $\delta_H$ (CDCl$_3$) 2.20-2.44 (3H, m), 2.77, (1H, d dd), 3.00 (3H, s), 3.42 (1H, m), 3.6-3.8 (1H, m), 6.44 (1H, ddd), 7.61 (1H, dd), 7.75, 7.81 (4H, 2×d), 8.37 (1H, s), 8.71 (1H, d).

Also the slower running epimer (D119b) (54 mg);

300 MHz $^1$H NMR $\delta_H$ (CDCl$_3$) 2.13 (1H, ddd), 2.32 (1H, m), 2.56 (1H, ddd), 2.84-3.00 (1H, m), 2.97 (3H, s), 3.44 (1H, dt), 3.75 (1H, dd), 6.49 (1H, ddd), 7.60 (1H, dd), 7.75, 7.81 (4H, 2×d), 8.37 (1H, s), 8.83 (1H, d).

Description 120

(5R)-3,3-Difluoro-7-methyl-2-[4-[4-(trifluoromethyl)phenyl]-2-pyridyl]-1,7-diazaspiro[4.4]non-1-en-6-one (D120)

Selectfluor (1500.01 mg, 4.23 mmol) was added to a dry vial charged with (5S)-7-methyl-2-[4-[4-(trifluoromethyl)phenyl]-2-pyridyl]-1,7-diazaspiro[4.4]non-1-en-6-one (which may be prepared as described in Description 118) (339.99 mg, 0.9100 mmol) in anhydrous MeCN (5 mL). trifluoroacetic acid (0.04 mL, 0.5300 mmol) was added to the solution. The vial was sealed under nitrogen and was heated to 90° C. for 20 h. The reaction mixture was allowed to cool to room temperature whence it was poured into sodium hydroxide (20 mL, 10 mmol). The mixture was left to stir for 10 min and extracted with ether. The combined organic layer was dried (sodium sulfate), filtered and the filtrate was evaporated to give crude brown oil (289 mg). The crude residue was purified by silica gel chromatography (10 g $SiO_2$) eluting with ethyl acetate in iso-hexane (10-100%), followed by purification using a ChiralPak AD-H column eluting with ethanol/n-heptane (20%:80%) to give a colourless oil, (5R)-3,3-difluoro-7-methyl-2-[4-[4-(trifluoromethyl)phenyl]-2-pyridyl]-1,7-diazaspiro[4.4]non-1-en-6-one (D120) (22 mg, 0.0537 mmol, 5.9% yield);

300 MHz $^1$H NMR $\delta_H$ (CDCl$_3$) 2.28-2.54 (3H, m), 3.01 (3H, s), 3.17 (1H, q), 3.44 (1H, dt), 3.82 (1H, q), 7.64 (1H, dd), 7.79 (4H, s), 8.31 (1H, s), 8.89 (1H, d).

Description 121

2-(4-Bromo-5-ethyl-2-pyridyl)-7-methyl-1,7-diazaspiro[4.4]non-1-en-6-one (D121)

To a stirred solution of phenyl vinyl sulfone (7307.08 mg, 43.44 mmol) in methanol (80 mL) was added 3-amino-1-methyl-pyrrolidin-2-one (4958.41 mg, 43.44 mmol), 4-bromo-5-ethyl-pyridine-2-carbaldehyde (CAS: 1256833-98-3) (9300 mg, 43.44 mmol) and calcium triflate (734.57 mg, 2.17 mmol). The reaction was stirred for 10 minutes, and then the reaction was cooled to −10° C., and then triethylamine (6.04 mL, 43.44 mmol) was added dropwise. The reaction was then stirred at room temperature for 4 hours. The reaction was concentrated in vacuo, and redissolved in THF (150 mL). The reaction was cooled to 00° C., and to the reaction mixture was added potassium tert-butoxide (14622.41 mg, 130.31 mmol) portionwise. The reaction was then stirred for 2 hours while allowing to warm to room temperature. The reaction was then filtered through celite, and the celite was washed with DCM (150 mL). The filtrate was then concentrated in vacuo. The residue was purified by column chromatography over silica (340 g, Biotage SNAP cartridge), eluting with EtOAc:isohexane from 0% to 100%. Fractions containing the desired product were combined and concentrated in vacuo to give 2-(4-bromo-5-ethyl-2-pyridyl)-7-methyl-1,7-diazaspiro[4.4]non-1-en-6-one (D121) (3091 mg, 9.1931 mmol, 21.2% yield) as a brown oil approximately 85% pure and used directly in the next step;

$^1$H NMR (300 MHz, CDCl$_3$) δ: 1.28 (t, 3H), 1.85-1.95 (m, 1H), 2.11-2.21 (m, 1H), 2.40-2.48 (m, 1H), 2.51-2.60 (m, 1H), 2.81 (q, 2H), 2.96 (s, 3H), 3.17-3.43 (m, 3H), 3.64-3.72 (m, 1H), 8.32 (s, 1H), 8.44 (s, 1H).

Description 122, 123 and 124

(2R,5S)-2-(4-Bromo-5-ethyl-2-pyridyl)-7-methyl-1,7-diazaspiro[4.4]nonan-6-one (D122), (2S,5R)-2-(4-Bromo-5-ethyl-2-pyridyl)-7-methyl-1,7-diazaspiro[4.4]nonan-6-one (D123) and a 1:1 mixture of (2S,5S)-2-(4-Bromo-5-ethyl-2-pyridyl)-7-methyl-1,7-diazaspiro[4.4]nonan-6-one and its enantiomer (D124)

To a cooled (−10° C.) solution of 2-(4-bromo-5-ethyl-2-pyridyl)-7-methyl-1,7-diazaspiro[4.4]-non-1-en-6-one (which may be prepared as described in Description 121) (2612 mg, 7.77 mmol) in DCM (20 mL) was added concentrated hydrochloric acid (0.67 mL, 7.77 mmol) followed by sodium triacetoxyborohydride (6590.92 mg, 31.1 mmol). The reaction was then allowed to warm up to room temperature over 2 hours. The reaction was quenched by addition of aqueous saturated Na$_2$CO$_3$ (40 mL) and the organics were separated using a hydrophobic frit. The organics were then concentrated in vacuo. The residue was dissolved in DCM (2 mL), and loaded onto silica (100 g, Biotage SNAP cartridge), the silica was then eluted with (80:20:2 EtOAc:MeOH:0.88 M NH$_3$):EtOAc from 0% to 100%. Fractions containing major trans isomer were combined and concentrated in vacuo, to give a 1:1 mixture of (2R,5S)-2-(4-bromo-5-ethyl-2-pyridyl)-7-methyl-1,7-diazaspiro[4.4]nonan-6-one and its enantiomer (1804 mg, 2.6667 mmol, 68.6% yield);

$^1$H NMR (300 MHz, CDCl$_3$) δ: 1.25 (t, 3H), 1.82-1.95 (m, 2H), 2.00-2.24 (m, 3H), 2.43-2.55 (m, 1H), 2.75 (q, 2H), 2.92 (s, 3H), 3.25-3.38 (m, 2H), 4.67 (t, 1H), 7.71 (s, 1H), 8.33 (s, 1H).

Fractions containing cis isomer were combined and concentrated in vacuo to give a 1:1 mixture of (2S,5S)-2-(4-bromo-5-ethyl-2-pyridyl)-7-methyl-1,7-diazaspiro[4.4]nonan-6-one and its enantiomer (D124) (460 mg, 1.36 mmol, 17.5% yield);

$^1$H NMR (300 MHz, CDCl$_3$) δ: 1.24 (t, 3H), 1.76-1.84 (m, 1H), 1.97-2.21 (m, 4H), 2.26-2.37 (m, 1H), 2.74 (q, 2H), 2.92 (s, 3H), 3.26-3.41 (m, 2H), 4.34 (t, 1H), 7.79 (s, 1H), 8.34 (s, 1H).

The racemic (2R,5S)/(2S,5R) mixture was dissolved in a mixture of ethanol (9 mL) and heptane (9 mL) and was chirally separated over a ChiralPak IA column eluting with 30% EtOH:Heptane, The first to elute material was isolated as (2R,5S)-2-(4-bromo-5-ethyl-2-pyridyl)-7-methyl-1,7-diazaspiro[4.4]nonan-6-one (D122) (359 mg, 1.0614 mmol) as an orange oil M/Z: 338.0, 340.1 [M+H]$^+$ in ES+

The slower to elute isomer was isolated as (2S,5R)-2-(4-bromo-5-ethyl-2-pyridyl)-7-methyl-1,7-diazaspiro[4.4]nonan-6-one (D123) (389 mg, 1.1501 mmol) as an orange oil M/Z: 338, 340 [M+H]$^+$ in ES+.

Descriptions 125 and 126

(6S,9S)-2-(4-Bromo-2-pyridyl)-9-methyl-1,8-diazaspiro[4.5]dec-1-en-7-one (D125) and (6R,9S)-2-(4-Bromo-2-pyridyl)-9-methyl-1,8-diazaspiro[4.5]dec-1-en-7-one (D126)

To a mixture of (6S)-3-amino-6-methyl-piperidin-2-one hydrochloride [Free base CAS 1354207-78-5](945 mg, 5.74 mmol), 4-bromopyridine-2-carbaldehyde (1067.72 mg, 5.74 mmol) and vinylsulfonylbenzene (1M in THF) (5.74 mL, 5.74 mmol) in methanol was added calcium triflate (1941.43 mg, 5.74 mmol). This was stirred for two minutes and then triethylamine (2.39 mL, 17.22 mmol) was added giving a solution. The mixture was stirred at room temperature overnight. The reaction mixture was evaporated. The residues were dissolved in THF (5 mL) and potassium tert-butoxide (3864.61 mg, 34.44 mmol) was added and the mixture stirred over 2 hrs. The reaction mixture was quenched with acetic acid and the resulting thick precipitate was filtered over kieselguhr. The filtrate was evaporated to a brown oil. This was dissolved in DCM and washed with sat. aq. sodium bicarbonate and brine, dried over magnesium sulphate, filtered and evaporated to a brown foaming gum, (1.808 g). Purification by silica gel column chromatography (0-10% MeOH in EtOAc) yielded a brown solid, (715 mg) as a mixture of diastereoisomers. These were separated by chiral prep-HPLC using a Chiralpak IA column and eluting with 30:70 EtOH:heptanes giving a faster eluting isomer (6S,9S)-2-(4-bromo-2-pyridyl)-9-methyl-1,8-diazaspiro[4.5]dec-1-en-7-one (D125) (181 mg);

300 MHz $^1$H NMR $\delta_H$ (CDCl$_3$): 1.32 (3H, d), 1.74 (1H, m), 1.88-1.97 (2H, m), 2.03-2.17 (2H, m), 2.70 (1H, ddd), 3.09-3.45 (2H, m), 3.61-3.78 (1H, m), 5.61 (1H, br.s), 7.50 (1H, dd), 8.39 (1H, d), 8.06 (1H, d);

Optical rotation $\alpha[^D/_{22}]=+107$ (c=1, CHCl$_3$).

The slower eluting isomer (6R,9S)-2-(4-bromo-2-pyridyl)-9-methyl-1,8-diazaspiro[4.5]dec-1-en-7-one (D126) (320 mg) was also isolated;

300 MHz $^1$H NMR $\delta_H$ (CDCl$_3$): 1.26 (3H, d), 1.51-1.64 (1H, m), 1.82-1.98 (2H, m), 2.09-2.18 (1H, m), 2.26 (1H, dt), 2.45-2.55 (1H, m), 3.17-3.39 (2H, m), 3.68-3.79 (1H, m), 5.7 (1H, br.s), 7.50 (1H, dd), 8.42-8.48 (2H, m);

Optical rotation $\alpha[^D/_{22}]=-73$ (c=1, CHCl$_3$).

Description 127

(6S,9S)-2-[4-(5-Ethoxy-2-fluoro-phenyl)-2-pyridyl]-9-methyl-1,8-diazaspiro[4.5]dec-1-en-7-one (D127)

To a solution of (6S,9S)-2-(4-bromo-2-pyridyl)-9-methyl-1,8-diazaspiro[4.5]dec-1-en-7-one (which may be prepared as described in Description 125) (181 mg, 0.5600 mmol) in 1,2-dimethoxyethane (4 mL) and water (1 mL) was added (5-ethoxy-2-fluoro-phenyl)boronic acid (113.68 mg, 0.6200 mmol) and sodium carbonate (178.62 mg, 1.69 mmol). The mixture was degassed with a stream of nitrogen then bis(triphenylphosphine)palladium (II) dichloride (19.71 mg, 0.0300 mmol) was added and the mixture was stirred at 120° C. in a microwave over 20 mins. The reaction mixture diluted with DCM and passed over a hydrophobic frit. The organic filtrate was evaporated to a dark brown oil and purified by silica gel column chromatography (0-10% MeOH in EtOAc) yielding a brown gum (6S,9S)-2-[4-(5-ethoxy-2-fluoro-phenyl)-2-pyridyl]-9-methyl-1,8-diazaspiro[4.5]dec-1-en-7-one (204 mg) (D127);

300 MHz $^1$H NMR $\delta_H$ (CDCl$_3$): 1.31 (3H, d), 1.71-1.81 (1H, m), 1.85-1.96 (1H, m), 2.05-2.20 (1H, m), 2.68-2.78 (1H, m), 3.28-3.52 (2H, m), 3.61-3.72 (1H, m), 4.14 (1H, q), 5.62 (1H, br.s), 6.91 (1H, dt), 7.03 (1H, dd), 7.11 (1H, t), 7.54 (1H, m), 8.33 (1H, s), 8.20 (1H, d).

Description 128

(6S,9S)-2-[4-(5-Ethoxy-2-fluoro-phenyl)-2-pyridyl]-9-methyl-1,8-diazaspiro[4.5]decan-7-one (D128)

To a solution of (6S,9S)-2-[4-(5-ethoxy-2-fluoro-phenyl)-2-pyridyl]-9-methyl-1,8-diazaspiro[4.5]dec-1-en-7-one (which may be prepared as described in Description 127) (204 mg, 0.5300 mmol) in DCM (5 mL) cooled in an ice-bath was added conc. HCl (0.06 mL, 0.6400 mmol) then sodium triacetoxyborohydride (453.4 mg, 2.14 mmol). The mixture was stirred in an ice-bath over 1 hr then at room temperature overnight. The reaction mixture washed with sat. aq. sodium bicarbonate and passed over a hydrophobic frit. The organic filtrate was evaporated to yield a yellow gum which was dissolved in methanol, passed down an SCX column, washed with methanol and eluted with 1M ammonia in methanol. The combined ammonia fractions were evaporated to give a yellow gum, (163 mg) (6S,9S)-2-[4-(5-ethoxy-2-fluoro-phenyl)-2-pyridyl]-9-methyl-1,8-diazaspiro[4.5]decan-7-one (D128) as a 0.8:1 mixture of isomers;

M/Z: 384 (M+H$^+$).

Descriptions 129 and 130 tert-Butyl (2S,6S,9S)-2-[4-(5-ethoxy-2-fluoro-phenyl)-2-pyridyl]-9-methyl-7-oxo-1,8-diazaspiro[4.5]decane-1-carboxylate (D129) and tert-Butyl (2R,6S,9S)-2-[4-(5-ethoxy-2-fluoro-phenyl)-2-pyridyl]-9-methyl-7-oxo-1,8-diazaspiro[4.5]decane-1-carboxylate (D130)

To a solution of (6S,9S)-2-[4-(5-ethoxy-2-fluoro-phenyl)-2-pyridyl]-9-methyl-1,8-diazaspiro[4.5]decan-7-one (which may be prepared as described in Description 128) (163.mg, 0.4300 mmol) in DCM (5 mL) was added triethylamine (0.06 mL, 0.4300 mmol) and tert-butoxycarbonyl tert-butyl carbonate (92.77 mg, 0.4300 mmol). The solution was stirred at 50° C. overnight. A further portion of tert-butoxycarbonyl tert-butyl carbonate (92.77 mg, 0.4300 mmol) was added and the solution stirred at 50° C. over 2 days. A third portion of tert-butoxycarbonyl tert-butyl carbonate (92.77 mg, 0.4300 mmol) was added and the mixture stirred at the same temperature overnight.

The cooled reaction mixture was purified by column chromatography (0-10% MeOH in EtOAc) yielding two fractions. The faster eluting isomer, tert-butyl (2R,6S,9S)-2-[4-(5-ethoxy-2-fluoro-phenyl)-2-pyridyl]-9-methyl-7-oxo-1,8-diazaspiro[4.5]decane-1-carboxylate (D130) (122 mg) was isolated after a retention time of 1.71 mins by reverse phase HPLC;

M/Z: 484 (M+H$^+$)

The slower eluting isomer, tert-butyl (2S,6S,9S)-2-[4-(5-ethoxy-2-fluoro-phenyl)-2-pyridyl]-9-methyl-7-oxo-1,8-diazaspiro[4.5]decane-1-carboxylate (D129) (69 mg) was isolated after a retention time of 2.42 mins by reverse phase HPLC;

M/Z: 484 (M+H$^+$)

Description 131

Methyl 4-(5-ethoxy-2-fluoro-phenyl)-6-methoxy-pyridine-2-carboxylate (D131)

Sodium (18 mg, 0.7800 mmol) was added to stirred, dry methanol (4 mL) in a 10 ml flask under N$_2$ at ambient temperature. When all the sodium had dissolved, 6-chloro-4-(5-ethoxy-2-fluoro-phenyl)pyridine-2-carbonitrile (which may be prepared as described in Description 113) (100 mg, 0.3600 mmol) was added. The yellow suspension was heated at block temp of 60° C. for 18 h with a reflux condenser attached. After 18 h, the reaction mixture was then transferred to a microwave vial, sealed and heated in a microwave oven at 100° C. for 1 h to give component A. Separately, sodium (16 mg, 0.700 mmol) was added to stirred, dry methanol (1 mL) in a microwave vial under N$_2$ at ambient temperature. When all the sodium had dissolved, 6-chloro-4-(5-ethoxy-2-fluoro-phenyl)pyridine-2-carbonitrile (20 mg, 72 µmol) (which may be prepared as described in Description 113) was added. The vial was sealed and heated in an oil bath at 50° C. for 3 h. The vial was then micowaved for 1 h at 100° C. This material was combined with component A and diluted with MeOH to give a total reaction volume of 9 ml. Water (1.5 ml) was added followed by AcOH (2 ml). The colourless solution was stirred at ambient temperature for 16 h. After 16 h the reaction was concentrated and the residue dissolved in DCM (30 ml) and washed with satd. aq. NaHCO$_3$ (50 ml). The organic phase was dried (MgSO$_4$) and evaporated to a colourless oil, which was dried to give methyl 4-(5-ethoxy-2-fluoro-phenyl)-6-methoxy-pyridine-2-carboxylate (D131) (111 mg, 84%);

300 MHz $^1$H NMR $\delta_H$ (CDCl$_3$) 1.45 (3H, t), 4.0 (3H, s), 4.06 (2H, q), 4.09 (3H, s), 6.93 (1H, dt), 6.99 (1H, dd), 7.08-7.15 (2H, m), 7.94 (1H, s).

Description 132

4-(5-Ethoxy-2-fluoro-phenyl)-6-methoxy-pyridine-2-carbaldehyde (D132)

1M DIBAL in toluene (7.53 mL, 7.53 mmol) was added dropwise over 10 mins to a stirred solution of methyl 4-(5-ethoxy-2-fluoro-phenyl)-6-methoxy-pyridine-2-carboxylate (which may be prepared as described in Description 131) (1.15 g, 3.77 mmol) in dry THF (20 mL) at −75° C. The reaction was stirred at this temp for 2 h then EtOH (175 µL) was added to quench. After 1 min the reaction mixture was poured into saturated Rochelle salt solution (100 ml) and water (50 ml). The mixture was warmed to ambient temperature then extracted with EtOAc (3×50 ml). Filtration under suction through celite was necessary to clear the emulsion. The combined organic extracts were dried (MgSO$_4$) and evaporated to 4-(5-ethoxy-2-fluoro-phenyl)-6-methoxy-pyridine-2-carbaldehyde (D132) a slightly coloured oil (970 mg);

300 MHz $^1$H NMR $\delta_H$ (CDCl$_3$) 1.45 (3H, t), 4.07 (2H, q), 4.09 (3H, s), 6.91-7.01 (2H, m), 7.12 (1H, t), 7.19 (1H, s), 7.77 (1H, s), 10.03 (1H, s).

Description 133

(5S)-2-[4-(5-Ethoxy-2-fluoro-phenyl)-6-methoxy-2-pyridyl]-7-methyl-1,7-diazaspiro[4.4]non-1-en-6-one (D133S) and (5R)-2-[4-(5-Ethoxy-2-fluoro-phenyl)-6-methoxy-2-pyridyl]-7-methyl-1,7-diazaspiro[4.4]non-1-en-6-one (D133R)

3 A molecular sieve (6 g, 3.5 mmol) was weighed into a RB flask with stirrer bar. The flask was heated for 10 mins under vacuum with a hot air gun to dry the sieves. When the flask was cool, a solution of 4-(5-ethoxy-2-fluoro-phenyl)-6-methoxy-pyridine-2-carbaldehyde (which may be prepared as described in Description 132) (963 mg, 3.5 mmol) in dry DCM (20 mL) was added under N$_2$ and 3-amino-1-methyl-pyrrolidin-2-one (399.34 mg, 3.5 mmol) was then added to the flask. The mixture was gently stirred under N$_2$ at ambient temp for 23 h. The reaction was filtered through celite under suction to remove the sieves and they were washed with DCM (5×15 ml). The filtrate was evaporated to a colorless oil. This was dissolved in dry THF (30 mL) and to this stirred solution under N$_2$ was added vinylsulfonyl-benzene (588.46 mg, 3.5 mmol) then silver acetate (584 mg, 0.18 mL, 3.5 mmol). The mixture was wrapped in foil to protect from light and stirred at ambient temp for 3 minutes then DBU (0.52 mL, 3.5 mmol) was added dropwise over 3 mins and the mixture left to stir for 3.5 h. The mixture was then filtered under suction through celite and washed through with THF (5×10 ml). The filtrate was evaporated to a dark residue and dried. The residue was dissolved in fresh THF (30 ml, not dried) under N$_2$ and the soln was cooled in an ice bath and to it was added 1.7M potassium t-butoxide in THF (6.17 mL, 10.5 mmol) over 5 minutes giving a sludgey mixture. The mixture was stirred at this temperature for 2 h then acetic acid (0.6 mL, 10.5 mmol) was added over 1 minute. The mixture was stirred at ambient temp for 20 minutes then filtered under suction through celite and washed through with THF until washings were colourless. The filtrate was evaporated to a viscous black oil, which was purified by SiO$_2$ column chromatography. The oil was dissolved in DCM (10 ml) and the solution was applied to a 100 g cartridge which was then eluted on a Biotage SP4 system with a gradient of MeOH/EtOAc (0-5%). Relevant fractions were pooled and evaporated to racemic 2-[4-(5-Ethoxy-2-fluoro-phenyl)-6-methoxy-2-pyridyl]-7-methyl-1,7-diazaspiro[4.4]non-1-en-6-one (608 mg, 44% yield);

300 MHz $^1$H NMR $\delta_H$ (CDCl$_3$) 1.43 (3H, t), 1.89 (1H, m), 2.16 (1H, m), 2.39-2.59 (2H, m), 2.96 (3H, s), 3.23-3.48 (3H, m), 3.66 (1H, q), 4.00 (3H, s), 4.06 (2H, q), 6.88 (1H, dt), 6.98-7.10 (3H, m), 7.91 (1H, s).

This was separated into enantiomers by AD-H chiralPak HPLC eluting with EtOH/heptane 5:95 to give the faster eluting isomer (5S)-2-[4-(5-Ethoxy-2-fluoro-phenyl)-6-methoxy-2-pyridyl]-7-methyl-1,7-diazaspiro[4.4]non-1-en-6-one (D133S) (108 mg);

Optical rotation α[$^D/_{20}$]=−70.0 (c=1, CHCl$_3$).

A slower eluting isomer was isolated_(5R)-2-[4-(5-ethoxy-2-fluoro-phenyl)-6-methoxy-2-pyridyl]-7-methyl-1,7-diazaspiro[4.4]non-1-en-6-one (D133R) (50 mg);

Optical rotation α[$^D/_{20}$]=+70.0 (c=1, CHCl$_3$).

Description 134

(2R,5S)-2-[4-(2-Fluoro-5-hydroxy-phenyl)-2-pyridyl]-7-methyl-1,7-diazaspiro[4.4]nonan-6-one (D134)

To a solution of (2R,5S)-2-(4-bromo-2-pyridyl)-7-methyl-1,7-diazaspiro[4.4]nonan-6-one (which may be prepared as described in Description 4) (140 mg, 0.4513 mmol) in MeCN (1.5 mL) and water (0.3000 mL) in a Smith microwave vessel was added (2-fluoro-5-hydroxy-phenyl)boronic acid (0.0774 g, 0.4965 mmol), bis(triphenylphosphine)palladium (II) dichloride (0.0095 g, 0.0135 mmol) and sodium carbonate (0.0957 g, 0.9027 mmol). The reaction vessel was sealed and purged with nitrogen. The reaction mixture was heated by microwave at 100° C. for 40 min. The reaction mixture was treated with water and was extracted with DCM twice and the organic layers were collected by passing down a PhaseSep cartridge. Evaporation of solvents gave an amber oil, It was further purified by silica gel chromatography (11 g KPNH silica cartridge) eluting with ethyl acetate in iso-hexane (20-100%) followed by methanol in ethyl acetate (0-18%) to give the desired product (2R,5S)-2-[4-(2-fluoro-5-hydroxy-phenyl)-2-pyridyl]-7-methyl-1,7-diazaspiro[4.4]nonan-6-one (D134) (0.1200 g, 0.3515 mmol, 77.9% yield) as cream solid;

300 MHz $^1$H NMR $\delta_H$ (CDCl$_3$) 1.86-2.29 (6H, m), 2.50 (1H, m), 2.94 (3H, s), 3.28-2.43 (2H, m), 4.68 (1H, t), 5.3 (1H, br.s), 6.82-6.90 (2H, m), 7.02 (1H, t), 7.28-7.31 (1H, m), 7.46 (1H, s), 8.55 (1H, d).

Description 135

2,5-Dimethyl-4-nitro-1-oxido-pyridin-1-ium (D135)

To a nitrating mixture of sulphuric acid (24 mL) and nitric acid (12 mL) cooled to 0° C. was added 2,5-dimethyl-1-oxido-pyridin-1-ium (CAS: 4986-05-4) (8.4 g, 68.21 mmol). The solution was allowed to warm to room temperature and stirred over 30 mins then heated to 110° C. and stirred over 5 hrs. The reaction mixture was cooled and poured onto ice. The aqueous solution was made basic with solid sodium carbonate, giving a precipitate. The aqueous was extracted into DCM (3x), and the combined extracts were dried over magnesium sulphate, filtered and evaporated to yield a yellow solid, 2,5-dimethyl-4-nitro-1-oxido-pyridin-1-ium (D135) (9.8 g, 58.3 mmol, 85.4% yield);

300 MHz $^1$H NMR $\delta_H$ (CDCl$_3$) 2.54 (3H, s), 2.59 (3H, s), 8.03 (1H, s), 8.21 (1H, s).

Description 136

4-Bromo-2,5-dimethyl-1-oxido-pyridin-1-ium (D136)

To a solution of acetyl bromide (43.09 mL, 582.81 mmol) in acetic acid (70 mL) was added 2,5-dimethyl-4-nitro-1-oxido-pyridin-1-ium (which may be prepared as described in Description 135) (9.8 g, 58.28 mmol) dropwise over 5 mins. After addition, the mixture was stirred at 80° C. overnight. The reaction mixture was poured on to ice and the solution basified to pH 8 with cold 2M sodium hydroxide. The aqueous layer was extracted with DCM (3x). The combined organics were washed with brine, dried over magnesium sulphate, filtered and evaporated to a pale yellow solid, 4-bromo-2,5-dimethyl-1-oxido-pyridin-1-ium (D136) (12.3 g);

300 MHz $^1$H NMR $\delta_H$ (CDCl$_3$) 2.29 (3H, s), 2.45 (3H, s), 7.41 (1H, s), 8.13 (1H, s).

Description 137

4-Bromo-3,6-dimethyl-pyridine-2-carbonitrile (D137)

To a Smith microwave vial was added 4-bromo-2,5-dimethyl-1-oxido-pyridin-1-ium (which may be prepared as described in Description 136), (300 mg, 1.48 mmol), diethoxyphosphorylformonitrile (0.9 mL, 5.94 mmol) and triethylamine (0.41 mL, 2.97 mmol) in anhydrous MeCN (1 mL). The reaction mixture was heated by microwave at 80° C. for 1 h. The reaction mixture was evaporated and the crude dark oil was purified on silica gel chromatography (10 g SiO$_2$) eluting with ethyl acetate in iso-hexane (0-80%). Evaporation of desired fractions gave 4-bromo-3,6-dimethyl-pyridine-2-carbonitrile (D137) (218 mg, 1.0329 mmol, 69.6% yield) as colourless solid;

300 MHz $^1$H NMR $\delta_H$ (CDCl$_3$) 2.55 (3H, s), 2.61 (3H, s), 7.59 (1H, s).

Description 138

4-(5-Ethoxy-2-fluoro-phenyl)-3,6-dimethyl-pyridine-2-carbonitrile (D138)

To a solution of 4-bromo-3,6-dimethyl-pyridine-2-carbonitrile (which may be prepared as described in Description 137) (3.82 g, 18.099 mmol) in MeCN (45 mL) and water (5 mL) in a Smith microwave vessel was added (5-ethoxy-2-fluoro-phenyl)boronic acid (3.6627 g, 19.909 mmol), bis(triphenylphosphine)palladium (II) dichloride (0.3811 g, 0.5430 mmol) and sodium carbonate (3.8367 g, 36.198 mmol). The reaction vessel was sealed and purged with nitrogen. The reaction mixture was heated by microwave at 100° C. for 25 min. The reaction mixture was treated with water and was extracted with DCM twice and the organic layers were collected by passing down a PhaseSep cartridge The solvent was removed by evaporation and the residue was purified by silica gel chromatography (100 g SiO$_2$) eluting with ethyl acetate in iso-hexane (10-60%). Evaporation of desired fractions gave 4-(5-ethoxy-2-fluoro-phenyl)-3,6-dimethyl-pyridine-2-carbonitrile (D138) (4.76 g, 17.61 mmol, 97.3% yield);

300 MHz $^1$H NMR $\delta_H$ (CDCl$_3$) 1.45 (3H, t), 2.40 (3H, s), 2.60 (3H, s), 4.04 (2H, d), 6.70 (1H, dd), 6.96 (1H, m), 7.12 (1H, t), 7.25 (1H, s).

Description 139

Ethyl 4-(5-ethoxy-2-fluoro-phenyl)-3,6-dimethyl-pyridine-2-carboxylate (D139)

To a stirred solution of 4-(5-ethoxy-2-fluoro-phenyl)-3,6-dimethyl-pyridine-2-carbonitrile (which may be prepared as described in Description 138) (4.76 g, 17.61 mmol) in ethanol (25 mL) was added 8M sodium hydroxide (13.21 mL, 105.66 mmol). The resulting mixture was left to stir at 100° C. for 5 h. The reaction mixture was cooled and concentrated. The pH was adjusted to 1 with the careful addition of 5M aq. HCl. The reaction mixture was extracted with DCM and the organic layers were collected by passing down a PhaseSep cartridge. Evaporation of solvent under reduced pressure gave a colourless oily solid. This was dissolved in ethanol (60 mL) and sulfuric acid (5.18 mL, 96.73 mmol) was added. The resulting mixture was left to stir under reflux for 24 h. The solution was allowed to cool and concentrated. It was quenched with crushed ice and treated with 2M aq. NaOH to give pH=7. The mixture was extracted with DCM twice and the combined organic layers dried over sodium sulfate, filtered and evaporated. The crude residue was purified by silica gel chromatography (50 g SiO$_2$) eluting with ethyl acetate in iso-hexane (10-70%). Evaporation of desired fractions gave ethyl 4-(5- ethoxy-2-fluoro-phenyl)-3,6-dimethyl-pyridine-2-carboxylate (D139) (5.51 g, 17.363 mmol, 98.6% yield) as colourless solid;

300 MHz $^1$H NMR $\delta_H$ (CDCl$_3$) 1.41-1.48 (6H, 2×t), 2.28 (3H, s), 2.61 (3H, s), 4.04 (2H, q), 4.49 (2H, q), 6.70 (1H, dd), 6.92 (1H, dt), 7.08 (1H, t), 7.15 (1H, s).

Description 140

[4-(5-Ethoxy-2-fluoro-phenyl)-3,6-dimethyl-2-pyridyl]methanol (D140)

To a stirred solution of ethyl 4-(5-ethoxy-2-fluoro-phenyl)-3,6-dimethyl-pyridine-2-carboxylate (which may be prepared as described in Description 139) (5.51 g, 17.36 mmol) in absolute ethanol (45 mL) under nitrogen at 25° C., was added sodium borohydride (3.28 g, 86.81 mmol) in portions over 40 min. The resulting mixture was left to stir for another 3 h. It was treated with crushed ice (80 mL) and the pH was carefully adjusted to 7 with the addition of 2M HCl. The reaction mixture was extracted with DCM and the organic layers were washed with brine then collected by passing down a PhaseSep cartridge. Evaporation of the volatiles gave [4-(5-ethoxy-2-fluoro-phenyl)-3,6-dimethyl-2-pyridyl]-methanol (D140) (4.33 g, 15.727 mmol, 90.6% yield) as colourless oil;

300 MHz $^1$H NMR $\delta_H$ (CDCl$_3$) 1.42 (3H, t), 2.03 (3H, s), 2.58 (3H, s), 4.04 (2H, q), 4.71 (2H, s), 5.15 (1H, br.s), 6.72 (1H, dd), 6.91 (1H, dt), 6.99 (1H, s), 7.08 (1H, t).

Description 141

4-(5-Ethoxy-2-fluoro-phenyl)-3,6-dimethyl-pyridine-2-carbaldehyde (D141)

To a solution of oxalyl chloride (1.46 mL, 17.3 mmol) in DCM (50 mL) cooled to −78° C. was added dropwise, a solution of dimethyl sulfoxide (2.68 mL, 37.74 mmol) in DCM (5 mL). After addition, the solution was stirred for 15 mins. A solution of [4-(5-ethoxy-2-fluoro-phenyl)-3,6-dimethyl-2-pyridyl]methanol (which may be prepared as described in Description 140) (4.33 g, 15.73 mmol) in DCM (10 mL) was then added dropwise over about 5 mins. The mixture was allowed to stir at −78° C. for 2 hrs. Triethylamine (8.74 mL, 62.91 mmol) was added dropwise giving a precipitate and this was allowed to warm to room temperature over one hour. The reaction mixture was washed with water and brine, dried over magnesium sulphate and evaporated. The crude residue was purified by silica gel chromatography (50 g SiO$_2$) eluting with ethyl acetate in iso-hexane (0-40%). Evaporation of desired fractions gave 4-(5-ethoxy-2-fluoro-phenyl)-3,6-dimethyl-pyridine-2-carbaldehyde (D141) (2.89 g, 10.574 mmol, 67.2% yield) as a yellow solid;

300 MHz $^1$H NMR $\delta_H$ (CDCl$_3$) 1.44 (3H, t), 2.48 (3H, s), 2.56 (3H, s), 4.04 (2H, q), 6.72 (1H, dd), 6.94 (1H, dt), 7.10 (1H, t), 7.24 (1H, s), 10.25 (1H, s).

Description 142

2-[4-(5-Ethoxy-2-fluoro-phenyl)-3,6-dimethyl-2-pyridyl]-7-methyl-1,7-diazaspiro[4.4]non-1-en-6-one (D142)

To a stirred mixture of 4-(5-ethoxy-2-fluoro-phenyl)-3,6-dimethyl-pyridine-2-carbaldehyde (which may be prepared as described in Description 141) (2980 mg, 10.904 mmol) and 3-amino-1-methyl-pyrrolidin-2-one (508.12 mg, 4.4514 mmol) in anhydrous DCM (10 mL) at room temperature, was added magnesium sulfate (3937.5 mg, 32.711 mmol). The resulting mixture was left to stir at room temperature for 3 h. The reaction mixture was filtered through a plug of cotton wool and the filtrate was washed with brine. The organic layer was collected by means of a PhaseSep cartridge. Evaporation of solvent under reduced pressure gave yellow oil, 3-[(E)-[4-(5-ethoxy-2-fluoro-phenyl)-3,6-dimethyl-2-pyridyl]methyleneamino]-1-methyl-pyrrolidin-2-one (3.97 g, 10.746 mmol, 98.6% yield). To a portion of this material (3920 mg, 10.611 mmol) in anhydrous THF (35 mL) under nitrogen at room temperature, was added phenyl vinyl sulfone (2141.9 mg, 12.733 mmol) and silver acetate (1771.1 mg, 10.611 mmol). The resulting mixture was left to stir in the dark for 10 min. DBU (0.7932 mL, 5.3055 mmol) was added. The resulting mixture was left to stir in the dark for 2 h. The dark filtrate was evaporated and further dried under house vac. It was purified by silica gel chromatography (100 g SiO$_2$) eluting with ethyl acetate in iso-hexane (30-100%) followed by methanol in ethyl acetate (0-15%). Evaporation of desired fractions gave 3-(benzenesulfonyl)-2-[4-(5-ethoxy-2-fluoro-phenyl)-3,6-dimethyl-2-pyridyl]-7-methyl-1,7-diazaspiro[4.4]nonan-6-one (3880 mg, 7.2166 mmol, 68.0% yield) as brown solid. To a stirred solution of this material in anhydrous THF (30 mL) under nitrogen at 0° C., was added potassium tert-butoxide (4048.9 mg, 36.083 mmol). The resulting mixture was left to stir for 2 h and acetic acid (2.07 mL, 36.08 mmol) was added. Stirring was continued for 15 min at room temperature. Evaporation of solvent under reduced pressure gave a dark oily residue. It was purified by silica gel chromatography (50 g SiO$_2$) eluting with ethyl acetate in iso-hexane (30-100%). Evaporation of desired fractions gave brown oil, 2-[4-(5-ethoxy-2-fluoro-phenyl)-3,6-dimethyl-2-pyridyl-7-methyl-1,7-diazaspiro[4.4]non-1-en-6-one (D142) (543 mg, 1.373 mmol, 19.0% yield);

300 MHz $^1$H NMR $\delta_H$ (CDCl$_3$) 1.42 (3H, t), 1.91 (1H, m), 2.08 (1H, m), 2.30 (3H, s), 2.46-2.59 (2H, m), 2.58 (3H, s), 2.94 (3H, s), 3.28-3.42 (3H, m), 3.62 (1H, q), 4.01 (2H, q), 6.69 (1H, dd), 6.90 (1H, dt), 7.03 (1H, s), 7.06 (1H, t).

Description 143

1-[4-Fluoro-3-(4,4,5,5-tetramethyl-1,3,2-dioxaborolan-2-yl)phenyl]propan-1-one (D143)

To a solution of 1-(3-bromo-4-fluoro-phenyl)propan-1-one [CAS: 202865-82-5](500 mg, 2.16 mmol) in dry DMF (6 mL) in a microwave vial was added potassium acetate (0.41 mL, 6.49 mmol), 4,4,5,5-tetramethyl-2-(4,4,5,5-tetramethyl-1,3,2-dioxaborolan-2-yl)-1,3,2-dioxaborolane (824.27 mg, 3.25 mmol), and Pd(dppf)Cl$_2$.CH$_2$Cl$_2$ (176.72 mg, 0.2200 mmol). The reaction was degassed by means of a stream of nitrogen bubbling into the solution for 15 mins. The mixture was then heated to 120° C. for 40 minutes in a microwave. The reaction was partitioned between EtOAc (20 mL) and water (80 mL), and the organics were separated, washed with brine (30 mL), dried over MgSO$_4$, filtered and concentrated in vacuo to yield a purple oil. The residue was loaded onto silica (25 g, SNAP cartridge), which was eluted with a gradient from 0% to 30% EtOAc:isohexane. Fractions containing desired product were combined and concentrated in vacuo to give 1-[4-fluoro-3-(4,4,5,5-tetramethyl-1,3,2-dioxaborolan-2-yl)phenyl]propan-1-one (D143) (622 mg, 2.0127 mmol, 93% yield) as brown oil which turned to beige solid on standing;

300 MHz $^1$H NMR $\delta_H$ (CDCl$_3$) 1.24 (3H, t), 1.39 (12H, s), 3.04 (2H, q), 7.12 (1H, t), 8.10 (1H, m), 8.37 (1H, m).

Description 144

4-Bromo-5,6-dimethyl-pyridine-2-carbonitrile (D144)

A mixture of 4-bromo-2,3-dimethyl-1-oxido-pyridin-1-ium (15.8 g, 78.2 mmol) (which may be prepared as described in Description 5) and dimethyl sulfate (8.88 mL, 93.84 mmol) in MeCN (36 mL) was stirred at block temp of 70° C. under $N_2$ for 3.25 h. The reaction mixture was evaporated to an oil which was stirred with $Et_2O$ (2×50 ml) and the solvent was decanted from the oil. The oil was dried in vacuo and dissolved in water (105 mL) and then was added over 25 mins to a stirred solution of potassium cyanide (20.37 g, 312.79 mmol) in water (75 mL), cooled in a salt-ice Dewar bath (range during addition −5 to 0° C.). The turbid mixture was stirred in the ice/salt bath whilst it warmed slowly to ambient temperature overnight. The beige precipitate was then filtered under suction and washed with water (3×50 ml) and pressed dry. This moist solid was then dissolved in DCM (300 ml), dried ($Na_2SO_4$), filtered and evaporated to a beige solid, approximately 90% pure 4-bromo-5,6-dimethyl-pyridine-2-carbonitrile (D144) by NMR;

300 MHz $^1$H NMR $\delta_H$ (CDCl$_3$) 2.48 (3H, s), 2.64 (3H, s), 7.28 (1H, s), 7.74 (1H, s).

Description 145 tert-Butyl (2S,5S)-7-methyl-6-oxo-2-[4-[3-(trifluoromethoxy)phenyl]-2-pyridyl]-1,7-diazaspiro[4.4]nonane-1-carboxylate (D145)

A solution of crude (2S,5S)-7-methyl-2-[4-[3-(trifluoromethoxy)phenyl]-2-pyridyl]-1,7-diazaspiro[4.4]nonan-6-one (which may be isolated as described in Example 2b) (111 mg, 0.2800 mmol) in DCM (3 mL) containing a proportion of the (2R)-isomer was treated with Boc$_2$O (0.08 g, 0.3700 mmol) and the mixture was stirred at room temperature overnight. The solvent was evaporated and the residue was purified by chromatography using a Biotage SNAP 10 g cartridge, eluting with ethyl acetate, to give the title compound (D145) as a white solid (124.5 mg);

M/Z: 392 (M+H$^+$) 492.

Example 1

(2R,5S)-7-Methyl-2-[4-[3-(trifluoromethoxy)phenyl]-2-pyridyl]-1,7-diazaspiro[4.4]nonan-6-one hydrochloride (E1)

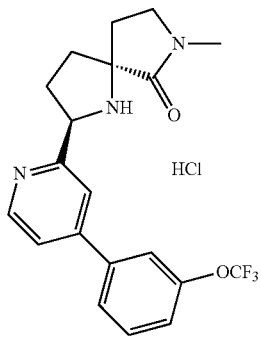 [SMILES: CN1CC[C@@]2(CC[C@H](c3cc(-c4cccc(OC(F)(F)F)c4)ccn3)N2)C1=O ; Cl]

To a solution of (2R,5S)-2-(4-bromo-2-pyridyl)-7-methyl-1,7-diazaspiro[4.4]nonan-6-one (which may be prepared as described in Description 4) (22 mg, 0.0709 mmol) in MeCN (1 mL) and water (0.2000 mL) in a Smith microwave vessel was added [3-(trifluoromethoxy)phenyl]boronic acid (14.605 mg, 0.0709 mmol), bis(triphenylphosphine)palladium (II) dichloride (2.4891 mg, 0.0035 mmol) and sodium carbonate (15.035 mg, 0.1418 mmol). The reaction vessel was sealed and purged with nitrogen. The reaction mixture was heated by microwave at 100° C. for 25 minutes. The reaction mixture was treated with water and was extracted with DCM twice and the organic layers were collected by passing down a PhaseSep cartridge. It was further eluted on an SCX-2 cartridge (0.5 g) and washed with DCM followed by MeOH. The desired product was eluted off the cartridge with ammonia in MeOH (0.2 M). Evaporation of solvents gave an amber oil. It was further purified by preparative HPLC (ChiralPak AD-H) column, eluting with ethanol/n-heptane (1:3) to give the desired product as an amber oil;

300 MHz $^1$H NMR $\delta_H$ (CDCl$_3$) 1.86-2.28 (5H, m), 2.50-2.62 (1H, m), 2.8 (1H, br s), 2.91 (3H, s), 2.25-3.89 (2H, m), 4.77 (1H, t), 7.29 (1H, d), 7.32 (1H, d), 7.48 (1H, t), 7.53 (1H, q), 7.60 (1H, d), 7.70 (1H, s), 8.62 (1H, d).

This was converted to the (2R,5S)-7-methyl-2-[4-[3-(trifluoromethoxy)phenyl]-2-pyridyl]-1,7-diazaspiro[4.4]nonan-6-one hydrochloride (E1) by addition of HCl (1 M in diethyl ether) to a DCM solution of the free base. Evaporation followed by further drying under reduced pressure gave an amber solid. The latter was further dried under reduced pressure at 400° C. to give the title compound in 58% yield;

M/Z: 392 (M+H$^+$).

Example 1a

(2R,5S)-7-Methyl-2-[4-[3-(trifluoromethoxy)phenyl]-2-pyridyl]-1,7-diazaspiro[4.4]nonan-6-one hemisulfate hydrate (E1a)

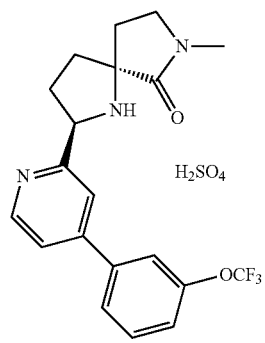

Method A:
tert-Butyl (2R,5S)-7-methyl-6-oxo-2-[4-[3-(trifluoromethoxy)phenyl]-2-pyridyl]-1,7-diazaspiro[4.4]nonane-1-carboxylate (which may be prepared as described in Description 109) (2.85 g, 5.8 mmol) was added to a solution of 4M HCl in dioxane (10 mL, 40 mmol) in DCM (20 mL) at 20° C. and the reaction stirred for 18 hours. The solvent was evaporated and the residue was suspended in DCM. This was treated with sat. aq. NaHCO$_3$ and the phases separated. The aqueous layer was washed with DCM (3x) and the combined organic layer was dried (Na$_2$SO$_4$) and the solvent evaporated to afford an amber oil (2.32 g). This was purified on a 100 g SNAP cartridge, using 0 to 10% MeOH in EtOAc. desired clean product fractions were collected and the solvent evaporated to afford (2R,5S)-7-methyl-2-[4-[3-(trifluoromethoxy)phenyl]-2-pyridyl]-1,7-diazaspiro[4.4]nonan-6-one as a pale yellow oil identical to that prepared in Example 1.

Sulphuric acid (0.26 mL, 4.6 mmol) was added to a solution of this material (1.8 g, 4.6 mmol) in DCM (17 mL) at 20° C. and the reaction stirred for 5 mins. The solvent was evaporated and the residue was dissolved in deionised water. This was freeze dried for 20 hours to give (2R,5S)-7-methyl-2-[4-[3-(trifluoromethoxy)phenyl]-2-pyridyl]-1,7-diazaspiro[4.4]nonan-6-one hemisulfate hydrate (E1a) (2.14 g) as a colourless solid;

300 MHz $^1$H NMR $\delta_H$ (MeOD) 2.26-2.49 (4H, m), 2.70 (1H, dt), 2.82-2.91 (1H, m), 2.98 (3H, s), 3.56 (2H, dd), 5.31 (1H, m), 7.46 (1H, d), 7.68 (1H, t), 7.82 (1H, s), 7.77 (1H, dd), 7.83 (1H, d), 7.87 (1H, s), 8.73 (1H, d).

Method B:
A solution of (5S)-7-methyl-2-[4-[3-(trifluoromethoxy)phenyl]-2-pyridyl]-1,7-diazaspiro[4.4]non-1-en-6-one (which may be prepared as described in Description 108) (5.77 g, 14.82 mmol) in DCM (75 mL) was cooled to −78° C. under nitrogen and a solution of borane tert-butylamine complex (1.43 g, 16.44 mmol) in DCM (15 ml) was added dropwise maintaining the internal temperature below −70° C. over 10 mins. The mixture was stirred at −78° C. for 90 mins and then the cooling bath was removed and 5M hydrochloric acid (30 mL, 150 mmol) was added via the dropping funnel over 1-2 mins. The mixture was brought to 25-30° C. with a water bath and the mixture stirred vigourously for 30 mins. More DCM (200 ml) was added and the mixture was then slowly poured into a beaker containing sodium carbonate (17.28 g, 163.01 mmol) in water (150 ml) and the mixture was stirred for 10 mins. The layers were sepated and the aqueous layer (pH 9) was re-extracted with DCM (2×150 ml). The combined organic layers were washed with brine, dried ($Na_2SO_4$) and concentrated to give a yellow gum, a 15:1 mixture of (2R,5S) and (2S,5S) isomers. This mixture was separated by chromatography using a Biotage SNAP 340 g cartridge eluting with 5% of 0.5M methanolic ammonia in ethyl acetate (isocratic) to obtain the major isomer (2R,5S)-7-methyl-2-[4-[3-(trifluoromethoxy)phenyl]-2-pyridyl]-1,7-diazaspiro[4.4]nonan-6-one (5.76 g), increasing to 10% of 0.5M methanolic ammonia to elute the minor (2S,5S)-7-methyl-2-[4-[3-(trifluoromethoxy)phenyl]-2-pyridyl]-1,7-diazaspiro[4.4]nonan-6-one isomer (111 mg) which was contaminated by traces of the (2R,5S) isomer. The (2R,5S) isomer was identical spectroscopically to that prepared in Example 1. This was converted to the salt form: sulphuric acid (0.75 mL, 13.48 mmol) was added to a solution of (2R,5S)-7-methyl-2-[4-[3-(trifluoromethoxy)phenyl]-2-pyridyl]-1,7-diazaspiro[4.4]nonan-6-one (5.27 g, 13.48 mmol) in DCM (70 mL) at 20° C. and the reaction stirred for 5 mins. The solvent was evaporated and the residue was triturated with diethyl ether and dried. This solid (approx. 6 g) was dissolved in acetone (30 ml) and then added dropwise to diethyl ether (600 ml) with rapid stirring. The mixture was stirred for 10 mins then the solid was collected by filtration and dried in a vacuum oven at 50° C. overnight. The solid was dissolved in deionised water (~60 ml), filtered and freeze dried and then dried in a vacuum oven at 50° C. for 3 hrs to give the title material (E1a) as a beige solid, (5.9 g) identical spectroscopically to that prepared by method A.

The following Examples were prepared in a similar manner to Example 1 with the modifications being the use of alternative boronic acids noted:

| Example | Structure | Name | Analysis | Modification |
|---|---|---|---|---|
| E2 | 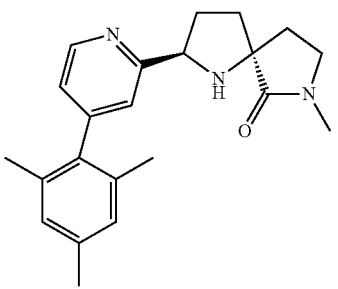 | (2R,5S)-7-Methyl-2-[4-(2,4,6-trimethylphenyl)-2-pyridyl]-1,7-diazaspiro-[4.4]nonan-6-one hydrochloride | M/Z: 350 (M + H$^+$) | (2,4,6-trimethyl-phenyl)-boronic acid |
| E3 | 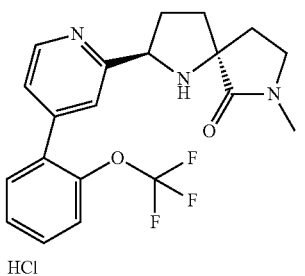 [SMILES: CN1CC[C@@]2(CC[C@H](c3cc(-c4ccccc4OC(F)(F)F)ccn3)N2)C1=O ; Cl] | (2R,5S)-7-Methyl-2-[4-[2-(trifluoromethoxy)-phenyl]-2-pyridyl]-1,7-diazaspiro-[4.4]nonan-6-one hydrochloride | M/Z: 392 (M + H$^+$) | [2-(trifluoromethoxy)-phenyl] boronic acid |

-continued

| Example | Structure | Name | Analysis | Modification |
|---|---|---|---|---|
| E4 | 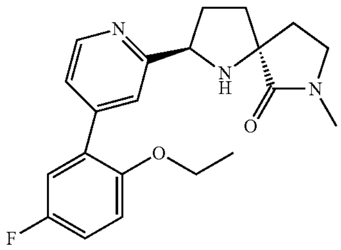 | (2R,5S)-2-[4-(2-Ethoxy-5-fluoro-phenyl)-pyridin-2-yl]-7-methyl-1,7-diaza-spiro[4.4]nonan-6-one hydrochloride | M/Z: 370 (M + H$^+$) | (2-ethoxy-5-fluoro-phenyl)boronic acid |
| E5 | 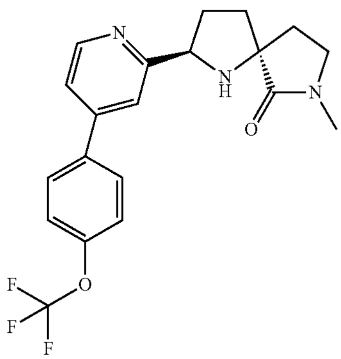 | (2R,5S)-7-Methyl-2-[4-(4-trifluoro-methoxy-phenyl)-pyridin-2-yl]-1,7-diaza-spiro[4.4]nonan-6-one hydrochloride | M/Z: 392 (M + H$^+$) | [4-(trifluoromethoxy)-phenyl]boronic acid |
| E6 | 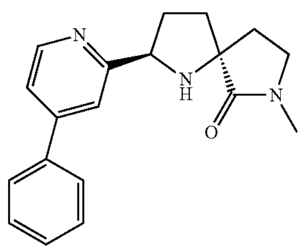 | (2R,5S)-7-Methyl-2-(4-phenyl-pyridin-2-yl)-1,7-diaza-spiro[4.4]nonan-6-one hydrochloride | M/Z: 308 (M + H$^+$) | phenylboronic acid |
| E7 | 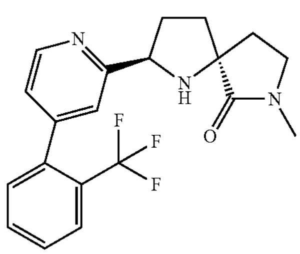 | (2R,5S)-7-Methyl-2-[4-[2-(trifluoro-methyl)phenyl]-2-pyridyl]-1,7-diazaspiro[4.4]nonan-6-one hydrochloride | M/Z: 376 (M + H$^+$) | [2-(trifluoromethyl)-phenyl]boronic acid |
| E8 | 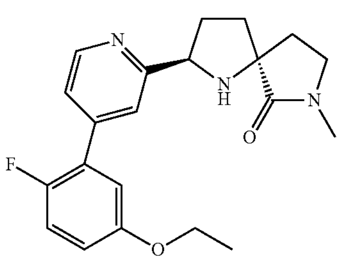 | (2R,5S)-2-[4-(5-Ethoxy-2-fluoro-phenyl)-2-pyridyl]-7-methyl-1,7-diazaspiro[4.4]nonan-6-one hydrochloride | M/Z: 370 (M + H$^+$) | (5-ethoxy-2-fluoro-phenyl)boronic acid |

-continued

| Example | Structure | Name | Analysis | Modification |
|---|---|---|---|---|
| E9 | 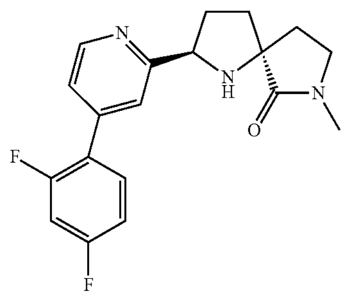 | (2R,5S)-2-[4-(2,4-Difluorophenyl)-2-pyridyl]-7-methyl-1,7-diazaspiro[4.4]nonan-6-one hydrochloride | M/Z: 344 (M + H+) | (2,4-difluorophenyl)-boronic acid |
| E10 | 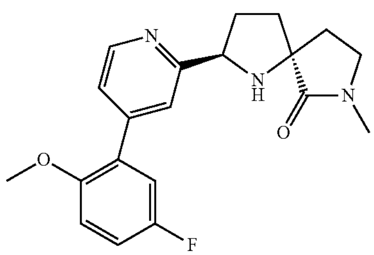 | (2R,5S)-2-[4-(5-Fluoro-2-methoxy-phenyl)-2-pyridyl]-7-methyl-1,7-diazaspiro[4.4]nonan-6-one hydrochloride | M/Z: 356 (M + H+) | (5-fluoro-2-methoxy-phenyl)boronic acid |
| E11 | 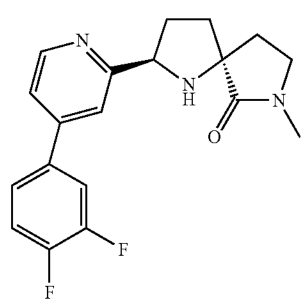 | (2R,5S)-2-[4-(3,4-Difluorophenyl)-2-pyridyl]-7-methyl-1,7-diazaspiro[4.4]nonan-6-one hydrochloride | M/Z: 344 (M + H+) | (3,4-difluorophenyl)-boronic acid |
| E12 | 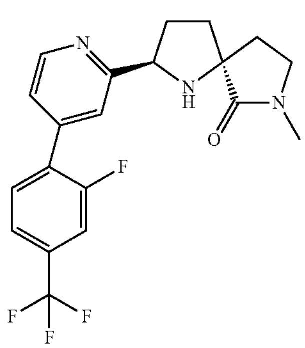 | (2R,5S)-2-[4-[2-Fluoro-4-(trifluoromethyl)phenyl]-2-pyridyl]-7-methyl-1,7-diazaspiro[4.4]nonan-6-one hydrochloride | M/Z: 394 (M + H+) | [2-fluoro-4-(trifluoromethyl)-phenyl]boronic acid |

| Example | Structure | Name | Analysis | Modification |
|---|---|---|---|---|
| E13 | (structure) | (2R,5S)-2-[4-(4-Chlorophenyl)-2-pyridyl]-7-methyl-1,7-diazaspiro[4.4]nonan-6-one hydrochloride | M/Z: 342, 344 (M + H⁺) | (4-chlorophenyl)boronic acid |

Examples 14 and 15

(2R,5R)-7-Methyl-2-[3-methyl-4-[4-(trifluoromethyl)phenyl]-2-pyridyl]-1,7-diazaspiro[4.4]nonan-6-one hydrochloride (E14) and (2S,5R)-7-Methyl-2-[3-methyl-4-[4-(trifluoromethyl)phenyl]-2-pyridyl]-1,7-diazaspiro[4.4]nonan-6-one hydrochloride (E15)

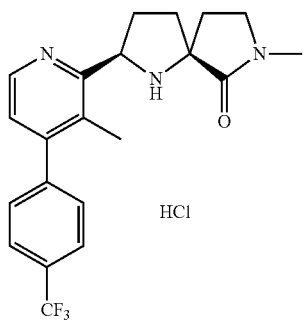

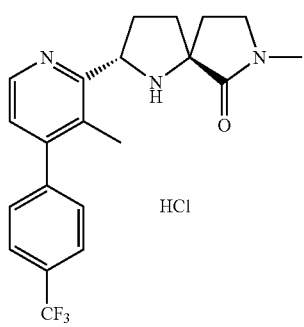

To a solution of (5R)-2-(4-bromo-3-methyl-2-pyridyl)-7-methyl-1,7-diazaspiro[4.4]nonan-6-one (which may be prepared as described in Description 10) in 1,2-dimethoxyethane (2 mL) and water (0.50 mL) in a microwave vial was added sodium carbonate (137.3 mg, 1.3 mmol) and 4-(trifluoromethyl)phenylboronic acid (123.02 mg, 0.6500 mmol). To the reaction was then added bis(triphenylphosphine)palladium (II) dichloride (15.15 mg, 0.0200 mmol) and the reaction was sealed and heated in the microwave at 130° C. for 15 minutes.

The reaction was partitioned between EtOAc (30 mL) and water (30 mL). The organic phase was separated, washed with brine (20 mL), and dried over MgSO₄. The residue was loaded onto a silica SNAP 10 g cartridge, and eluted with 100% EtOAc (15 Column volumes), the column was then eluted with a gradient from DCM to 90:10 DCM:MeOH. The two desired compounds co-eluted. The material was dissolved in ethanol:heptane (50%, 1 mL), and separated using chiral HPLC (ChiralPak AD-H), eluting with 30% EtOH: Heptane. Fractions containing the faster running component were combined and evaporated to yield (2R,5R)-7-methyl-2-[3-methyl-4-[4-(trifluoromethyl)phenyl]-2-pyridyl]-1,7-diazaspiro[4.4]nonan-6-one (19 mg, 0.0488 mmol, 22.6% yield);

300 MHz ¹H NMR $\delta_H$ (CDCl₃) 1.76-1.92 (2H, m), 2.03-2.11 (1H, m), 2.20-2.43 (3H, m), 2.22 (3H, s), 2.94 (3H, s), 3.29-3.39 (1H, m), 3.40-3.49 (1H, m), 4.0 (1H, br s), 4.46-4.54 (1H, m), 7.01 (1H, d), 7.43 (2H, d), 7.72 (2H, d), 8.47 (1H, d).

This residue was dissolved in acetone (1 mL) and HCl in ether (1 N, 48 μL) was added. The mixture was concentrated in vacuo and azeotroped twice with acetone to give the hydrochloride salt (E14);

M/Z: 390 (M+H⁺).

Fractions containing the second eluting peak were combined and concentrated in vacuo to yield (2S,5R)-7-methyl-2-[3-methyl-4-[4-(trifluoromethyl)phenyl]-2-pyridyl]-1,7-diazaspiro[4.4]nonan-6-one (12 mg, 0.0308 mmol, 14.3% yield);

300 MHz ¹H NMR $\delta_H$ (CDCl₃) 1.75-1.94 (2H, m), 2.23-2.42 (3H, m), 2.4 (1H, br s), 2.46-2.60 (1H, m), 2.24 (3H, s), 2.89 (3H, s), 3.26-3.34 (1H, m), 3.42-3.50 (1H, m), 4.84-4.91 (1H, m), 7.01 (1H, d), 7.41 (2H, d), 7.70 (2H, d), 8.42 (1H, d).

This was dissolved in acetone (1 mL) and HCl in ether (1 N, 31 μL) was added, the mixture concentrated in vacuo and azeotroped twice with acetone to give the hydrochloride salt (E15);

M/Z: 390 (M+H⁺).

Examples 16 and 17

(2S,5S)-7-Methyl-2-[3-methyl-4-[4-(trifluoromethyl)phenyl]-2-pyridyl]-1,7-diazaspiro[4.4]nonan-6-one hydrochloride (E16) and (2R,5S)-7-Methyl-2-[3-methyl-4-[4-(trifluoromethyl)phenyl]-2-pyridyl]-1,7-diazaspiro[4.4]nonan-6-one hydrochloride (E17)

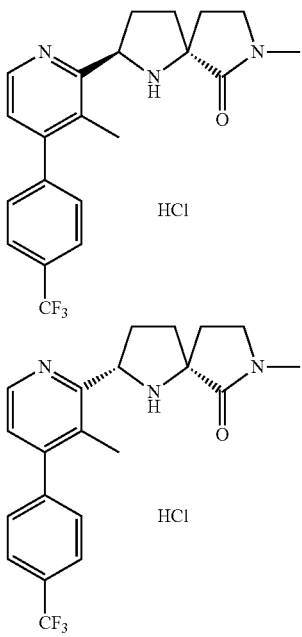 [SMILES: Cc1c(-c2ccc(C(F)(F)F)cc2)ccnc1[C@H]1CC[C@@]2(CCN(C)C2=O)N1 ; Cl ; Cc1c(-c2ccc(C(F)(F)F)cc2)ccnc1[C@@H]1CC[C@@]2(CCN(C)C2=O)N1 ; Cl]

(5S)-3-(4-Bromo-3-methyl-2-pyridyl)-8-methyl-4,8-diazaspiro[4.4]nonan-9-one (250 mg, 0.3900 mmol) (which may be prepared as described in Description 11) was subjected to the experimental conditions described in Example 14/15 but afforded a mixture of epimers of (5S)-7-methyl-2-[3-methyl-4-[4-(trifluoromethyl)phenyl]-2-pyridyl]-1,7-diazaspiro[4.4]nonan-6-one (140 mg, 0.1798 mmol, 46.6% yield). To a proportion of this material (120 mg, 0.1500 mmol) in MeCN (1.5 mL) was added triethylamine (0.04 mL, 0.3100 mmol) followed by tert-butoxycarbonyl tert-butyl carbonate (67.25 mg, 0.3100 mmol). The reaction was then stirred at room temperature for 16 hours. The reaction was thus concentrated in vacuo and redissolved in DCM, and loaded onto silca (SNAP 25 g column). The column was then eluted with EtOAc:isohexane 0% to 100%, to give a fast running component A. The column was then eluted with (10:90 MeOH:DCM) in DCM, 0% to 100%. Fractions containing the slower component were combined and concentrated in vacuo to give a pale orange oil, B. Component A was then dissolved in HCl in dioxane (4 M, 3 mL) and the reaction was stirred for 16 hours at room temperature. The reaction was concentrated in vacuo, and the residue was azeotroped with acetone (2×5 mL). The residue was then taken up in MeOH (2 mL) and loaded onto an SCX cartridge (2 g). Eluting the SCX cartridge with MeOH (16 mL) and subsequently with NH$_3$/MeOH (0.5 M, 8 mL) eluted the desired product as the free base in the methanolic ammonia fractions. Concentration in vacuo yielded the desired product (2R,5S)-7-methyl-2-[3-methyl-4-[4-(trifluoromethyl)phenyl]-2-pyridyl]-1,7-diazaspiro[4.4]nonan-6-one (40 mg, 0.1027 mmol, 66.7% yield). To a proportion of this material (39 mg, 0.1000 mmol) was added HCl in ether (0.1 mL, 0.1000 mmol) (1 eq) and the reaction was concentrated in vacuo. The residue was then azeotroped twice with acetone (2×5 mL) and dried under vacuum, at (40° C.) for 4 hours to afford the hydrochloride salt (E17);

M/Z: 390 (M+H$^+$).

Component B was then dissolved in HCl in dioxane (4 M, 3 mL) and the reaction was stirred for 3 hours at room temperature. The reaction was concentrated in vacuo, and the residue was azeotroped with acetone (2×5 mL). The residue was then taken up in MeOH (2 mL) and loaded onto an SCX cartridge (2 g). Eluting the SCX cartridge with MeOH (16 mL) and subsequently with NH$_3$/MeOH (0.5 M, 8 mL) eluted the desired product as the free base in the methanolic ammonia fractions. Concentration in vacuo yielded the desired product (2S,5S)-7-methyl-2-[3-methyl-4-[4-(trifluoromethyl)phenyl]-2-pyridyl]-1,7-diazaspiro[4.4]nonan-6-one (20 mg, 0.0514 mmol, 33.334% yield). To this was added HCl in ether (0.05 mL, 0.0500 mmol) and the reaction mixture was concentrated in vacuo. The residue was then azeotroped twice with acetone (2×5 mL) and dried under vacuum, at (40° C.) for 4 hours to afford the hydrochloride salt (E16);

M/Z: 390 (M+H$^+$).

Example 18

(2S,5R)-7-Methyl-2-[3-methyl-4-[4-fluorophenyl]-2-pyridyl]-1,7-diazaspiro[4.4]nonan-6-one hydrochloride (E18)

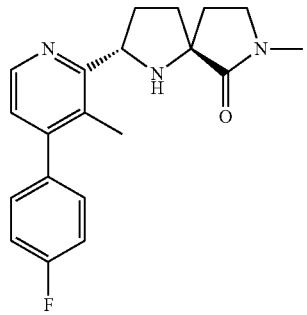 [SMILES: Cc1c(-c2ccc(F)cc2)ccnc1[C@@H]1CC[C@]2(CCN(C)C2=O)N1]

This compound was prepared from (5R)-2-(4-bromo-3-methyl-2-pyridyl)-7-methyl-1,7-diazaspiro[4.4]-nonan-6-one (which may be prepared as described in Description 10) using 4-fluorophenylboronic acid in place of 4-trifluoromethylphenyboronic acid by the method of Example 16;

M/Z: 340 (M+H$^+$).

Example 19 and Example 20

(2R,5S)-2-[4-(4-Fluorophenyl)-3-methyl-2-pyridyl]-7-methyl-1,7-diazaspiro[4.4]nonan-6-one hydrochloride (E19) and (2S,5S)-2-[4-(4-Fluorophenyl)-3-methyl-2-pyridyl]-7-methyl-1,7-diazaspiro[4.4]nonan-6-one hydrochloride (E20)

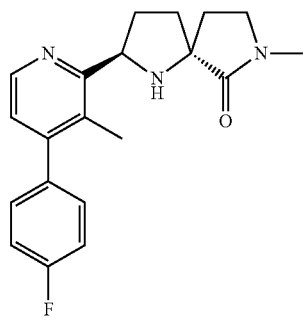

-continued

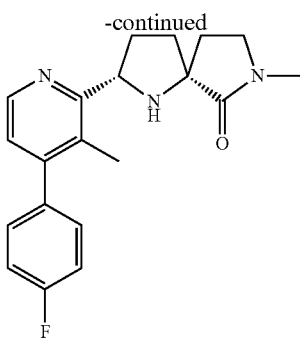

These compounds were prepared from (5S)-3-(4-bromo-3-methyl-2-pyridyl)-8-methyl-4,8-diazaspiro[4.4]-nonan-9-one (which may be prepared as described in Description 11) using 4-fluorophenylboronic acid in place of 4-trifluoromethylphenyboronic acid by the method of Example 16;
E19 M/Z: 340 (M+H+);
E20 M/Z: 340 (M+H+).

Example 21 and Example 22

2-[2-Methyl-6-[(2S,5R)-7-methyl-6-oxo-1,7-diazaspiro[4.4]-nonan-2-yl]-4-pyridyl]-4-(trifluoromethyl)-benzonitrile hydrochloride (E21) and 2-[2-Methyl-6-[(2R,5R)-7-methyl-6-oxo-1,7-diazaspiro[4.4]-nonan-2-yl]-4-pyridyl]-4-(trifluoromethyl)-benzonitrile hydrochloride (E22)

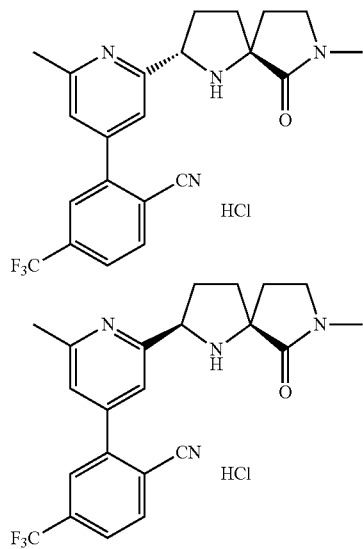

To a stirred solution of 2-[2-methyl-6-[(5R)-7-methyl-6-oxo-1,7-diazaspiro[4.4]non-1-en-2-yl]-4-pyridyl]-4-(trifluoromethyl)benzonitrile (which may be prepared as described in Description 14) (52 mg, 0.1300 mmol) in anhydrous DCM (6 mL) under nitrogen at 0° C. was added concentrated hydrochloric acid (0.01 mL, 0.1500 mmol). After stirring for 5 minutes, sodium triacetoxyborohydride (106.89 mg, 0.5000 mmol) was added portionwise. The resulting suspension was at 0° C. for 1 hour and at room temperature for a further 90 minutes. An aqueous solution of sodium carbonate (6 mL) was added and the mixture stirred for 15 minutes. The reaction mixture was extracted with dichloromethane twice and passed through a phase separation cartridge. The organic solution was concentrated at reduced pressure to give a yellow oil. This was purified by silica gel chromatography eluting with 0-10% methanol in ethyl acetate. The less polar diastereoisomer was isolated as a yellow oil (33 mg);

300 MHz $^1$H NMR $\delta_H$ (CDCl$_3$) 1.85-2.25 (6H, m), 2.5-2.65 (1H, m), 2.67 (3H, s), 2.93 (3H, s), 3.27-3.39 (2H, m), 4.75-4.82 (1H, m), 7.16 (1H, s), 7.63 (1H, s), 7.78 (2H, t), 7.95 (1H, d).

This was dissolved in DCM (3 mL) and 1M HCl in diethyl ether (0.08 mL, 0.0800 mmol) was added and the reaction mixture stirred for 10 minutes. The reaction mixture was concentrated at reduced pressure and then triturated with diethyl ether to give a colourless solid 2-[2-methyl-6-[(2S,5R)-7-methyl-6-oxo-1,7-diazaspiro[4.4]nonan-2-yl]-4-pyridyl]-4-(trifluoromethyl)-benzonitrile hydrochloride (E21) (34 mg);

M/Z: 415 (M+H+).

The more polar diastereoisomer was isolated as a yellow gum (9 mg) following additional chromatographic purification;

300 MHz $^1$H NMR $\delta_H$ (CDCl$_3$) 1.7 (1H, br s), 1.80-1.90 (1H, m), 2.04-2.23 (4H, m), 2.35-2.45 (1H, m), 2.14 (3H, s), 2.92 (3H, s), 3.29-3.45 (2H, m), 4.50 (1H, t), 7.23 (1H, s), 7.67 (1H, s), 7.80 (2H, t), 7.95 (1H, d).

To a solution of this in DCM (3 mL) was added 1M HCl in diethyl ether (0.02 mL, 0.0200 mmol) and the reaction mixture stirred for 10 minutes. The reaction mixture was concentrated at reduced pressure and then triturated with diethyl ether to give 2-[2-methyl-6-[(2R,5R)-7-methyl-6-oxo-1,7-diazaspiro[4.4]nonan-2-yl]-4-pyridyl]-4-(trifluoromethyl)-benzonitrile hydrochloride (E22) as a colourless solid (7 mg);

M/Z: 415 (M+H+).

The following Examples were prepared in a similar manner to Examples 21 and 22 with the modifications noted:

| Example | Structure | Name | Analysis | Modification |
|---|---|---|---|---|
| E23 | 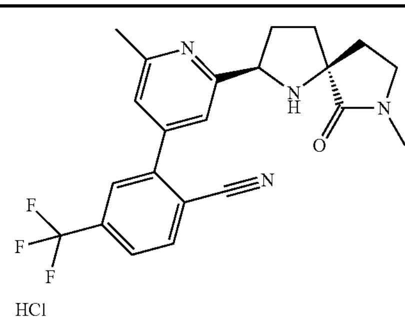 | 2-[2-Methyl-6-[(2R,5S)-7-methyl-6-oxo-1,7-diazaspiro[4.4]nonan-2-yl]-4-pyridyl]-4-(trifluoromethyl)benzonitrile hydrochloride | M/Z: 415 (M + H+) | Using D14S in place of D14R |

-continued

| Example | Structure | Name | Analysis | Modification |
|---|---|---|---|---|
| E24 | 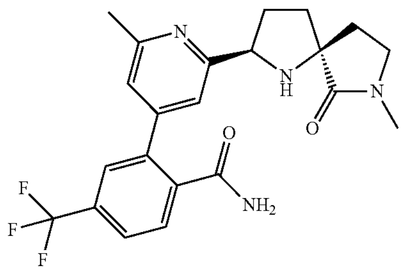 | 2-[2-Methyl-6-[(2R,5S)-7-methyl-6-oxo-1,7-diazaspiro[4.4]nonan-2-yl]-4-pyridyl]-4-(trifluoromethyl)benzamide hydrochloride | M/Z: 433 (M + H⁺) | Using D15R in place of D14S |
| E25 | 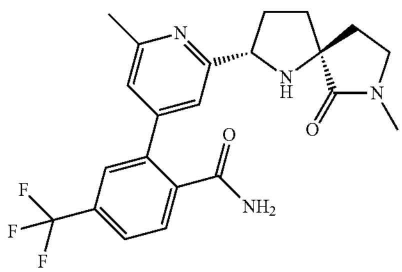 | 2-[2-Methyl-6-[(2S,5S)-7-methyl-6-oxo-1,7-diazaspiro[4.4]nonan-2-yl]-4-pyridyl]-4-(trifluoromethyl)benzamide hydrochloride | M/Z: 433 (M + H⁺) | Using D15R in place of D14S |
| E26 | 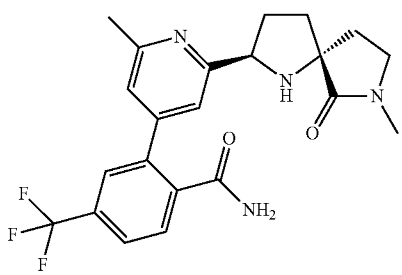 | 2-[2-Methyl-6-[(2R,5R)-7-methyl-6-oxo-1,7-diazaspiro[4.4]nonan-2-yl]-4-pyridyl]-4-(trifluoromethyl)benzamide hydrochloride | M/Z: 433 (M + H⁺) | Using D15R in place of D14R |
| E27 | 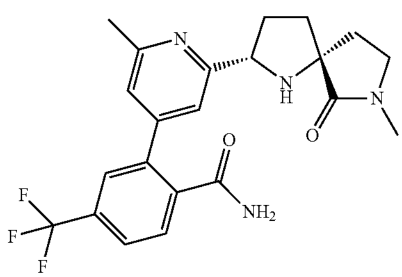 | 2-[2-Methyl-6-[(2S,5R)-7-methyl-6-oxo-1,7-diazaspiro[4.4]nonan-2-yl]-4-pyridyl]-4-(trifluoromethyl)benzamide hydrochloride | M/Z: 433 (M + H⁺) | Using D15R in place of D14R |
| E28 | 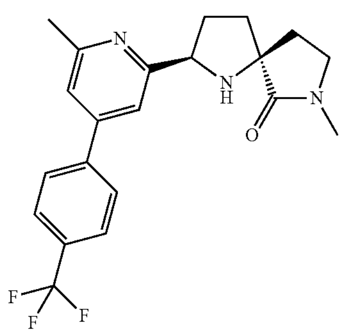 | (2R,5S)-7-Methyl-2-[6-methyl-4-[4-(trifluoromethyl)phenyl]-2-pyridyl]-1,7-diazaspiro[4.4]nonan-6-one hydrochloride | M/Z: 390 (M + H⁺) | Using D17S in place of D14R |

| Example | Structure | Name | Analysis | Modification |
|---------|-----------|------|----------|--------------|
| E29 | 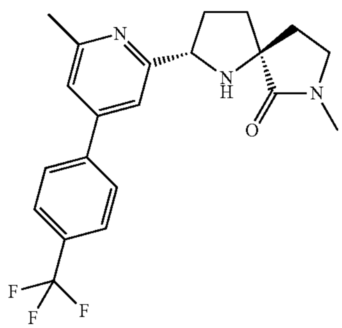 | (2S,5S)-7-Methyl-2-[6-methyl-4-[4-(trifluoromethyl)phenyl]-2-pyridyl]-1,7-diazaspiro[4.4]nonan-6-one hydrochloride | M/Z: 390 (M + H$^+$) | Using D17S in place of D14R |
| E30 | 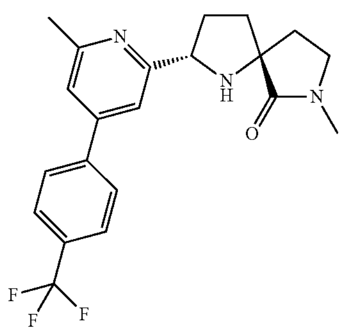 | (2S,5R)-7-Methyl-2-[6-methyl-4-[4-(trifluoromethyl)phenyl]-2-pyridyl]-1,7-diazaspiro[4.4]nonan-6-one hydrochloride | M/Z: 390 (M + H$^+$) | Using D17R in place of D14R |
| E31 | 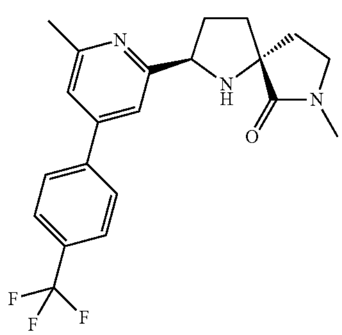 | (2R,5R)-7-Methyl-2-[6-methyl-4-[4-(trifluoromethyl)phenyl]-2-pyridyl]-1,7-diazaspiro[4.4]nonan-6-one hydrochloride | M/Z: 390 (M + H$^+$) | Using D17R in place of D14R |

Example 32 and Example 33

(2R,5S)-2-[4-(2-Fluoro-phenyl)-pyridin-2-yl]-7-methyl-1,7-diaza-spiro[4.4]nonan-6-one hydrochloride (E32) and (2S,5S)-2-[4-(2-Fluoro-phenyl)-pyridin-2-yl]-7-methyl-1,7-diaza-spiro[4.4]nonan-6-one hydrochloride (E33)

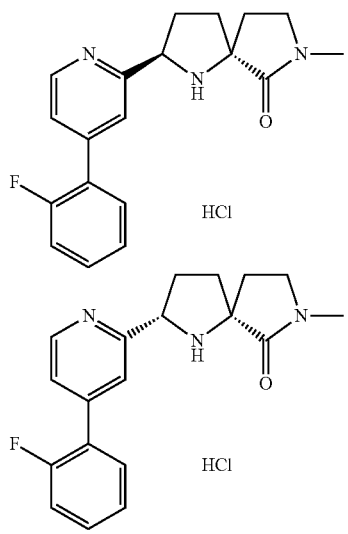

To a stirred solution of (2S)-2-[4-(2-fluoro-phenyl)-pyridin-2-yl]-7-methyl-1,7-diaza-spiro[4.4]non-1-en-6-one (which may be prepared as described in Description 18) (458 mg, 1.42 mmol) in anhydrous THF (5 mL) under nitrogen at 0° C., was added concentrated hydrochloric acid (0.12 mL, 1.42 mmol). This was followed by the addition of lithium borohydride (154.18 mg, 7.08 mmol). The mixture was left to stir at 00° C. for 2 hours. Saturated ammonium chloride (2 mL) was added to the reaction mixture. Stirring was continued for 10 minutes. The reaction mixture was extracted with DCM twice and the organic layers were collected by passing down a PhaseSep cartridge. Evaporation of solvent under reduced pressure gave a colourless oil. The latter was suspended in 5 M HCl (2 mL) and heated to 90° C. for 30 minutes. It was cooled to 00° C. whence the pH was adjusted with the careful addition of 2 M NaOH to 8. The reaction mixture was extracted with DCM twice and the organic layers were collected by passing down a PhaseSep cartridge. Evaporation of solvent under reduced pressure gave a colourless oil. This crude residue was purified by silica gel chromatography (9 g $SiO_2$) eluting with methanol in ethyl acetate in isohexane.

Evaporation of desired fractions gave product as diastereomixture (476 mg). The two isomers were separated by ChiralPak AD-H column HPLC using as eluent ethanol/n-heptane (20:80) to give the first to elute component (2S,5S)-2-[4-(2-fluoro-phenyl)-pyridin-2-yl]-7-methyl-1,7-diaza-spiro[4.4]nonan-6-one as colourless oil;

Optical rotation $\alpha[^D/_{22}]=-40.9$ (c=1, $CHCl_3$).

A DCM solution of the free base was treated with 1 M equivalent of 1 M HCl in ether, the solution evaporated and dried in vacuo at 50° C. to give the hydrochloride salt (E33) (233 mg, 0.7161 mmol, 50.6% yield) as an off-white solid. The second to elute component (2R,5S)-2-[4-(2-fluoro-phenyl)-pyridin-2-yl]-7-methyl-1,7-diaza-spiro[4.4]nonan-6-one was obtained as a colourless oil;

Optical rotation $\alpha[^D/_{22}]=+8.5$ (c=1, $CHCl_3$).

A DCM solution of this free base was treated with 1 M equivalent of 1 M HCl in ether, the solution evaporated and dried in vacuo at 50° C. to give the hydrochloride salt (E32) (51 mg, 0.1567 mmol, 11.1% yield) as an off white solid.

The following Examples were prepared in a similar manner to Examples E32 and E33 with the modifications noted:

| Example | Structure | Name | Analysis | Modification |
|---|---|---|---|---|
| E34 | 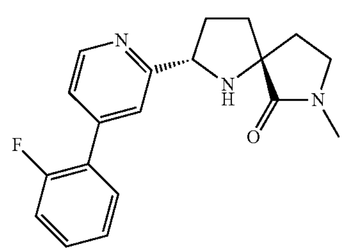 | (2S,5R)-2-[4-(2-Fluoro-phenyl)-pyridin-2-yl]-7-methyl-1,7-diaza-spiro[4.4]nonan-6-one hydrochloride | M/Z: 326 (M + H⁺) | Using D3R in place of D3S |
| E35 | 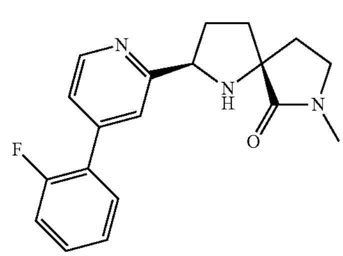 | (2R,5R)-2-[4-(2-Fluoro-phenyl)-pyridin-2-yl]-7-methyl-1,7-diaza-spiro[4.4]nonan-6-one hydrochloride | M/Z: 326 (M + H⁺) | Using D3R in place of D3S |

Examples E36 and E37

(2S,5S)-2-[4-[4-(Trifluoromethyl)phenyl]-2-pyridyl]-1,7-diazaspiro[4.4]nonan-6-one hydrochloride (E36) and (2R,5S)-2-[4-[4-(Trifluoromethyl)phenyl]-2-pyridyl]-1,7-diazaspiro[4.4]nonan-6-one hydrochloride (E37)

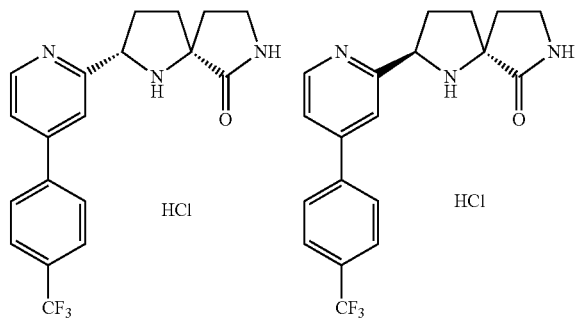

To a stirred solution of (5S)-2-[4-[4-(trifluoromethyl)phenyl]-2-pyridyl]-1,7-diazaspiro[4.4]non-1-en-6-one (which may be prepared as described in Description 20)(177 mg, 0.4900 mmol) in anhydrous DCM (10 mL) under nitrogen at 0° C. was added concentrated hydrochloric acid (0.05 mL, 0.5900 mmol). After stirring for 10 minutes, sodium triacetoxyborohydride (417.57 mg, 1.97 mmol) was added portionwise. The resulting suspension was allowed to stir at room temperature for 2 hours. An aqueous solution of sodium carbonate (6 mL) was added and the mixture stirred for 15 minutes. The reaction mixture was extracted with dichloromethane twice and passed through a phase separation cartridge. The organic solution was concentrated at reduced pressure to give a yellow solid (171 mg). A proportion of this material (165 mg, 0.4600 mmol) in MeCN (3 mL) was treated with triethylamine (0.06 mL, 0.4600 mmol) followed by tert-butoxycarbonyl tert-butyl carbonate (99.65 mg, 0.4600 mmol). The reaction mixture was stirred for 16 hours at room temperature. A further quantity of Boc$_2$O (50 mg) was added and the reaction stirred for a further 5 hours. Further quantities of tert-butoxycarbonyl tert-butyl carbonate (99.65 mg, 0.4600 mmol) and triethylamine (0.06 mL, 0.4600 mmol) were added and the reaction mixture stirred for 16 hours. The reaction mixture was concentrated at reduced pressure. The products were purified by silica gel chromatography eluting with EtOAc followed by gradient elution with 0-10% MeOH in EtOAc.

The less polar compound (eluting in EtOAc) was isolated as a pale yellow oil (49 mg) which was further purified by chiral HPLC using a Chiralpak AD-H preparative column using 20% EtOH/heptane to give tert-butyl (2S,5S)-6-oxo-2-[4-[4-(trifluoromethyl)phenyl]-2-pyridyl]-1,7-diazaspiro[4.4]nonane-1-carboxylate (18 mg) as a colourless solid;

M/Z: 462 (M+H$^+$).

The more polar component, also a pale yellow oil (101 mg) was further purified by chiral HPLC using a Chirakpak AD-H preparative column using 20% EtOH/heptane to give tert-butyl (2R,5S)-6-oxo-2-[4-[4-(trifluoromethyl)phenyl]-2-pyridyl]-1,7-diazaspiro[4.4]nonane-1-carboxylate as a colourless solid (45 mg);

M/Z: 462 (M+H$^+$).

4 M HCl in dioxane (3 mL, 12 mmol) was added to tert-butyl (2S,5S)-6-oxo-2-[4-[4-(trifluoromethyl)phenyl]-2-pyridyl]-1,7-diazaspiro[4.4]nonane-1-carboxylate (18 mg, 0.0400 mmol) and the reaction mixture stirred for 16 hours. The mixture was concentrated at reduced pressure and then re-dissolved in methanol. The solution was applied to an SCX column which was eluted with methanol, followed by 0.5 M ammonia in methanol. Basic product containing fractions were combined and concentrated to give (2S,5S)-2-[4-[4-(trifluoromethyl)phenyl]-2-pyridyl]-1,7-diazaspiro[4.4]nonan-6-one as a colourless oil (14 mg);

300 MHz $^1$H NMR $\delta_H$ (CDCl$_3$) 1.87-1.96 (1H, m), 2.05-2.47 (6H, m), 3.20-3.48 (2H, m), 4.56 (1H, t), 5.85 (1H, br s), 7.39 (1H, d), 7.80 (4H, abq), 8.01 (1H, s), 8.68 (1H, d).

A solution of this oil in DCM (3 mL) was added to 1M HCl in diethyl ether (0.04 mL, 0.0400 mmol) and the reaction mixture stirred for 10 minutes. The reaction mixture was concentrated at reduced pressure and then triturated with diethyl ether to give hydrochloride salt (E36) as a colourless solid (15 mg);

M/Z: 362 (M+H$^+$).

4 M HCl in dioxane (3 mL, 12 mmol) was added to the tert-butyl (2R,5S)-6-oxo-2-[4-[4-(trifluoromethyl)phenyl]-2-pyridyl]-1,7-diazaspiro[4.4]nonane-1-carboxylate and the reaction mixture stirred for 16 hours. The mixture was concentrated at reduced pressure and then re-dissolved in methanol. The solution was applied to an SCX column which was eluted with methanol, followed by 0.5 M ammonia in methanol. Basic product containing fractions were combined and concentrated to give (2R,5S)-2-[4-[4-(trifluoromethyl)phenyl]-2-pyridyl]-1,7-diazaspiro[4.4]nonan-6-one as a colourless solid (36 mg);

300 MHz $^1$H NMR $\delta_H$ (CDCl$_3$) 1.7 (1H, br s), 1.95-2.06 (3H, m), 2.10-2.39 (3H, m), 2.51-2.62 (1H, m), 3.30-3.47 (2H, m), 4.79 (1H, t), 5.65 (1H, br s), 7.40 (1H, d), 7.75 (1H, s), 7.77 (1H, s), 8.67 (1H, d).

To a solution of this in DCM (3 mL) was added 1 M HCl in diethyl ether (0.1 mL, 0.1000 mmol) and the reaction mixture stirred for 10 minutes. The reaction mixture was concentrated at reduced pressure and the product triturated with diethyl ether to give the hydrochloride salt (E37) as a colourless solid (32 mg);

M/Z: 362 (M+H$^+$).

The following Examples were prepared in a similar manner to Examples E36 and E37 with the modifications and alternative boronic acids noted:

| Example | Structure | Name | Analysis | Modification |
|---|---|---|---|---|
| E38 | HCl | (2S,5S)-2-[4-[2-Fluoro-4-(trifluoro-methyl)phenyl]-2-pyridyl]-1,7-diazaspiro[4.4]nonan-6-one hydrochloride | M/Z: 380 (M + H⁺) | Using (2-fluoro-4-trifluoromethyl-phenyl boronic acid |
| E39 | HCl | (2R,5S)-2-[4-[2-Fluoro-4-(trifluoro-methyl)phenyl]-2-pyridyl]-1,7-diazaspiro[4.4]nonan-6-one hydrochloride | M/Z: 380 (M + H⁺) | Using (2-fluoro-4-trifluoromethyl-phenyl boronic acid |
| E40 | HCl | (2S,5S)-7-Methyl-2-[5-methyl-4-[4-(trifluoromethyl)phenyl]-2-pyridyl]-1,7-diazaspiro[4.4]nonan-6-one hydrochloride | M/Z: 390 (M + H⁺) | Using D23S in place of D19 |
| E41 | HCl | (2R,5S)-7-Methyl-2-[5-methyl-4-[4-(trifluoromethyl)phenyl]-2-pyridyl]-1,7-diazaspiro[4.4]nonan-6-one hydrochloride | M/Z: 390 (M + H⁺) | Using D23S in place of D19 |

| Example | Structure | Name | Analysis | Modification |
|---|---|---|---|---|
| E42 | (structure shown) HCl | (2R,5R)-7-Methyl-2-[5-methyl-4-[4-(trifluoromethyl)phenyl]-2-pyridyl]-1,7-diazaspiro[4.4]nonan-6-one hydrochloride | M/Z: 390 (M + H$^+$) | Using D23R in place of D19 |
| E43 | (structure shown) HCl | (2S,5R)-7-Methyl-2-[5-methyl-4-[4-(trifluoromethyl)phenyl]-2-pyridyl]-1,7-diazaspiro[4.4]nonan-6-one hydrochloride | M/Z: 390 (M + H$^+$) | Using D23R in place of D19 |
| E44 | (structure shown) HCl | (2S,5S)-8,8-Dimethyl-2-[4-[4-(trifluoromethyl)phenyl]-2-pyridyl]-1,7-diazaspiro[4.4]nonan-6-one hydrochloride | M/Z: 390 (M + H$^+$) | Using D30S in place of D19S |

| Example | Structure | Name | Analysis | Modification |
|---------|-----------|------|----------|--------------|
| E45 | HCl | (2R,5S)-8,8-Dimethyl-2-[4-[4-(trifluoromethyl)phenyl]-2-pyridyl]-1,7-diazaspiro[4.4]nonan-6-one hydrochloride | M/Z: 390 (M + H⁺) | Using D30S in place of D19S |
| E46 | HCl | (2R,5R)-8,8-Dimethyl-2-[4-[4-(trifluoromethyl)phenyl]-2-pyridyl]-1,7-diazaspiro[4.4]nonan-6-one hydrochloride | M/Z: 390 (M + H⁺) | Using D30R in place of D19R |
| E47 | HCl | (2S,5R)-8,8-Dimethyl-2-[4-[4-(trifluoromethyl)phenyl]-2-pyridyl]-1,7-diazaspiro[4.4]nonan-6-one hydrochloride | M/Z: 390 (M + H⁺) | Using D30R in place of D19R |

The following Examples were prepared in a similar manner to Examples E21 and E22 with the modifications noted:

| Example | Structure | Name | Analysis | Modification |
|---|---|---|---|---|
| E48 | 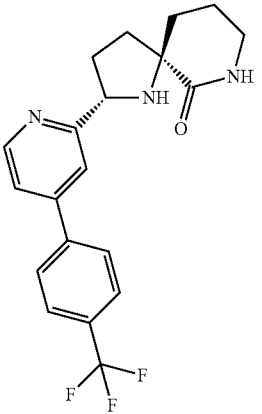 HCl | (2S,5R)-2-[4-(4-Trifluoromethyl-phenyl)-pyridin-2-yl]-1,7-diaza-spiro[4.5]decan-6-one hydrochloride | M/Z: 376 (M + H$^+$) | Using D31R in place of D14R |
| E49 | 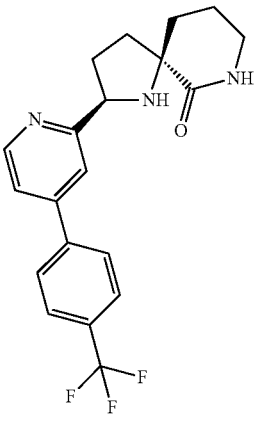 HCl | (2R,5R)-2-[4-(4-Trifluoromethyl-phenyl)-pyridin-2-yl]-1,7-diaza-spiro[4.5]decan-6-one hydrochloride | M/Z: 376 (M + H$^+$) | Using D31R in place of D14R |
| E50 | 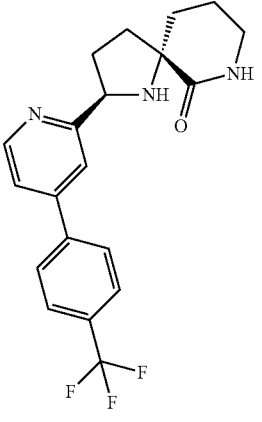 HCl | (2R,5S)-2-[4-(4-Trifluoromethyl-phenyl)-pyridin-2-yl]-1,7-diaza-spiro[4.5]decan-6-one hydrochloride | M/Z: 376 (M + H$^+$); Single crystal X-ray crystallography | Using D31S in place of D14S |

-continued

| Example | Structure | Name | Analysis | Modification |
|---|---|---|---|---|
| E51 | (structure shown, HCl salt) | (2S,5S)-2-[4-(4-Trifluoromethyl-phenyl)-pyridin-2-yl]-1,7-diaza-spiro[4.5]decan-6-one hydrochloride | M/Z: 376 (M + H$^+$) | Using D31S in place of D14S |

The following Examples were prepared in a similar manner to Examples E48 to E51 with the modifications noted:

| Example | Structure | Name | Analysis | Modification |
|---|---|---|---|---|
| E52 | (structure shown, HCl salt) | (2R,5S)-7-Methyl-2-[4-(4-trifluoromethyl-phenyl)-pyridin-2-yl]-1,7-diaza-spiro[4.4]nonan-6-one hydrochloride | M/Z: 376 (M + H$^+$) | Using 3-amino-1-methyl-pyrrolidin-2-one in place of 3-amino-piperidin-2-one |
| E53 | (structure shown, HCl salt) | (2S,5S)-7-Methyl-2-[4-(4-trifluoromethyl-phenyl)-pyridin-2-yl]-1,7-diaza-spiro[4.4]nonan-6-one hydrochloride | M/Z: 376 (M + H$^+$) | Using 3-amino-1-methyl-pyrrolidin-2-one in place of 3-amino-piperidin-2-one |

-continued

| Example | Structure | Name | Analysis | Modification |
|---|---|---|---|---|
| E54 | 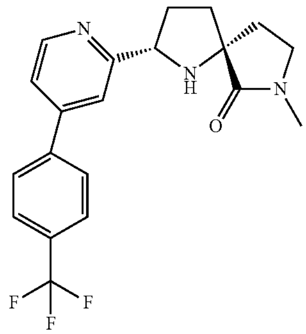 | (2S,5R)-7-Methyl-2-[4-(4-trifluoromethyl-phenyl)-pyridin-2-yl]-1,7-diaza-spiro[4.4]nonan-6-one hydrochloride | M/Z: 376 (M + H$^+$) | Using 3-amino-1-methyl-pyrrolidin-2-one in place of 3-amino-piperidin-2-one |
| E55 | 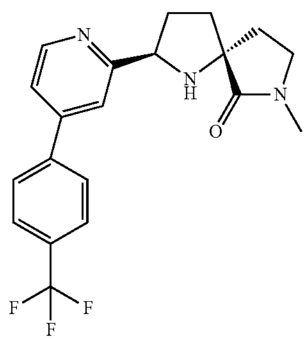 | (2R,5R)-7-Methyl-2-[4-(4-trifluoromethyl-phenyl)-pyridin-2-yl]-1,7-diaza-spiro[4.4]nonan-6-one hydrochloride | M/Z: 376 (M + H$^+$) | Using 3-amino-1-methyl-pyrrolidin-2-one in place of 3-amino-piperidin-2-one |

The following Examples were prepared in a similar manner to Examples E21 and E22 with the modifications noted:

| Example | Structure | Name | Analysis | Modification |
|---|---|---|---|---|
| E56 | 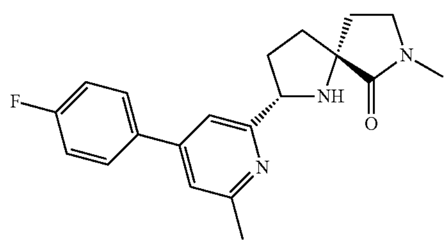 | (2S,5R)-2-[4-(4-Fluorophenyl)-6-methyl-2-pyridyl]-7-methyl-1,7-diazaspiro[4.4]nonan-6-one hydrochloride | M/Z: 340 (M + H$^+$) | Using D33R in place of D14R |
| E57 | 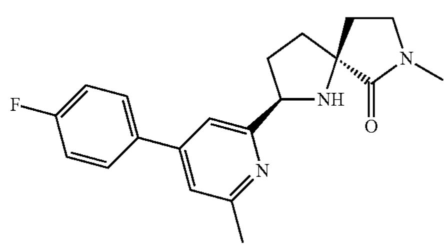 | (2R,5S)-2-[4-(4-Fluorophenyl)-6-methyl-2-pyridyl]-7-methyl-1,7-diazaspiro[4.4]nonan-6-one hydrochloride | M/Z: 340 (M + H$^+$) | As Example 56 but using D32S in place of D32R |

-continued

| Example | Structure | Name | Analysis | Modification |
|---|---|---|---|---|
| E58 | HCl | (2R,5S)-2-[5-Fluoro-4-[4-(trifluoromethyl)phenyl]-2-pyridyl]-7-methyl-1,7-diazaspiro[4.4]nonan-6-one hydrochloride | M/Z: 394 (M + H$^+$) | Using D35S in place of D13 |
| E59 | HCl | (2S,5S)-2-[5-Fluoro-4-[4-(trifluoromethyl)phenyl]-2-pyridyl]-7-methyl-1,7-diazaspiro[4.4]nonan-6-one hydrochloride | M/Z: 394 (M + H$^+$) | Using D35S in place of D13 |
| E60 | HCl | (2S,5R)-2-[5-Fluoro-4-[4-(trifluoromethyl)phenyl]-2-pyridyl]-7-methyl-1,7-diazaspiro[4.4]nonan-6-one hydrochloride | M/Z: 394 (M + H$^+$) | Using D35R in place of D13 |

| Example | Structure | Name | Analysis | Modification |
|---|---|---|---|---|
| E61 | HCl | (2R,5R)-2-[5-Fluoro-4-[4-(trifluoromethyl)phenyl]-2-pyridyl]-7-methyl-1,7-diazaspiro[4.4]nonan-6-one hydrochloride | M/Z: 394 (M + H⁺) | Using D35R in place of D13 |
| E62 | HCl | (2R,5S)-2-[5-tert-Butoxy-4-[4-(trifluoromethyl)-phenyl]-2-pyridyl]-7-methyl-1,7-diazaspiro[4.4]nonan-6-one hydrochloride | M/Z: 448 (M + H⁺) | Using D37S in place of D14R |
| E63 | HCl | (2S,5S)-2-[5-tert-Butoxy-4-[4-(trifluoromethyl)-phenyl]-2-pyridyl]-7-methyl-1,7-diazaspiro[4.4]nonan-6-one hydrochloride | M/Z: 448 (M + H⁺) | Using D37S in place of D14R |

| Example | Structure | Name | Analysis | Modification |
|---|---|---|---|---|
| E64 | 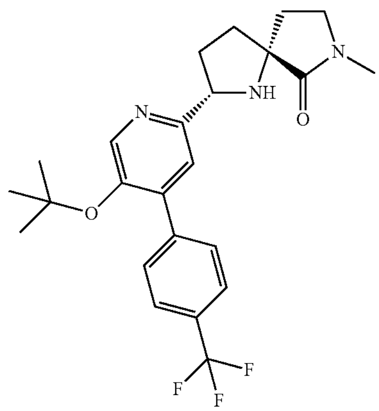 | (2S,5R)-2-[5-tert-Butoxy-4-[4-(trifluoromethyl)-phenyl]-2-pyridyl]-7-methyl-1,7-diazaspiro[4.4]nonan-6-one hydrochloride | M/Z: 448 (M + H$^+$) | Using D37R in place of D14R |
| E65 | 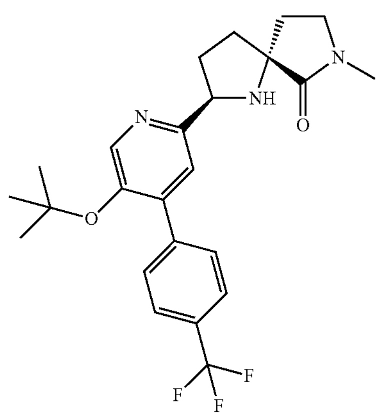 | (2R,5R)-2-[5-tert-Butoxy-4-[4-(trifluoromethyl)-phenyl]-2-pyridyl]-7-methyl-1,7-diazaspiro[4.4]nonan-6-one hydrochloride | M/Z: 448 (M + H$^+$) | Using D37R in place of D14R |

The following Examples were prepared in a similar manner to Examples E32 and E33 with the modifications and alternative boronic acids noted:

| Example | Structure | Name | Analysis | Modification |
|---|---|---|---|---|
| E66 | 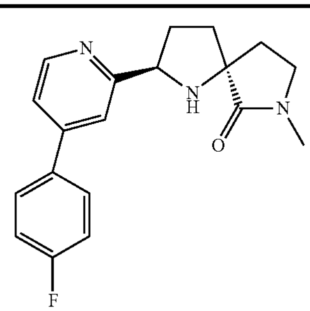 | (2R,5S)-2-[4-(4-Fluorophenyl)-2-pyridyl]-7-methyl-1,7-diazaspiro[4.4]nonan-6-one hydrochloride | M/Z: 326 (M + H$^+$) | Using 4-fluorophenyl-boronic acid |

-continued

| Example | Structure | Name | Analysis | Modification |
|---|---|---|---|---|
| E67 | 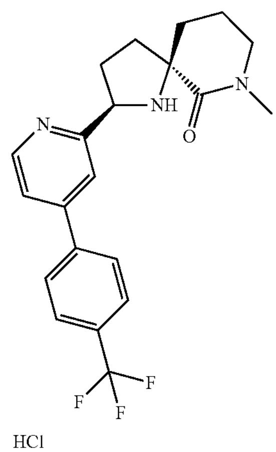 [SMILES: CN1CCC[C@@]2(CC[C@H](c3cc(-c4ccc(C(F)(F)F)cc4)ccn3)N2)C1=O ; Cl] | (2R,5R)-7-Methyl-2-[4-(4-trifluoromethyl-phenyl)-pyridin-2-yl]-1,7-diaza-spiro[4.5]decan-6-one hydrochloride | M/Z: 390 (M + H$^+$) | Using 3-amino-1-methyl-piperidin-2-one in place of 3-amino-1-methyl-pyrrolidin-2-one |
| E68 | 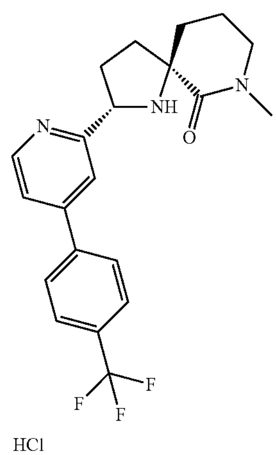 [SMILES: CN1CCC[C@@]2(CC[C@@H](c3cc(-c4ccc(C(F)(F)F)cc4)ccn3)N2)C1=O ; Cl] | (2S,5R)-7-Methyl-2-[4-(4-trifluoromethyl-phenyl)-pyridin-2-yl]-1,7-diaza-spiro[4.5]decan-6-one hydrochloride | M/Z: 390 (M + H$^+$) | Using 3-amino-1-methyl-piperidin-2-one in place of 3-amino-1-methyl-pyrrolidin-2-one |
| E69 | 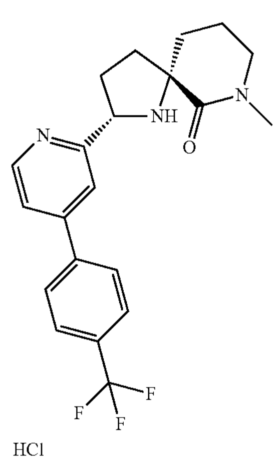 [SMILES: CN1CCC[C@]2(CC[C@@H](c3cc(-c4ccc(C(F)(F)F)cc4)ccn3)N2)C1=O ; Cl] | (2S,5S)-7-Methyl-2-[4-(4-trifluoromethyl-phenyl)-pyridin-2-yl]-1,7-diaza-spiro[4.5]decan-6-one hydrochloride | M/Z: 390 (M + H$^+$) | Using 3-amino-1-methyl-piperidin-2-one in place of 3-amino-1-methyl-pyrrolidin-2-one |

-continued

| Example | Structure | Name | Analysis | Modification |
|---|---|---|---|---|
| E70 | 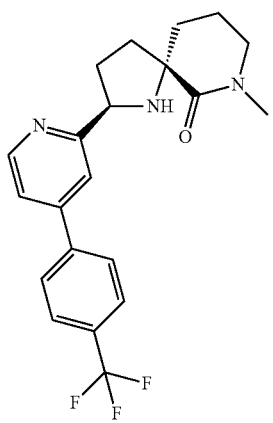 HCl | (2R,5S)-7-Methyl-2-[4-(4-trifluoromethyl-phenyl)-pyridin-2-yl]-1,7-diaza-spiro[4.5]decan-6-one hydrochloride | M/Z: 390 (M + H$^+$) | Using 3-amino-1-methyl-piperidin-2-one in place of 3-amino-1-methyl-pyrrolidin-2-one |
| E71 | 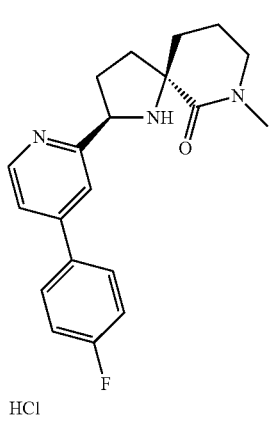 [SMILES: CN1CCC[C@@]2(CC[C@H](c3cc(-c4ccc(F)cc4)ccn3)N2)C1=O ; Cl] HCl | (2R,5R)-2-[4-(4-Fluoro-phenyl)-pyridin-2-yl]-7-methyl-1,7-diaza-spiro[4.5]decan-6-one hydrochloride | M/Z: 340 (M + H$^+$) | As Example 67 but using 4-fluoro-phenyl-boronic acid |
| E72 | 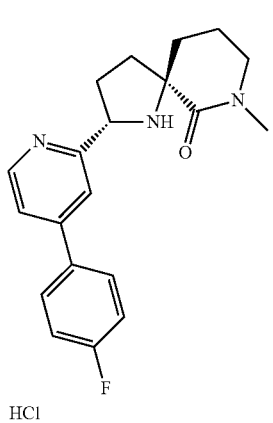 [SMILES: CN1CCC[C@@]2(CC[C@@H](c3cc(-c4ccc(F)cc4)ccn3)N2)C1=O ; Cl] HCl | (2S,5R)-2-[4-(4-Fluoro-phenyl)-pyridin-2-yl]-7-methyl-1,7-diaza-spiro[4.5]decan-6-one hydrochloride | M/Z: 340 (M + H$^+$) | As Example 68 but using 4-fluoro-phenyl-boronic acid |

| Example | Structure | Name | Analysis | Modification |
|---|---|---|---|---|
| E73 | 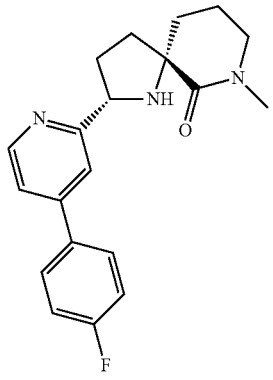 HCl | (2S,5S)-2-[4-(4-Fluoro-phenyl)-pyridin-2-yl]-7-methyl-1,7-diaza-spiro[4.5]decan-6-one hydrochloride | M/Z: 340 (M + H+) | As Example 69 but using 4-fluoro-phenyl-boronic acid |
| E74 | 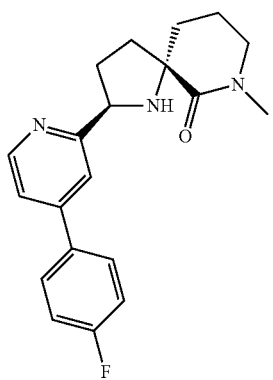 HCl | (2R,5S)-2-[4-(4-Fluoro-phenyl)-pyridin-2-yl]-7-methyl-1,7-diaza-spiro[4.5]decan-6-one hydrochloride | M/Z: 340 (M + H+) | As Example 70 but using 4-fluoro-phenyl-boronic acid |

The following Examples were prepared in a similar manner to Example 1 with the modifications being the use of alternative boronic acids and esters noted:

| Example | Structure | Name | Analysis | Modification |
|---|---|---|---|---|
| E75 | 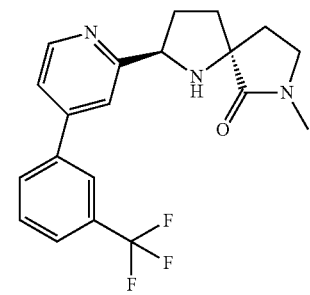 [SMILES: CN1CC[C@@]2(CC[C@H](c3cc(-c4cccc(C(F)(F)F)c4)ccn3)N2)C1=O] HCl | (2R,5S)-7-Methyl-2-[4-[3-(trifluoromethyl)phenyl]-2-pyridyl]-1,7-diazaspiro[4.4]nonan-6-one hydrochloride | M/Z: 376 (M + H+) | [3-(trifluoromethyl)-phenyl]boronic acid |

-continued

| Example | Structure | Name | Analysis | Modification |
|---|---|---|---|---|
| E76 | 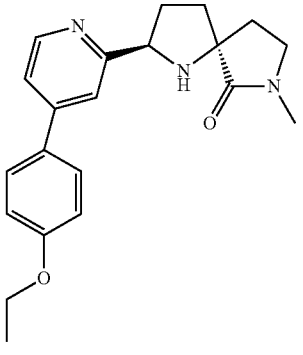 [SMILES: CCOc1ccc(-c2ccnc([C@H]3CC[C@@]4(CCN(C)C4=O)N3)c2)cc1] HCl | (2R,5S)-2-[4-(4-Ethoxyphenyl)-2-pyridyl]-7-methyl-1,7-diazaspiro[4.4]nonan-6-one hydrochloride | M/Z: 352 (M + H$^+$) | (4-ethoxyphenyl)-boronic acid |
| E77 | 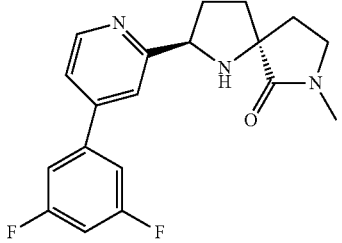 [SMILES: CN1CC[C@@]2(CC[C@H](c3cc(-c4cc(F)cc(F)c4)ccn3)N2)C1=O] HCl | (2R,5S)-2-[4-(3,5-Difluorophenyl)-2-pyridyl]-7-methyl-1,7-diazaspiro[4.4]nonan-6-one hydrochloride | M/Z: 344 (M + H$^+$) | (3,5-difluorophenyl)-boronic acid |
| E78 | 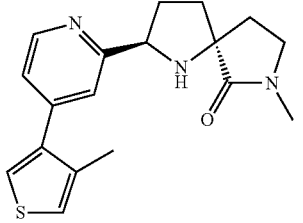 [SMILES: Cc1cscc1-c1ccnc([C@H]2CC[C@@]3(CCN(C)C3=O)N2)c1] HCl | (2R,5S)-7-Methyl-2-[4-(4-methyl-3-thienyl)-2-pyridyl]-1,7-diazaspiro[4.4]nonan-6-one hydrochloride | M/Z: 328 (M + H$^+$) | (4-methyl-3-thienyl)-boronic acid |
| E79 | 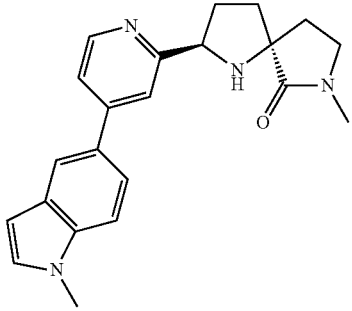 [SMILES: CN1CC[C@@]2(CC[C@H](c3cc(-c4ccc5c(ccn5C)c4)ccn3)N2)C1=O] HCl | (2R,5S)-7-Methyl-2-[4-(1-methylindol-5-yl)-2-pyridyl]-1,7-diazaspiro[4.4]nonan-6-one hydrochloride | M/Z: 361 (M + H$^+$) | (1-methylindol-5-yl)boronic acid |

-continued

| Example | Structure | Name | Analysis | Modification |
|---|---|---|---|---|
| E80 | 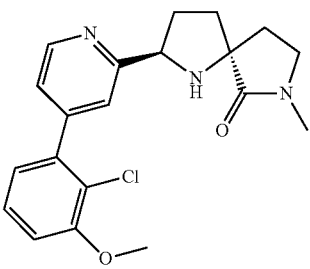 [SMILES: COc1cccc(-c2ccnc([C@H]3CC[C@@]4(CCN(C)C4=O)N3)c2)c1Cl] HCl | (2R,5S)-2-[4-(2-Chloro-3-methoxy-phenyl)-2-pyridyl]-7-methyl-1,7-diazaspiro[4.4]nonan-6-one hydrochloride | M/Z: 372, 374 (M + H$^+$) | 2-(2-chloro-3-methoxy-phenyl)-4,4,5,5-tetramethyl-1,3,2-dioxaborolane |
| E81 | 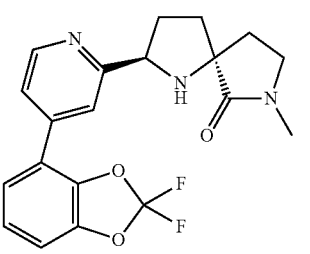 [SMILES: CN1CC[C@@]2(CC[C@H](c3cc(-c4cccc5c4OC(F)(F)O5)ccn3)N2)C1=O] HCl | (2R,5S)-2-[4-(2,2-Difluoro-1,3-benzodioxol-4-yl)-2-pyridyl]-7-methyl-1,7-diazaspiro[4.4]nonan-6-one hydrochloride | M/Z: 388 (M + H$^+$) | (2,2-difluoro-1,3-benzodioxol-4-yl)boronic acid |
| E82 | 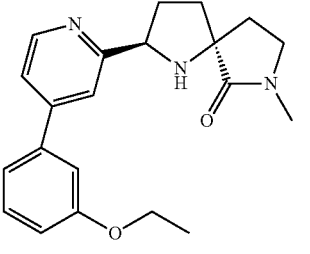 [SMILES: CCOc1cccc(-c2ccnc([C@H]3CC[C@@]4(CCN(C)C4=O)N3)c2)c1] HCl | (2R,5S)-2-[4-(3-Ethoxyphenyl)-2-pyridyl]-7-methyl-1,7-diazaspiro[4.4]nonan-6-one hydrochloride | M/Z: 352 (M + H$^+$) | (3-ethoxyphenyl)-boronic acid |
| E83 | 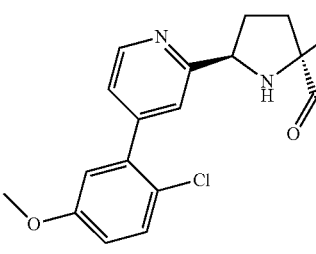 HCl | (2R,5S)-2-[4-(2-Chloro-5-methoxy-phenyl)-2-pyridyl]-7-methyl-1,7-diazaspiro[4.4]nonan-6-one hydrochloride | M/Z: 372, 374 (M + H$^+$) | 2-chloro-5-methoxyphenyl-boronic acid |
| E84 | 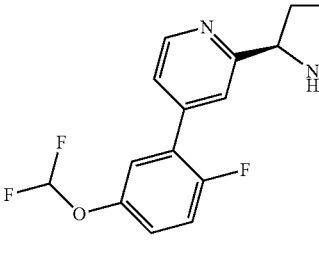 HCl | (2R,5S)-2-[4-[5-(Difluoromethoxy)-2-fluoro-phenyl]-2-pyridyl]-7-methyl-1,7-diazaspiro[4.4]nonan-6-one hydrochloride | M/Z: 392 (M + H$^+$) | 2-[5-(difluoromethoxy)-2-fluoro-phenyl]-4,4,5,5-tetramethyl-1,3,2-dioxaborolane (D38) |

The following Examples were prepared in a similar manner to Example E56 with the alternative aryl bromide noted:

| Example | Structure | Name | Analysis | Modification |
|---|---|---|---|---|
| E85 | 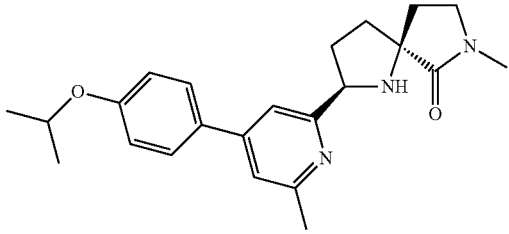<br>HCl | (2R,5S)-2-[4-(4-Isopropoxyphenyl)-6-methyl-2-pyridyl]-7-methyl-1,7-diazaspiro[4.4]nonan-6-one hydrochloride | M/Z: 390 (M + H$^+$) | Using 4-isopropoxy-phenyl-bromide |
| E86 | 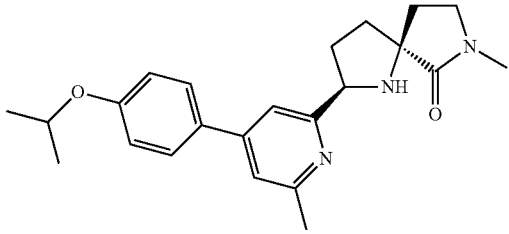 [SMILES: Cc1cc(-c2ccc(OC(C)C)cc2)cc([C@H]2CC[C@@]3(CCN(C)C3=O)N2)n1]<br>HCl | (2S,5S)-2-[4-(4-Isopropoxyphenyl)-6-methyl-2-pyridyl]-7-methyl-1,7-diazaspiro[4.4]nonan-6-one hydrochloride | M/Z: 380 (M + H$^+$) | Using 4-isopropoxy-phenyl-bromide |
| E87 | 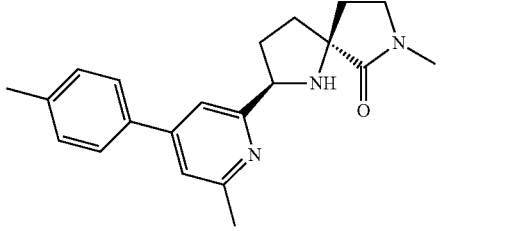<br>HCl | (2R,5S)-7-Methyl-2-[6-methyl-4-(p-tolyl)-2-pyridyl]-1,7-diazaspiro[4.4]nonan-6-one hydrochloride | M/Z: 336 (M + H$^+$) | Using 4-methyl-phenyl-bromide |
| E88 | 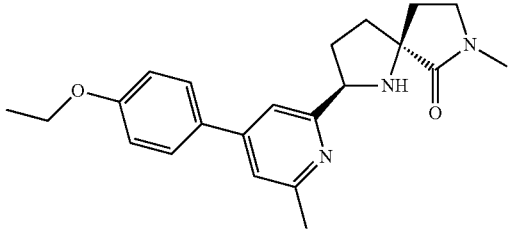 [SMILES: CCOc1ccc(-c2cc(C)nc([C@H]3CC[C@@]4(CCN(C)C4=O)N3)c2)cc1]<br>HCl | (2S,5S)-2-[4-(4-Ethoxyphenyl)-6-methyl-2-pyridyl]-7-methyl-1,7-diazaspiro[4.4]nonan-6-one hydrochloride | M/Z: 366 (M + H$^+$) | Using 4-ethoxy-phenyl-bromide |
| E89 | 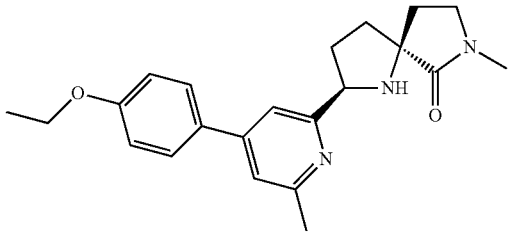 [SMILES: CCOc1ccc(-c2cc(C)nc([C@H]3CC[C@@]4(CCN(C)C4=O)N3)c2)cc1]<br>HCl | (3R,5S)-3-[4-(4-Ethoxyphenyl)-6-methyl-2-pyridyl]-8-methyl-4,8-diazaspiro[4.4]nonan-9-one hydrochloride | M/Z: 366 (M + H$^+$) | Using 4-ethoxy-phenyl-bromide |

The following Examples were prepared in a similar manner to Examples E21 and E22 with the alternative boronic acids noted:

| Example | Structure | Name | Analysis | Modification |
|---|---|---|---|---|
| E90 | HCl | (3R,5R)-3-[4-[2-Methoxy-4-(trifluoromethyl)phenyl]-6-methyl-2-pyridyl]-8-methyl-4,8-diazaspiro[4.4]nonan-9-one hydrochloride | M/Z: 420 (M + H$^+$) | Using 2-methoxy-4-trifluoromethyl-phenyl-boronic acid |
| E91 | HCl | (3S,5R)-3-[4-[2-Methoxy-4-(trifluoromethyl)phenyl]-6-methyl-2-pyridyl]-8-methyl-4,8-diazaspiro[4.4]nonan-9-one hydrochloride | M/Z: 420 (M + H$^+$) | Using 2-methoxy-4-trifluoromethyl-phenyl-boronic acid |
| E92 | HCl | (2S,5S)-2-[4-(5-Ethoxy-2-fluoro-phenyl)-6-methyl-pyridin-2-yl]-7-methyl-1,7-diaza-spiro[4.4]nonan-6-one hydrochloride | M/Z: 384 (M + H$^+$) | Using 2-fluoro-5-ethoxy-phenyl-boronic acid |
| E93 | HCl | (2R,5S)-2-[4-(5-Ethoxy-2-fluoro-phenyl)-6-methyl-pyridin-2-yl]-7-methyl-1,7-diaza-spiro[4.4]nonan-6-one hydrochloride | M/Z: 384 (M + H$^+$) | Using 2-fluoro-5-ethoxy-phenyl-boronic acid |

Example 94

(2R,5S)-2-[6-Methyl-4-[4-(trifluoromethyl)phenyl]-2-pyridyl]-1,7-diazaspiro[4.4]nonan-6-one hydrochloride (E94)

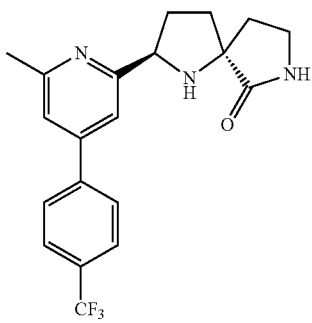 [SMILES: Cc1cc(-c2ccc(C(F)(F)F)cc2)cc([C@H]2CC[C@@]3(CCNC3=O)N2)n1]

1 M tetra-n-butylammonium fluoride in THF (1.43 mL, 1.43 mmol) then ethylenediamine (0.19 mL, 2.87 mmol) were successively added to a stirred solution of (2R,5S)-2-[6-methyl-4-[4-(trifluoromethyl)-phenyl]-2-pyridyl]-7-(2-trimethylsilylethoxymethyl)-1,7-diazaspiro[4.4]nonan-6-one (which may be prepared as described in Description 45) (145 mg, 0.2900 mmol) in dry THF (4 mL) in a 20 mL microwave vial. It was then sealed under $N_2$ and heated in a microwave reactor at 120° C. for 0.5 hours (3 bar pressure recorded). Further 1 M tetra-n-butylammonium fluoride in THF (1.43 mL, 1.43 mmol) was added and the solution microwaved for a further 0.5 hours at 120° C. More 1 M tetra-n-butylammonium fluoride in THF (1.43 mL, 1.43 mmol) was added and the solution microwaved for a further 0.5 hours at 120° C. More 1 M tetra-n-butylammonium fluoride in THF (1.43 mL, 1.43 mmol) was added and the solution microwaved for a further 0.5 hours at 120° C. The reaction mixture was evaporated to a residue which was dissolved in EtOAc (25 mL) and the solution washed with water (2×20 mL). The latter was re-extracted with EtOAc (2×20 mL) and the combined organic extracts were dried ($MgSO_4$) and evaporated to an oil, which was dried at room temperature under vaccum overnight. The oil separated into a colourless mobile phase and a light yellow, viscous, immobile oil. The former was removed to leave the viscous oil. This was purified by silica gel column chromatography. The oil was dissolved in DCM (3 mL) and the solution applied to a 10 g cartridge which was eluted on a Biotage SP4 system with a gradient of solvent A:DCM (0-80%) where solvent A=MeOH/DCM/1 M $NH_3$-MeOH (10:90:4). Relevant fractions were pooled and evaporated to a light yellow oil which was stirred with iso-hexane (2×2 mL), which was decanted leaving an insoluble oil. This was dissolved in DCM (2 mL) and 1 M HCl in $Et_2O$ (190 µL, 1.05 equivalent) was added. The solution was evaporated to a foam. To the foam was added $Et_2O$ (2 mL) and the mixture was stirred for 2 hours until a cream solid was obtained. The supernatant was decanted off and the solid was dried at room temperature under vacuum overnight to form (2R,5S)-2-[6-methyl-4-[4-(trifluoro-methyl)phenyl]-2-pyridyl]-1,7-diazaspiro-[4.4]nonan-6-one hydrochloride (E94) (50 mg);

M/Z: 376 (M+H$^+$).

The following Examples were prepared in a similar manner to Example E94 with the modifications and alternative boronic acids noted:

| Example | Structure | Name | Analysis | Modification |
|---|---|---|---|---|
| E95 | | (2S,5R)-2-[6-Methyl-4-[4-(trifluoromethyl)phenyl]-2-pyridyl]-1,7-diazaspiro[4.4]nonan-6-one hydrochloride | M/Z: 376 (M + H$^+$) | Using D43R in place of D43S |
| E96 | | (2R,5R)-2-[6-Methyl-4-[4-(trifluoromethyl)phenyl]-2-pyridyl]-1,7-diazaspiro[4.4]nonan-6-one hydrochloride | M/Z: 376 (M + H$^+$); single crystal X-ray crystallography | Using D43R in place of D43S |

-continued

| Example | Structure | Name | Analysis | Modification |
|---|---|---|---|---|
| E97 | 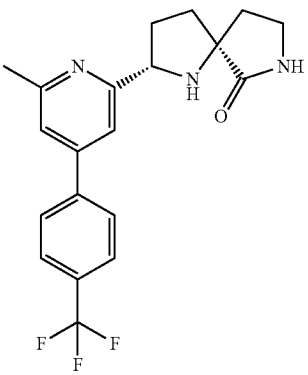 [SMILES: Cc1cc(-c2ccc(C(F)(F)F)cc2)cc([C@@H]2CC[C@@]3(CCNC3=O)N2)n1] HCl | (2S,5S)-2-[6-Methyl-4-[4-(trifluoromethyl)phenyl]-2-pyridyl]-1,7-diazaspiro[4.4]nonan-6-one hydrochloride | M/Z: 376 (M + H$^+$) | Using D44 in place of D45 |
| E98 | 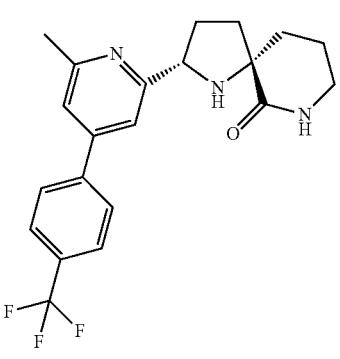 [SMILES: Cc1cc(-c2ccc(C(F)(F)F)cc2)cc([C@@H]2CC[C@]3(CCCNC3=O)N2)n1] HCl | (2S,5S)-2-[6-Methyl-4-(4-trifluoromethyl-phenyl)-pyridin-2-yl]-1,7-diaza-spiro[4.5]decan-6-one hydrochloride | M/Z: 388 (M + H$^+$) | Using 3-aminopiperidin-2-one in place of 3-aminopyrrolidin-2-one |
| E99 | 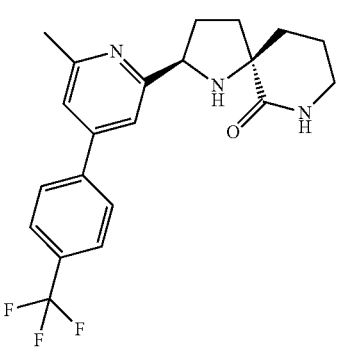 [SMILES: Cc1cc(-c2ccc(C(F)(F)F)cc2)cc([C@H]2CC[C@@]3(CCCNC3=O)N2)n1] HCl | (2R,5R)-2-[6-Methyl-4-(4-trifluoromethyl-phenyl)-pyridin-2-yl]-1,7-diaza-spiro[4.5]decan-6-one hydrochloride | M/Z: 388 (M + H$^+$) | Using 3-aminopiperidin-2-one in place of 3-aminopyrrolidin-2-one |
| E100 | 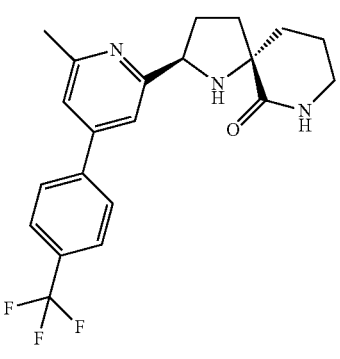 [SMILES: Cc1cc(-c2ccc(C(F)(F)F)cc2)cc([C@H]2CC[C@]3(CCCNC3=O)N2)n1] HCl | (2R,5S)-2-[6-Methyl-4-(4-trifluoromethyl-phenyl)-pyridin-2-yl]-1,7-diaza-spiro[4.5]decan-6-one hydrochloride | M/Z: 388 (M + H$^+$) | Using 3-aminopiperidin-2-one in place of 3-aminopyrrolidin-2-one |

-continued

| Example | Structure | Name | Analysis | Modification |
|---|---|---|---|---|
| E101 | 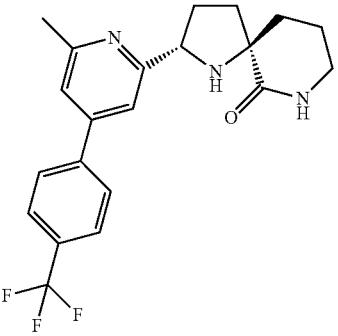 [SMILES: Cc1cc(-c2ccc(C(F)(F)F)cc2)cc([C@@H]2CC[C@@]3(CCCNC3=O)N2)n1] HCl | (2S,5R)-2-[6-Methyl-4-(4-trifluoromethyl-phenyl)-pyridin-2-yl]-1,7-diaza-spiro[4.5]decan-6-one hydrochloride | M/Z: 388 (M + H$^+$) | Using 3-aminopiperidin-2-one in place of 3-aminopyrrolidin-2-one |
| E102 | 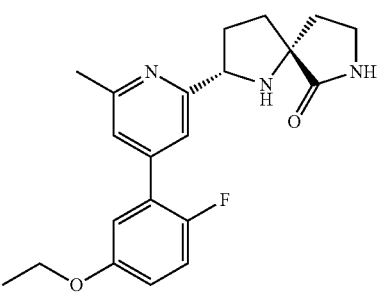 [SMILES: CCOc1ccc(F)c(-c2cc(C)nc([C@@H]3CC[C@]4(CCNC4=O)N3)c2)c1] HCl | (2S,5R)-2-[4-(5-Ethoxy-2-fluoro-phenyl)-6-methyl-2-pyridyl]-1,7-diazaspiro[4.4]nonan-6-one hydrochloride | M/Z: 370 (M + H$^+$) | As E95 Using 2-fluoro-5-ethoxyphenyl boronic acid |
| E103 | 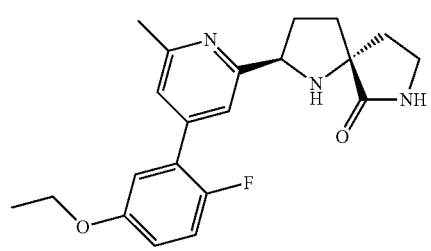 [SMILES: CCOc1ccc(F)c(-c2cc(C)nc([C@H]3CC[C@]4(CCNC4=O)N3)c2)c1] HCl | (2R,5R)-2-[4-(5-Ethoxy-2-fluoro-phenyl)-6-methyl-2-pyridyl]-1,7-diazaspiro[4.4]nonan-6-one hydrochloride | M/Z: 370 (M + H$^+$) | As E96 using 2-fluoro-5-ethoxyphenyl boronic acid |
| E104 | 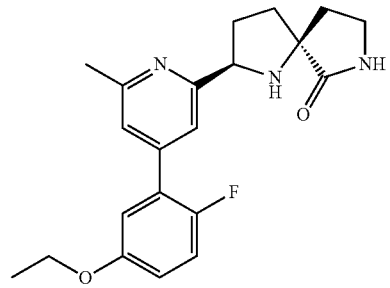 [SMILES: CCOc1ccc(F)c(-c2cc(C)nc([C@H]3CC[C@@]4(CCNC4=O)N3)c2)c1] HCl | (2R,5S)-2-[4-(5-Ethoxy-2-fluoro-phenyl)-6-methyl-2-pyridyl]-1,7-diazaspiro[4.4]nonan-6-one hydrochloride | M/Z: 370 (M + H$^+$) | As E94 using 2-fluoro-5-ethoxyphenyl boronic acid |

| Example | Structure | Name | Analysis | Modification |
|---|---|---|---|---|
| E105 | 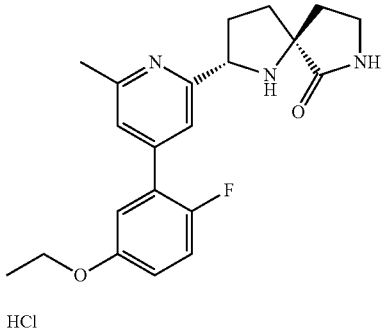 HCl | (2S,5S)-2-[4-(5-Ethoxy-2-fluoro-phenyl)-6-methyl-2-pyridyl]-1,7-diazaspiro[4.4]nonan-6-one hydrochloride | M/Z: 370 (M + H⁺) | As E97 using 2-fluoro-5-ethoxyphenyl boronic acid |
| E106 | 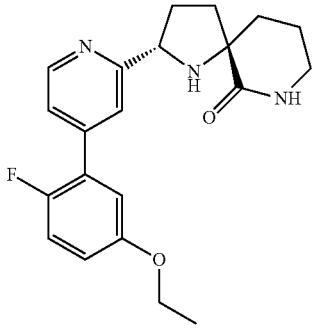 [SMILES: CCOc1ccc(F)c(-c2ccnc([C@@H]3CC[C@]4(CCCNC4=O)N3)c2)c1] HCl | (2S,5S)-2-[4-(5-Ethoxy-2-fluoro-phenyl)-pyridin-2-yl]-1,7-diaza-spiro[4.5]decan-6-one hydrochloride | M/Z: 370 (M + H⁺) | Using D49 in place of D45 |
| E107 | 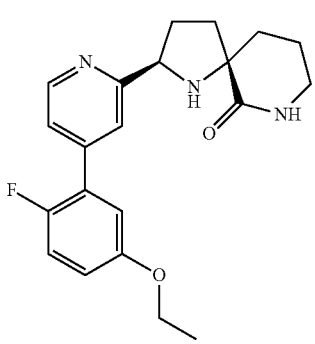 [SMILES: CCOc1ccc(F)c(-c2ccnc([C@H]3CC[C@]4(CCCNC4=O)N3)c2)c1] HCl | (2R,5S)-2-[4-(5-Ethoxy-2-fluoro-phenyl)-pyridin-2-yl]-1,7-diaza-spiro[4.5]decan-6-one hydrochloride | M/Z: 370 (M + H⁺) | Using D50 in place of D45 |

The following Examples were prepared in a similar manner to Examples E106 and E107 with the modifications and alternative boronic acids noted:

| Example | Structure | Name | Analysis | Modification |
|---|---|---|---|---|
| E108 | 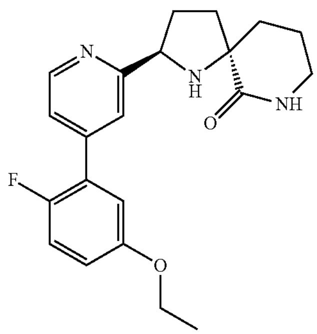 [SMILES: CCOc1ccc(F)c(-c2ccnc([C@H]3CC[C@@]4(CCCNC4=O)N3)c2)c1] | (2R,5R)-2-[4-(5-Ethoxy-2-fluoro-phenyl)-pyridin-2-yl]-1,7-diaza-spiro[4.5]decan-6-one hydrochloride | M/Z: 370 (M + H$^+$) | Using D47R in place of D47S |
| E109 | 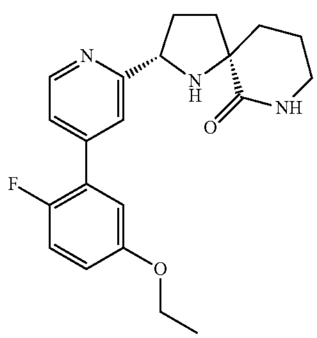 [SMILES: CCOc1ccc(F)c(-c2ccnc([C@@H]3CC[C@@]4(CCCNC4=O)N3)c2)c1] | (2S,5R)-2-[4-(5-Ethoxy-2-fluoro-phenyl)-pyridin-2-yl]-1,7-diaza-spiro[4.5]decan-6-one hydrochloride | M/Z: 370 (M + H$^+$) | Using D47R in place of D47S |
| E110 | 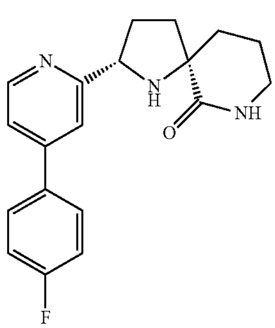 [SMILES: O=C1NCCC[C@@]12CC[C@@H](c1cc(-c3ccc(F)cc3)ccn1)N2] | (2S,5R)-2-[4-(4-Fluoro-phenyl)-pyridin-2-yl]-1,7-diaza-spiro[4.5]decan-6-one hydrochloride | M/Z: 326 (M + H$^+$) | Using D47R in place of D47S and 4-fluorophenyl-boronic acid |
| E111 | 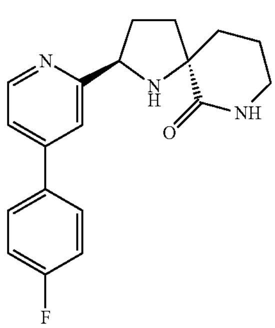 [SMILES: O=C1NCCC[C@@]12CC[C@H](c1cc(-c3ccc(F)cc3)ccn1)N2] | (2R,5R)-2-[4-(4-Fluoro-phenyl)-pyridin-2-yl]-1,7-diaza-spiro[4.5]decan-6-one hydrochloride | M/Z: 326 (M + H$^+$) | Using Using D47R in place of D47S and 4-fluorophenyl-boronic acid |

-continued

| Example | Structure | Name | Analysis | Modification |
|---|---|---|---|---|
| E112 | 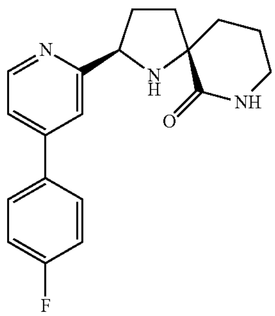 [SMILES: O=C1NCCC[C@]12CC[C@H](c1cc(-c3ccc(F)cc3)ccn1)N2] | (2R,5S)-2-[4-(4-Fluoro-phenyl)-pyridin-2-yl]-1,7-diaza-spiro[4.5]decan-6-one hydrochloride | M/Z: 326 (M + H+) | Using 4-fluorophenyl-boronic acid |
| E113 | 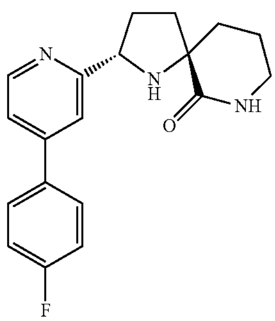 [SMILES: O=C1NCCC[C@]12CC[C@@H](c1cc(-c3ccc(F)cc3)ccn1)N2] | (2S,5S)-2-[4-(4-Fluoro-phenyl)-pyridin-2-yl]-1,7-diaza-spiro[4.5]decan-6-one hydrochloride | M/Z: 326 (M + H+) | Using 4-fluorophenyl-boronic acid |
| E114 | 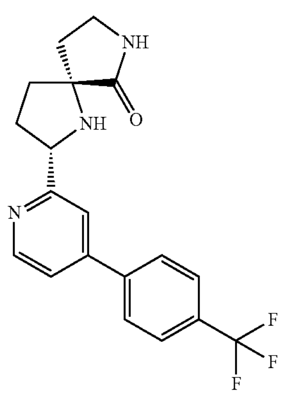 [SMILES: O=C1NCC[C@]12CC[C@@H](c1cc(-c3ccc(C(F)(F)F)cc3)ccn1)N2] | (2S,5R)-2-[4-[4-(Trifluoromethyl)phenyl]-2-pyridyl]-1,7-diazaspiro[4.4]nonan-6-one hydrochloride | M/Z: 362 (M + H+) | Usinf D42R in place of D47S and 4-trifluoromethyl phenylboronic acid |
| E115 | 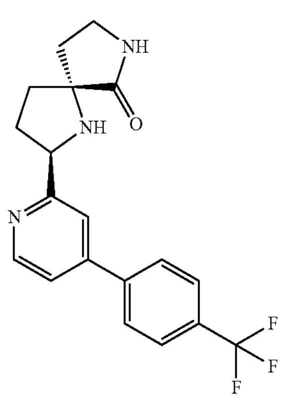 [SMILES: O=C1NCC[C@]12CC[C@H](c1cc(-c3ccc(C(F)(F)F)cc3)ccn1)N2] | (2R,5R)-2-[4-[4-(Trifluoromethyl)phenyl]-2-pyridyl]-1,7-diazaspiro[4.4]nonan-6-one hydrochloride | M/Z: 362 (M + H+) | Using D42R in place of D47S and 4-trifluoromethyl phenylboronic acid |

-continued

| Example | Structure | Name | Analysis | Modification |
|---|---|---|---|---|
| E116 | 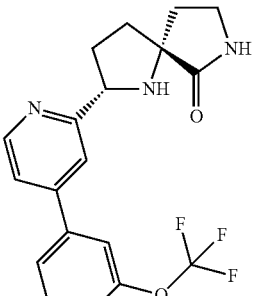 HCl | (2S,5R)-2-[4-[3-(Trifluoromethoxy)phenyl]-2-pyridyl]-1,7-diazaspiro[4.4]nonan-6-one hydrochloride | M/Z: 378 (M + H$^+$) | Using D42R in place of D47S and 3-trifluoromethoxyphenylboronic acid |
| E117 | 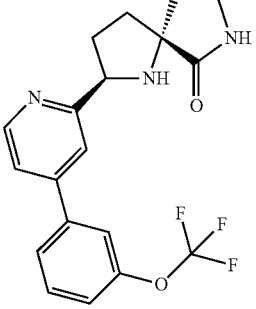 HCl | (2R,5R)-2-[4-[3-(Trifluoromethoxy)phenyl]-2-pyridyl]-1,7-diazaspiro[4.4]nonan-6-one hydrochloride | M/Z: 378 (M + H$^+$) | Using D42R in place of D47S and 3-trifluoromethoxyphenylboronic acid |
| E118 | 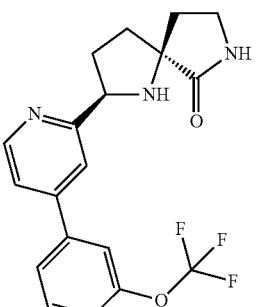 HCl | (2R,5S)-2-[4-[3-(Trifluoromethoxy)phenyl]-2-pyridyl]-1,7-diazaspiro[4.4]nonan-6-one hydrochloride | M/Z: 378 (M + H$^+$) | Using D42S in place of D47S and 3-trifluoromethoxyphenylboronic acid |
| E119 | 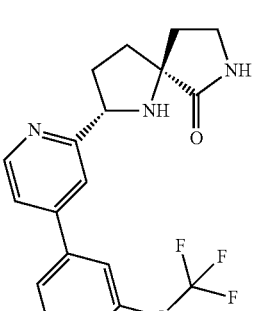 HCl | (2S,5S)-2-[4-[3-(Trifluoromethoxy)phenyl]-2-pyridyl]-1,7-diazaspiro[4.4]nonan-6-one hydrochloride | M/Z: 378 (M + H$^+$) | Using D42S in place of D47S and 3-trifluoromethoxyphenylboronic acid |

The following Examples were prepared in a similar manner to Examples 21 and 22 with the modifications noted:

| Example | Structure | Name | Analysis | Modification |
|---|---|---|---|---|
| E120 | 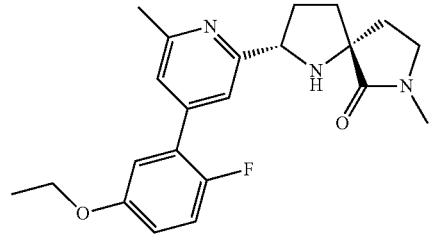 [SMILES: CCOc1ccc(F)c(-c2cc(C)nc([C@@H]3CC[C@]4(CCN(C)C4=O)N3)c2)c1] HCl | (2S,5R)-2-[4-(5-Ethoxy-2-fluoro-phenyl)-6-methyl-pyridin-2-yl]-7-methyl-1,7-diaza-spiro[4.4]nonan-6-one hydrochloride | M/Z: 384 (M + H$^+$) | Using 2-fluoro-5-ethoxy-phenyl-boronic acid |
| E121 | 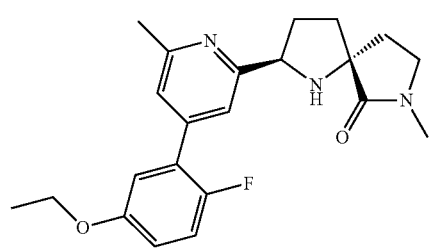 [SMILES: CCOc1ccc(F)c(-c2cc(C)nc([C@H]3CC[C@]4(CCN(C)C4=O)N3)c2)c1] HCl | (2R,5R)-2-[4-(5-Ethoxy-2-fluoro-phenyl)-6-methyl-pyridin-2-yl]-7-methyl-1,7-diaza-spiro[4.4]nonan-6-one hydrochloride | M/Z: 384 (M + H$^+$) | Using 2-fluoro-5-ethoxy-phenyl-boronic acid |
| E122 | 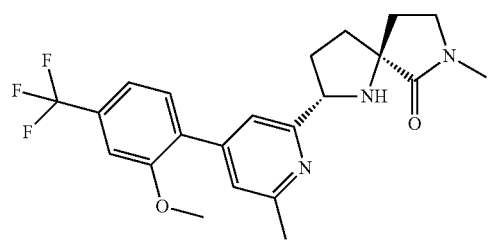 HCl | (2S,5S)-2-[4-[2-Methoxy-4-(trifluoromethyl)phenyl]-6-methyl-2-pyridyl]-7-methyl-1,7-diazaspiro[4.4]nonan-6-one hydrochloride | M/Z: 384 (M + H$^+$) | Using 2-methoxy-4-trifluoro-methylphenyl-boronic acid |
| E123 | 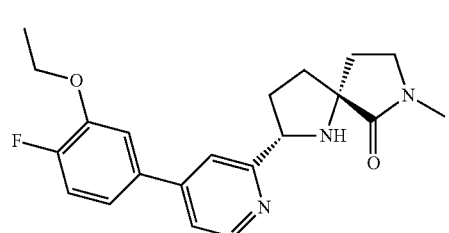 HCl | (2S,5R)-2-[4-(3-Ethoxy-4-fluoro-phenyl)-6-methyl-2-pyridyl]-7-methyl-1,7-diazaspiro[4.4]nonan-6-one hydrochloride | M/Z: 384 (M + H$^+$) | Using 3-ethoxy-4-fluorophenyl-boronic acid |
| E124 | 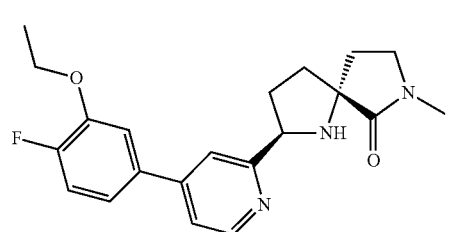 HCl | (2R,5R)-2-[4-(3-Ethoxy-4-fluoro-phenyl)-6-methyl-2-pyridyl]-7-methyl-1,7-diazaspio[4.4]nonan-6-one hydrochloride | M/Z: 384 (M + H$^+$) | Using 3-ethoxy-4-fluorophenyl-boronic acid |

-continued

| Example | Structure | Name | Analysis | Modification |
|---|---|---|---|---|
| E125 | HCl | (2R,5S)-2-[4-(3-Ethoxy-4-fluorophenyl)-6-methyl-2-pyridyl]-7-methyl-1,7-diazaspiro[4.4]nonan-4-one hydrochloride | M/Z: 384 (M + H$^+$) | Using 3-ethoxy-4-fluorophenyl-boronic acid |
| E126 | HCl | (2S,5S)-2-[4-(3-Ethoxy-4-fluorophenyl)-6-methyl-2-pyridyl]-7-methyl-1,7-diazaspiro[4.4]nonan-6-one hydrochloride | M/Z: 384 (M + H$^+$) | Using 3-ethoxy-4-fluorophenyl-boronic acid |
| E127 | HCl | (2R,5S)-7-Methyl-2-[6-methyl-4-[3-(trifluoromethoxy)phenyl]-2-pyridyl]-1,7-diazaspiro[4.4]nonan-6-one hydrochloride | M/Z: 406 (M + H$^+$) | Using 3-trifluoromethoxyphenyl-boronic acid |
| E128 | HCl | (2S,5R)-7-Methyl-2-[6-methyl-4-[3-(trifluoromethoxy)phenyl]-2-pyridyl]-1,7-diazaspiro[4.4]nonan-6-one hydrochloride | M/Z: 406 (M + H$^+$) | Using 3-trifluoromethoxyphenyl-boronic acid |

The following Examples were prepared in a similar manner to Examples 40-43 with the modifications and alternative boronic acids noted:

| Example | Structure | Name | Analysis | Modification |
|---|---|---|---|---|
| E129 | 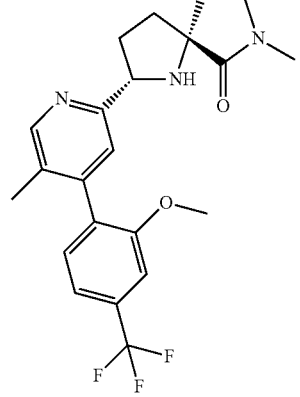 HCl | (2S,5R)-2-[4-[2-Methoxy-4-(trifluoromethyl)phenyl]-5-methyl-2-pyridyl]-7-methyl-1,7-diazaspiro[4.4]nonan-6-one hydrochloride | M/Z: 420 (M + H$^+$) | Using 2-methoxy-4-trifluoromethyphenyl-boronic acid |
| E130 | 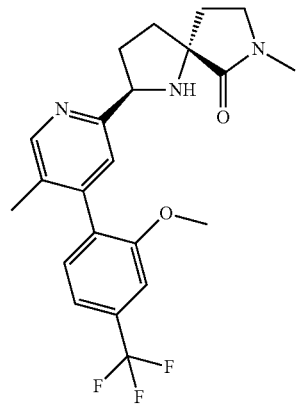 HCl | (2R,5R)-2-[4-[2-Methoxy-4-(trifluoromethyl)phenyl]-5-methyl-2-pyridyl]-7-methyl-1,7-diazaspiro[4.4]nonan-6-one hydrochloride | M/Z: 420 (M + H$^+$) | Using 2-methoxy-4-trifluoromethylphenyl-boronic acid |
| E131 | 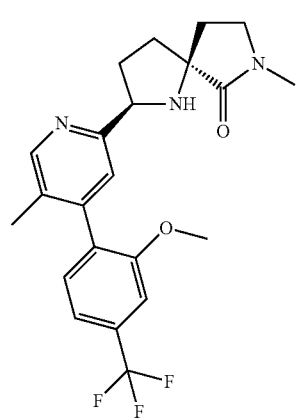 HCl | (2R,5S)-2-[4-[2-Methoxy-4-(trifluoromethyl)phenyl]-5-methyl-2-pyridyl]-7-methyl-1,7-diazaspiro[4.4]nonan-6-one hydrochloride | M/Z: 420 (M + H$^+$) | Using 2-methoxy-4-trifluoromethylphenyl-boronic acid |

-continued

| Example | Structure | Name | Analysis | Modification |
|---|---|---|---|---|
| E132 | 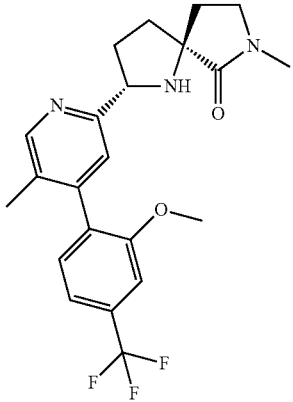 HCl | (2S,5S)-2-[4-[2-Methoxy-4-(trifluoromethyl)phenyl]-5-methyl-2-pyridyl]-7-methyl-1,7-diazaspiro[4.4]nonan-6-one hydrochloride | M/Z: 420 (M + H$^+$) | Using 2-methoxy-4-trifluoro-methylphenyl-boronic acid |
| E133 | 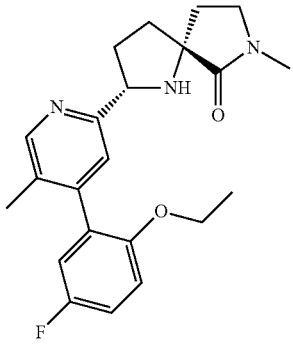 HCl | (2S,5R)-2-[4-(5-Ethoxy-2-fluoro-phenyl)-5-methyl-2-pyridyl]-7-methyl-1,7-diazaspiro[4.4]nonan-6-one hydrochloride | M/Z: 384 (M + H$^+$) | Using 2-ethoxy-5-fluorophenyl boronic acid ronic acid |
| E134 | 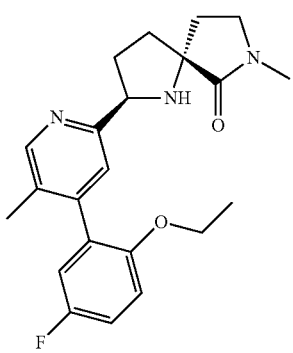 HCl | (2R,5R)-2-[4-(5-Ethoxy-2-fluoro-phenyl)-5-methyl-2-pyridyl]-7-methyl-1,7-diazaspiro[4.4]nonan-6-one hydrochloride | M/Z: 384 (M + H$^+$) | Using 2-ethoxy-5-fluorophenyl boronic acid |

-continued

| Example | Structure | Name | Analysis | Modification |
|---|---|---|---|---|
| E135 | | (2R,5S)-2-[4-(5-Ethoxy-2-fluoro-phenyl)-5-methyl-2-pyridyl]-7-methyl-1,7-diazaspiro[4.4]nonan-6-one hydrochloride | M/Z: 384 (M + H+) | Using 2-thoxy-5-fluorophenyl boronic acid |
| E136 | | (2S,5S)-2-[4-(5-Ethoxy-2-fluoro-phenyl)-5-methyl-2-pyridyl]-7-methyl-1,7-diazaspiro[4.4]nonan-6-one hydrochloride | M/Z: 384 (M + H+) | Using 2-ethoxy-5-fluorophenyl boronic acid |
| E137 | | (2R,5S)-2-[4-(5-Ethoxy-2-fluoro-phenyl)-5-methyl-2-pyridyl]-7-methyl-1,7-diazaspiro[4.4]nonan-6-one hydrochloride | M/Z: 384 (M + H+) | Using 2-fluoro-5-ethoxy-phenylboronic acid |
| E138 | | (2S,5S)-2-[4-(5-Ethoxy-2-fluoro-phenyl)-5-methyl-2-pyridyl]-7-methyl-1,7-diazaspiro[4.4]nonan-6-one hydrochloride | M/Z: 384 (M + H+) | Using 2-fluoro-5-ethoxy-phenylboronic acid |

| Example Structure | Name | Analysis | Modification |
|---|---|---|---|
| E139 | (2S,5R)-2-[4-(5-Ethoxy-2-fluoro-phenyl)-5-methyl-2-pyridyl]-7-methyl-1,7-diazaspiro[4.4]nonan-6-one hydrochloride | M/Z: 384 (M + H⁺) | Using 2-fluoro-5-ethoxy-phenylboronic acid |
| E140 | (2R,5R)-2-[4-(5-Ethoxy-2-fluoro-phenyl)-5-methyl-2-pyridyl]-7-methyl-1,7-diazaspiro[4.4]nonan-6-one hydrochloride | M/Z: 384 (M + H⁺) | Using 2-fluoro-5-ethoxy-phenylboronic acid |

The following Examples were prepared in a similar manner to Examples 21 and 22 with the modifications noted:

| Example Structure | Name | Analysis | Modification |
|---|---|---|---|
| E141 | (2R,5R)-2-[4-(5-Ethoxy-2-fluoro-phenyl)-5,6-dimethyl-2-pyridyl]-7-methyl-1,7-diazaspiro[4.4]nonan-6-one hydrochloride | M/Z: 398 (M + H⁺) | Using D54R in place of D14S |

-continued

| Example | Structure | Name | Analysis | Modification |
|---------|-----------|------|----------|--------------|
| E142 | HCl | (2S,5S)-2-[4-(5-Ethoxy-2-fluoro-phenyl)-5,6-dimethyl-2-pyridyl]-7-methyl-1,7-diazaspiro[4.4]nonan-6-one hydrochloride | M/Z: 398 (M + H$^+$) | Using D54S in place of D14S |
| E143 | HCl | (2S,5R)-2-[4-(5-Ethoxy-2-fluoro-phenyl)-5,6-dimethyl-2-pyridyl]-7-methyl-1,7-diazaspiro[4.4]nonan-6-one hydrochloride | M/Z: 398 (M + H$^+$) | Using D54R in place of D14R |
| E144 | HCl | (2R,5S)-2-[4-(5-Ethoxy-2-fluoro-phenyl)-5,6-dimethyl-2-pyridyl]-7-methyl-1,7-diazaspiro[4.4]nonan-6-one hydrochloride | M/Z: 398 (M + H$^+$) | Using D54S in place of D14S |

Example 145 and Example 146

(2S,5R)-2-[4-(5-Ethoxy-2-fluoro-phenyl)-2-pyridyl]-7-methyl-1,7-diazaspiro[4.4]nonan-6-one hydrochloride (E145) and (2R,5R)-2-[4-(5-Ethoxy-2-fluoro-phenyl)-2-pyridyl]-7-methyl-1,7-diazaspiro[4.4]nonan-6-one hydrochloride (E146)

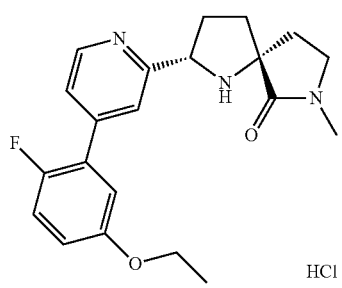

HCl

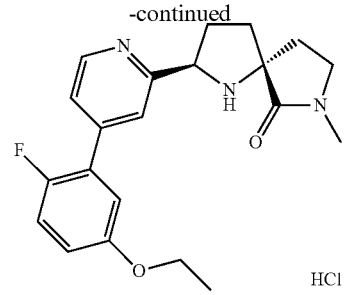

HCl

These were prepared by the methods described in Example 21 and 22 but using D55 in place of D14R. (2S,5R)-2-[4-(5-ethoxy-2-fluoro-phenyl)-2-pyridyl]-7-methyl-1,7-diazaspiro[4.4]-nonan-6-one was characterised as a free base;
300 MHz $^1$H NMR $\delta_H$ (CDCl$_3$) 1.45 (3H, t), 1.85-2.26 (6H, m), 2.50-2.61 (1H, m), 2.92 (3H, s), 3.24-3.39 (2H, m), 4.06 (2H, q), 4.78 (1H, q), 6.90 (1H, dt), 6.97 (1H, dd), 7.10 (1H, t), 7.33 (1H, d), 7.58 (1H, s), 8.60 (1H, s).
The hydrochloride (E145) gave an M/Z: 370 (M+H$^+$).
Likewise (2R,5R)-2-[4-(5-ethoxy-2-fluoro-phenyl)-2-pyridyl]-7-methyl-1,7-diazaspiro[4.4]nonan-6-one free base;
300 MHz $^1$H NMR $\delta_H$ (CDCl$_3$) 1.44 (3H, t), 1.83 (2H, ddd), 2.05-2.25 (4H, m), 2.32-2.42 (1H, m), 2.92 (3H, s), 3.0 (1H, br.s). 3.28-3.43 (2H, m), 4.08 (2H, q), 4.45 (1H, t), 6.90 (1H, dt), 7.04 (1H, dd), 7.1 (1H, t), 7.37 (1H, d), 7.74 (1H, s), 8.62 (1H, d).
The hydrochloride (E146) gave an M/Z: 370 (M+H+).

The following Examples were prepared in a similar manner to Examples 145 and 146 with the modifications and alternative boronic acids noted:

| Example | Structure | Name | Analysis | Modification |
|---|---|---|---|---|
| E147 | 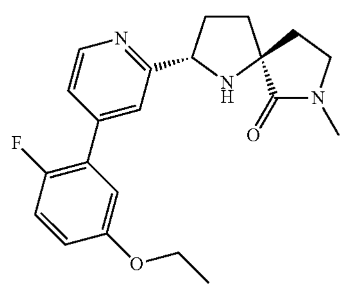 [SMILES: CCOc1ccc(F)c(-c2ccnc([C@@H]3CC[C@@]4(CCN(C)C4=O)N3)c2)c1] | (2S,5S)-2-[4-(5-Ethoxy-2-fluoro-phenyl)-2-pyridyl]-7-methyl-1,7-diazaspiro[4.4]nonan-6-one hydrochloride | M/Z: 370 (M + H$^+$). | Using D3S in place of D3R |
| E148 | 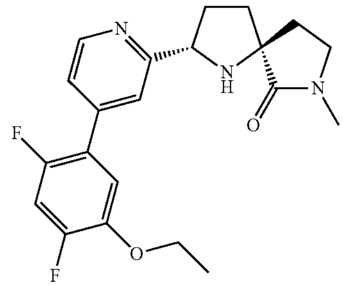 [SMILES: CCOc1cc(-c2ccnc([C@@H]3CC[C@@]4(CCN(C)C4=O)N3)c2)c(F)cc1F] | (2S,5S)-2-[4-(5-Ethoxy-2,4-difluoro-phenyl)-2-pyridyl]-7-methyl-1,7-diazaspiro[4.4]nonan-6-one hydrochloride | M/Z: 388 (M + H$^+$) | Using D3S in place of D3R and 2,4-difluoro-5-ethoxy-phenylboronic acid |

-continued

| Example | Structure | Name | Analysis | Modification |
|---|---|---|---|---|
| E149 | 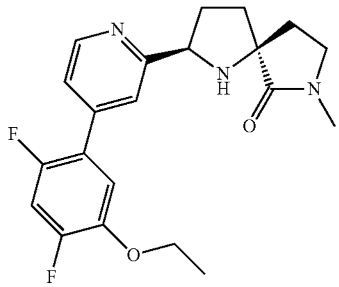 [SMILES: CCOc1cc(-c2ccnc([C@H]3CC[C@@]4(CCN(C)C4=O)N3)c2)c(F)cc1F] | (2R,5S)-2-[4-(5-Ethoxy-2,4-difluoro-phenyl)-2-pyridyl]-7-methyl-1,7-diazaspiro[4.4]nonan-6-one hydrochloride | M/Z: 388 (M + H+) | Using D3S in place of D3R and 2,4-difluoro-5-ethoxy-phenylboronic acid |
| E150 | 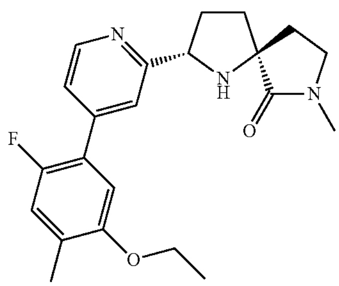 [SMILES: CCOc1cc(-c2ccnc([C@@H]3CC[C@@]4(CCN(C)C4=O)N3)c2)c(F)cc1C] | (2S,5S)-2-[4-(5-Ethoxy-2-fluoro-4-methyl-phenyl)-2-pyridyl]-7-methyl-1,7-diazaspiro[4.4]nonan-6-one hydrochloride | M/Z: 384 (M + H+) | Using D3S in place of D3R and 5-ethoxy-2-fluoro-4-methyl-phenylboronic acid |
| E151 | 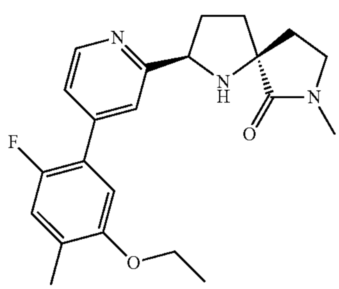 [SMILES: CCOc1cc(-c2ccnc([C@H]3CC[C@@]4(CCN(C)C4=O)N3)c2)c(F)cc1C] | (2R,5S)-2-[4-(5-Ethoxy-2-fluoro-4-methyl-phenyl)-2-pyridyl]-7-methyl-1,7-diazaspiro[4.4]nonan-6-one hydrochloride | M/Z: 384 (M + H+) | Using D3S in place of D3R and 5-ethoxy-2-fluoro-4-methyl-phenylboronic acid |
| E152 | 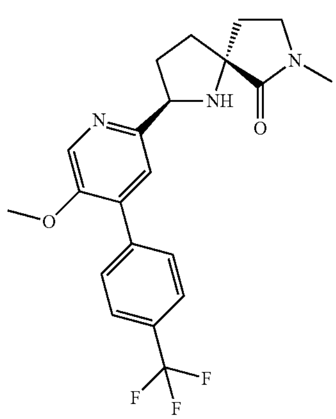 | (2R,5R)-2-[5-Methoxy-4-[4-(trifluoromethyl)phenyl]-2-pyridyl]-7-methyl-1,7-diazaspiro[4.4]nonan-6-one hydrochloride | M/Z: 406 (M + H+) | Using D56 in place of D55 and 4-trifluoromethyl-phenylboronic acid |

-continued

| Example | Structure | Name | Analysis | Modification |
|---|---|---|---|---|
| E153 | (structure with HCl) | (2S,5R)-2-[5-Methoxy-4-[4-(trifluoromethyl)phenyl]-2-pyridyl]-7-methyl-1,7-diazaspiro[4.4]nonan-6-one hydrochloride | M/Z: 406 (M + H$^+$) | Using D56 in place of D55 and 4-trifluoromethylphenyl-boronic acid |
| E154 | (structure with HCl) | (2S,5S)-2-[5-Methoxy-4-[4-(trifluoromethyl)phenyl]-2-pyridyl]-7-methyl-1,7-diazaspiro[4.4]nonan-6-one hydrochloride | M/Z: 406 (M + H$^+$) | As E152 but using D35S in place of D35R and 4-trifluoromethylphenyl-boronic acid |
| E155 | (structure with HCl) | (2R,5S)-2-[5-Methoxy-4-[4-(trifluoromethyl)phenyl]-2-pyridyl]-7-methyl-1,7-diazaspiro[4.4]nonan-6-one hydrochloride | M/Z: 406 (M + H$^+$) | As E153 but using D35S in place of D35R and 4-trifluoromethylphenyl-boronic acid |

The following Examples were prepared in a similar manner to Example 1 with the modifications noted, including the use of alternative boronic acids and esters:

| Example | Structure | Name | Analysis | Modification |
|---|---|---|---|---|
| E156 | | (2R,5S)-2-[4-(4-Difluoromethoxy-2-fluoro-phenyl)-pyridin-2-yl]-7-methyl-1,7-diaza-spiro[4.4]nonan-6-one hydrochloride | M/Z: 392 (M + H$^+$) | 4-Difluoromethoxy-2-fluorophenylboronic acid |
| E157 | | (2R,5S)-7-Methyl-2-[4-(1-methyl-1H-indol-3-yl)-pyridin-2-yl]-1,7-diaza-spiro[4.4]nonan-6-one hydrochloride | M/Z: 361 (M + H$^+$) | 1-Methyl-3-(4,4,5,5-tetramethyl-1,3,2-dioxaborolan-2-yl)indole |
| E158 | | (2R,5S)-2-[4-(2-Ethoxy-3-fluoro-phenyl)-2-pyridyl]-7-methyl-1,7-diazaspiro[4.4]nonan-6-one hydrochloride | M/Z: 370 (M + H$^+$) | 2-Ethoxy-3-fluorophenylboronic acid |
| E159 | | (2R,5S)-2-[4-(2-Fluoro-5-isopropyl-phenyl)-2-pyridyl]-7-methyl-1,7-diazaspiro[4.4]nonan-6-one hydrochloride | M/Z: 368 (M + H$^+$) | (2-fluoro-5-isopropyl-phenyl)boronic acid |

-continued

| Example | Structure | Name | Analysis | Modification |
|---|---|---|---|---|
| E160 | 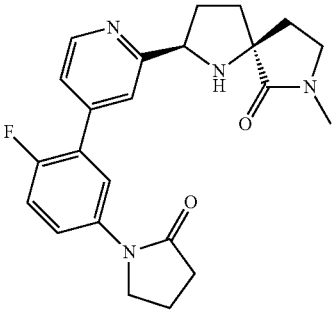 [SMILES: CN1CC[C@@]2(CC[C@H](c3cc(-c4cc(N5CCCC5=O)ccc4F)ccn3)N2)C1=O] HCl | (2R,5S)-2-[4-[2-Fluoro-5-(2-oxopyrrolidin-1-yl)phenyl]-2-pyridyl]-7-methyl-1,7-diazaspiro[4.4]nonan-6-one hydrochloride | M/Z: 409 (M + H⁺) | 1-[4-fluoro-3-(4,4,5,5-tetramethyl-1,3,2-dioxaborolan-2-yl)phenyl]pyrrolidin-2-one D59 |
| E161 | 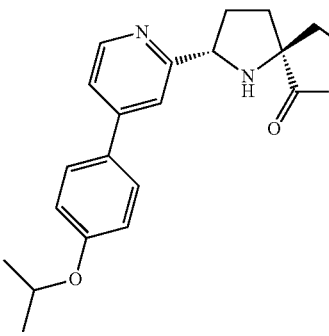 HCl | (2S,5S)-2-[4-(4-Isopropoxyphenyl)-2-pyridyl]-7-methyl-1,7-diazaspiro[4.4]nonan-6-one hydrochloride | M/Z: 366 (M + H⁺) | Using D4S and (4-isopropoxyphenyl) boronic acid |
| E162 | 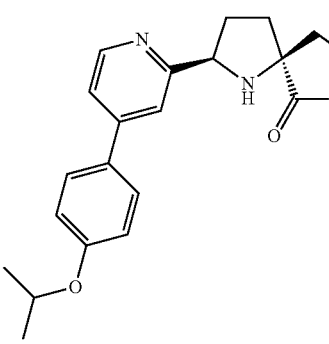 HCl | (2R,5S)-2-[4-(4-Isopropoxyphenyl)-2-pyridyl]-7-methyl-1,7-diazaspiro[4.4]nonan-6-one hydrochloride | M/Z: 366 (M + H⁺) | (4-isopropoxyphenyl) boronic acid |
| E163 | 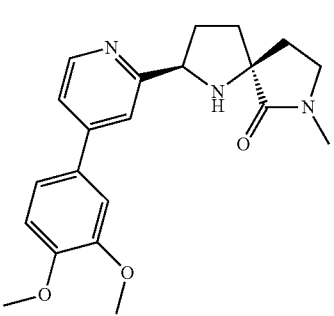 HCl | (2R,5S)-2-[4-(3,4-Dimethoxyphenyl)-2-pyridyl]-7-methyl-1,7-diazaspiro[4.4]nonan-6-one hydrochloride | M/Z: 368 (M + H⁺) | (3,4-dimethoxyphenyl) boronic acid |

-continued

| Example | Structure | Name | Analysis | Modification |
|---|---|---|---|---|
| E164 | 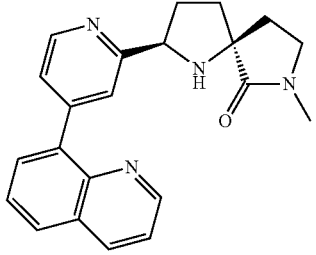 [SMILES: CN1CC[C@@]2(CC[C@H](c3cc(-c4cccc5cccnc45)ccn3)N2)C1=O] HCl | (2R,5S)-7-Methyl-2-[4-(8-quinolyl)-2-pyridyl]-1,7-diazaspiro[4.4]nonan-6-one hydrochloride | M/Z: 359 (M + H⁺) | 8-quinolinylboronic acid |
| E165 | 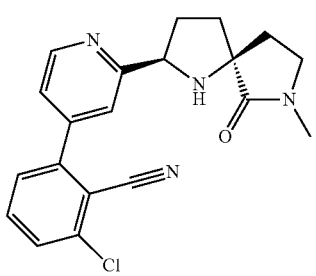 [SMILES: CN1CC[C@@]2(CC[C@H](c3cc(-c4cccc(Cl)c4C#N)ccn3)N2)C1=O] HCl | 2-Chloro-6-[2-[(2R,5S)-7-methyl-6-oxo-1,7-diazaspiro[4.4]nonan-2-yl]-4-pyridyl]benzonitrile hydrochloride | M/Z: 367, 369 (M + H⁺) | (3-chloro-2-cyano-phenyl)boronic acid |
| E166 | 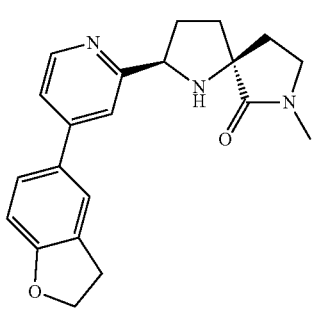 [SMILES: CN1CC[C@@]2(CC[C@H](c3cc(-c4ccc5c(c4)CCO5)ccn3)N2)C1=O] HCl | (2R,5S)-2-[4-(2,3-Dihydrobenzofuran-5-yl)-2-pyridyl]-7-methyl-1,7-diazaspiro[4.4]nonan-6-one hydrochloride | M/Z: 350 (M + H⁺) | 2,3-dihydrobenzofuran-5-ylboronic acid |
| E167 | 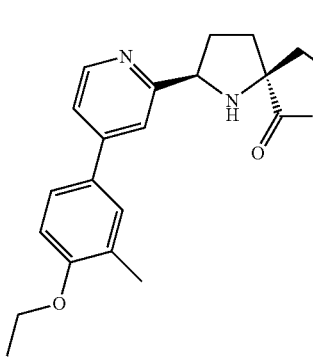 HCl | (2R,5S)-2-[4-(4-Ethoxy-3-methyl-phenyl)-2-pyridyl]-7-methyl-1,7-diazaspiro[4.4]nonan-6-one hydrochloride | M/Z: 366 (M + H⁺) | (4-ethoxy-3-methyl-phenyl)boronic acid |

| Example | Structure | Name | Analysis | Modification |
|---|---|---|---|---|
| E168 | 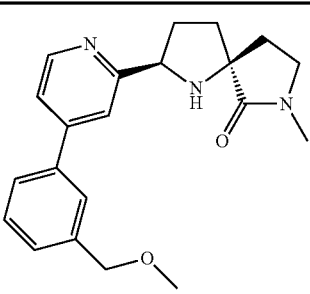 HCl | (2R,5S)-2-[4-[3-(methoxymethyl)phenyl]-2-pyridyl]-7-methyl-1,7-diazaspiro[4.4]nonan-6-one hydrochloride | M/Z: 352 (M + H$^+$) | [3-(methoxymethyl)phenyl]boronic acid |
| E169 | 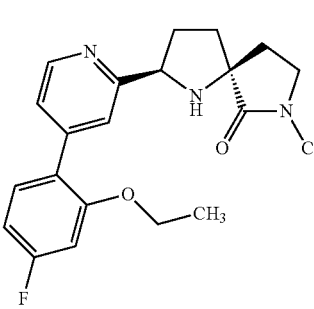 HCl | (2R,5S)-2-[4-(2-Ethoxy-4-fluoro-phenyl)-2-pyridyl]-7-methyl-1,7-diazaspiro[4.4]nonan-6-one hydrochloride | M/Z: 370 (M + H$^+$) | (2-ethoxy-4-fluoro-phenyl)boronic acid |
| E170 | 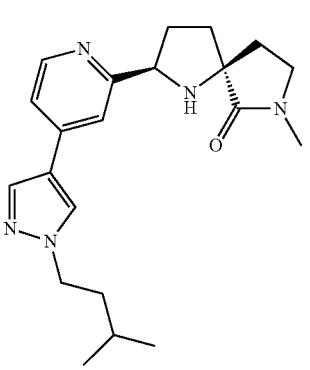 [SMILES: CC(C)CCn1cc(-c2ccnc([C@H]3CC[C@@]4(CCN(C)C4=O)N3)c2)cn1] HCl | (2R,5S)-2-[4-(1-Isopentylpyrazol-4-yl)-2-pyridyl]-7-methyl-1,7-diazaspiro[4.4]nonan-6-one hydrochloride | M/Z: 368 (M + H$^+$) | (1-isopentylpyrazol-4-yl)boronic acid |
| E171 | 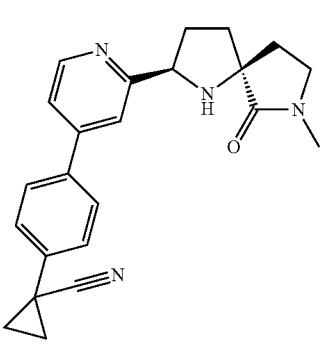 [SMILES: CN1CC[C@@]2(CC[C@H](c3cc(-c4ccc(C5(C#N)CC5)cc4)ccn3)N2)C1=O] HCl | 1-[4-[2-[(2R,5S)-7-Methyl-6-oxo-1,7-diazaspiro[4.4]nonan-2-yl]-4-pyridyl]phenyl]cyclopropanecarbonitrile hydrochloride | M/Z: 373 (M + H$^+$) | [4-(1-cyanocyclopropyl)phenyl]boronic acid |

-continued

| Example | Structure | Name | Analysis | Modification |
|---|---|---|---|---|
| E172 | HCl | (2R,5S)-2-[4-(2,2-Difluoro-1,3-benzodioxol-5-yl)-2-pyridyl]-7-methyl-1,7-diazaspiro[4.4]nonan-6-one hydrochloride | M/Z: 388 (M + H$^+$) | (2,2-difluoro-1,3-benzodioxol-5-yl)boronic acid |
| E173 | HCl | (2R,5S)-7-Methyl-2-[4-(3-pyrazol-1-ylphenyl)-2-pyridyl]-1,7-diazaspiro[4.4]nonan-6-one hydrochloride | M/Z: 374 (M + H$^+$) | (3-pyrazol-1-ylphenyl)boronic acid |
| E174 | HCl | (2R,5S)-2-[4-(3,5-Dimethylphenyl)-2-pyridyl]-7-methyl-1,7-diazaspiro[4.4]nonan-6-one hydrochloride | M/Z: 336 (M + H$^+$) | 3,5-dimethylphenyl boronic acid |
| E175 | HCl | (2R,5S)-2-[4-(5-Ethoxy-2,3-difluoro-phenyl)-2-pyridyl]-7-methyl-1,7-diazaspiro[4.4]nonan-6-one hydrochloride | M/Z: 388 (M + H$^+$) | 2-(5-ethoxy-2,3-difluoro-phenyl)-4,4,5,5-tetramethyl-1,3,2-dioxaborolane D63 |

-continued

| Example | Structure | Name | Analysis | Modification |
|---|---|---|---|---|
| E176 | 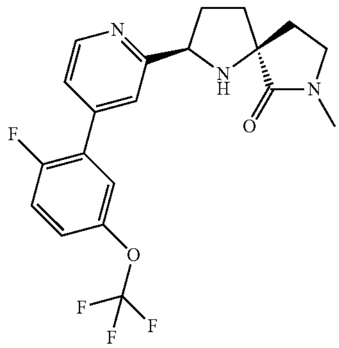 [SMILES: CN1CC[C@@]2(CC[C@H](c3cc(-c4cc(OC(F)(F)F)ccc4F)ccn3)N2)C1=O] | (2R,5S)-2-[4-[2-Fluoro-5-(trifluoromethoxy)phenyl]-2-pyridyl]-7-methyl-1,7-diazaspiro[4.4]nonan-6-one hydrochloride | M/Z: 410 (M + H⁺) | [2-fluoro-5-(trifluoromethoxy)phenyl]boronic acid |
| E177 | 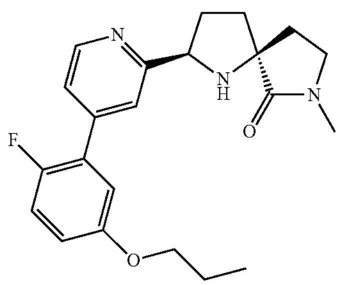 [SMILES: CCCOc1ccc(F)c(-c2ccnc([C@H]3CC[C@@]4(CCN(C)C4=O)N3)c2)c1] | (2R,5S)-2-[4-(2-Fluoro-5-propoxy-phenyl)-2-pyridyl]-7-methyl-1,7-diazaspiro[4.4]nonan-6-one hydrochloride | M/Z: 384 (M + H⁺) | 2-fluoro-5-propoxyphenylboronic acid |
| E178 | 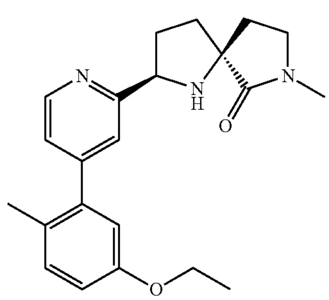 | (2R,5S)-2-[4-(5-Ethoxy-2-methyl-phenyl)-2-pyridyl]-7-methyl-1,7-diazaspiro[4.4]nonan-6-one hydrochloride | M/Z: 366 (M + H⁺) | 2-(5-ethoxy-2-methyl-phenyl)-4,4,5,5-tetramethyl-1,3,2-dioxaborolane D65 |
| E179 | 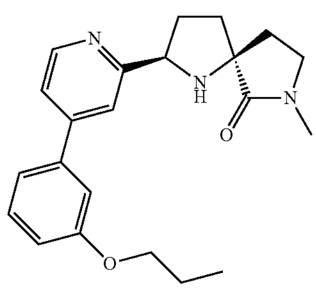 [SMILES: CCCOc1cccc(-c2ccnc([C@H]3CC[C@@]4(CCN(C)C4=O)N3)c2)c1] | (2R,5S)-7-Methyl-2-[4-(3-propoxyphenyl)-2-pyridyl]-1,7-diazaspiro[4.4]nonan-6-one hydrochloride | M/Z: 366 (M + H⁺) | (3-propoxyphenyl)boronic acid |

-continued

| Example | Structure | Name | Analysis | Modification |
|---|---|---|---|---|
| E180 | 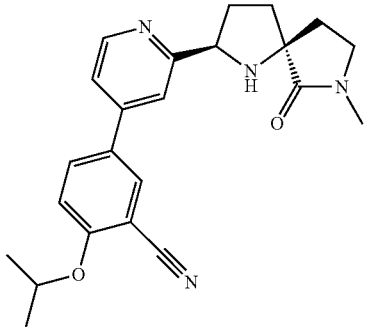 [SMILES: CC(C)Oc1ccc(-c2ccnc([C@H]3CC[C@@]4(CCN(C)C4=O)N3)c2)cc1C#N] HCl | 2-Isopropoxy-5-[2-[(2R,5S)-7-methyl-6-oxo-1,7-diazaspiro[4.4]nonan-2-yl]-4-pyridyl]benzonitrile hydrochloride | M/Z: 391 (M + H$^+$) | (3-cyano-4-isopropoxy-phenyl)boronic acid |
| E181 | 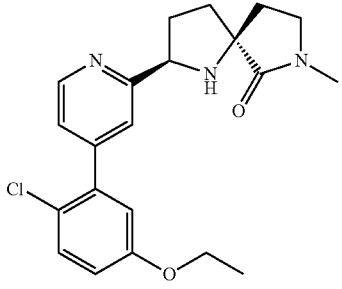 [SMILES: CCOc1ccc(Cl)c(-c2ccnc([C@H]3CC[C@@]4(CCN(C)C4=O)N3)c2)c1] HCl | (2R,5S)-2-[4-(2-Chloro-5-ethoxy-phenyl)-2-pyridyl]-7-methyl-1,7-diazaspiro[4.4]nonan-6-one hydrochloride | M/Z: 366, 368 (M + H$^+$) | 2-(2-chloro-5-ethoxy-phenyl)-4,4,5,5-tetramethyl-1,3,2-dioxaborolane |
| E182 | 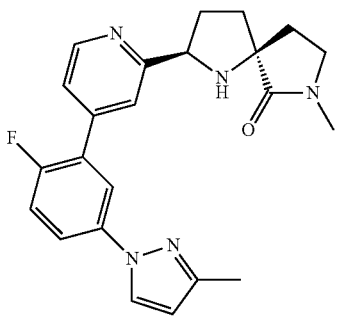 [SMILES: Cc1ccn(-c2ccc(F)c(-c3ccnc([C@H]4CC[C@@]5(CCN(C)C5=O)N4)c3)c2)n1] HCl | (2R,5S)-2-[4-[2-Fluoro-5-(3-methylpyrazol-1-yl)phenyl]-2-pyridyl]-7-methyl-1,7-diazaspiro[4.4]nonan-6-one hydrochloride | M/Z: 406 (M + H$^+$) | 1-[4-fluoro-3-(4,4,5,5-tetramethyl-1,3,2-dioxaborolan-2-yl)phenyl]-3-methyl-pyrazole D70 |
| E183 | 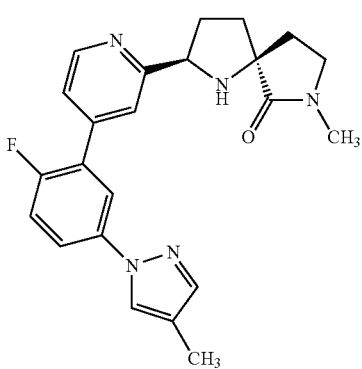 [SMILES: Cc1cnn(-c2ccc(F)c(-c3ccnc([C@H]4CC[C@@]5(CCN(C)C5=O)N4)c3)c2)c1] HCl | (2R,5S)-2-[4-[2-Fluoro-5-(4-methylpyrazol-1-yl)phenyl]-2-pyridyl]-7-methyl-1,7-diazaspiro[4.4]nonan-6-one hydrochloride | M/Z: 406 (M + H$^+$) | Using method of E182 but with D86 |

-continued

| Example | Structure | Name | Analysis | Modification |
|---|---|---|---|---|
| E184 | 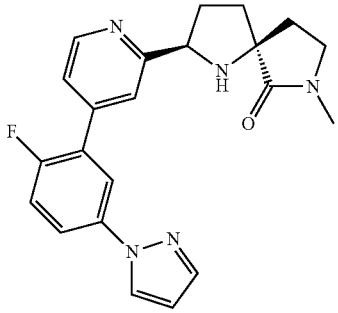 [SMILES: CN1CC[C@@]2(CC[C@H](c3cc(-c4cc(-n5cccn5)ccc4F)ccn3)N2)C1=O] HCl | (2R,5S)-2-[4-(2-Fluoro-5-pyrazol-1-yl-phenyl)-2-pyridyl]-7-methyl-1,7-diazaspiro[4.4]nonan-6-one hydrochloride | M/Z: 392 (M + H⁺) | 1-[4-fluoro-3-(4,4,5,5-tetramethyl-1,3,2-dioxaborolan-2-yl)phenyl]pyrazole D74 |
| E185 | 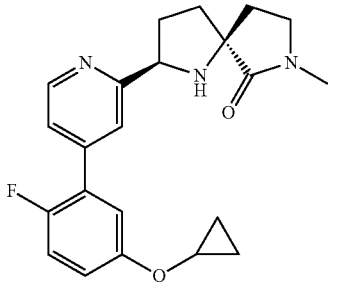 [SMILES: CN1CC[C@@]2(CC[C@H](c3cc(-c4cc(OC5CC5)ccc4F)ccn3)N2)C1=O] HCl | (2R,5S)-2-[4-[5-(Cyclopropoxy)-2-fluoro-phenyl]-2-pyridyl]-7-methyl-1,7-diazaspiro[4.4]nonan-6-one hydrochloride | M/Z: 382 (M + H⁺) | 2-[5-(cyclopropoxy)-2-fluoro-phenyl]-4,4,5,5-tetramethyl-1,3,2-dioxaborolane D75 |
| E186 | 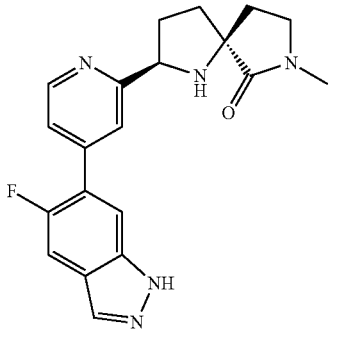 [SMILES: CN1CC[C@@]2(CC[C@H](c3cc(-c4cc5[nH]ncc5cc4F)ccn3)N2)C1=O] HCl | (2R,5S)-2-[4-(5-Fluoro-1H-indazol-6-yl)-2-pyridyl]-7-methyl-1,7-diazaspiro[4.4]nonan-6-one hydrochloride | M/Z: 366 (M + H⁺) | (5-fluoro-1H-indazol-6-yl)boronic acid |
| E187 | 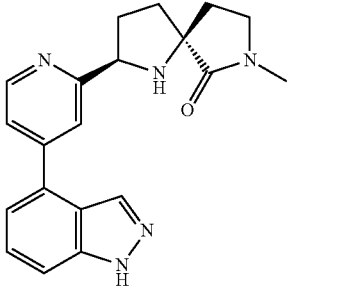 [SMILES: CN1CC[C@@]2(CC[C@H](c3cc(-c4cccc5[nH]ncc45)ccn3)N2)C1=O] HCl | (2R,5S)-2-[4-(1H-Indazol-4-yl)-2-pyridyl]-7-methyl-1,7-diazaspiro[4.4]nonan-6-one hydrochloride | M/Z: 348 (M + H⁺) | 1H-indazol-4-ylboronic acid |

-continued

| Example | Structure | Name | Analysis | Modification |
|---|---|---|---|---|
| E188 | HCl | (2R,5S)-2-[4-[2-Fluoro-5-(methoxymethyl)phenyl]-2-pyridyl]-7-methyl-1,7-diazaspiro[4.4]nonan-6-one hydrochloride | M/Z: 370 (M + H$^+$) | 2-[2-fluoro-5-(methoxymethyl)phenyl]-4,4,5,5-tetramethyl-1,3,2-dioxaborolane D76 |
| E189 | HCl | (2R,5S)-2-[4-[5-(Ethoxymethyl)-2-fluoro-phenyl]-2-pyridyl]-7-methyl-1,7-diazaspiro[4.4]nonan-6-one hydrochloride | M/Z: 384 (M + H$^+$) | 2-[5-(ethoxymethyl)-2-fluoro-phenyl]-4,4,5,5-tetramethyl-1,3,2-dioxaborolane D77 |
| E190 | HCl | (2R,5S)-2-[4-(3,4-Diethoxyphenyl)-2-pyridyl]-7-methyl-1,7-diazaspiro[4.4]nonan-6-one hydrochloride | M/Z: 396 (M + H$^+$) | 2-(3,4-diethoxyphenyl)-4,4,5,5-tetramethyl-1,3,2-dioxaborolane |
| E191 | HCl | (2R,5S)-2-[4-[2-Fluoro-5-(1-methylpyrazol-4-yl)phenyl]-2-pyridyl]-7-methyl-1,7-diazaspiro[4.4]nonan-6-one hydrochloride | M/Z: 406 (M + H$^+$) | 4-[4-fluoro-3-(4,4,5,5-teramethyl-1,3,2-dioxaborolan-2-yl)phenyl]-1-methyl-pyrazole D81 |

-continued

| Example | Structure | Name | Analysis | Modification |
|---|---|---|---|---|
| E192 | 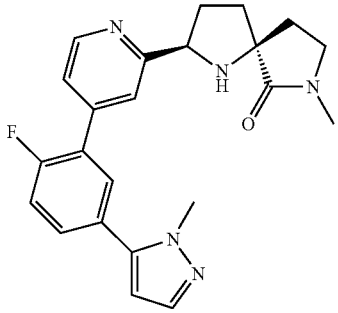 [SMILES: CN1CC[C@@]2(CC[C@H](c3cc(-c4cc(-c5ccnn5C)ccc4F)ccn3)N2)C1=O] HCl | (2R,5S)-2-[4-[2-Fluoro-5-(2-methylpyrazol-3-yl)phenyl]-2-pyridyl]-7-methyl-1,7-diazaspiro[4.4]nonan-6-one hydrochloride | M/Z: 406 (M + H$^+$) | 5-[4-fluoro-3-(4,4,5,5-tetramethyl-1,3,2-dioxaborolane-2-yl)phenyl]-1-methyl-pyrazole D85 |
| E193 | 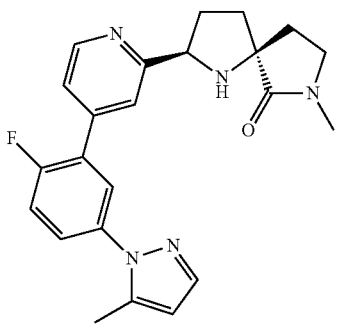 [SMILES: Cc1ccnn1-c1ccc(F)c(-c2ccnc([C@H]3CC[C@@]4(CCN(C)C4=O)N3)c2)c1] HCl | (2R,5S)-2-[4-[2-Fluoro-5-(5-methylpyrazol-1-yl)phenyl]-2-pyridyl]-7-methyl-1,7-diazaspiro[4.4]nonan-6-one hydrochloride | M/Z: 406 (M + H$^+$) | 1-[4-fluoro-3-(4,4,5,5-tetramethyl-1,3,2-dioxaborolan-2-yl)phenyl]-5-methyl-pyrazole D88 |
| E194 | 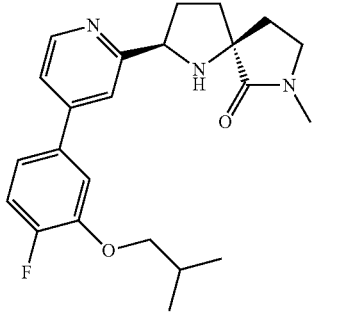 [SMILES: CC(C)COc1cc(-c2ccnc([C@H]3CC[C@@]4(CCN(C)C4=O)N3)c2)ccc1F] HCl | (2R,5S)-2-[4-(4-Fluoro-3-isobutoxy-phenyl)-2-pyridyl]-7-methyl-1,7-diazaspiro[4.4]nonan-6-one hydrochloride | M/Z: 398 (M + H$^+$) | 2-(4-fluoro-3-isobutoxy-phenyl)-4,4,5,5-tetramethyl-1,3,2-dioxaborolane D89 |

The following Examples were prepared in a similar manner to Example 1 but using D91 in place of D4R with the further modifications noted, including the use of alternative boronic acids and esters:

| Example | Structure | Name | Analysis | Modification |
|---|---|---|---|---|
| E195 | 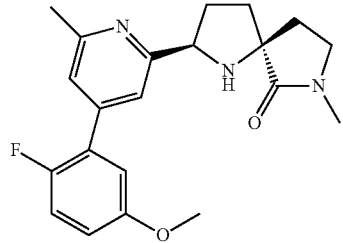 HCl | (2R,5S)-2-[4-(2-Fluoro-5-methoxy-phenyl)-6-methyl-2-pyridyl]-7-methyl-1,7-diazaspiro[4.4]nonan-6-one hydrochloride | M/Z: 370 (M + H$^+$) | (2-fluoro-5-methoxy-phenyl)boronic acid |

| Example | Structure | Name | Analysis | Modification |
|---|---|---|---|---|
| E196 | 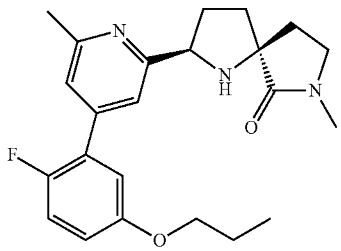 | (2R,5S)-2-[4-(2-Fluoro-5-propoxy-phenyl)-6-methyl-2-pyridyl]-7-methyl-1,7-diazaspiro[4.4]nonan-6-one hydrochloride | M/Z: 398 (M + H⁺) | (2-fluoro-5-propoxy-phenyl)boronic acid |
| E197 | 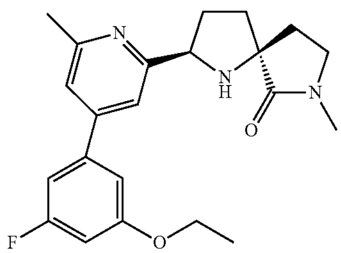 | (2R,5S)-2-[4-(3-Ethoxy-5-fluoro-phenyl)-6-methyl-2-pyridyl]-7-methyl-1,7-diazaspiro[4.4]nonan-6-one hydrochloride | M/Z: 384 (M + H⁺) | (3-ethoxy-5-fluoro-phenyl)boronic acid |
| E198 | 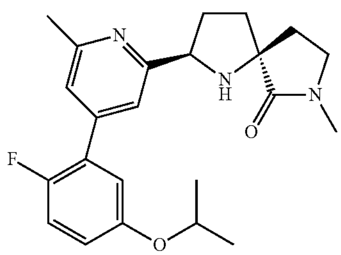 | (2R,5S)-2-[4-(2-Fluoro-5-isopropoxy-phenyl)-6-methyl-2-pyridyl]-7-methyl-1,7-diazaspiro[4.4]nonan-6-one hydrochloride | M/Z: 398 (M + H⁺) | (2-fluoro-5-isopropoxy-phenyl)boronic acid |
| E199 | 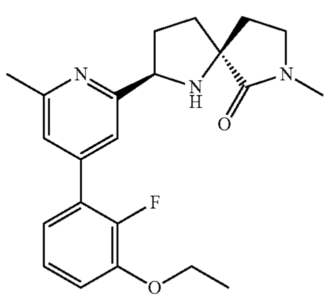 | (2R,5S)-2-[4-(3-Ethoxy-2-fluoro-phenyl)-6-methyl-2-pyridyl]-7-methyl-1,7-diazaspiro[4.4]nonan-6-one hydrochloride | M/Z: 384 (M + H⁺) | (3-ethoxy-2-fluoro-phenyl)boronic acid |
| E200 | 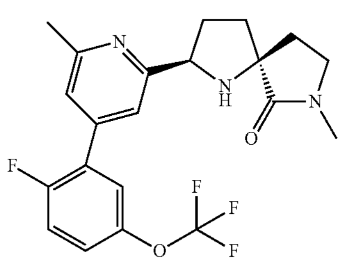 | (2R,5S)-2-[4-[2-Fluoro-5-(trifluoromethoxy)phenyl]-6-methyl-2-pyridyl]-7-methyl-1,7-diazaspiro[4.4]nonan-6-one hydrochloride | M/Z: 424 (M + H⁺) | [2-fluoro-5-(trifluoromethoxy)phenyl]boronic acid |

| Example | Structure | Name | Analysis | Modification |
|---|---|---|---|---|
| E201 | HCl | (2S,5R)-2-[4-(2-Fluoro-5-propoxy-phenyl)-6-methyl-2-pyridyl]-7-methyl-1,7-diazaspiro[4.4]nonan-6-one hydrochloride | M/Z: 398 (M + H⁺) | Using D90 in place of D91 and (2-fluoro-5-propoxy-phenyl)boronic acid |
| E202 | HCl | (2R,5S)-2-[4-(5-Ethoxy-2-fluoro-4-methyl-phenyl)-6-methyl-2-pyridyl]-7-methyl-1,7-diazaspiro[4.4]nonan-6-one hydrochloride | M/Z: 398 (M + H⁺) | (5-ethoxy-2-fluoro-4-methyl-phenyl)boronic acid D94 |
| E203 | HCl | (2R,5S)-2-[4-[2-Fluoro-5-(2-oxopyrrolidin-1-yl)phenyl]-6-methyl-2-pyridyl]-7-methyl-1,7-diazaspiro[4.4]nonan-6-one hydrochloride | M/Z: 423 (M + H⁺) | 1-[4-fluoro-3-(4,4,5,5-tetramethyl-1,3,2-dioxaborolan-2-yl)phenyl]pyrrolidin-2-one D59 |
| E204 | HCl | (2R,5S)-2-[4-(5-Ethyl-2-fluoro-phenyl)-6-methyl-2-pyridyl]-7-methyl-1,7-diazaspiro[4.4]nonan-6-one hydrochloride | M/Z: 328 (M + H⁺) | (5-ethyl-2-fluoro-phenyl)boronic acid [CAS: 900175-03-3] |
| E205 | HCl | (2R,5S)-2-[4-(3-Ethylphenyl)-6-methyl-2-pyridyl]-7-methyl-1,7-diazaspiro[4.4]nonan-6-one hydrochloride | M/Z: 350 (M + H⁺) | (3-ethyl-phenyl)boronic acid |

-continued

| Example | Structure | Name | Analysis | Modification |
|---|---|---|---|---|
| E206 | HCl | (2R,5S)-2-[4-(3-Ethyl-2-fluoro-phenyl)-6-methyl-2-pyridyl]-7-methyl-1,7-diazaspiro[4.4]nonan-6-one hydrochloride | M/Z: 368 (M + H⁺) | (3-ethyl-2-fluoro-phenyl)boronic acid [CAS: 1383575-71-0] |
| E207 | HCl | (2R,5S)-2-[4-(3-Ethoxyphenyl)-6-methyl-2-pyridyl]-7-methyl-1,7-diazaspiro[4.4]nonan-6-one hydrochloride | M/Z: 366 (M + H⁺) | (3-ethoxyphenyl)boronic acid |
| E208 | HCl | (2S,5R)-2-[4-(5-Fluoro-2,3-dihydrobenzofuran-6-yl)-6-methyl-2-pyridyl]-7-methyl-1,7-diazaspiro[4.4]nonan-6-one hydrochloride | M/Z: 382 (M + H⁺) | Using D90 in place of D91 and 2-(5-fluoro-2,3-dihydrobenzofuran-6-yl)-4,4,5,5-tetramethyl-1,3,2-dioxaborolane D97 |
| E209 | HCl | (2S,5R)-2-[4-(6-Isopropoxy-3-pyridyl)-6-methyl-2-pyridyl]-7-methyl-1,7-diazaspiro[4.4]nonan-6-one hydrochloride | M/Z: 381 (M + H⁺) | Using D90 in place of D91 and (6-isopropoxy-3-pyridyl)boronic acid |

| Example | Structure | Name | Analysis | Modification |
|---|---|---|---|---|
| E210 | 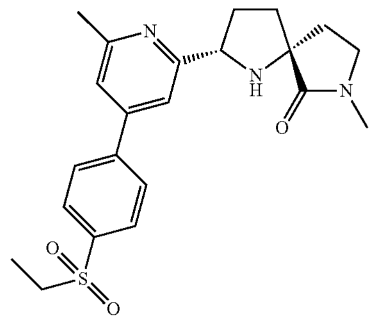 | (2S,5R)-2-[4-(4-Ethylsulfonylphenyl)-6-methyl-2-pyridyl]-7-methyl-1,7-diazaspiro[4.4]nonan-6-one hydrochloride | M/Z: 414 (M + H⁺) | Using D90 in place of D91 and (4-ethylsulfonyl-phenyl)boronic acid |
| E211 | 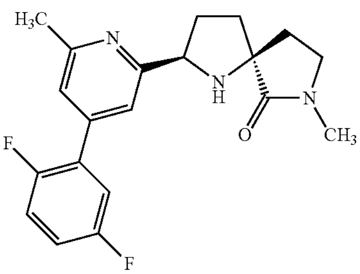 | (2R,5S)-2-[4-(2,5-Difluorophenyl)-6-methyl-2-pyridyl]-7-methyl-1,7-diazaspiro[4.4]nonan-6-one hydrochloride | M/Z: 358 (M + H⁺) | (2,5-difluorophenyl) boronic acid |

Example 212

(2R,5R)-2-[4-(5-Ethoxy-2-fluoro-phenyl)-3-methyl-2-pyridyl]-7-methyl-1,7-diazaspiro[4.4]nonan-6-one hydrochloride (E212)

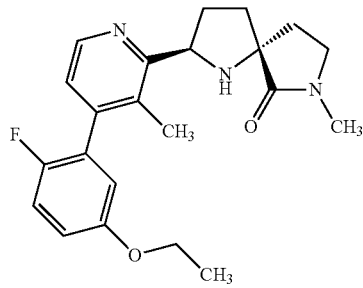 [SMILES: CCOc1ccc(F)c(-c2ccnc([C@H]3CC[C@]4(CCN(C)C4=O)N3)c2C)c1]

A solution of tert-butyl (2R,5R)-2-[4-(5-ethoxy-2-fluoro-phenyl)-3-methyl-2-pyridyl]-7-methyl-6-oxo-1,7-diazaspiro[4.4]nonane-1-carboxylate (which may be prepared as described in Description 100)(74.2 mg, 0.1500 mmol) in 4M HCl in dioxane (0.38 mL, 1.53 mmol) was stirred for 2 hours. The reaction was then concentrated in vacuo. The residue was loaded onto an SCX cartridge which was eluted with MeOH and 0.5 M methanolic ammonia. The basic fractions were combined and concentrated in vacuo to give (2R,5R)-2-[4-(5-ethoxy-2-fluoro-phenyl)-3-methyl-2-pyridyl]-7-methyl-1,7-diazaspiro[4.4]nonan-6-one (55.6 mg, 0.1450 mmol, 94.524% yield) as a colourless oil (5182RTS331-A1, >95% pure);

$^1$H NMR (300 MHz, CDCl$_3$) δ: 1.42 (t, 3H), 1.80-1.93 (m, 2H), 2.03-2.12 (m, 1H), 2.18 (s, 3H), 2.21-2.42 (m, 2H), 2.94 (s, 3H), 3.28-3.48 (m, 3H), 3.5 (br.s, 1H), 4.01 (q, 2H), 4.53 (t, 1H), 6.70 (dd, 1H), 6.89 (dt, 1H), 7.02 (d, 1H), 7.05 (t, 1H), 8.44 (d, 1H).

To a solution of this material (55.6 mg, 0.1500 mmol) in DCM (2 mL) was added HCl in ether (0.15 mL, 0.1500 mmol) and the reaction was concentrated in a vacuum oven (50° C., <100 mbar) to give the title compound (E212);

M/Z: 384.0 [M+H+].

The following compounds were prepared by the method of Example 212 with the modifications shown:

| Example | Structure | Name | Analysis | Modification |
|---|---|---|---|---|
| E213 | 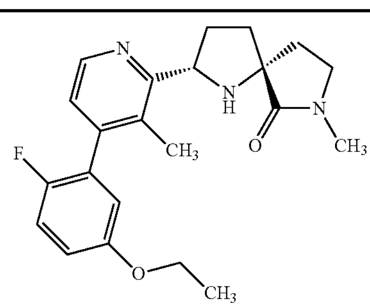 | (2S,5R)-2-[4-(5-Ethoxy-2-fluoro-phenyl)-3-methyl-2-pyridyl]-7-methyl-1,7-diazaspiro[4.4]nonan-6-one hydrochloride | M/Z: 384 (M + H⁺) | Using D99 in place of D98 |

-continued

| Example | Structure | Name | Analysis | Modification |
| --- | --- | --- | --- | --- |
| E214 | 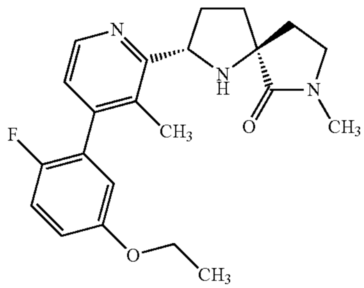 | (2S,5S)-2-[4-(5-Ethoxy-2-fluoro-phenyl)-3-methyl-2-pyridyl]-7-methyl-1,7-diazaspiro[4.4]nonan-6-one hydrochloride | M/Z: 384 (M + H$^+$) | Using D11 in place of D10 |
| E215 | 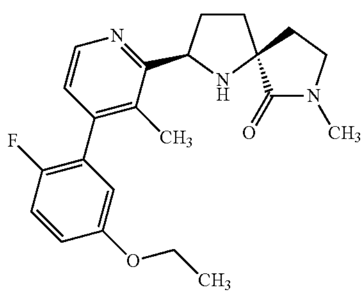 | (2R,5S)-2-[4-(5-Ethoxy-2-fluoro-phenyl)-3-methyl-2-pyridyl]-7-methyl-1,7-diazaspiro[4.4]nonan-6-one hydrochloride | M/Z: 384 (M + H$^+$) | Using D11 in place of D10 |

The following Examples were made by the method of Examples 44 and 45 but using the modifications noted:

| Example | Structure | Name | Analysis | Modification |
| --- | --- | --- | --- | --- |
| E216 | 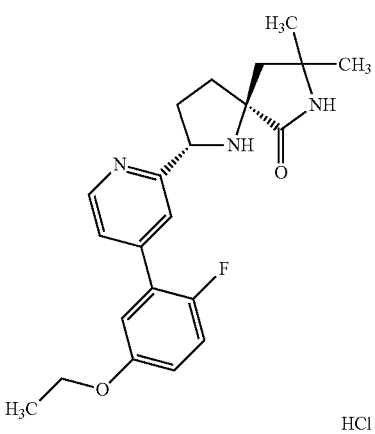 [SMILES: CCOc1ccc(F)c(-c2ccnc([C@@H]3CC[C@@]4(CC(C)(C)NC4=O)N3)c2)c1 ; Cl] | (2S,5S)-2-[4-(5-Ethoxy-2-fluoro-phenyl)-2-pyridyl]-8,8-dimethyl-1,7-diazaspiro[4.4]nonan-6-one hydrochloride | M/Z: 384 (M + H$^+$) | Using D30S and (5-ethoxy-2-fluorophenyl)-boronic acid |

-continued

| Example | Structure | Name | Analysis | Modification |
|---|---|---|---|---|
| E217 | 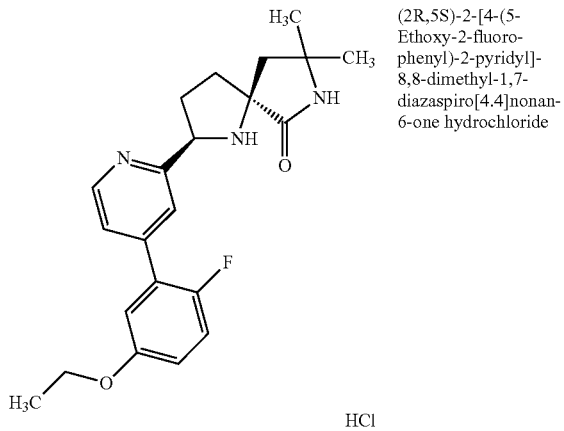 | (2R,5S)-2-[4-(5-Ethoxy-2-fluoro-phenyl)-2-pyridyl]-8,8-dimethyl-1,7-diazaspiro[4.4]nonan-6-one hydrochloride | M/Z: 384 (M + H$^+$) | Using D30S and 5-ethoxy-2-fluorophenyl)-boronic acid |
| E218 | 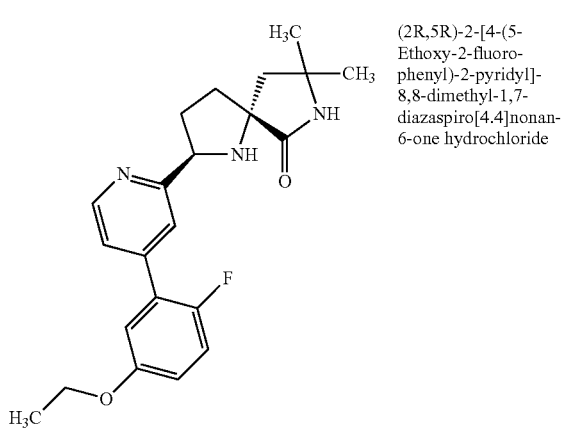 | (2R,5R)-2-[4-(5-Ethoxy-2-fluoro-phenyl)-2-pyridyl]-8,8-dimethyl-1,7-diazaspiro[4.4]nonan-6-one hydrochloride | M/Z: 384 (M + H$^+$) | Using D30R and 5-ethoxy-2-fluorophenyl)-boronic acid |
| E219 | 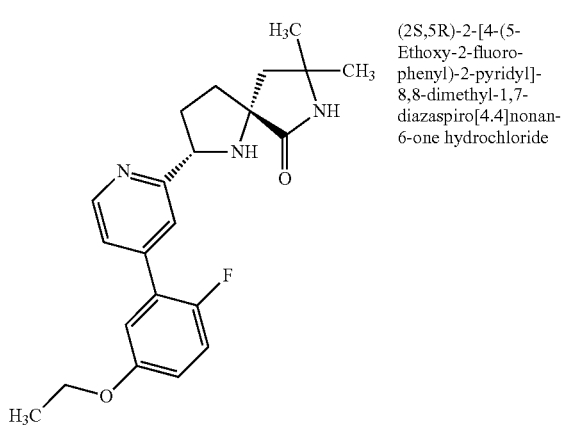 | (2S,5R)-2-[4-(5-Ethoxy-2-fluoro-phenyl)-2-pyridyl]-8,8-dimethyl-1,7-diazaspiro[4.4]nonan-6-one hydrochloride | M/Z: 384 (M + H$^+$) | Using D30R and 5-ethoxy-2-fluropheny)-boronic acid |

Example 220

(2R,5R)-2-[4-(2-Fluoro-5-hydroxy-phenyl)-2-pyridyl]-8,8-dimethyl-1,7-diazaspiro[4.4]nonan-6-one (E220)

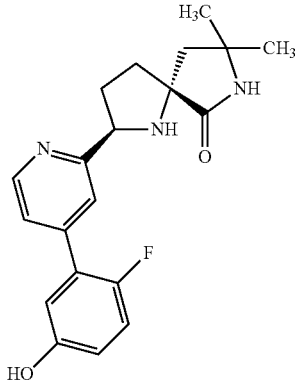 [SMILES: CC1(C)C[C@]2(CC[C@H](c3cc(-c4cc(O)ccc4F)ccn3)N2)C(=O)N1]

A solution of (2R,5R)-2-[4-(5-ethoxy-2-fluoro-phenyl)-2-pyridyl]-8,8-dimethyl-1,7-diazaspiro[4.4]nonan-6-one (which may be prepared as described in Example 218) (1.9 mg, 0.0100 mmol) in DCM (0.1000 mL) was coooled to −78° C. and treated with BBr$_3$ in DCM (7 µL, 0.0100 mmol) and then the mixture was allowed to warm to room temp. After 1 hr, more BBr$_3$ in DCM (0.07 ml, 0.07 mmol) was added and stirring was continued for a further 1 hr. Methanol was added and the product was trapped on an SCX cartridge (0.5 g). After eluting with methanol, the product was released from the resin with 1M NH$_3$ in methanol.

Evaporation gave 1.7 mg of (2R,5R)-2-[4-(2-fluoro-5-hydroxy-phenyl)-2-pyridyl]-8,8-dimethyl-1,7-diazaspiro[4.4]nonan-6-one (E220);

M/Z: 356 (M+H$^+$).

The following Examples were prepared in a similar manner to Examples E58 and E59 with the modifications and alternative boronic acids noted:

| Example | Structure | Name | Analysis | Modification |
|---|---|---|---|---|
| E221 | 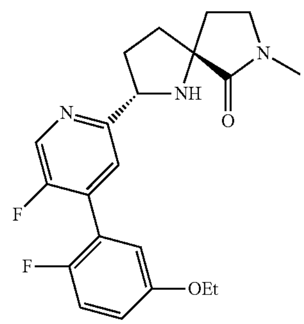 | (2S,5R)-2-[4-(5-Ethoxy-2-fluoro-phenyl)-5-fluoro-2-pyridyl]-7-methyl-1,7-diazaspiro[4.4]nonan-6-one hydrochloride | M/Z: 388 (M + H$^+$) | Using (D35R) and (2-fluoro-5-ethoxyphenyl) boronic acid |
| E222 | 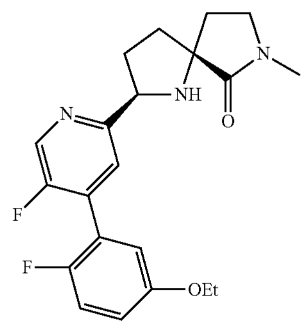 | (2R,5R)-2-[4-(5-Ethoxy-2-fluoro-phenyl)-5-fluoro-2-pyridyl]-7-methyl-1,7-diazaspiro[4.4]nonan-6-one hydrochloride | M/Z: 388 (M + H$^+$) | Using (D35R) and (2-fluoro-5-ethoxyphenyl) boronic acid |
| E223 | 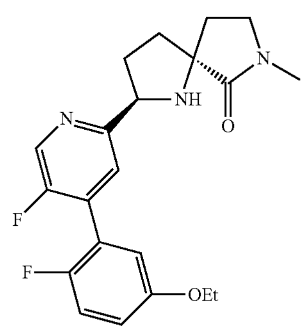 | (2R,5S)-2-[4-(5-Ethoxy-2-fluoro-phenyl)-5-fluoro-2-pyridyl]-7-methyl-1,7-diazaspiro[4.4]nonan-6-one hydrochloride | M/Z: 388 (M + H$^+$) | Using (D35S) and (2-fluoro-5-ethoxyphenyl) boronic acid |

-continued

| Example | Structure | Name | Analysis | Modification |
|---|---|---|---|---|
| E224 | 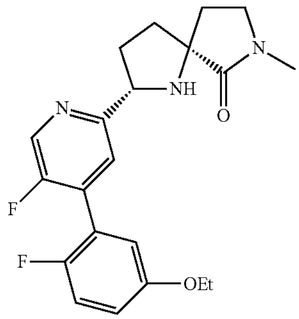 | (2S,5S)-2-[4-(5-Ethoxy-2-fluorophenyl)-5-fluoro-2-pyridyl]-7-methyl-1,7-diazaspiro[4.4]nonan-6-one hydrochloride | M/Z: 388 (M + H$^+$) | Using (D35S) and (2-fluoro-5-ethoxyphenyl) boronic acid |

Example 225

(2R,5S)-1,7-Dimethyl-2-[4-[4-(trifluoromethyl)phenyl]-2-pyridyl]-1,7-diazaspiro[4.4]nonan-6-one hydrochloride (E225)

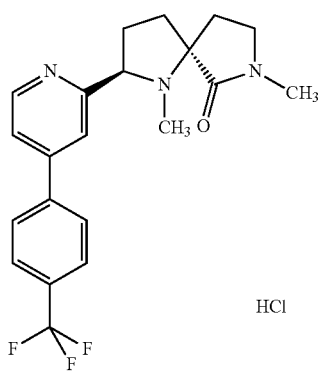 [SMILES: CN1CC[C@@]2(CC[C@H](c3cc(-c4ccc(C(F)(F)F)cc4)ccn3)N2C)C1=O ; Cl]

To a solution of (2R,5S)-7-methyl-2-[4-[4-(trifluoromethyl)phenyl]-2-pyridyl]-1,7-diazaspiro[4.4]nonan-6-one hydrochloride (which may be prepared as described in Example 52) (21 mg, 0.0500 mmol) in methanol (0.5000 mL) was added 3 meq of 3.7% formalin solution and sodium triacetoxyborohydride (16.21 mg, 0.0800 mmol) and the mixture was stirred for 1 h. The mixture was evaporated and partitioned between satd. aq. NaHCO$_3$ (2 ml) and MDC (3×5 ml) and the residue purified on an SCX-2 cartridge (0.5 g) eluting with MeOH to 2% aq NH$_3$ in MeOH to give (2R,5S)-1,7-dimethyl-2-[4-[4-(trifluoromethyl)phenyl]-2-pyridyl]-1,7-diazaspiro[4.4]nonan-6-one, a clear oil (16.9 mg);

300 MHz $^1$H NMR $\delta_H$ (CDCl$_3$) 1.88-2.07 (2H, m), 2.11-2.42 (4H, m), 2.29 (3H, s), 2.53-2.63 (1H, m), 2.89 (3H, m), 3.26-3.42 (2H, m), 4.50 (1H, t), 7.48 (1H, d), 7.61 (1H, s), 7.76 (4H, s), 8.70 (1H, d).

The material was treated with 1M HCl in Et$_2$O (80 µl) and evaporated to give the hydrochloride salt (E225);

M/Z 390 (M+H$^+$)

The following examples were prepared by a similar method to Example 225 using the alternative secondary amines indicated in the table in place of E52

| Example | Structure | Name | Analysis | Modification |
|---|---|---|---|---|
| E226 | 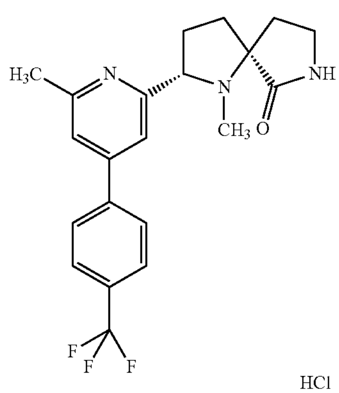 [SMILES: Cc1cc(-c2ccc(C(F)(F)F)cc2)cc([C@@H]2CC[C@@]3(CCNC3=O)N2C)n1 ; Cl] | (2S,5S)-1-Methyl-2-[6-methyl-4-[4-(trifluoromethyl)phenyl]-2-pyridyl]-1,7-diazaspiro[4.4]nonan-6-one hydrochloride | M/Z: 390 (M + H$^+$) | Using E97 |

| Example | Structure | Name | Analysis | Modification |
|---|---|---|---|---|
| E227 | 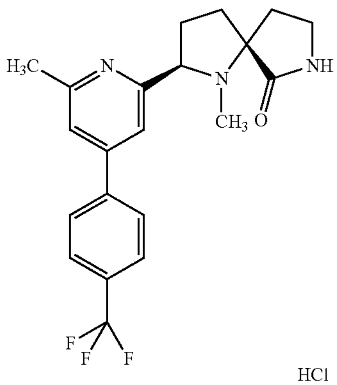 [SMILES: Cc1cc(-c2ccc(C(F)(F)F)cc2)cc([C@H]2CC[C@]3(CCNC3=O)N2C)n1 ; Cl] | (2R,5R)-1-Methyl-2-[6-methyl-4-[4-(trifluoromethyl)phenyl]-2-pyridyl]-1,7-diazaspiro[4.4]nonan-6-one hydrochloride | M/Z: 390 (M + H$^+$) | Using E96 |
| E228 | 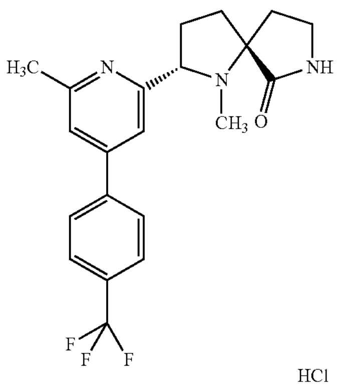 [SMILES: Cc1cc(-c2ccc(C(F)(F)F)cc2)cc([C@@H]2CC[C@]3(CCNC3=O)N2C)n1 ; Cl] | (2S,5R)-1-Methyl-2-[6-methyl-4-[4-(trifluoromethyl)phenyl]-2-pyridyl]-1,7-diazaspiro[4.4]nonan-6-one hydrochloride | M/Z: 390 (M + H$^+$) | Using E95 |
| E229 | 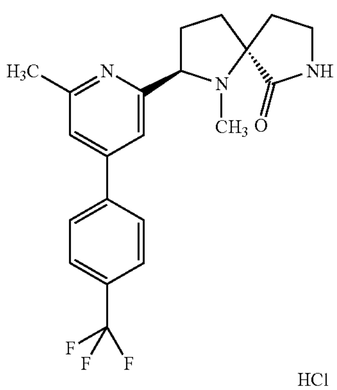 [SMILES: Cc1cc(-c2ccc(C(F)(F)F)cc2)cc([C@H]2CC[C@@]3(CCNC3=O)N2C)n1 ; Cl] | (2R,5S)-1-Methyl-2-[6-methyl-4-[4-(trifluoromethyl)phenyl]-2-pyridyl]-1,7-diazaspiro[4.4]nonan-6-one hydrochloride | M/Z: 390 (M + H$^+$) | Using E94 |
| E230 | 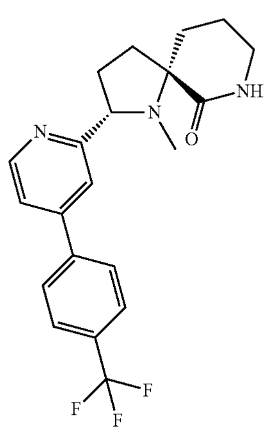 | (2S,6S)-1-Methyl-2-[4-[4-(trifluoromethyl)phenyl]-2-pyridyl]-1,8-diazaspiro[4.5]decan-7-one hydrochloride | M/Z: 390 (M + H$^+$) | Using E51 |

-continued

| Example | Structure | Name | Analysis | Modification |
|---|---|---|---|---|
| E231 | 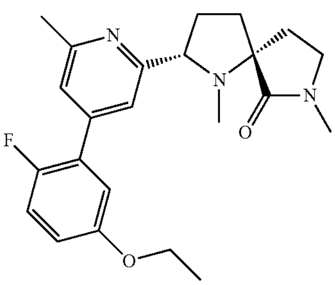 | (2S,5R)-2-[4-(5-Ethoxy-2-fluoro-phenyl)-6-methyl-2-pyridyl]-1,7-dimethyl-1,7-diazaspiro-[4.4]nonan-6-one hydrochloride | M/Z: 398 (M + H+) | Using E120 |
| E232 | 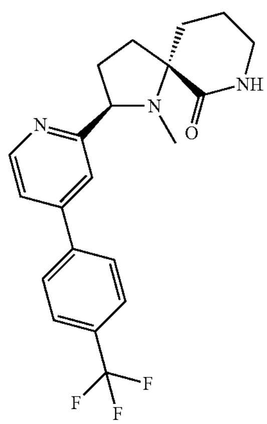 | (2R,6S)-1-Methyl-2-[4-[4-(trifluoromethyl)phenyl]-2-pyridyl]-1,8-diazaspiro[4.5]decan-7-one hydrochloride | M/Z: 390 (M + H+) | Using E50 |

Example 233

(2S,6S)-1-Ethyl-2-[4-[4-(trifluoromethyl)phenyl]-2-pyridyl]-1,8-diazaspiro[4.5]decan-7-one hydrochloride (E233)

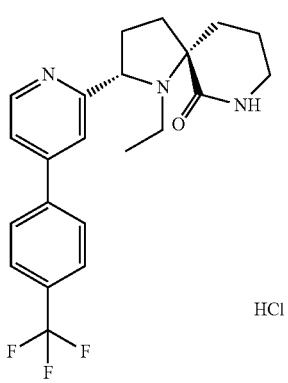 [SMILES: CCN1[C@H](c2cc(-c3ccc(C(F)(F)F)cc3)ccn2)CC[C@]12CCCNC2=O ; Cl]

Iodoethane (0.01 mL, 0.1500 mmol) was added to a mixture of (2S,6S)-2-[4-[4-(trifluoromethyl)phenyl]-2-pyridyl]-1,8-diazaspiro[4.5]decan-7-one (49.87 mg, 0.1300 mmol) (which may be prepared as described in Example 51) and potassium carbonate (36.72 mg, 0.2700 mmol) in DCM (2 mL) at 200° C. in a sealed microwave vial and the reaction was stirred for 18 hrs. Additional EtI (2 eq.) and DMF (0.5000 mL) was added and the reaction was stirred for 12 days. The solid K₂CO₃ was filtered off, washed with a little DCM and the combine organics evaporated to afford an orange oil. This was purified using a Biotage SP4 silica column, eluting with 0 to 10% MeOH/EtOAc to afford (2S,6S)-1-ethyl-2-[4-[4-(trifluoromethyl)phenyl]-2-pyridyl]-1,8-diazaspiro[4.5]decan-7-one (36 mg, 0.0892 mmol, 67.2% yield) as a yellow oil;

300 MHz $^1$H NMR $\delta_H$ (CDCl₃) 0.8 (3H, t), 1.69-2.33 (7H, m), 2.68-2.91 (3H, m), 3.28-3.35 (2H, m), 4.57 (1H, dd), 5.95 (1H, br.s), 7.34 (1H, dd), 7.76 (4H, s), 7.84 (1H, d), 8.64 (1H, d).

1M HCl in Et₂O (0.09 mL, 0.0900 mmol) was added to a solution of this material in DCM (1 mL) at 20° C. and the reaction was stood for 5 mins. The solvent was blown down with N₂ to afford (2S,6S)-1-ethyl-2-[4-[4-(trifluoromethyl)phenyl]-2-pyridyl]-1,8-diazaspiro[4.5]decan-7-one hydrochloride (E233) as a light brown solid;

M/Z: 404 (M+H+).

The following Examples were prepared by the method of Examples 21 and 22 using alternative imines in place of D14R

| Example | Structure | Name | Analysis | Modification |
|---|---|---|---|---|
| E234 | 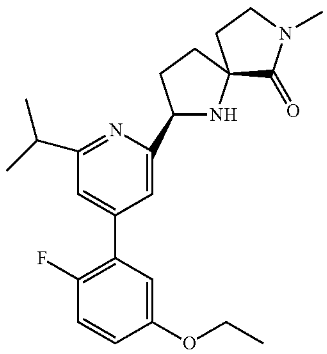 | (2R,5R)-2-[4-(5-Ethoxy-2-fluoro-phenyl)-6-isopropyl-2-pyridyl]-7-methyl-1,7-diazaspiro[4.4]nonan-6-one hydrochloride | M/Z: 412 (M + H$^+$) | Using D117R |
| E235 | 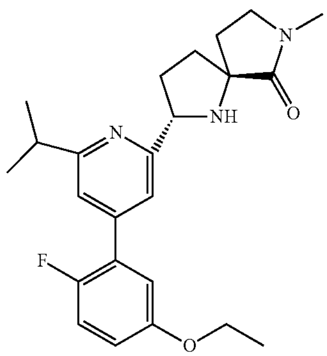 | (2S,5R)-2-[4-(5-Ethoxy-2-fluoro-phenyl)-6-isopropyl-2-pyridyl]-7-methyl-1,7-diazaspiro[4.4]nonan-6-one hydrochloride | M/Z: 412 (M + H$^+$) | Using D117R |
| E236 | 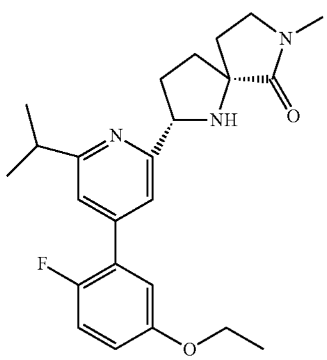 | (2S,5S)-2-[4-(5-Ethoxy-2-fluoro-phenyl)-6-isopropyl-2-pyridyl]-7-methyl-1,7-diazaspiro[4.4]nonan-6-one hydrochloride | M/Z: 412 (M + H$^+$) | Using D117S |
| E237 | 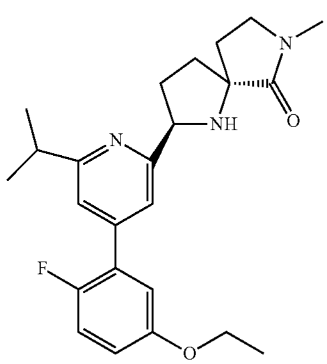 | (2R,5S)-2-[4-(5-Ethoxy-2-fluoro-phenyl)-6-isopropyl-2-pyridyl]-7-methyl-1,7-diazaspiro[4.4]nonan-6-one hydrochloride | M/Z: 412 (M + H$^+$) | Using D117S |

Example 238 and Example 239

(2S,3S,5R)-3-Fluoro-7-methyl-2-[4-[4-(trifluoromethyl)phenyl]-2-pyridyl]-1,7-diazaspiro[4.4]nonan-6-one hydrochloride (E238) and (2S,3R,5R)-3-Fluoro-7-methyl-2-[4-[4-(trifluoromethyl)phenyl]-2-pyridyl]-1,7-diazaspiro[4.4]nonan-6-one (E239)

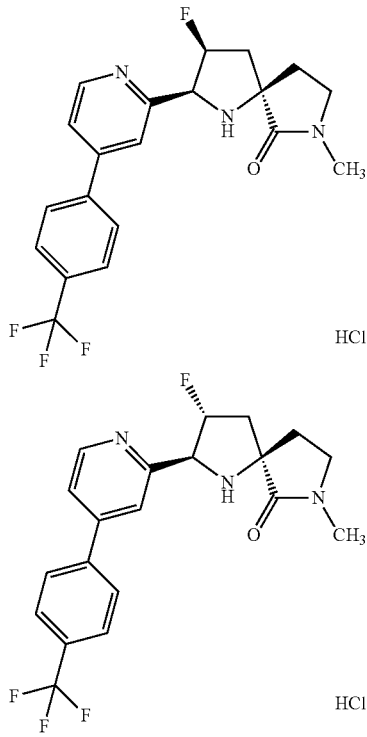

To a stirred solution of (5R)-3-fluoro-7-methyl-2-[4-[4-(trifluoromethyl)phenyl]-2-pyridyl]-1,7-diazaspiro[4.4]non-1-en-6-one (which may be prepared as described in Description 119) (54 mg, 0.1400 mmol) in anhydrous DCM (2 mL) under nitrogen at 0° C., was added concentrated hydrochloric acid (0.01 mL, 0.1500 mmol). After 10 min of stirring, sodium triacetoxyborohydride (116.99 mg, 0.5500 mmol) was added portionwise. The resulting suspension was left to stir at room temperature for 2 h. The mixture was left to stir for 30 min. Saturated aq. sodium hydrogen carbonate was added. The reaction mixture was extracted with DCM twice and the organic layers were washed with brine, dried over sodium sulfate, filtered and the filtrate was evaporated under reduced pressure to give an amber oil. The crude residue was purified by silica gel chromatography (10 g SiO₂) eluting with ethyl acetate in iso-hexane (0-100%). Evaporation of desired fractions gave mixed isomers and a major slower running product, tentatively assigned (2S,3S,5R)-3-fluoro-7-methyl-2-[4-[4-(trifluoromethyl)phenyl]-2-pyridyl]-1,7-diazaspiro[4.4]nonan-6-one although the absolute and relative stereochemistries of the 2 and 3 position are uncertain;

300 MHz ¹H NMR $\delta_H$ (CDCl₃) 2.19-2.64 (5H, m), 2.94 (3H, s), 3.33 (1H, m), 3.46 (1H, m), 4.96 (1H, dd), 5.52 (1H, dt), 7.42 (1H, dd), 7.76-7.78 (5H, m), 8.68 (1H, d), which was converted to the corresponging HCl salt (E238) (47 mg);

M/Z: 394 (M+H⁺).

In a similar manner, the epimer (D119a) (27 mg) was converted to a major slower eluting product tentatively assigned (2S,3R,5R)-3-fluoro-7-methyl-2-[4-[4-(trifluoromethyl)phenyl]-2-pyridyl]-1,7-diazaspiro[4.4]nonan-6-one;

300 MHz ¹H NMR $\delta_H$ (CDCl₃) 2.09 (1H, ddd), 2.17-2.35 (3H, m), 2.58 (1H, dd), 2.97 (3H, s), 3.32-3.50 (2H, m), 4.40 (1H, dd), 5.53 (1H, dt), 7.45 (1H, d), 7.66 (1H, s), 7.76 (4H, s), 8.70 (1H, d) which was converted to a hydrochloride salt (E239) (11 mg);

M/Z: 394 (M+H⁺).

Example 240

(5R)-3,3-Difluoro-7-methyl-2-[4-[4-(trifluoromethyl)phenyl]-2-pyridyl]-1,7-diazaspiro[4.4]nonan-6-one hydrochloride (E240)

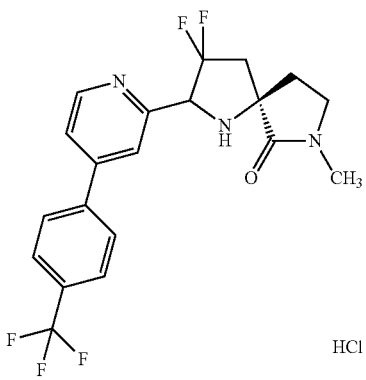 [SMILES: CN1CC[C@@]2(CC(F)(F)C(c3cc(-c4ccc(C(F)(F)F)cc4)ccn3)N2)C1=O ; Cl]

To a stirred solution of (5R)-3,3-difluoro-7-methyl-2-[4-[4-(trifluoromethyl)phenyl]-2-pyridyl]-1,7-diazaspiro[4.4]non-1-en-6-one (which may be prepared as described in Description 120) (18.99 mg, 0.0500 mmol) in anhydrous DCM (2 mL) under nitrogen at -10° C., was added concentrated hydrochloric acid (0.01 mL, 0.1400 mmol). After 10 min of stirring, sodium triacetoxyborohydride (68.84 mg, 0.3200 mmol) was added. The resulting suspension was left to stir at room temperature for 30 h. Saturated sodium hydrogen carbonate was added. The reaction mixture was extracted with DCM and the organic layers were washed with brine, dried over sodium sulfate, filtered and the filtrate was evaporated under reduced pressure to give an amber oil (17 mg). The mixture was separated by semi-preparative hplc using a ChiralPak IA column (250×20 mm) with ethanol/n-heptane (14%:86%) to give (5R)-3,3-difluoro-7-methyl-2-[4-[4-(trifluoromethyl)phenyl]-2-pyridyl]-1,7-diazaspiro[4.4]nonan-6-one as a ~2:3 mixture of diastereoisomers as a colourless oil;

300 MHz ¹H NMR $\delta_H$ (CDCl₃) 2.25-2.42 (3H, m), 2.68-2.90 (1H, m), 2.95, 2.98 (3H, 2×d), 3.29-3.57 (2H, m), 4.62, 5.04 (1H, 2×m), 7.49 (1H, app.d), 7.69 (1H, app.q), 7.77, 7.79 (4H, 2×s), 8.70, 8.82 (1H, 2×d).

This was dissolved in DCM and treated with 1M HCl in ether (1 eq.). Evaporation of volatiles gave a yellow solid, (5R)-3,3-difluoro-7-methyl-2-[4-[4-(trifluoromethyl)phenyl]-2-pyridyl]-1,7-diazaspiro[4.4]nonan-6-one hydrochloride (E240) (1.58 mg, 0.0038 mmol, 8.3% yield);

M/Z: 412 (M+H+).

Example 241 and Example 242

(2R,5S)-2-[4-(5-Ethoxy-2-fluoro-phenyl)-5-ethyl-2-pyridyl]-7-methyl-1,7-diazaspiro[4.4]nonan-6-one hydrochloride (E241) and (2S,5R)-2-[4-(5-Ethoxy-2-fluoro-phenyl)-5-ethyl-2-pyridyl]-7-methyl-1,7-diazaspiro[4.4]nonan-6-one hydrochloride (E242)

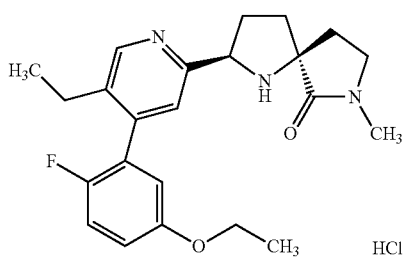

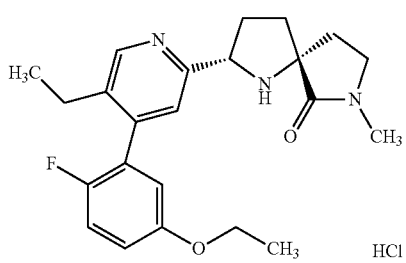

To a microwave vial containing a solution of (5-ethoxy-2-fluoro-phenyl)boronic acid (54.39 mg, 0.3000 mmol) in MeCN (1 mL) and water (0.2000 mL) was added (2R,5S)-2-(4-bromo-5-ethyl-2-pyridyl)-7-methyl-1,7-diazaspiro[4.4]nonan-6-one (which may be prepared as described in Description 122) (80 mg, 0.2400 mmol), sodium carbonate (50.12 mg, 0.4700 mmol) and bis(triphenylphosphine)palladium (II) dichloride (8.2 mg, 0.0100 mmol). The microwave vial was sealed and heated at 140° C. for 15 minutes. The reaction was concentrated in vacuo and loaded onto a silica column (10 g, Biotage SNAP cartridge). The silica column was then eluted with a gradient of (80:20:2 EtOAc:MeOH: 0.88M NH$_3$):EtOAc from 0% to 100%. Fractions containing desired product were combined and concentrated in vacuo to give (2R,5S)-2-[4-(5-ethoxy-2-fluoro-phenyl)-5-ethyl-2-pyridyl]-7-methyl-1,7-diazaspiro[4.4]nonan-6-one (69.9 mg, 0.1759 mmol, 74.4% yield) as a colourless oil;

$^1$H NMR (300 MHz, CDCl$_3$) δ: 1.05 (t, 3H), 1.39 (t, 3H), 1.81-2.19 (m, 5H), 2.42-2.56 (m, 3H), 2.69 (s, 1H), 2.86 (s, 3H), 3.20-3.33 (m, 2H), 3.99 (q, 2H), 4.67 (t, 1H), 6.69 (dd, 1H), 6.86 (dt, 1H), 7.03 (t, 1H), 7.26 (s, 1H), 8.45 (s, 1H).

This was dissolved in dichloromethane in DCM (2 mL) and HCl in ether (0.18 mL, 0.1800 mmol) (1 eq) was added and the reaction was concentrated in a vacuum oven (50° C., <100 mbar). The residue was triturated with tBME (3 mL), and the residue was concentrated in vacuo to give (E241) as a solid (76.6 mg);

M/Z: 398 (M+H+).

By the same method, the antipode (D123) was converted to (2S,5R)-2-[4-(5-Ethoxy-2-fluoro-phenyl)-5-ethyl-2-pyridyl]-7-methyl-1,7-diazaspiro[4.4]nonan-6-one;

$^1$H NMR (300 MHz, CDCl$_3$) δ: 1.05 (t, 3H), 1.38 (t, 3H), 1.80-2.18 (m, 5H), 2.41-2.56 (m, 3H), 2.73 (s, 1H), 2.85 (s, 3H), 3.19-3.32 (m, 2H), 3.98 (q, 2H), 4.66 (t, 1H), 6.69 (dd, 1H), 6.85 (dt, 1H), 7.02 (t, 1H), 7.25 (s, 1H), 8.45 (s, 1H), which was correspondingly converted to its hydrochloride salt (E242);

M/Z: 398 (M+H+).

Example 243

(2R,6S,9S)-2-[4-(5-Ethoxy-2-fluoro-phenyl)-2-pyridyl]-9-methyl-1,8-diazaspiro[4.5]decan-7-one hydrochloride (E243)

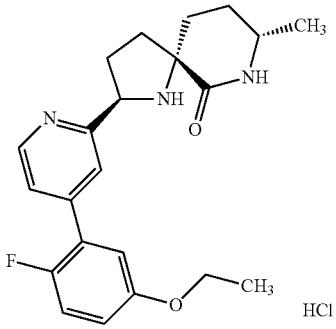 [SMILES: CCOc1ccc(F)c(-c2ccnc([C@H]3CC[C@]4(CC[C@H](C)NC4=O)N3)c2)c1 ; Cl]

To a solution of tert-butyl (2R,6S,9S)-2-[4-(5-ethoxy-2-fluoro-phenyl)-2-pyridyl]-9-methyl-7-oxo-1,8-diazaspiro[4.5]decane-1-carboxylate (which may be prepared as described in Description 130) (61 mg, 0.1300 mmol) in DCM (2 mL) was added 4M HCl in dioxane (0.5 mL, 2 mmol). The mixture was stood at room temperature over 2 days. The reaction mixture was evaporated and the residues dissolved in methanol and passed down an SCX column, washed through with methanol and eluted with 0.5M ammonia in methanol. The combined ammonia fractions were evaporated to yield (2R,6S,9S)-2-[4-(5-ethoxy-2-fluoro-phenyl)-2-pyridyl]-9-methyl-1,8-diazaspiro[4.5]decan-7-one as a yellow gum, (47 mg);

300 MHz $^1$H NMR δ$_H$ (CDCl$_3$); 1.25 (3H, d), 1.45 (3H, t), 1.71-1.83 (3H, m), 1.38-2.16 (3H, m), 2.33 (1H, m), 2.48 (1H, tt), 3.4 (1H, br.s), 3.61 (1H, q), 4.06 (2H, q), 4.38 (1H, dd), 5.07 (1H, br.s), 6.89 (1H, dt), 6.98 (1H, dd), 7.00 (1H, t), 7.35 (1H, d), 7.55 (1H, s), 8.64 (1H, d), To a solution of this freebase in DCM was added (1 eq.) of 4M HCl in dioxane (30 μL). The solution was stood at room temperature for 1 hr then evaporated and dried under vacuum overnight to give hydrochloride salt (E243) as yellow solid, (52 mg);

M/Z: 384 (M+H$^+$).

The following Examples were prepared by the method of Example 243 using the modifications noted:

| Example | Structure | Name | Analysis | Modification |
|---|---|---|---|---|
| E244 | 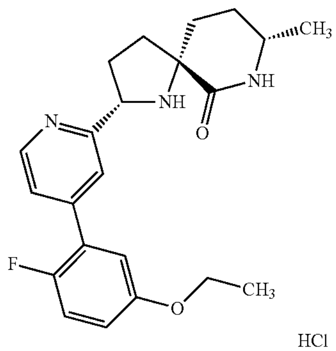 [SMILES: CCOc1ccc(F)c(-c2ccnc([C@@H]3CC[C@]4(CC[C@H](C)NC4=O)N3)c2)c1 ; Cl] | (2S,6S,9S)-2-[4-(5-Ethoxy-2-fluoro-phenyl)-2-pyridyl]-9-methyl-1,8-diazaspiro[4.5]decan-7-one hydrochloride | M/Z: 384 (M + H⁺) | Using D129 in place of D130 |
| E245 | 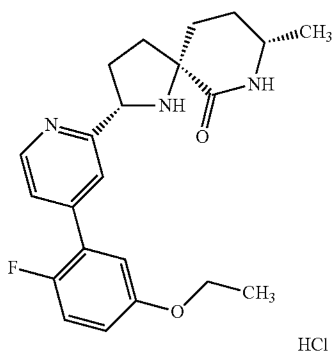 [SMILES: CCOc1ccc(F)c(-c2ccnc([C@@H]3CC[C@@]4(CC[C@H](C)NC4=O)N3)c2)c1 ; Cl] | (2S,6R,9S)-2-[4-(5-Ethoxy-2-fluoro-phenyl)-2-pyridyl]-9-methyl-1,8-diazaspiro[4.5]decan-7-one hydrochloride | M/Z: 384 (M + H⁺) | Using D126 in place of D125 |
| E246 | 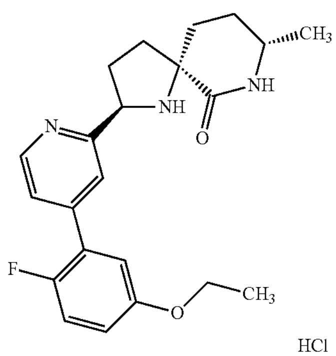 [SMILES: CCOc1ccc(F)c(-c2ccnc([C@H]3CC[C@@]4(CC[C@H](C)NC4=O)N3)c2)c1 ; Cl] | (2R,6R,9S)-2-[4-(5-Ethoxy-2-fluoro-phenyl)-2-pyridyl]-9-methyl-1,8-diazaspiro[4.5]decan-7-one hydrochloride | M/Z: 384 (M + H⁺) | Using D126 in place of D125 |

Examples 247 and 248

(2R,5R)-2-[4-(5-Ethoxy-2-fluoro-phenyl)-6-methoxy-2-pyridyl]-7-methyl-1,7-diazaspiro[4.4]nonan-6-one hydrochloride (E247) and (2S,5R)-2-[4-(5-Ethoxy-2-fluoro-phenyl)-6-methoxy-2-pyridyl]-7-methyl-1,7-diazaspiro[4.4]nonan-6-one

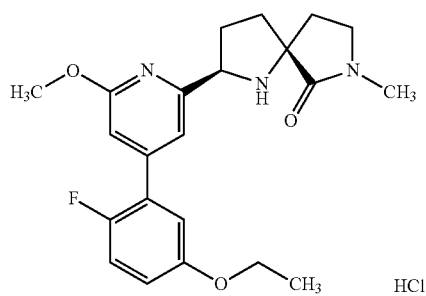

Concentrated hydrochloric acid (0.01 mL, 0.1400 mmol) was added to an ice-cooled, stirred solution of (5R)-2-[4-(5-ethoxy-2-fluoro-phenyl)-6-methoxy-2-pyridyl]-7-methyl-1,7-diazaspiro[4.4]non-1-en-6-one (which may be prepared as described in Description 133) (50 mg, 0.1300 mmol) in dry DCM (2 mL) under N₂. After leaving 3-5 minutes sodium triacetoxyborohydride (106.65 mg, 0.5000 mmol) was added portionwise over 3 mins. After stirring for 30 mins, the ice bath was removed and the mixture was stirred at ambient temp for 1.75 h. Satd. aq. NaHCO₃ solution (15 ml) was added and the reaction mixture was stirred for 15 minutes. The mixture was then extracted with DCM (3×15 ml) and the combined organic extracts were dried (Na₂SO₄) and evaporated to an oil, which was purified by silica gel column chromatography: the oil was dissolved in DCM (2 ml) and the solution was applied to a 10 g cartridge which was then eluted on a Biotage SP4 system with a gradient of Solvent A/EtOAc (0-50%) where Solvent A=0.5M NH₃-MeOH (8:92). Two components were collected and evaporated to oils. The faster funning isomer was (2S,5R)-2-[4-(5-ethoxy-2-fluoro-phenyl)-6-methoxy-2-pyridyl]-7-methyl-1,7-diazaspiro[4.4]nonan-6-one (30.6 mg);

300 MHz ¹H NMR δ$_H$ (CDCl₃) 1.44 (3H, t), 1.79 (1H, m), 1.99-2.27 (5H, m), 2.48 (1H, m), 2.91 (3H, s), 3.26-3.39 (2H, m), 3.98 (3H, s), 4.04 (2H, q), 4.64 (1H, q), 6.78 (1H, s), 6.89 (1H, dt), 6.95 (1H, dd), 7.08 (1H, t), 7.19 (1H, s).

1M hydrogen chloride in Et₂O (0.08 mL, 0.0800 mmol) was added to this material (30 mg, 0.080 mmol) in DCM (1 mL). The solution was evaporated to an oily residue which was stirred with Et₂O (3 ml) and re-evaporated. This was repeated a number of times to get a solid residue which was dried to give hydrochloride salt (E248) as a solid;

M/Z: 400 (M+H⁺).

The slower running isomer was (2R,5R)-2-[4-(5-ethoxy-2-fluoro-phenyl)-6-methoxy-2-pyridyl]-7-methyl-1,7-diazaspiro[4.4]nonan-6-one (9 mg);

300 MHz ¹H NMR δ$_H$ (CDCl₃) 1.44 (3H, t), 1.83 (1H, m), 2.02-2.38 (8H, m), 2.95 (1H, s), 3.29-3.45 (2H, m), 4.04 (3H, s) 4.05 (2H, q), 4.34 (1H, t), 6.82 (1H, s), 6.88 (1H, dt), 6.97 (1H, dd), 7.08 (1H, t), 7.11 (1H, s).

1M hydrogen chloride in Et₂O (0.02 mL, 0.0200 mmol) was added to a stirred solution of (2R,5R)-2-[4-(5-ethoxy-2-fluoro-phenyl)-6-methoxy-2-pyridyl]-7-methyl-1,7-diazaspiro[4.4]nonan-6-one (8 mg, 0.0200 mmol) in DCM (1 mL). The solution was evaporated to an oily residue which was stirred with Et₂O (3 ml) and re-evaporated. This was repeated a number of times to give hydrochloride salt (E247) as a solid;

M/Z: 400 (M+H⁺).

The following Examples were prepared in a similar manner to Examples 247 and 248 using the alternative intermediate indicated:

| Example | Structure | Name | Analysis | Modification |
|---|---|---|---|---|
| E249 | 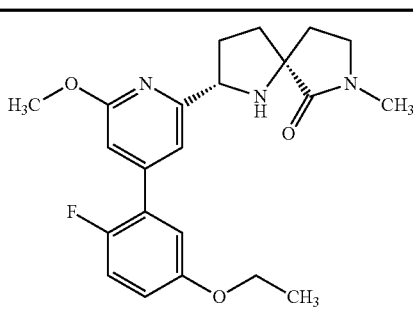 | (2S,5S)-2-[4-(5-Ethoxy-2-fluoro-phenyl)-6-methoxy-2-pyridyl]-7-methyl-1,7-diazaspiro[4.4]nonan-6-one hydrochloride | M/Z: 400 (M + H⁺) | Using D133S in place of D133R |
| E250 | 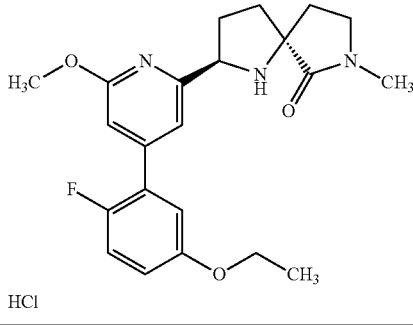 | (2R,5S)-2-[4-(5-Ethoxy-2-fluoro-phenyl)-6-methoxy-2-pyridyl]-7-methyl-1,7-diazaspiro[4.4]nonan-6-one hydrochloride | M/Z: 400 (M + H⁺) | Using D133S in place of D133R |

Example 251

(2R,5S)-2-[4-[2-Fluoro-5-(2-fluoroethoxyl)phenyl]-2-pyridyl]-7-methyl-1,7-diazaspiro[4.4]nonan-6-one hydrochloride (E251)

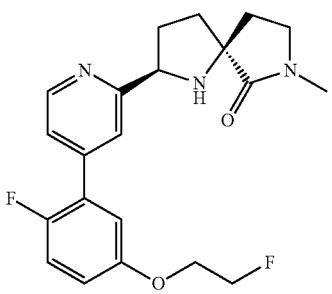 [SMILES: CN1CC[C@@]2(CC[C@H](c3cc(-c4cc(OCCF)ccc4F)ccn3)N2)C1=O]

To a Smith microwave vial was added (2R,5S)-2-[4-(2-fluoro-5-hydroxy-phenyl)-2-pyridyl]-7-methyl-1,7-diazaspiro[4.4]nonan-6-one (which may be prepared as described in Description 134) (66.5 mg, 0.1900 mmol), triphenyl phosphine (102.19 mg, 0.3900 mmol), Di-tert-butyl azodicarboxylate ((89.71 mg, 0.3900 mmol) and 2-fluoroethanol (0.02 mL, 0.2900 mmol) in THF (0.5000 mL). Toluene (1 mL) was added. The reaction mixture was heated by microwave at 120° C. for 45 min. The reaction mixture was eluted on an SCX-2 cartrige (0.5 g) and washed with DCM followed MeOH. The desired product was eluted off the cartridge with ammonia in MeOH (0.2M). Evaporation of solvents gave colourless oil. The crude residue was purified by silica gel chromatography (KPNH silica 11 g) eluting with ethyl acetate in iso-hexane (10-100%) followed by methanol in ethyl acetate (0-18%). Evaporation of desired fractions gave colourless oil. It was further purified by a ChiralPak IA column eluting with ethanol/n-heptane (20%:80%) to give 2R,5S)-2-[4-[2-fluoro-5-(2-fluoroethoxyl)phenyl]-2-pyridyl]-7-methyl-1,7-diazaspiro[4.4]nonan-6-one;

300 MHz $^1$H NMR $\delta_H$ (CDCl$_3$) 1.86-2.26 (5H, m), 2.37 (1H, br.s), 2.50-2.60 (1H, m), 2.91 (3H, s), 3.25-3.39 (2H, m), 4.20 (1H, t), 4.30 (1H, t), 4.70 (1H, t), 4.77 (1H, t), 4.86 (1H, t), 6.95 (1H, dt), 7.03 (1H, dd), 7.13 (1H, t), 7.33 (1H, d), 7.68 (1H, s), 8.61 (1H, d).

This was dissolved in DCM and treated with 1M HCl in ether (1 eq.). Evaporation of volatiles gave (2R,5S)-2-[4-[2-fluoro-5-(2-fluoroethoxyl)phenyl]-2-pyridyl]-7-methyl-1,7-diazaspiro-[4.4]nonan-6-one (E251) (42 mg, 0.1030 mmol, 52.9% yield) as a cream solid.

M/Z: 388 (M+H$^+$)

The following Examples were prepared in a similar manner to Example 251 using the alternative alcohols tabulated below:

| Example | Structure | Name | Analysis | Modification |
|---|---|---|---|---|
| E252 | 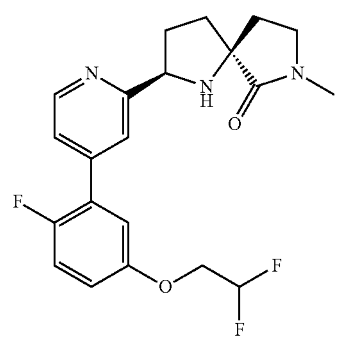 | (2R,5S)-2-[4-[5-(2,2-Difluoroethoxy)-2-fluoro-phenyl]-2-pyridyl]-7-methyl-1,7-diazaspiro[4.4]nonan-6-one hydrochloride | M/Z: 406 (M + H$^+$) | Using 2,2-difluoroethanol in place of 2-fluoroethanol |
| E253 | 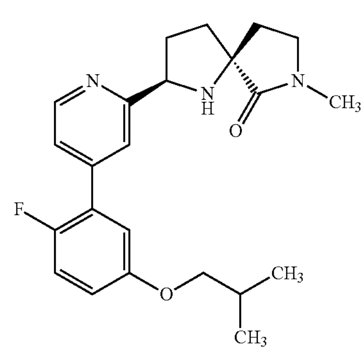 | (2R,5S)-2-[4-(2-Fluoro-5-isobutoxy-phenyl)-2-pyridyl]-7-methyl-1,7-diazaspiro[4.4]nonan-6-one hydrochloride | M/Z: 398 (M + H$^+$) | Using isobutanol in place of 2-fluoroethanol |

-continued

| Example | Structure | Name | Analysis | Modification |
|---|---|---|---|---|
| E254 | 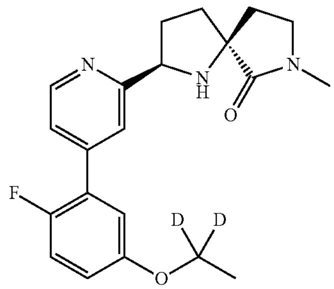 | (2R,5S)-2-[4-[5-(1,1-Dideuterioethoxy)-2-fluoro-phenyl]-2-pyridyl]-7-methyl-1,7-diazaspiro[4.4]nonan-6-one hydrochloride | M/Z: 372 (M + H⁺) | Using 1,1-dideuterioethanol in place of 2-fluoroethanol |
| E255 | 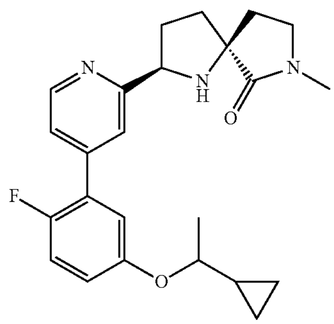 | (2R,5S)-2-[4-[5-(1-(Cyclopropyl)ethoxy)-2-fluoro-phenyl]-2-pyridyl]-7-methyl-1,7-diazaspiro[4.4]nonan-6-one hydrochloride | M/Z: 410 (M + H⁺) | Using 1-cyclopropylethanol in place of 2-fluoroethanol |

Example 256

2-[4-(5-Ethoxy-2-fluoro-phenyl)-3,6-dimethyl-2-pyridyl]-7-methyl-1,7-diazaspiro[4.4]nonan-6-one hydrochloride (E256)

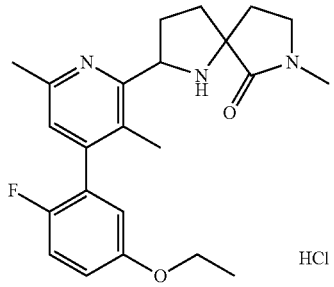 [SMILES: CCOc1ccc(F)c(-c2cc(C)nc(C3CCC4(CCN(C)C4=O)N3)c2C)c1 ; Cl]

To a stirred solution of 2-[4-(5-ethoxy-2-fluoro-phenyl)-3,6-dimethyl-2-pyridyl]-7-methyl-1,7-diazaspiro[4.4]non-1-en-6-one (which may be prepared as described in Description 142) (543 mg, 1.37 mmol) in anhydrous DCM (8 mL) under nitrogen at 0° C. was added concentrated hydrochloric acid (0.13 mL, 1.51 mmol). After 10 min of stirring, sodium triacetoxyborohydride (1.16 g, 5.49 mmol) was added portionwise. The resulting suspension was left to stir at room temperature for 2 h. Saturated aq. sodium hydrogen carbonate was added. The mixture was left to stir for 30 min. The reaction mixture was extracted with DCM twice and the combined organic layers were washed with brine, dried over sodium sulfate, filtered and the filtrate was evaporated under reduced pressure to give amber oil. The material was purified using KPNH SiO₂ chromatography, eluting with methanol in ethyl acetate (0-15%) to give an amber oil. This was purified by means of an SCX-2 cartrige (0.5 g) and the latter was eluted with DCM followed by MeOH. The desired product was eluted off the cartridge with ammonia in MeOH (0.2M). Evaporation of solvents gave, 2-[4-(5-ethoxy-2-fluoro-phenyl)-3,6-dimethyl-2-pyridyl]-7-methyl-1,7-diazaspiro[4.4]nonan-6-one (E256) as a colourless oil, an approximately 3:2 mixture of diastereomers;

M/Z: 398 (M+H⁺).

This mix was converted to the corresponding HCl salts. 1M HCl in ether ((1 eq.)) was added to the free base in DCM. Evaporation of volatiles gave yellow solid which was further dried under vacuum at 40° C. for 5 h. to give 2-[4-(5-ethoxy-2-fluoro-phenyl)-3,6-dimethyl-2-pyridyl]-7-methyl-1,7-diazaspiro[4.4]nonan-6-one hydrochloride (E256) (18.5 mg, 0.0442 mmol, 87.9% yield);

M/Z: 398 (M+H⁺).

Example 257

(2R,5S)-2-[4-(2-Fluoro-5-propanoyl-phenyl)-2-pyridyl]-7-methyl-1,7-diazaspiro[4.4]nonan-6-one hydrochloride (E257)

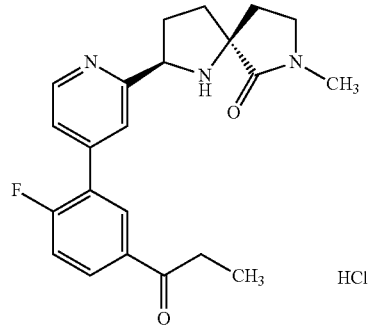 [SMILES: CCC(=O)c1ccc(F)c(-c2ccnc([C@H]3CC[C@@]4(CCN(C)C4=O)N3)c2)c1 ; Cl]

To a solution of 1-[4-fluoro-3-(4,4,5,5-tetramethyl-1,3,2-dioxaborolan-2-yl)phenyl]propan-1-one (which can be prepared as described in Description 143) (44.832 mg, 0.1612 mmol) in MeCN (1.5 mL) and water (0.3000 mL) in a Smith microwave vessel was added (2R,5S)-2-(4-bromo-2-pyridyl)-7-methyl-1,7-diazaspiro[4.4]nonan-6-one (50 mg, 0.1612 mmol) (which may be prepared as described in Description 4), bis(triphenylphosphine)palladium (II) dichloride (0.0034 g, 0.0048 mmol) and sodium carbonate (0.0342 g, 0.3224 mmol). The reaction vessel was sealed and purged with nitrogen. The reaction mixture was heated by microwave at 100° C. for 40 min. The reaction mixture was treated with water and was extracted with DCM twice and the organic layers were collected by passing down a PhaseSep cartridge. Evaporation of solvents gave an amber oil, It was further purified by silica gel chromatography (11 g KPNH silica cartridge) eluting with ethyl acetate in iso-hexane (20-100%) followed by methanol in ethyl acetate (0-18%) to give the desired product (2R,5S)-2-[4-(2-fluoro-5-propanoyl-phenyl)-2-pyridyl]-7-methyl-1,7-diazaspiro[4.4]nonan-6-one (32.7 mg, 0.0857 mmol, 53.2% yield) as cream solid.

300 MHz $^1$H NMR $\delta_H$ (CDCl$_3$) 1.27 (3H, t), 1.86-2.25 (5H, m), 2.55 (1H, m), 2.86 (1H, bs.s), 2.92 (3H, s), 3.04 (2H, q), 3.26-3.39 (2H, m), 4.78 (1H, t), 7.27 (1H, t), 7.35 (1H, d), 7.72 (1H, s), 8.03 (1H, dt), 8.13 (1H, dd), 8.65 (1H, d).

The free base was converted to the corresponging HCl salts using 1M HCl in ether ((1 eq.)) to give cream solid (2R,5S)-2-[4-(2-fluoro-5-propanoyl-phenyl)-2-pyridyl]-7-methyl-1,7-diazaspiro[4.4]nonan-6-one hydrochloride (E257).

M/Z: 382 (M+H+).

Examples 258 and 259

(2R,5S)-2-[4-(1-Ethyl-5-fluoro-indazol-6-yl)-2-pyridyl]-7-methyl-1,7-diazaspiro[4.4]nonan-6-one hydrochloride (E258) and (2R,5S)-2-[4-(2-Ethyl-5-fluoro-indazol-6-yl)-2-pyridyl]-7-methyl-1,7-diazaspiro[4.4]nonan-6-one hydrochloride (E259)

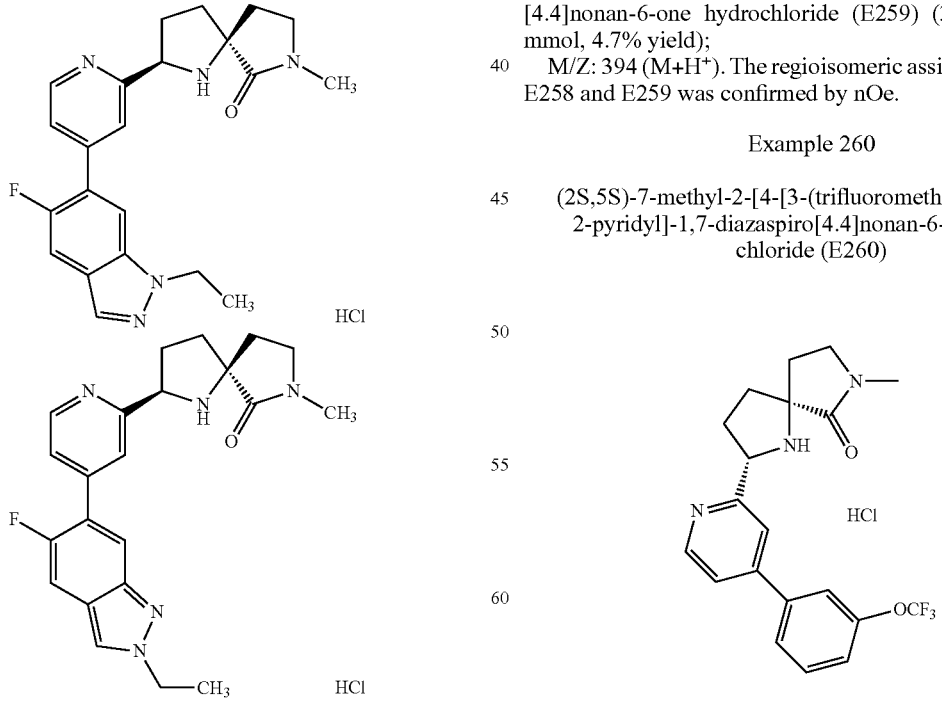

To a Smith microwave vial was added (2R,5S)-2-[4-(5-fluoro-1H-indazol-6-yl)-2-pyridyl]-7-methyl-1,7-diazaspiro[4.4]nonan-6-one (which may be prepared as described in Example 186) (40 mg, 0.1100 mmol), di-tert-butyl azodicarboxylate (126.03 mg, 0.5500 mmol), ethanol (0.03 mL, 0.5500 mmol) and triphenyl phosphine (143.56 mg, 0.5500 mmol) in THF (1 mL). The reaction mixture was heated by microwave at 800° C. for 45 minutes. The reaction mixture was cooled and eluted on an SCX-2 cartrige (0.5 g) and washed with DCM followed by MeOH. The desired product was eluted off the cartridge with ammonia in MeOH (0.2M). Evaporation of solvents gave a colourless oil. The crude residue was purified by silica gel chromatography (silica 10 g) eluting with methanol (containing 10% 0.88 ammonia) in ethyl acetate (0-80%), to give the products as a mixture of isomers. These were separated by HPLC using a ChiralPak IA column and eluting with ethanol/n-heptane (20%:80%) to give (2R,5S)-2-[4-(1-ethyl-5-fluoro-indazol-6-yl)-2-pyridyl]-7-methyl-1,7-diazaspiro[4.4]nonan-6-one as the major isomer;

300 MHz $^1$H NMR $\delta_H$ (CDCl$_3$) 1.56 (3H, t), 1.88-2.28 (6H, m), 2.56 (1H, m), 2.92 (3H, s), 3.32 (2H, m), 4.48 (2H, q), 4.80 (1H, t), 7.39 (1H, d), 7.45-7.51 (2H, m), 7.74 (1H, s), 8.01 (1H, s), 8.66 (1H, d).

This free base was converted to the corresponding HCl salt using 1M HCl in ether (1 eq.) to give, (2R,5S)-2-[4-(1-ethyl-5-fluoro-indazol-6-yl)-2-pyridyl]-7-methyl-1,7-diazaspiro[4.4]nonan-6-one hydrochloride (E258) (6.87 mg, 0.0166 mmol, 15.2% yield);

M/Z: 394 (M+H$^+$)

The minor isomer was also isolated: (2R,5S)-2-[4-(2-ethyl-5-fluoro-indazol-6-yl)-2-pyridyl]-7-methyl-1,7-diazaspiro[4.4]nonan-6-one;

300 MHz $^1$H NMR $\delta_H$ (CDCl$_3$) 1.68 (3H, t), 1.85-2.30 (6H, m), 2.57 (1H, m), 2.92 (3H, s), 3.22-3.41 (2H, m), 4.51 (2H, q), 4.80 (1H, t), 7.35-7.42 (2H, m), 7.48-7.61 (1H, m), 7.73-7.82 (1H, m), 7.94 (1H, s), 8.62 (1H, d).

This was converted to the HCl salt (2R,5S)-2-[4-(2-ethyl-5-fluoro-indazol-6-yl)-2-pyridyl]-7-methyl-1,7-diazaspiro[4.4]nonan-6-one hydrochloride (E259) (3.4 mg, 0.0052 mmol, 4.7% yield);

M/Z: 394 (M+H$^+$). The regioisomeric assignment between E258 and E259 was confirmed by nOe.

Example 260

(2S,5S)-7-methyl-2-[4-[3-(trifluoromethoxy)phenyl]-2-pyridyl]-1,7-diazaspiro[4.4]nonan-6-one hydrochloride (E260)

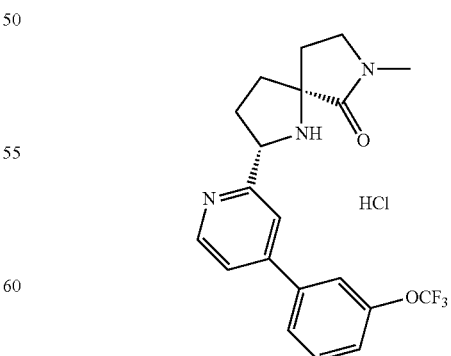

A solution of tert-butyl (2S,5S)-7-methyl-6-oxo-2-[4-[3-(trifluoromethoxy)phenyl]-2-pyridyl]-1,7-diazaspiro[4.4]nonane-1-carboxylate (which may be prepared as described in Description 145) (124.5 mg, 0.2500 mmol) in HCl in dioxan (3 mL, 12 mmol) was allowed to react at room temperature for 2 hrs. The solvent was evaporated and the residue was dissolved in methanol and passed through an SCX cartridge, washed with methanol and the product eluted with 0.5M $NH_3$ in methanol to give the free base as a clear gum (97 mg);

300 MHz $^1$H NMR $\delta_H$ (CDCl$_3$) 1.83-1.89 (1H, m), 2.13-2.21 (4H, m), 2.40 (1H, m), 2.9 (1H, br.s), 2.94 (3H, s), 3.30-3.43 (2H, m), 4.50 (1H, t), 7.31 (1H, d), 7.37 (1H, d), 7.53 (2H, t), 7.64 (1H, d), 7.87 (1H, s), 8.64 (1H, d).

A solution of this material in DCM (2 mL) was treated with HCl in ether (0.27 mL, 0.2700 mmol) and the mixture was allowed to stand at room temp for 2 minutes. The solvent was evaporated almost to dryness and then diethyl ether (20 ml) was added to precipitate the product. The solid was collected by filtration and then dried in the vacuum oven overnight at 45° C. to afford the title compound (E260) (84 mg);

M/Z: 392 (M+H$^+$).

Biological Assays

The compounds of the invention were tested in a QPatch NaV1.7 assay.

QPatch NaV1.7 Assay

HEK293-hNaV1.7 cells were grown in DMEM-F12+10% FBS culture media at 37° C. At a confluency of 50-70% cells were dissociated from culture flasks & triturated to ensure unicellular cell suspension; cell density was measured & adjusted to 2-3×10$^6$ cells/ml. Recordings were obtained using QPatch16x. The external solution was (in mM): NaCl, 128; KCl, 5; MgCl$_2$, 2; CaCl$_2$, 2; Glucose, 30; HEPES, 15; pH 7.3, 305-315 mOsm. Following seal formation and whole-cell access using internal solution (containing in mM: CsF, 135; EGTA/CsOH, 1/5; HEPES 10; NaCl, 10; pH 7.3, 310-320 mOsM), voltage pulse protocols were applied. Initially a steady state inactivation voltage protocol was used to determine the half-maximal voltage for steady state inactivation (V1/2 SSI). Two holding voltages were used to determine test drug inhibition: –90 mV, where most of the channels are in a closed state; and V1/2 SSI, where half of the channels are inactivated. Currents were elicited every seconds by stepping to a membrane potential of 0 mV for 20 ms. Four-point cumulative concentration responses were derived by determining the peak current amplitude at each concentration of test drug over 120 second application. Curves were fitted with the Hill equation yielding pIC50 values at –90 mV and V1/2 SSI holding potentials.

| Example Number | QP Nav1.7 –90 mV pIC50 | QP Nav1.7 SSI vhalf pIC50 |
|---|---|---|
| 1 | 4.3 | 5.5 |
| 2 | 3.7 | 4.7 |
| 3 | 4.2 | 5.1 |
| 4 | 3.7 | 4.9 |
| 5 | 4.6 | 5.4 |
| 6 | 3.8 | 4.5 |
| 7 | 4 | 4.5 |
| 8 | 5 | 6.1 |
| 9 | 3 | 4.2 |
| 10 | 2.4 | 4.3 |
| 11 | 3.7 | 4.6 |
| 12 | 4.3 | 5 |
| 13 | 4.6 | 5.2 |
| 14 | 4.2 | 5 |
| 15 | 4.6 | 5.2 |
| 16 | 4 | 4.9 |
| 17 | 4.7 | 5.5 |
| 18 | 3.1 | 4.5 |
| 19 | 4.3 | 5.2 |
| 20 | 3.5 | 4.5 |
| 21 | 3.1 | 4.5 |
| 22 | 3 | 3.8 |
| 23 | 3.2 | 4.1 |
| 24 | 3 | 3.4 |
| 25 |  | 2.8 |
| 26 |  | 3.1 |
| 27 |  | 1.4 |
| 28 | 4.5 | 5.3 |
| 29 | 3.9 | 4.7 |
| 30 | 4.4 | 5.3 |
| 31 | 4.1 | 4.7 |
| 32 | 3.6 | 4.4 |
| 33 | 3.9 | 4.4 |
| 34 | 3.6 | 3.8 |
| 35 | 3.4 | 4 |
| 36 | 4.7 | 6.1 |
| 37 | 4.6 | 6.1 |
| 38 | 4.2 | 5.1 |
| 39 | 4.1 | 4.7 |
| 40 | 4.3 | 5.8 |
| 41 | 4.6 | 5.7 |
| 42 | 4.6 | 5.7 |
| 43 | 4.4 | 5.5 |
| 44 | 4.3 | 5 |
| 45 | 4.4 | 5.5 |
| 46 | 5 | 6.1 |
| 47 | 4.5 | 4.9 |
| 48 | 4.6 | 5.7 |
| 49 | 4.3 | 5.4 |
| 50 | 5.6 | 6.6 |
| 51 | 4.6 | 5.3 |
| 52 | 4.6 | 5.2 |
| 53 | 4 | 4.4 |
| 54 | 4.2 | 4.4 |
| 55 | 4 | 4.7 |
| 56 | 4.1 | 5.0 |
| 57 | 4.1 | 5.4 |
| 58 | 4.2 | 5.9 |
| 59 | 4 | 5.5 |
| 60 | 4.1 | 5.4 |
| 61 | 4 | 5.2 |
| 62 | 4.1 | 5.7 |
| 63 | 4.1 | 5 |
| 64 | 4.3 | 5.5 |
| 65 | 4.5 | 5.8 |
| 66 | 3.9 | 5 |
| 67 | 4.5 | 5.4 |
| 68 | 4.6 | 5.3 |
| 69 | 4.5 | 5.1 |
| 70 | 4.9 | 6 |
| 71 | 3.9 | 4.7 |
| 72 | 3.8 | 4.7 |
| 73 | 3.7 | 4.7 |
| 74 | 4.2 | 5.1 |
| 75 | 3.9 | 4.7 |
| 76 | 4.2 | 5.4 |
| 77 | 3.5 | 4.5 |
| 78 | 3.8 | 4.9 |
| 79 | 3.4 | 4.5 |
| 80 | 3.5 | 3.7 |
| 81 | 3.7 | 5.5 |
| 82 | 3.7 | 5.1 |
| 83 | 3.7 | 4.5 |
| 84 | 3.7 | 4.7 |
| 85 | 5 | 6.5 |
| 86 | 4 | 5 |
| 87 | 3.9 | 5.2 |
| 88 | 3.5 | 4.5 |
| 89 | 4.3 | 5.5 |
| 90 | 5.2 | 6.5 |
| 91 | 4.4 | 5.7 |
| 92 | 4.4 | 5.6 |
| 93 | 4.4 | 5.4 |

| Example Number | QP Nav1.7 −90 mV pIC50 | QP Nav1.7 SSI vhalf pIC50 |
|---|---|---|
| 94 | 5.4 | 6.7 |
| 95 | 4 | 4.9 |
| 96 | 4.7 | 5.5 |
| 97 | 4.7 | 5.9 |
| 98 | 4.6 | 6.2 |
| 99 | 4.8 | 6 |
| 100 | 6.0 | 6.7 |
| 101 | 4.9 | 5.0 |
| 102 | 4.6 | 5.7 |
| 103 | 5.6 | 6.9 |
| 104 | 5.8 | 6.8 |
| 105 | 4.6 | 5.7 |
| 106 | 5.3 | 5.7 |
| 107 | 5.8 | 6.7 |
| 108 | 5.9 | 7.2 |
| 109 | 5.7 | 6.0 |
| 110 | 3.6 | 5.0 |
| 111 | 3.7 | 4.2 |
| 112 | 4.4 | 5.4 |
| 113 | 3.7 | 4.3 |
| 114 | 4.1 | 4.8 |
| 115 | 4.5 | 5.6 |
| 116 | 4.1 | 5.0 |
| 117 | 5.1 | 6.4 |
| 118 | 4.3 | 5.1 |
| 119 | 4.5 | 5.4 |
| 120 | 4.7 | 6.1 |
| 121 | 4.9 | 6.2 |
| 122 | 5.1 | 5.5 |
| 123 | 3.6 | 4.4 |
| 124 | 3.9 | 5.1 |
| 125 | 3.8 | 4.6 |
| 126 | 3.5 | 4.7 |
| 127 | 4.9 | 4.9 |
| 128 | 4.7 | 5.3 |
| 129 | 3.7 | 4.7 |
| 130 | 3.8 | 5.1 |
| 131 | 4.0 | 5.7 |
| 132 | 3.6 | 4.4 |
| 133 | 2.7 | 4.8 |
| 134 | 3.6 | 4.7 |
| 135 | 1.9 | 5.0 |
| 136 | 3.9 | 4.2 |
| 137 | 3.8 | 4.7 |
| 138 | 3.7 | 4.6 |
| 139 | 3.6 | 4.4 |
| 140 | 4.0 | 4.5 |
| 141 | 4.2 | 5.2 |
| 142 | 4.8 | 6.1 |
| 143 | 4.2 | 5.0 |
| 144 | 4.5 | 5.4 |
| 145 | 4.1 | 5.2 |
| 146 | 4.5 | 5.7 |
| 147 | 4.3 | 5.5 |
| 148 | 3.4 | 4.5 |
| 149 | 3.4 | 4.6 |
| 150 | 3.9 | 4.9 |
| 151 | 4.0 | 4.8 |
| 152 | 3.7 | 4.8 |
| 153 | 3.8 | 4.9 |
| 154 | 4.0 | 4.9 |
| 155 | 4.4 | 5.4 |
| 156 | 3.9 | 4.7 |
| 157 | 4.1 | 4.6 |
| 158 | 2.9 | 4.2 |
| 159 | 4.5 | 5.1 |
| 160 | 0.3 | 2.8 |
| 161 | 3.9 | 4.4 |
| 162 | 4.8 | 5.4 |
| 163 | 2.1 | |
| 164 | 2.9 | 4.4 |
| 165 | 3.8 | 4.0 |
| 166 | 2.7 | 3.9 |
| 167 | 4.4 | 4.4 |
| 168 | 3.5 | 3.8 |
| 169 | 3.9 | 5.2 |
| 170 | 3.4 | 4.6 |
| 171 | 3.8 | 4.3 |
| 172 | 3.5 | 4.5 |
| 173 | 3.7 | 4.9 |
| 174 | 3.9 | 4.6 |
| 175 | 3.7 | 4.8 |
| 176 | 3.7 | 4.7 |
| 177 | 4.9 | 6.4 |
| 178 | 3.2 | 4.6 |
| 179 | 4.5 | 6.1 |
| 180 | 3.0 | 4.7 |
| 181 | 4.0 | 5.3 |
| 182 | 4.0 | 4.8 |
| 183 | 4.2 | 5.5 |
| 184 | 3.9 | 5.0 |
| 185 | 4.2 | 5.1 |
| 186 | 2.2 | 3.8 |
| 187 | 3.0 | 3.7 |
| 188 | 3.3 | 4.0 |
| 189 | 3.6 | 4.6 |
| 190 | 2.0 | 4.0 |
| 191 | 3.4 | 4.6 |
| 192 | | 3.0 |
| 193 | 2.3 | 4.3 |
| 194 | 4.8 | 6.0 |
| 195 | 4.0 | 5.3 |
| 196 | 5.8 | 7.0 |
| 197 | 4.3 | 5.3 |
| 198 | 4.2 | 5.3 |
| 199 | 3.8 | 4.6 |
| 200 | 4.5 | 5.7 |
| 201 | 5.3 | 6.9 |
| 202 | 4.5 | 5.5 |
| 203 | 2.7 | 3.6 |
| 204 | 4.5 | 5.3 |
| 205 | 4.2 | 5.2 |
| 206 | 4.2 | 5.0 |
| 207 | 4.1 | 5.2 |
| 208 | 3.8 | 4.0 |
| 209 | 4.6 | 5.5 |
| 210 | | 3.4 |
| 211 | 3.6 | 4.6 |
| 212 | 4.2 | 5.3 |
| 213 | 4.2 | 5.2 |
| 214 | 4.5 | 5.4 |
| 215 | 3.9 | 4.9 |
| 216 | 4.5 | 5.3 |
| 217 | 4.6 | 5.4 |
| 218 | 5.2 | 6.3 |
| 219 | 4.3 | 5.1 |
| 220 | 3.7 | 4.3 |
| 221 | 3.5 | 4.5 |
| 222 | 3.4 | 4.6 |
| 223 | 3.8 | 4.6 |
| 224 | 4.0 | 4.8 |
| 225 | 3.6 | 4.6 |
| 226 | 2.8 | 4.9 |
| 227 | 3.8 | 4.9 |
| 228 | 4.7 | 5.5 |
| 229 | 4.2 | 5.5 |
| 230 | 4.6 | 5.9 |
| 231 | 4.9 | 6.0 |
| 232 | 5.1 | 5.9 |
| 233 | 4.5 | 4.9 |
| 234 | 6.0 | 7.3 |
| 235 | 4.8 | 5.7 |
| 236 | 5.2 | 6.2 |
| 237 | 5.6 | 6.5 |
| 238 | 4.3 | 5.7 |
| 239 | 3.6 | 4.8 |
| 240 | 4.5 | 5.8 |
| 241 | 4.0 | 4.8 |
| 242 | 4.0 | 4.7 |
| 243 | 4.8 | 5.9 |

-continued

| Example Number | QP Nav1.7 −90 mV pIC50 | QP Nav1.7 SSI vhalf pIC50 |
|---|---|---|
| 244 | 4.4 | 5.5 |
| 245 | 4.4 | 5.3 |
| 246 | 4.8 | 6.0 |
| 247 | 4.7 | 5.9 |
| 248 | 4.5 | 5.3 |
| 249 | 4.8 | 5.9 |
| 250 | 4.7 | 5.9 |
| 251 | 3.4 | 4.4 |
| 252 | 4.1 | 4.9 |
| 253 | 5.5 | 7.1 |
| 254 | 4.3 | 5.2 |
| 255 | 4.0 | 5.0 |
| 256 | 4.7 | 5.6 |
| 257 | 2.6 | 4.2 |
| 258 | 1.4 | 4.5 |
| 259 | 3.8 | 2.9 |

The invention claimed is:
1. A compound of formula (I) or a pharmaceutically acceptable salt thereof:

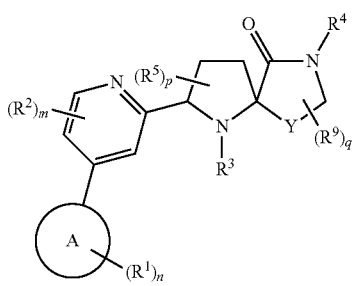

wherein:
Ring A represents a phenyl ring;
n represents an integer selected from 0 to 4;
each $R^1$ independently represents $C_{1-6}$ alkyl, $C_{2-6}$ alkenyl, $C_{2-6}$ alkynyl, halogen, halo$C_{1-6}$ alkyl, $C_{1-6}$ alkoxy, —$CH_2$—$C_{1-6}$ alkoxy, halo$C_{1-6}$ alkoxy, —C(=O)—$C_{1-6}$ alkyl, —Z—$C_{3-8}$ cycloalkyl, —Z— phenyl, —$SO_2C_{1-6}$ alkyl, —CN, —OH, —CONR$^6$R$^7$, —NR$^6$R$^7$, wherein said $C_{3-8}$ cycloalkyl or phenyl group of $R^1$ may be optionally substituted by one or more (e.g. 1, 2 or 3) $R^8$ groups and wherein n represents an integer greater than 1, said $R^1$ groups represent no more than one —Z—$C_{3-8}$ cycloalkyl or one —Z-phenyl group;
Z represents a bond or a linker selected from —O—, —$CH_2$—, —$CH_2$—O—, —OCH($CH_3$)— or —O—$CH_2$—;
$R^6$ and $R^7$ independently represent hydrogen or $C_{1-6}$ alkyl;
$R^8$ represents $C_{1-6}$ alkyl, $C_{2-6}$ alkenyl, $C_{2-6}$alkynyl, halogen, halo$C_{1-6}$ alkyl, $C_{1-6}$ alkoxy, halo$C_{1-6}$ alkoxy, —CN, —NR$^6$R$^7$ or =O;
m represents an integer selected from 0 to 3;
each $R^2$ independently represents $C_{1-6}$ alkyl, $C_{2-6}$ alkenyl, $C_{2-6}$ alkynyl, halogen, halo $C_{1-6}$alkyl, $C_{1-6}$ alkoxy, halo$C_{1-6}$ alkoxy, —CN or —NR$^7$R$^8$;
$R^3$ represents hydrogen or $C_{1-6}$ alkyl;
$R^4$ represents hydrogen or $C_{1-6}$ alkyl;
each $R^5$ independently represents $C_{1-3}$ alkyl or fluoro;
each $R^9$ independently represents $C_{1-3}$alkyl;
Y represents —$CH_2$—; and
p and q independently represent an integer from 0 to 3.

2. A compound as defined in claim 1 or a pharmaceutically acceptable salt thereof, which is other than 7-methyl-2-[4-[3-(trifluoromethoxy)phenyl]-2-pyridyl]-1,7-diazaspiro[4.4]nonan-6-one.

3. A compound as defined in claim 1 or a pharmaceutically acceptable salt thereof, wherein n represents an integer selected from 0 to 3 and $R^1$ independently represents methyl, ethyl, isopropyl or isopentyl, fluorine, chlorine, $CF_3$, —O-methyl, —O—$CH_2$—$CH_3$, —O—$CD_2$-$CH_3$, —O-propyl, —O-butyl, —O—CH(Me)$_2$, —O—$CH_2$—CH(Me)$_2$), —O—$CF_3$, —OCHF$_2$, —OCH$_2$CHF$_2$—OCH$_2$CH$_2$F, —$CH_2$—O—$CF_3$, —$CH_2$OMe, —$CH_2$OEt, —$SO_2$Et, —C(=O)-Et, -cyclopropyl, —O-cyclopropyl, —O-ethylcyclopropyl, —OCH($CH_3$)-cyclopropyl, —O-phenyl, —O—$CH_2$-phenyl, —$CH_2$—O-phenyl), —CN, —OH, —CONH$_2$, or —N(Me)$_2$), wherein said phenyl or $C_{3-8}$ cycloalkyl groups are optionally substituted by one or more $R^8$ groups.

4. A compound as defined in claim 1 or a pharmaceutically acceptable salt thereof, wherein m represents an integer selected from 0 to 2 and $R^2$ independently represents $C_{1-6}$ alkyl, halogen or $C_{1-6}$alkoxy.

5. A compound as defined in claim 1 or a pharmaceutically acceptable salt thereof, wherein $R^3$ represents hydrogen, methyl or ethyl.

6. A compound as defined in claim 1 or a pharmaceutically acceptable salt thereof, wherein $R^4$ represents hydrogen or methyl.

7. A compound as defined in claim 1 or a pharmaceutically acceptable salt thereof, wherein p represents 0 to 2 and $R^5$ represents fluoro.

8. A compound as defined in claim 1 or a pharmaceutically acceptable salt thereof, wherein q represents 0 to 2 and $R^9$ represents methyl.

9. A compound as defined in claim 1, which is selected from a compound of
(2R,5S)-7-methyl-2-[4-(2,4,6-trimethylphenyl)-2-pyridyl]-1,7-diazaspiro-[4.4]nonan-6-one hydrochloride;
(2R,5S)-7-methyl-2-[4-[2-(trifluoromethoxy)-phenyl]-2-pyridyl]-1,7-diazaspiro[4.4]nonan-6-one hydrochloride;
(2R,5S)-2-[4-(2-ethoxy-5-fluoro-phenyl)-pyridin-2-yl]-7-methyl-1,7-diaza-spiro[4.4]nonan-6-one hydrochloride;
(2R,5S)-7-methyl-2-[4-(4-trifluoro-methoxy-phenyl)-pyridin-2-yl]-1,7-diaza-spiro[4.4]nonan-6-one hydrochloride;
(2R,5S)-7-methyl-2-(4-phenyl-pyridin-2-yl)-1,7-diaza-spiro[4.4]nonan-6-one hydrochloride;
(2R,5S)-7-methyl-2-[4-[2-(trifluoro-methyl)phenyl]-2-pyridyl]-1,7-diazaspiro[4.4]nonan-6-one hydrochloride;
(2R,5S)-2-[4-(5-ethoxy-2-fluoro-phenyl)-2-pyridyl]-7-methyl-1,7-diazaspiro[4.4]nonan-6-one hydrochloride;
(2R,5S)-2-[4-(2,4-difluorophenyl)-2-pyridyl]-7-methyl-1,7-diazaspiro[4.4]nonan-6-one hydrochloride;
(2R,5S)-2-[4-(5-fluoro-2-methoxy-phenyl)-2-pyridyl]-7-methyl-1,7-diazaspiro[4.4]nonan-6-one hydrochloride;
(2R,5S)-2-[4-(3,4-difluorophenyl)-2-pyridyl]-7-methyl-1,7-diazaspiro[4.4]nonan-6-one hydrochloride;
(2R,5S)-2-[4-[2-fluoro-4-(trifluoromethyl)phenyl]-2-pyridyl]-7-methyl-1,7-diazaspiro[4.4]nonan-6-one hydrochloride;
(2R,5S)-2-[4-(4-chlorophenyl)-2-pyridyl]-7-methyl-1,7-diazaspiro[4.4]nonan-6-one hydrochloride;

(2R,5R)-7-methyl-2-[3-methyl-4-[4-(trifluoromethyl)phenyl]-2-pyridyl]-1,7-diazaspiro[4.4]nonan-6-one hydrochloride;
(2S,5R)-7-methyl-2-[3-methyl-4-[4-(trifluoromethyl)phenyl]-2-pyridyl]-1,7-diazaspiro[4.4]nonan-6-one hydrochloride;
(2S,5S)-7-methyl-2-[3-methyl-4-[4-(trifluoromethyl)phenyl]-2-pyridyl]-1,7-diazaspiro[4.4]nonan-6-one hydrochloride;
(2R,5S)-7-methyl-2-[3-methyl-4-[4-(trifluoromethyl)phenyl]-2-pyridyl]-1,7-diazaspiro[4.4]nonan-6-one hydrochloride;
(2S,5R)-7-methyl-2-[3-methyl-4-[4-fluorophenyl]-2-pyridyl]-1,7-diazaspiro[-4.4]nonan-6-one hydrochloride;
(2R,5S)-2-[4-(4-fluorophenyl)-3-methyl-2-pyridyl]-7-methyl-1,7-diazaspiro[-4.4]nonan-6-one hydrochloride;
(2S,5S)-2-[4-(4-fluorophenyl)-3-methyl-2-pyridyl]-7-methyl-1,7-diazaspiro[-4.4]nonan-6-one hydrochloride;
2-[2-methyl-6-[(2S,5R)-7-methyl-6-oxo-1,7-diazaspiro[4.4]-nonan-2-yl]-4-py-ridyl]-4-(trifluoromethyl)-benzonitrile hydrochloride;
2-[2-methyl-6-[(2R,5R)-7-methyl-6-oxo-1,7-diazaspiro[4.4]-nonan-2-yl]-4-p-yridyl]-4-(trifluoromethyl)-benzonitrile hydrochloride;
2-[2-methyl-6-[(2R,5S)-7-methyl-6-oxo-1,7-diazaspiro[4.4]nonan-2-yl]-4-pyridyl]-4-(trifluoromethyl)benzonitrile hydrochloride;
2-[2-methyl-6-[(2R,5S)-7-methyl-6-oxo-1,7-diazaspiro[4.4]nonan-2-yl]-4-pyridyl]-4-(trifluoromethyl)benzamide hydrochloride;
2-[2-methyl-6-[(2S,5S)-7-methyl-6-oxo-1,7-diazaspiro[4.4]nonan-2-yl]-4-pyridyl]-4-(trifluoromethyl)benzamide hydrochloride;
2-[2-methyl-6-[(2R,5R)-7-methyl-6-oxo-1,7-diazaspiro[4.4]nonan-2-yl]-4-pyridyl]J-4-(trifluoromethyl)benzamide hydrochloride;
2-[2-methyl-6-[(2S,5R)-7-methyl-1-oxo-1,7-diazaspiro[4.4]nonan-2-yl]-4-pyridyl]-4-(trifluoromethyl)benzamide hydrochloride;
(2R,5S)-7-methyl-2-[6-methyl-4-[4-trifluoromethyl)phenyl]-2-pyridyl]-1,7-diazaspiro[4.4]nonan-6-one hydrochloride;
(2S,5S)-7-methyl-2-[6-methyl-4-[4-(trifluoromethyl)phenyl]-2-pyridyl]-1,7-diazaspiro[4.4]nonan-6-one hydrochloride;
(2S,5R)-7-methyl-2-[6-methyl-4-[4-(trifluoromethyl)phenyl]-2-pyridyl]-1,7-diazaspiro[4.4]nonan-6-one hydrochloride;
(2R,5R)-7-methyl-2-[6-methyl-4-[4-(trifluoromethyl)phenyl]-2-pyridyl]-1,7-diazaspiro[4.4]nonan-6-one hydrochloride;
(2R,5S)-2-[4-(2-fluoro-phenyl)-pyridin-2-yl]-7-methyl-1,7-diaza-spiro[4.4]-nonan-6-one hydrochloride;
(2S,5S)-2-[4-(2-fluoro-phenyl)-pyridin-2-yl]-7-methyl-1,7-diaza-spiro[4.4-]nonan-6-one hydrochloride;
(2S,5R)-2-[4-(2-fluoro-phenyl)-pyridin-2-yl]-7-methyl-1,7-diaza-spiro[4.4]nonan-6-one hydrochloride;
(2R,5R)-2-[4-(2-fluoro-phenyl)-pyridin-2-yl]-7-methyl-1,7-diaza-spiro[4.4]nonan-6-one hydrochloride;
(2S,5S)-2-[4-[4-(trifluoromethyl)phenyl]-2-pyridyl]-1,7-diazaspiro[4.4]non-an-6-one hydrochloride;
(2R,5S)-2-[4-[4-(trifluoromethyl)phenyl]-2-pyridyl]-1,7-diazaspiro[4.4]no-nan-6-one hydrochloride;
(2S,5S)-2-[4-[2-fluoro-4-(trifluoro-methyl)phenyl]-2-pyridyl]-1,7-diazaspiro[4.4]nonan-6-one hydrochloride;
(2R,5S)-2-[4-[2-fluoro-4-(trifluoro-methyl)phenyl]-2-pyridyl]-1,7-diazaspiro[4.4]nonan-6-one hydrochloride;
(2S,5S)-7-methyl-2-[S-methyl-4-[4-(trifluoromethyl)phenyl]-2-pyridyl]-1,97-diazaspiro[4.4]nonan-6-one hydrochloride;
(2R,5S)-7-methyl-2-[5-methyl-4-[4-(trifluoromethyl)phenyl]-2-pyridyl]-1,7-diazaspiro[4.4]nonan-6-one hydrochloride;
(2R,5R)-7-methyl-2-[5-methyl-4-[4-(trifluoromethyl)phenyl]-2-pyridyl]-1,7-diazaspiro[4.4]nonan-6-one hydrochloride;
(2S,5R)-7-methyl-2-[5-methyl-4-[4-(trifluoromethyl)phenyl]-2-pyridyl]-1,7-diazaspiro[4.4]nonan-6-one hydrochloride;
(2S,5S)-8,8-dimethyl-2-[4-[4-(trifluoromethyl)phenyl]-2-pyridyl]-1,7-diazaspiro[4.4]nonan-6-one hydrochloride;
(2R,5S)-8,8-dimethyl-2-[4-[4-(trifluoromethyl)phenyl]-2-pyridyl]-1,7-diazaspiro[4.4]nonan-6-one hydrochloride;
(2R,5R)-8,8-dimethyl-2-[4-[4-(trifluoromethyl)phenyl]-2-pyridyl]-1,7-diazaspiro[4.4]nonan-6-one hydrochloride;
(2S,5R)-8,8-dimethyl-2-[4-[4-(trifluoromethyl)phenyl]-2-pyridyl]-1,7-diazaspiro[4.4]nonan-6-one hydrochloride;
(2S,5R)-2-[4-(4-trifluoromethyl-phenyl)-pyridin-2-yl]-1,7-diaza-spiro[4.5]decan-6-one hydrochloride;
(2R,5R)-2-[4-(4-trifluoromethyl-phenyl)-pyridin-2-yl]-1,7-diaza-spiro[4.5]decan-6-one hydrochloride;
(2R,5S)-2-[4-(4-trifluoromethyl-phenyl)-pyridin-2-yl]-1,7-diaza-spiro[4.5]decan-6-one hydrochloride;
(2S,5S)-2-[4-(4-trifluoromethyl-phenyl)-pyridin-2-yl]-1,7-diaza-spiro[4.5]decan-6-one hydrochloride;
(2R,5S)-7-methyl-2-[4-(4-trifluoromethyl-phenyl)-pyridin-2-yl]-1,7-diaza-spiro[4.4]nonan-6-one hydrochloride;
(2S,5S)-7-methyl-2-[4-(4-trifluoromethyl-phenyl)-pyridin-2-yl]-1,7-diaza-spiro[4.4]nonan-6-one hydrochloride;
(2S,5R)-7-methyl-2-[4-(4-trifluoromethyl-phenyl)-pyridin-2-yl]-1,7-diaza-spiro[4.4]nonan-6-one hydrochloride;
(2R,5R)-7-methyl-2-[4-(4-trifluoromethyl-phenyl)-pyridin-2-yl]-1,7-diaza-spiro[4.4]nonan-6-one hydrochloride;
(2S,5R)-2-[4-(4-fluorophenyl)-6-methyl-2-pyridyl]-7-methyl-1,7-diazaspiro[4.4]nonan-6-one hydrochloride;
(2R,5S)-2-[4-(4-fluorophenyl)-6-methyl-2-pyridyl]-7-methyl-1,7-diazaspiro[4.4]nonan-6-one hydrochloride;
(2R,5S)-2-[5-fluoro-4-[4-(trifluoromethyl)phenyl]-2-pyridyl]-7-methyl-1,7-diazaspiro[4.4]nonan-6-one hydrochloride;
(2S,5S)-2-[5-fluoro-4-[4-(trifluoromethyl)phenyl]-2-pyridyl]-7-methyl-1,7-diazaspiro[4.4]nonan-6-one hydrochloride;
(2S,5R)-2-[5-fluoro-4-[4-(trifluoromethyl)phenyl]-2-pyridyl]-7-methyl-1,7-diazaspiro[4.4]nonan-6-one hydrochloride;
(2R,5R)-2-[5-fluoro-4-[4-(trifluoromethyl)phenyl]-2-pyridyl]-7-methyl-1,7-diazaspiro[4.4]nonan-6-one hydrochloride;
(2R,5S)-2-[5-tert-Butoxy-4-[4-(trifluoromethyl)-phenyl]-2-pyridyl]-7-methyl-1,7-diazaspiro[4.4]nonan-6-one hydrochloride;

(2S,5S)-2-[5-tert-Butoxy-4-[4-(trifluoromethyl)-phenyl]-2-pyridyl]-7-methyl-1,7-diazaspiro[4.4]nonan-6-one hydrochloride;
(2S,5R)-2-[5-tert-Butoxy-4-[4-(trifluoromethyl)-phenyl]-2-pyridyl]-7-methyl-1,7-diazaspiro[4.4]nonan-6-one hydrochloride;
(2R,5R)-2-[5-tert-Butoxy-4-[4-(trifluoromethyl)-phenyl]-2-pyridyl]-7-methyl-1,7-diazaspiro[4.4]nonan-6-one hydrochloride;
(2R,5S)-2-[4-(4-fluorophenyl)-2-pyridyl]-7-methyl-1,7-diazaspiro[4.4]nonan-6-one hydrochloride;
(2R,5R)-7-methyl-2-[4-(4-trifluoromethyl-phenyl)-pyridin-2-yl]-1,7-diaza-spiro[4.5]decan-6-one hydrochloride;
(2S,5R)-7-methyl-2-[4-(4-trifluoromethyl-phenyl)-pyridin-2-yl]-1,7-diaza-spiro[4.5]decan-6-one hydrochloride;
(2S,5S)-7-methyl-2-[4-(4-trifluoromethyl-phenyl)-pyridin-2-yl]-1,7-diaza-spiro[4.5]decan-6-one hydrochloride;
(2R,5S)-7-methyl-2-[4-(4-trifluoromethyl-phenyl)-pyridin-2-yl]-1,7-diaza-spiro[4.5]decan-6-one hydrochloride;
(2R,5R)-2-[4-(4-fluoro-phenyl)-pyridin-2-yl]-7-methyl-1,7-diaza-spiro[4.5]decan-6-one hydrochloride;
(2S,5R)-2-[4-(4-fluoro-phenyl)-pyridin-2-yl]-7-methyl-1,7-diaza-spiro[4.5]decan-6-one hydrochloride;
(2S,5S)-2-[4-(4-fluoro-phenyl)-pyridin-2-yl]-7-methyl-1,7-diaza-spiro[4.5]decan-6-one hydrochloride;
(2R,5S)-2-[4-(4-fluoro-phenyl)-pyridin-2-yl]-7-methyl 1,7-diaza-spiro[4.5]decan-6-one hydrochloride;
(2R,5S)-7-methyl-2-[4-[3-(trifluoromethyl)phenyl]-2-pyridyl]-1,7-diazaspiro[4.4]nonan-6-one hydrochloride;
(2R,5S)-2-[4-(4-ethoxyphenyl)-2-pyridyl]-7-methyl-1,7-diazaspiro[4.4]nonan-6-one hydrochloride;
(2R,5S)-2-[4-(3,5-difluorophenyl)-2-pyridyl]-7-methyl-1,7-diazaspiro[4.4]nonan-6-one hydrochloride;
(2R,5S)-2-[4-(2-Chloro-3-methoxy-phenyl)-2-pyridyl]-7-methyl-1,7-diazaspiro[4.4]nonan-6-one hydrochloride;
(2R,5S)-2-[4-(3-ethoxyphenyl)-2-pyridyl]-7-methyl-1,7-diazaspiro[4.4]nonan-6-one hydrochloride;
(2R,5S)-2-[4-(2-Chloro-5-methoxy-phenyl)-2-pyridyl]-7-methyl-1,7-diazaspiro[4.4]nonan-6-one hydrochloride;
(2R,5S)-2-[4-[5-(difluoromethoxy)-2-fluoro-phenyl]-2-pyridyl]-7-methyl-1,7-diazaspiro[4.4]nonan-6-one hydrochloride;
(2R,5S)-2-[4-(4-isopropoxyphenyl)-6-methyl-2-pyridyl]-7-methyl-1,7-diazaspiro[4.4]nonan-6-one hydrochloride;
(2S,5S)-2-[4-(4-isopropoxyphenyl)-6-methyl-2-pyridyl]-7-methyl-1,7-diazaspiro[4.4]nonan-6-one hydrochloride;
(2R,5S)-7-methyl-2-[6-methyl-4-(p-tolyl)-2-pyridyl]-1,7-diazaspiro[4.4]nonan-6-one hydrochloride;
(2S,5S)-2-[4-(4-ethoxyphenyl)-6-methyl-2-pyridyl]-7-methyl-1,7-diazaspiro[4.4]nonan-6-one hydrochloride;
(3R,5S)-3-[4-(4-ethoxyphenyl)-6-methyl-2-pyridyl]-8-methyl-4,8-diazaspiro[4.4]nonan-9-one hydrochloride;
(3R,5R)-3-[4-[2-methoxy-4-(trifluoromethyl)phenyl]-6-methyl-2-pyridyl]-8-methyl-4,8-diazaspiro[4.4]nonan-9-one hydrochloride;
(3S,5R)-3-[4-[2-methoxy-4-(trifluoromethyl)phenyl]-6-methyl-2-pyridyl]-8-methyl-4,8-diazaspiro[4.4]nonan-9-one hydrochloride;
(2S,5S)-2-[4-(5-ethoxy-2-fluoro-phenyl)-6-methyl-pyridin-2-yl]-7-methyl-1,7-diazaspiro[4.4]nonan-6-one hydrochloride;
(2R,5S)-2-[4-(5-ethoxy-2-fluoro-phenyl)-6-methyl-pyridin-2-yl]-7-methyl-1,7-diaza-spiro[4.4]nonan-6-one hydrochloride;
(2R,5S)-2-[6-methyl-4-[4-(trifluoromethyl)phenyl]-2-pyridyl]-1,7-diazaspiro[4.4]nonan-6-one hydrochloride;
(2S,5R)-2-[6-methyl-4-[4-(trifluoromethyl)phenyl]-2-pyridyl]-1,7-diazaspiro[4.4]nonan-6-one hydrochloride;
(2R,5R)-2-[6-methyl-4-[4-(trifluoromethyl)phenyl]-2-pyridyl]-1,7-diazaspiro[4.4]nonan-6-one hydrochloride;
(2S,5S)-2-[6-methyl-4-[4-(trifluoromethyl)phenyl]-2-pyridyl]-1,7-diazaspiro[4.4]nonan-6-one hydrochloride;
(2S,5S)-2-[6-methyl-4-(4-trifluoromethyl-phenyl)-pyridin-2-yl]-1,7-diaza-spiro[4.5]decan-6-one hydrochloride;
(2R,5R)-2-[6-methyl-4-(4-trifluoromethyl-phenyl)-pyridin-2-yl]-1,7-diaza-spiro[4.5]decan-6-one hydrochloride;
(2R,5S)-2-[6-methyl-4-(4-trifluoromethyl-phenyl)-pyridin-2-yl]-1,7-diaza-spiro[4.5]decan-6-one hydrochloride;
(2S,5R)-2-[6-methyl-4-(4-trifluoromethyl-phenyl)-pyridin-2-yl]-1,7-diaza-spiro[4.5]decan-6-one hydrochloride;
(2S,5R)-2-[4-(5-ethoxy-2-fluoro-phenyl)-6-methyl-2-pyridyl]-1,7-diazaspiro[4.4]nonan-6-one hydrochloride;
(2R,5R)-2-[4-(5-ethoxy-2-fluoro-phenyl)-6-methyl-2-pyridyl]-1,7-diazaspiro[4.4]nonan-6-one hydrochloride;
(2R,5S)-2-[4-(5-ethoxy-2-fluoro-phenyl)-6-methyl-2-pyridyl]-1,7-diazaspiro[4.4]nonan-6-one hydrochloride;
(2S,5S)-2-[4-(5-ethoxy-2-fluoro-phenyl)-6-methyl-2-pyridyl]-1,7-diazaspiro[4.4]nonan-6-one hydrochloride;
(2S,5S)-2-[4-(5-ethoxy-2-fluoro-phenyl)-pyridin-2-yl]-1,7-diaza-spiro[4.5]decan-6-one hydrochloride;
(2R,5S)-2-[4-(5-ethoxy-2-fluoro-phenyl)-pyridin-2-yl]-1,7-diaza-spiro[4.5]decan-6-one hydrochloride;
(2R,5R)-2-[4-(5-ethoxy-2-fluoro-phenyl)-pyridin-2-yl]-1,7-diaza-spiro[4.5]decan-6-one hydrochloride;
(2S,5R)-2-[4-(5-ethoxy-2-fluoro-phenyl)-pyridin-2-yl]-1,7-diaza-spiro[4.5]decan-6-one hydrochloride;
(2S,5R)-2-[4-(4-fluoro-phenyl)-pyridin-2-yl]-1,7-diaza-spiro[4.5]decan-6-one hydrochloride;
(2R,5R)-2-[4-(4-fluoro-phenyl)-pyridin-2-yl]-1,7-diaza-spiro[4.5]decan-6-one hydrochloride;
(2R,5S)-2-[4-(4-fluoro-phenyl)-pyridin-2-yl]-1,7-diaza-spiro[4.5]decan-6-one hydrochloride;
(2S,5S)-2-[4-(4-fluoro-phenyl)-pyridin-2-yl]-1,7-diaza-spiro[4.5]decan-6-one hydrochloride;
(2S,5R)-2-[4-[4-(trifluoromethyl)phenyl]-2-pyridyl]-1,7-diazaspiro[4.4]nonan-6-one hydrochloride;
(2R,5R)-2-[4-[4-(trifluoromethyl)phenyl]-2-pyridyl]-1,7-diazaspiro[4.4]nonan-6-one hydrochloride;
(2S,5R)-2-[4-[3-(trifluoromethoxy)phenyl]-2-pyridyl]-1,7-diazaspiro[4.4]nonan-6-one hydrochloride;
(2R,5R)-2-[4-[3-(trifluoromethoxy)phenyl]-2-pyridyl]I 17-diazaspiro[4.4]nonan-6-one hydrochloride;
(2R,5S)-2-[4-[3-(trifluoromethoxy)phenyl]-2-pyridyl]-1,7-diazaspiro[4.4]nonan-6-one hydrochloride;
(2S,5S)-2-[4-[3-(trifluoromethoxy)phenyl]-2-pyridyl]-1,7-diazaspiro[4.4]nonan-6-one hydrochloride;
(2S,5R)-2-[4-(5-ethoxy-2-fluoro-phenyl)-6-methyl-pyridin-2-yl]-7-methyl-1,7-diaza-spiro[4.4]nonan-6-one hydrochloride;
(2R,5R)-2-[4-(5-ethoxy-2-fluoro-phenyl)-6-methyl-pyridin-2-yl]-7-methyl-1,7-diaza-spiro[4.4]nonan-6-one hydrochloride;

(2S,5S)-2-[4-[2-methoxy-4-(trifluoromethyl)phenyl]-6-methyl-2-pyridyl]-7-methyl-1,7-diazaspiro[4.4]nonan-6-one hydrochloride;
(2S,5R)-2-[4-(3-ethoxy-4-fluoro-phenyl)-6-methyl-2-pyridyl]-7-methyl-1,7-diazaspiro[4.4]nonan-6-one hydrochloride;
(2R,5R)-2-[4-(3-ethoxy-4-fluoro-phenyl)-6-methyl-2-pyridyl]-7-methyl-1,7-diazaspiro[4.4]nonan-6-one hydrochloride;
(2R,5S)-2-[4-(3-ethoxy-4-fluoro-phenyl)-6-methyl-2-pyridyl]-7-methyl-1,7-diazaspiro[4.4]nonan-4-one hydrochloride;
(2S,5S)-2-[4-(3-ethoxy-4-fluoro-phenyl)-6-methyl-2-pyridyl]-7-methyl-1,7-diazaspiro[4.4]nonan-6-one hydrochloride;
(2R,5S)-7-methyl-2-[6-methyl-4-[3-(trifluoromethoxy)phenyl]-2-pyridyl]-1,7-diazaspiro[4.4]nonan-6-one hydrochloride;
(2S,5R)-7-methyl-2-[6-methyl-4-[3-(trifluoromethoxy)phenyl]-2-pyridyl]-1,7-diazaspiro[4.4]nonan-6-one hydrochloride;
(2S,5R)-2-[4-[2-methoxy-4-(trifluoromethyl)phenyl]-5-methyl-2-pyridyl]-7-methyl-17-diazaspiro[4.4]nonan-6-one hydrochloride;
(2R,5R)-2-[4-[2-methoxy-4-(trifluoromethyl)phenyl]-5-methyl-2-pyridyl]-7-methyl-1,7-diazaspiro[4.4]nonan-6-one hydrochloride;
(2R,5S)-2-[4-[2-methoxy-4-(trifluoromethyl)phenyl]-5-methyl-2-pyridyl]-7-methyl-1,7-diazaspiro[4.4]nonan-6-one hydrochloride;
(2S,5S)-2-[4-[2-methoxy-4-(trifluoromethyl)phenyl]-5-methyl-2-pyridyl]-7-methyl-1,7-diazaspiro[4.4]nonan-6-one hydrochloride;
(2S,5R)-2-[4-(5-ethoxy-2-fluoro-phenyl)-5-methyl-2-pyridyl]-7-methyl-1,7-diazaspiro[4.4]nonan-6-one hydrochloride;
(2R,5R)-2-[4-(5-ethoxy-2-fluoro-phenyl)-5-methyl-2-pyridyl]-7-methyl-1,7-diazaspiro[4.4]nonan-6-one hydrochloride;
(2R,5S)-2-[4-(5-ethoxy-2-fluoro-phenyl)-5-methyl-2-pyridyl]-7-methyl-1,7-diazaspiro[4.4]nonan-6-one hydrochloride;
(2S,5S)-2-[4-(5-ethoxy-2-fluoro-phenyl)-5-methyl-2-pyridyl]-7-methyl-1,7-diazaspiro[4.4]nonan-6-one hydrochloride;
(2R,5S)-2-[4-(5-ethoxy-2-fluoro-phenyl)-5-methyl-2-pyridyl]-7-methyl-1,7-diazaspiro[4.4]nonan-6-one hydrochloride;
(2S,5S)-2-[4-(5-ethoxy-2-fluoro-phenyl)-5-methyl-2-pyridyl]-7-methyl-1,7-diazaspiro[4.4]nonan-6-one hydrochloride;
(2S,5R)-2-[4-(5-ethoxy-2-fluoro-phenyl)-5-methyl-2-pyridyl]-7-methyl-1,2-diazaspiro[74.4]nonan-6-one hydrochloride;
(2R,5R)-2-[4-(5-ethoxy-2-fluoro-phenyl)-5-methyl-2-pyridyl]-7-methyl-1,7-diazaspiro[4.4]nonan-6-one hydrochloride;
(2R,5R)-2-[4-(5-ethoxy-2-fluoro-phenyl)-5,6-dimethyl-2-pyridyl]-7-methyl-1,7-diazaspiro[4.4]nonan-6-one hydrochloride;
(2S,5S)-2-[4-(5-ethoxy-2-fluoro-phenyl)-5,6-dimethyl-2-pyridyl]-7-methyl-1,7-diazaspiro[4.4]nonan-6-one hydrochloride;
(2S,5R)-2-[4-(5-ethoxy-2-fluoro-phenyl)-5,6-dimethyl-2-pyridyl]-7-methyl-1,7-diazaspiro[4.4]nonan-6-one hydrochloride;
(2R,5S)-2-[4-(5-ethoxy-2-fluoro-phenyl)-5,6-dimethyl-2-pyridyl]-7-methyl-1,7-diazaspiro[4.4]nonan-6-one hydrochloride;
(2S,5R)-2-[4-(5-ethoxy-2-fluoro-phenyl)-2-pyridyl]-7-methyl-1,7-diazaspiro-[4.4]nonan-6-one hydrochloride;
(2R,5R)-2-[4-(5-ethoxy-2-fluoro-phenyl)-2-pyridyl]-7-methyl-1,7-diazaspir-o[4.4]nonan-6-one hydrochloride;
(2S,5S)-2-[4-(5-ethoxy-2-fluoro-phenyl)-2-pyridyl]-7-methyl-1,7-diazaspiro[4.4]nonan-6-one hydrochloride;
(2S,5S)-2-[4-(5-ethoxy-2,4-difluoro-phenyl)-2-pyridyl]-7-methyl-1,7-diazaspiro[4.4]nonan-6-one hydrochloride;
(2R,5S)-2-[4-(5-ethoxy-2,4-difluoro-phenyl)-2-pyridyl]-7-methyl-1,7-diazaspiro[4.4]nonan-6-one hydrochloride;
(2S,5S)-2-[4-(5-ethoxy-2-fluoro-4-methyl-phenyl)-2-pyridyl]-7-methyl-1,7-diazaspiro[4.4]nonan-6-one hydrochloride;
(2R,5S)-2-[4-(5-ethoxy-2-fluoro-4-methyl-phenyl)-2-pyridyl]-7-methyl-1,7-diazaspiro[4.4]nonan-6-one hydrochloride;
(2R,5R)-2-[5-methoxy-4-[4-(trifluoromethyl)phenyl]-2-pyridyl]-7-methyl-1,7-diazaspiro[4.4]nonan-6-one hydrochloride;
(2S,5R)-2-[5-methoxy-4-[4-(trifluoromethyl)phenyl]-2-pyridyl]-7-methyl-1,7-diazaspiro[4.4]nonan-6-one hydrochloride;
(2S,5S)-2-[5-methoxy-4-[4-(trifluoromethyl)phenyl]-2-pyridyl]-7-methyl-1,7-diazaspiro[4.4]nonan-6-one hydrochloride;
(2R,5S)-2-[5-methoxy-4-[4-(trifluoromethyl)phenyl]-2-pyridyl]-7-methyl-1,7-diazaspiro[4.4]nonan-6-one hydrochloride;
(2R,5S)-2-[4-(4-difluoromethoxy-2-fluoro-phenyl)-pyridin-2-yl]-7-methyl-1,7-diaza-spiro[4.4]nonan-6-one hydrochloride;
(2R,5S)-2-[4-(2-ethoxy-3-fluoro-phenyl)-2-pyridyl]-7-methyl-1,7-diazaspiro[4.4]nonan-6-one hydrochloride;
(2R,5S)-2-[4-(2-fluoro-5-isopropyl-phenyl)-2-pyridyl]-7-methyl-1,7-diazaspiro[4.4]nonan-6-one hydrochloride;
(2S,5S)-2-[4-(4-isopropoxyphenyl)-2-pyridyl]-7-methyl-1,7-diazaspiro[4.4]nonan-6-one hydrochloride;
(2R,5S)-2-[4-(4-isopropoxyphenyl)-2-pyridyl]-7-methyl-1,7-diazaspiro[4.4]nonan-6-one hydrochloride;
(2R,5S)-2-[4-(3,4-dimethoxyphenyl)-2-pyridyl]-7-methyl-1,7-diazaspiro[4.4]nonan-6-one hydrochloride;
2-Chloro-6-[2-[(2R,5S)-7-methyl-6-oxo-1,7-diazaspiro[4.4]nonan-2-yl]-4-pyridyl]benzonitrile hydrochloride;
(2R,5S)-2-[4-(4-ethoxy-3-methyl-phenyl)-2-pyridyl]-7-methyl-1,7-diazaspiro[4.4]nonan-6-one hydrochloride;
(2R,5S)-2-[4-[3-(methoxymethyl)phenyl]-2-pyridyl]-7-methyl-1,7-diazaspiro[4.4]nonan-6-one hydrochloride;
(2R,5S)-2-[4-(2-ethoxy-4-fluoro-phenyl)-2-pyridyl]-7-methyl-1,7-diazaspiro[4.4]nonan-6-one hydrochoride;
1-[4-[2-[(2R,5S)-7-methyl-6-oxo-1,7-diazaspiro[4.4]nonan-2-yl]-4-pyridyl]phenyl]cyclopropanecarbonitrile hydrochloride;
(2R,5S)-2-[4-(3,5-dimethylphenyl)-2-pyridyl]-7-methyl-1,7-diazaspiro[4.4]nonan-6-one hydrochloride;
(2R,5S)-2-[4-(5-ethoxy-2,3-difluoro-phenyl)-2-pyridyl]-7-methyl-1,7-diazaspiro[4.4]nonan-6-one hydrochloride;
(2R,5S)-2-[4-[2-fluoro-5-(trifluoromethoxy)phenyl]-2-pyridyl]-7-methyl-1,7-diazaspiro[4.4]nonan-6-one hydrochloride;

(2R,5S)-2-[4-(2-fluoro-5-propoxy-phenyl)-2-pyridyl]-7-methyl-1,7-diazaspiro[4.4]nonan-6-one hydrochloride;
(2R,5S)-2-[4-(5-ethoxy-2-methyl-phenyl)-2-pyridyl]-7-methyl-1,7-diazaspiro[4.4]nonan-6-one hydrochloride;
(2R,5S)-7-methyl-2-[4-(3-propoxyphenyl)-2-pyridyl]-1,7-diazaspiro[4.4]nonan-6-one hydrochloride;
2-isopropoxy-5-[2-[(2R,5S)-7-methyl-6-oxo-1,7-diazaspiro[4.4]nonan-2-yl]-4-pyridyl]benzonitrile hydrochloride;
(2R,5S)-2-[4-(2-Chloro-5-ethoxy-phenyl)-2-pyridyl]-7-methyl-1,7-diazaspiro[4.4]nonan-6-one hydrochloride;
(2R,5S)-2-[4-[5-(Cyclopropoxy)-2-fluoro-phenyl]-2-pyridyl]-7-methyl-1,7-diazaspiro[4.4]nonan-6-one hydrochloride;
(2R,5S)-2-[4-[2-fluoro-5-(methoxymethyl)phenyl]-2-pyridyl]-7-methyl-1,7-diazaspiro[4.4]nonan-6-one hydrochloride;
(2R,5S)-2-[4-[5-(ethoxymethyl)-2-fluoro-phenyl]-2-pyridyl]-7-methyl-1,7-diazaspiro[4.4]nonan-6-one hydrochloride;
(2R,5S)-2-[4-(3,4-diethoxyphenyl)-2-pyridyl]-7-methyl-1,7-diazaspiro[4.4]nonan-6-one hydrochloride;
(2R,5S)-2-[4-(4-fluoro-3-isobutoxy-phenyl)-2-pyridyl]-7-methyl-1,7-diazaspiro[4.4]nonan-6-one hydrochloride;
(2R,5S)-2-[4-(2-fluoro-S-methoxy-phenyl)-6-methyl-2-pyridyl]-7-methyl-1,7-diazaspiro[4.4]nonan-6-one hydrochloride;
(2R,5S)-2-[4-(2-fluoro-5-propoxy-phenyl)-6-methyl-2-pyridyl]-7-methyl-1,7-diazaspiro[4.4]nonan-6-one hydrochloride;
(2R,5S)-2-[4-(3-ethoxy-5-fluoro-phenyl)-6-methyl-2-pyridyl]-7-methyl-17-diazaspiro[4.4]nonan-6-one hydrochloride;
(2R,5S)-2-[4-(2-fluoro-5-isopropoxy-phenyl)-6-methyl-2-pyridyl]-7-methyl-1,7-diazaspiro[4.4]nonan-6-one hydrochloride;
(2R,5S)-2-[4-(3-ethoxy-2-fluoro-phenyl)-6-methyl-2-pyridyl]-7-methyl-1,7-diazaspiro[4.4]nonan-6-one hydrochloride,
(2R,5S)-2-[4-[2-fluoro-5-(trifluoromethoxy)phenyl]-6-methyl-2-pyridyl]-7-methyl-1,7-diazaspiro[4.4]nonan-6-one hydrochloride;
(2S,5R)-2-[4-(2-fluoro-5-propoxy-phenyl)-6-methyl-2-pyridyl]-7-methyl-1,7-diazaspiro[4.4]nonan-6-one hydrochloride;
(2R,5S)-2-[4-(5-ethoxy-2-fluoro-4-methyl-phenyl)-6-methyl-2-pyridyl]-7-methyl-1,7-diazaspiro[4.4]nonan-6-one hydrochloride;
(2R,5S)-2-[4-(5-ethyl-2-fluoro-phenyl)-6-methyl-2-pyridyl]-7-methyl-1,7-diazaspiro[4.4]nonan-6-one hydrochloride;
(2R,5S)-2-[4-(3-ethylphenyl)-6-methyl-2-pyridyl]-7-methyl-1,7-diazaspiro[4.4]nonan-6-one hydrochloride;
(2R,5S)-2-[4-(3-ethyl-2-fluoro-phenyl)-6-methyl-2-pyridyl]-7-methyl-1,7-diazaspiro[4.4]nonan-6-one hydrochloride;
(2R,5S)-2-[4-(3-ethoxyphenyl)-6-methyl-2-pyridyl]-7-methyl-1,7-diazaspiro[4.4]nonan-6-one hydrochloride;
(2S,5R)-2-[4-(4-ethylsulfonylphenyl)-6-methyl-2-pyridyl]-7-methyl-1,7-diazaspiro[4.4]nonan-6-one hydrochloride;
(2R,5S)-2-[4-(2,5-difluorophenyl)-6-methyl-2-pyridyl]-7-methyl-1,7-diazaspiro[4.4]nonan-6-one hydrochloride;
(2R,5R)-2-[4-(5-ethoxy-2-fluoro-phenyl)-3-methyl-2-pyridyl]-7-methyl-1,7-diazaspiro[4.4]nonan-6-one hydrochloride;
(2S,5R)-2-[4-(5-ethoxy-2-fluoro-phenyl)-3-methyl-2-pyridyl]-7-methyl-1,7-diazaspiro[4.4]nonan-6-one hydrochloride;
(2S,5S)-2-[4-(5-ethoxy-2-fluoro-phenyl)-3-methyl-2-pyridyl]-7-methy-1,7-diazaspiro[4.4]nonan-6-one hydrochloride;
(2R,5S)-2-[4-(5-ethoxy-2-fluoro-phenyl)-3-methyl-2-pyridyl]-7-methyl-1,7-diazaspiro[4.4]nonan-6-one hydrochloride;
(2S,5S)-2-[4-(5-ethoxy-2-fluoro-phenyl)-2-pyridyl]-8,8-dimethyl-1,7-diazaspiro[4.4]nonan-6-one hydrochloride;
(2R,5S)-2-[4-(5-ethoxy-2-fluoro-phenyl)-2-pyridyl]-8,8-dimethyl-1,7-diazaspiro[4.4]nonan-6-one hydrochloride;
(2R,5R)-2-[4-(5-ethoxy-2-fluoro-phenyl)-2-pyridyl]-8,8-dimethyl-1,7-diazaspiro[4.4]nonan-6-one hydrochloride;
(2S,5R)-2-[4-(5-ethoxy-2-fluoro-phenyl)-2-pyridyl]-8,8-dimethyl-1,7-diazaspiro[4.4]nonan-6-one hydrochloride;
(2R,5R)-2-[4-(2-fluoro-5-hydroxy-phenyl)-2-pyridyl]-8,8-dimethyl-1,7-diaza-spiro[4.4]nonan-6-one;
(2S,5R)-2-[4-(5-ethoxy-2-fluoro-phenyl)-5-fluoro-2-pyridyl]-7-methyl-1,7-diazaspiro[4.4]nonan-6-one hydrochloride;
(2R,5R)-2-[4-(5-ethoxy-2-fluoro-phenyl)-5-fluoro-2-pyridyl]-7-methyl-1,7-diazaspiro[4.4]nonan-6-one hydrochloride;
(2R,5S)-2-[4-(5-ethoxy-2-fluoro-phenyl)-5-fluoro-2-pyridyl]-7-methyl-1,7-diazaspiro[4.4]nonan-6-one hydrochloride;
(2S,5S)-2-[4-(5-ethoxy-2-fluoro-phenyl)-5-fluoro-2-pyridyl]-7-methyl-1,7-diazaspiro[4.4]nonan-6-one hydrochloride;
(2R,5S)-1,7-dimethyl-2-[4-[4-(trifluoromethyl)phenyl]-2-pyridyl]-1,7-diaza-spiro[4.4]nonan-6-one hydrochloride;
(2S,5S)-1-methyl-2-[6-methyl-4-[4-(trifluoromethyl)phenyl]-2-pyridyl]-1,7-diazaspiro[4.4]nonan-6-one hydrochloride;
(2R,5R)-1-methyl-2-[6-methyl-4-[4-(trifluoromethyl)phenyl]-2-pyridyl]-1,7-diazaspiro[4.4]nonan-6-one hydrochloride;
(2S,5R)-1I-methyl-2-[6-methyl-4-[4-(trifluoromethyl)phenyl]-2-pyridyl]-1,7-diazaspiro[4.4]nonan-6-one hydrochloride;
(2R,5S)-1-methyl-2-[6-methyl-4-[4-(trifluoromethyl)phenyl]-2-pyridyl]-1,7-diazaspiro[4.4]nonan-6-one hydrochloride;
(2S,5R)-2-[4-(5-ethoxy-2-fluoro-phenyl)-6-methyl-2-pyridyl]-1,7-dimethyl-1,7-diazaspiro-[4.4]nonan-6-one hydrochloride;
(2R,5R)-2-[4-(5-ethoxy-2-fluoro-phenyl)-6-isopropyl-2-pyridyl]-7-methyl-1,7-diazaspiro[4.4]nonan-6-one hydrochloride;
(2S,5R)-2-[4-(5-ethoxy-2-fluoro-phenyl)-6-isopropyl-2-pyridyl]-7-methyl-1,7-diazaspiro[4.4]nonan-6-one hydrochloride;
(2S,5S)-2-[4-(5-ethoxy-2-fluoro-phenyl)-6-isopropyl-2-pyridyl]-7-methyl-1,7-diazaspiro[4.4]nonan-6-one hydrochloride;

(2R,5S)-2-[4-(5-ethoxy-2-fluoro-phenyl)-6-isopropyl-2-pyridyl]-7-methyl-1,7-diazaspiro[4.4]nonan-6-one hydrochloride;
(2S,3S,5R)-3-fluoro-7-methyl-2-[4-[4-(trifluoromethyl)phenyl]-2-pyridyl]-1,7-diazaspiro[4.4]nonan-6-one hydrochloride;
(2S,3R,5R)-3-fluoro-7-methyl-2-[4-[4-(trifluoromethyl)phenyl]-2-pyridyl)-1,7-diazaspiro[4.4]nonan-6-one hydrochloride;
(5R)-3,3-difluoro-7-methyl-2-[4-[4-(trifluoromethyl)phenyl]-2-pyridyl]-1,-7-diazaspiro[4.4]nonan-6-one hydrochloride;
(2R,5S)-2-14-(5-ethoxy-2-fluoro-phenyl)-5-ethyl-2-pyridyl]-7-methyl-1,7-di-azaspiro[4.4]nonan-6-one hydrochloride;
(2S,5R)-2-[4-(5-ethoxy-2-fluoro-phenyl)-5-ethyl-2-pyridyl]-7-methyl-1,7-d-iazaspiro[4.4]nonan-6-one hydrochloride;
(2R,5R)-2-[4-(5-ethoxy-2-fluoro-phenyl)-6-methoxy-2-pyridyl]-7-methyl-1,7-diazaspiro[4.4]nonan-6-one hydrochloride;
(2S,5R)-2-[4-(5-ethoxy-2-fluoro-phenyl)-6-methoxy-2-pyridyl]-7-methyl-1,7-diazaspiro[4.4]nonan-6-one hydrochloride;
(2S,5S)-2-[4-(5-ethoxy-2-fluoro-phenyl)-6-methoxy-2-pyridyl]-7-methyl-1,7-diazaspiro[4.4]nonan-6-one hydrochloride;
(2R,5S)-2-[4-(5-ethoxy-2-fluoro-phenyl)-6i-ethoxy-2-pyridyl]-7-methyl-1,7-diazaspiro[4.4]nonan-6-one hydrochloride;
(2R,5S)-2-[4-[2-fluoro-5-(2-fluoroethoxyl)phenyl]-2-pyridyl]-7-methyl-1,7-diazaspiro[4.4]nonan-6-one hydrochloride;
(2R,5S)-2-[4-[5-(2,2-difluoroethoxy)-2-fluoro-phenyl]-2-pyridyl]-7-methyl-1,7-diazaspiro[4.4]nonan-6-one hydrochloride;
(2R,5S)-2-[4-(2-fluoro-5-isobutoxy-phenyl)-2-pyridyl]-7-methyl-1,7-diazaspiro[4.4]nonan-6-one hydrochloride;
(2R,5S)-2-[4-[5-(1,1-dideuterioethoxy)-2-fluoro-phenyl]-2-pyridyl]-7-methyl-1,7-diazaspiro[4.4]nonan-6-one hydrochloride;
(2R,5S)-2-[4-[5-(1-(Cyclopropyl)ethoxy)-2-fluoro-phenyl]-2-pyridyl]-7-methyl-1,7-diazaspiro[4.4]nonan-6-one hydrochloride;
2-[4-(5-ethoxy-2-fluoro-phenyl)-3,6-dimethyl-2-pyridyl]-7-methyl-1,7-diaza-spiro[4.4]nonan-6-one hydrochloride; or
(2R,5S)-2-[4-(2-fluoro-5-propanoyl-phenyl)-2-pyridyl]-7-methyl-1,7-diazasp-iro[4.4]nonan-6-one hydrochloride.

10. A pharmaceutical composition comprising a compound of formula (I) as defined in claim 1 or a pharmaceutically acceptable salt thereof with one or more pharmaceutically acceptable carrier(s), diluents(s) and/or excipient(s).

11. The compound of claim 3 or a pharmaceutically acceptable salt thereof, wherein each $R^8$ group is independently selected from the group fluorine, methyl, ethyl, —CN, =O or —O—CF$_3$.

12. A compound as defined in claim 1, which is selected from a compound of
(2R,5S)-7-methyl-2-[4-(2,4,6-trimethylphenyl)-2-pyridyl]-1,7-diazaspiro-[4.4]nonan-6-one;
(2R,5S)-7-methyl-2-[4-[2-(trifluoromethoxy)-phenyl]-2-pyridyl]-1,7-diazaspiro-[4.4]nonan-6-one;
(2R,5S)-2-[4-(2-ethoxy-5-fluoro-phenyl)-pyridin-2-yl]-7-methyl-1,7-diaza-spiro[4.4]nonan-6-one;
(2R,5S)-7-methyl-2-[4-(4-trifluoro-methoxy-phenyl)-pyridin-2-yl]-1,7-diaza-spiro[4.4]nonan-6-one,
(2R,5S)-7-methyl-2-(4-phenyl-pyridin-2-yl)-1,7-diazaspiro[4.4]nonan-6-one;
(2R,5S)-7-methyl-2-[4-[2-(trifluoro-methyl)phenyl]-2-pyridyl]-1,7-diazaspiro[4.4]nonan-6-one;
(2R,5S)-2-[4-(5-ethoxy-2-fluoro-phenyl)-2-pyridyl]-7-methyl-1,7-diazaspiro[4.4]nonan-6-one;
(2R,5S)-2-[4-(2,4-difluorophenyl)-2-pyridyl]-7-methyl-1,7-diazaspiro[4.4]nonan-6-one;
(2R,5S)-2-[4-(5-fluoro-2-methoxy-phenyl)-2-pyridyl]-7-methyl-1,7-diazaspiro[4.4]nonan-6-one;
(2R,5S)-2-[4-(3,4-difluorophenyl)-2-pyridyl]-7-methyl-1,7-diazaspiro[4.4]nonan-6-one;
(2R,5S)-2-[4-[2-fluoro-4-(trifluoromethyl)phenyl]-2-pyridyl]-7-methyl-1,7-diazaspiro[4.4]nonan-6-one;
(2R,5S)-2-[4-(4-chlorophenyl)-2-pyridyl]-7-methyl-1,7-diazaspiro[4.4]nonan-6-one;
(2R,5R)-7-methyl-2-[3-methyl-4-[4-(trifluoromethyl)phenyl]-2-pyridyl]-1,7-diazaspiro[4.4]nonan-6-one;
(2S,5R)-7-methyl-2-[3-methyl-4-[4-(trifluoromethyl)phenyl]-2-pyridyl]-1,7-diazaspiro[4.4]nonan-6-one;
(2S,5S)-7-methyl-2-[3-methyl-4-[4-(trifluoromethyl)phenyl]-2-pyridyl]-1,7-diazaspiro[4.4]nonan-6-one;
(2R,5S)-7-methyl-2-[3-methyl-4-[4-(trifluoromethyl)phenyl]-2-pyridyl]-1,7-diazaspiro[4.4]nonan-6-one;
(2S,5R)-7-methyl-2-[3-methyl-4-[4-fluorophenyl]-2-pyridyl]-1,7-diazaspiro[4.4]nonan-6-one;
(2R,5S)-2-[4-(4-fluorophenyl)-3-methyl-2-pyridyl]-7-methyl-1,7-diazaspiro[-4.4]nonan-6-one;
(2S,5S)-2-[4-(4-fluorophenyl)-3-methyl-2-pyridyl]-7-methyl-1,7-diazaspiro-[4.4]nonan-6-one;
2-[2-methyl-6-[(2S,5R)-7-methyl-6-oxo-1,7-diazaspiro[4.4]nonan-2-yl]-4-py-ridyl]-4-(trifluoromethyl)-benzonitrile;
2-[2-methyl-6-[(2R,5R)-7-methyl-6-oxo-1,7-diazaspiro[4.4]-nonan-2-yl]-4-p-yridyl]-4-(trifluoromethyl)-benzonitrile;
2-[2-methyl-6-[(2R,5S)-7-methyl-6-oxo-1,7-diazaspiro[4.4]nonan-2-yl]-4-pyridyl]-4-(trifluoromethyl)benzonitrile;
2-[2-methyl-6-[(2R,5S)-7-methyl-6-oxo-1,7-diazaspiro[4.4]nonan-2-yl]-4-pyridyl]-4-(trifluoromethyl)benzamide;
2-[2-methyl-6-[(2S,5S)-7-methyl-6-oxo-1,7-diazaspiro[4.4]nonan-2-yl]-4-pyridyl]-4-(trifluoromethyl)benzamide;
2-[2-methyl-6-[(2R,5R)-7-methyl-6-oxo-1,7-diazaspiro[4.4]nonan-2-yl]-4-pyridyl]-4-(trifluoromethyl)benzamide;
2-[2-methyl-6-[(2S,5R)-7-methyl-6-oxo-1,7-diazaspiro[4.4]nonan-2-yl]-4-pyridyl]-4-(trifluoromethyl)benzamide;
(2R,5S)-7-methyl-2-[6-methyl-4-[4-(trifluoromethyl)phenyl]-2-pyridyl]-1,7-diazaspiro[4.4]nonan-6-one;
(2S,5S)-7-methyl-2-[6-methyl-4-[4-(trifluoromethyl)phenyl]-2-pyridyl]-1,7-diazaspiro[4.4]nonan-6-one;
(2S,5R)-7-methyl-2-[6-methyl-4-[4-(trifluoromethyl)phenyl]-2-pyridyl]-1,7-diazaspiro[4.4]nonan-6-one;
(2R,5R)-7-methyl-2-[6-methyl-4-[4-(trifluoromethyl)phenyl]-2-pyridyl]-1,7-diazaspiro[4.4]nonan-6-one;
(2R,5S)-2-[4-(2-fluoro-phenyl)-pyridin-2-yl]-7-methyl-1,7-diaza-spiro[4.4]-nonan-6-one;
(2S,5S)-2-[4-(2-fluoro-phenyl)-pyridin-2-yl]-7-methyl-1,7-diaza-spiro[4.4.]nonan-6-one;
(2S,5R)-2-[4-(2-fluoro-phenyl)-pyridin-2-yl]-7-methyl-1,7-diaza-spiro[4.4]nonan-6-one;

(2R,5R)-2-[4-(2-fluoro-phenyl)-pyridin-2-yl]-7-methyl-1,7-diaza-spiro[4.4]nonan-6-one;
(2S,5S)-2-[4-[4-(trifluoromethyl)phenyl]-2-pyridyl]-1,7-diazaspiro[4.4]non-an-6-one;
(2R,5S)-2-[4-[4-(trifluoromethyl)phenyl]-2-pyridyl]-1,7-diazaspiro[4.4]no-nan-6-one;
(2S,5S)-2-[4-[2-fluoro-4-(trifluoro-methyl)phenyl]-2-pyridyl]-1,7-diazaspiro[4.4]nonan-6-one;
(2R,5S)-2-[4-[2-fluoro-4-(trifluoro-methyl)phenyl]-2-pyridyl]-1,7-diazaspiro[4.4]nonan-6-one;
(2S,5S)-7-methyl-2-[5-methyl-4-[4-(trifluoromethyl)phenyl]-2-pyridyl]-1,7-diazaspiro[4.4]nonan-6-one;
(2R,5S)-7-methyl-2-[5-methyl-4-[4-(trifluoromethyl)phenyl]-2-pyridyl]-1,7-diazaspiro[4.4]nonan-6-one;
(2R,5R)-7-methyl-2-[5-methyl-4-[4-(trifluoromethyl)phenyl]-2-pyridyl]-1,7-diazaspiro[4.4]nonan-6-one;
(2S,5R)-7-methyl-2-[5-methyl-4-[4-(trifluoromethyl)phenyl]-2-pyridyl]-1,7-diazaspiro[4.4]nonan-6-one;
(2S,5S)-8,8-dimethyl-2-[4-[4-(trifluoromethyl)phenyl]-2-pyridyl]-1,7-diazaspiro[4.4]nonan-6-one;
(2R,5S)-8,8-dimethyl-2-[4-[4-(trifluoromethyl)phenyl]-2-pyridyl]-1,7-diazaspiro[4.4]nonan-6-one;
(2R,5R)-8,8-dimethyl-2-[4-[4-(trifluoromethyl)phenyl]-2-pyridyl]-1,7-diazaspiro[4.4]nonan-6-one;
(2S,5R)-8,8-dimethyl-2-[4-[4-(trifluoromethyl)phenyl]-2-pyridyl]-1,7-diazaspiro[4.4]nonan-6-one;
(2S,5R)-2-[4-(4-trifluoromethyl-phenyl)-pyridin-2-yl]-1,7-diaza-spiro[4.5]decan-6-one;
(2R,5R)-2-[4-(4-trifluoromethyl-phenyl)-pyridin-2-yl]-1,7-diaza-spiro[4.5]decan-6-one;
(2R,5S)-2-[4-(4-trifluoromethyl-phenyl)-pyridin-2-yl]-1,7-diaza-spiro[4.5]decan-6-one;
(2S,5S)-2-[4-(4-trifluoromethyl-phenyl)-pyridin-2-yl]-1,7-diaza-spiro[4.5]decan-6-one;
(2R,5S)-7-methyl-2-[4-(4-trifluoromethyl-phenyl)-pyridin-2-yl]-1,7-diaza-spiro[4.4]nonan-6-one;
(2S,5S)-7-methyl-2-[4-(4-trifluoromethyl-phenyl)-pyridin-2-yl]-1,7-diaza-spiro[4.4]nonan-6-one;
(2S,5R)-7-methyl-2-[4-(4-trifluoromethyl-phenyl)-pyridin-2-yl]-1,7-diaza-spiro[4.4]nonan-6-one;
(2R,5R)-7-methyl-2-[4-(4-trifluoromethyl-phenyl)-pyridin-2-yl]-1,7-diaza-spiro[4.4]nonan-6-one;
(2S,5R)-2-[4-(4-fluorophenyl)-6-methyl-2-pyridyl]-7-methyl-1,7-diazaspiro[4.4]nonan-6-one;
(2R,5S)-2-[4-(4-fluorophenyl)-6-methyl-2-pyridyl]-7-methyl-1,7-diazaspiro[4.4]nonan-6-one;
(2R,5S)-2-[5-fluoro-4-[4-(trifluoromethyl)phenyl]-2-pyridyl]-7-methyl-1,7-diazaspiro[4.4]nonan-6-one;
(2S,5S)-2-[5-fluoro-4-[4-(trifluoromethyl)phenyl]-2-pyridyl]-7-methyl-1,7-diazaspiro[4.4]nonan-6-one;
(2S,5R)-2-[5-fluoro-4-[4-(trifluoromethyl)phenyl]-2-pyridyl]-7-methyl-1,7-diazaspiro[4.4]nonan-6-one;
(2R,5R)-2-[5-fluoro-4-[4-(trifluoromethyl)phenyl]-2-pyridyl]-7-methyl-1,7-diazaspiro[4.4]nonan-6-one;
(2R,5S)-2-[5-tert-Butoxy-4-[4-(trifluoromethyl)-phenyl]-2-pyridyl]-7-methyl-1,7-diazaspiro[4.4]nonan-6-one;
(2S,5S)-2-[5-tert-Butoxy-4-[4-(trifluoromethyl)-phenyl]-2-pyridyl]-7-methyl-1,7-diazaspiro[4.4]nonan-6-one;
(2S,5R)-2-[5S-tert-Butoxy-4-[4-(trifluoromethyl)-phenyl]-2-pyridyl]-7-methyl-1,7-diazaspiro[4.4]nonan-6-one;
(2R,5R)-2-[5-tert-Butoxy-4-[4-(trifluoromethyl)-phenyl]-2-pyridyl]-7-methyl-1,7-diazaspiro[4.4]nonan-6-one;
(2R,5S)-2-[4-(4-fluorophenyl)-2-pyridyl]-7-methyl-1,7-diazaspiro[4.4]nonan-6-one;
(2R,5R)-7-methyl-2-(4-(4-trifluoromethyl-phenyl)-pyridin-2-yl]-1,7-diaza-spiro[4.5]decan-6-one;
(2S,5R)-7-methyl-2-[4-(4-trifluoromethyl-phenyl)-pyridin-2-yl]-1,7-diaza-spiro[4.5]decan-6-one;
(2S,5S)-7-methyl-2-[4-(4-trifluoromethyl-phenyl)-pyridin-2-yl]-1,7-diaza-spiro[4.5]decan-6-one;
(2R,5S)-7-methyl-2-[4-(4-trifluoromethyl-phenyl)-pyridin-2-yl]-1,7-diaza-spiro[4.5]decan-6-one;
(2R,5R)-2-[4-(4-fluoro-phenyl)-pyridin-2-yl]-7-methyl-1,7-diaza-spiro[4.5]decan-6-one;
(2S,5R)-2-[4-(4-fluoro-phenyl)-pyridin-2-yl]-7-methyl-1,7-diaza-spiro[4.5]decan-6-one;
(2S,5S)-2-[4-(4-fluoro-phenyl)-pyridin-2-yl]-7-methyl-1,7-diaza-spiro[4.5]decan-6-one;
(2R,5S)-2-[4-(4-fluoro-phenyl)-pyridin-2-yl]-7-methyl-1,7-diaza-spiro[4.5]decan-6-one;
(2R,5S)-7-methyl-2-[4-[3-(trifluoromethyl)phenyl]-2-pyridyl]-1,7-diazaspiro[4.4]nonan-6-one;
(2R,5S)-2-[4-(4-ethoxyphenyl)-2-pyridyl]-7-methyl-1,7-diazaspiro[4.4]nonan-6-one;
(2R,5S)-2-[4-(3,5-difluorophenyl)-2-pyridyl]-7-methyl-1,7-diazaspiro[4.4]nonan-6-one;
(2R,5S)-2-[4-(2-Chloro-3-methoxy-phenyl)-2-pyridyl]-7-methyl-1,7-diazaspiro[4.4]nonan-6-one;
(2R,5S)-2-[4-(3-ethoxyphenyl)-2-pyridyl]-7-methyl-1,7-diazaspiro[4.4]nonan-6-one;
(2R,5S)-2-[4-(2-Chloro-5-methoxy-phenyl)-2-pyridyl]-7-methyl-1,7-diazaspiro[4.4]nonan-6-one;
(2R,5S)-2-[4-[5-(difluoromethoxy)-2-fluoro-phenyl]-2-pyridyl]-7-methyl-1,7-diazaspiro[4.4]nonan-6-one;
(2R,5S)-2-[4-(4-isopropoxyphenyl)-6-methyl-2-pyridyl]-7-methyl-1,7-diazaspiro[4.4]nonan-6-one;
(2S,5S)-2-[4-(4-isopropoxyphenyl)-6-methyl-2-pyridyl]-7-methyl-1,7-diazaspiro[4.4]nonan-6-one;
(2R,5S)-7-methyl-2-[6-methyl-4-(p-tolyl)-2-pyridyl]-1,7-diazaspiro[4.4]nonan-6-one;
(2S,5S)-2-[4-(4-ethoxyphenyl)-6-methyl-2-pyridyl]-7-methyl-1,7-diazaspiro[4.4]nonan-6-one;
(3R,5S)-3-[4-(4-ethoxyphenyl)-6-methyl-2-pyridyl]-8-methyl-4,8-diazaspiro[4.4]nonan-9-one;
(3R,5R)-3-[4-[2-methoxy-4-(trifluoromethyl)phenyl]-6-methyl-2-pyridyl]-8-methyl-4,8-diazaspiro[4.4]nonan-9-one;
(3S,5R)-3-[4-[2-methoxy-4-(trifluoromethyl)phenyl]-6-methyl-2-pyridyl]-8-methyl-4,8-diazaspiro[4.4]nonan-9-one;
(2S,5S)-2-[4-(5-ethoxy-2-fluoro-phenyl)-6-methyl-pyridin-2-yl]-7-methyl-1,7-diaza-spiro[4.4]nonan-6-one;
(2R,5S)-2-[4-(5-ethoxy-2-fluoro-phenyl)-6-methyl-pyridin-2-yl j-7-methyl-1,7-diaza-spiro[4.4]nonan-6-one;
(2R,5S)-2-[6-methyl-4-[4-(trifluoromethyl)phenyl]-2-pyridyl]-1,7-diazaspir-o[4.4]nonan-6-one;
(2S,5R)-2-[6-methyl-4-[4-(trifluoromethyl)phenyl]-2-pyridyl]-1,7-diazaspiro[4.4]nonan-6-one;
(2R,5R)-2-[6-methyl-4-[4-(trifluoromethyl)phenyl]-2-pyridyl]-1,7-diazaspiro[4.4]nonan-6-one;
(2S,5S)-2-[6-methyl-4-[4-(trifluoromethyl)phenyl]]-2-pyridyl]-1,7-diazaspiro[4.4]nonan-6-one;
(2S,5S)-2-[6-methyl-4-(4-trifluoromethyl-phenyl)-pyridin-2-yl]-1,7-diaza-spiro[4.5]decan-6-one;
(2R,5R)-2-[6-methyl-4-(4-trifluoromethyl-phenyl)-pyridin-2-yl]-1,7-diaza-spiro[4.5]decan-6-one;
(2R,5S)-2-[6-methyl-4-(4-trifluoromethyl-phenyl)-pyridin-2-yl]-1,7-diaza-spiro[4.5]decan-6-one;
(2S,5R)-2-[6-methyl-4-(4-trifluoromethyl-phenyl)-pyridin-2-yl]-1,7-diaza-spiro[4.5]decan-6-one;
(2S,5R)-2-[4-(5-ethoxy-2-fluoro-phenyl)-6-methyl-2-pyridyl]-1,7-diazaspiro[4.4]nonan-6-one;

(2R,5R)-2-[4-(5-ethoxy-2-fluoro-phenyl)-6-methyl-2-pyridyl]-1,7-diazaspiro[4.4]nonan-6-one;
(2R,5S)-2-[4-(5-ethoxy-2-fluoro-phenyl)-6-methyl-2-pyridyl]-1,7-diazaspiro[4.4]nonan-6-one;
(2S,5S)-2-[4-(5-ethoxy-2-fluoro-phenyl)-6-methyl-2-pyridyl]-1,7-diazaspiro[4.4]nonan-6-one;
(2S,5S)-2-[4-(5-ethoxy-2-fluoro-phenyl)-pyridin-2-yl]-1,7-diaza-spiro[4.5]decan-6-one;
(2R,5S)-2-[4-(5-ethoxy-2-fluoro-phenyl)-pyridin-2-yl]-1,7-diaza-spiro[4.5]decan-6-one;
(2R,5R)-2-[4-(5-ethoxy-2-fluoro-phenyl)-pyridin-2-yl]-1,7-diaza-spiro[4.5]decan-6-one;
(2S,5R)-2-[4-(5-ethoxy-2-fluoro-phenyl)-pyridin-2-yl]-1,7-diaza-spiro[4.5]decan-6-one;
(2S,5R)-2-[4-(4-fluoro-phenyl)-pyridin-2-yl]-1,7-diaza-spiro[4.5]decan-6-one;
(2R,5R)-2-[4-(4-fluoro-phenyl)-pyridin-2-yl]-1,7-diaza-spiro[4.5]decan-6-one;
(2R,5S)-2-[4-(4-fluoro-phenyl)-pyridin-2-yl]-1,7-diaza-spiro[4.5]decan-6-one;
(2S,5S)-2-[4-(4-fluoro-phenyl)-pyridin-2-yl]-1,7-diaza-spiro[4.5]decan-6-one;
(2S,5R)-2-[4-[4-(trifluoromethyl)phenyl]-2-pyridyl]-1,7-diazaspiro[4.4]nonan-6-one;
(2R,5R)-2-[4-[4-(trifluoromethyl)phenyl]-2-pyridyl)-1,7-diazaspiro[4.4]nonan-6-one;
(2S,5R)-2-[4-[3-(trifluoromethoxy)phenyl]-2-pyridyl]-1,7-diazaspiro[4.4]nonan-6-one;
(2R,5R)-2-[4-[3-(trifluoromethoxy)phenyl]-2-pyridyl]-1,7-diazaspiro[4.4]nonan-6-one;
(2R,5S)-2-[4-[3-(trifluoromethoxy)phenyl]-2-pyridyl]j-1,7-diazaspiro[4.4]nonan-6-one;
(2S,5S)-2-[4-[3-(trifluoromethoxy)phenyl]-2-pyridyl]-1,7-diazaspiro[4.4]nonan-6-one;
(2S,5R)-2-[4-(5-ethoxy-2-fluoro-phenyl)-6-methyl-pyridin-2-yl]-7-methyl-1,7-diaza-spiro[4.4]nonan-6-one;
(2R,5R)-2-[4-(5-ethoxy-2-fluoro-phenyl)-6-methyl-pyridin-2-yl]-7-methyl-1,7-diaza-spiro[4.4]nonan-6-one;
(2S,5S)-2-[4-[2-methoxy-4-(trifluoromethyl)phenyl]-6-methyl-2-pyridyl]-7-methyl-1,7-diazaspiro[4.4]nonan-6-one;
(2S,5R)-2-[4-(3-ethoxy-4-fluoro-phenyl)-6-methyl-2-pyridyl]-7-methyl-1,7-diazaspiro[4.4]nonan-6-one;
(2R,5R)-2-[4-(3-ethoxy-4-fluoro-phenyl)-6-methyl-2-pyridyl]-7-methyl-1,7-diazaspiro[4.4]nonan-6-one;
(2R,5S)-2-[4-(3-ethoxy-fluoro-phenyl)-6-methyl-2-pyridyl]-7-methyl-1,7-diazaspiro[4.4]nonan-4-one;
(2S,5S)-2-[4-(3-ethoxy-4-fluoro-phenyl)-6-methyl-2-pyridyl]-7-methyl-1,7-diazaspiro[4.4]nonan-6-one;
(2R,5S)-7-methyl-2-[6-methyl-4-[3-(trifluoromethoxy)phenyl]-2-pyridyl]-1,7-diazaspiro[4.4]nonan-6-one;
(2S,5R)-7-methyl-2-[6-methyl-4-[3-(trifluoromethoxy)phenyl]-2-pyridyl]-1,7-diazaspiro[4.4]nonan-6-one;
(2S,5R)-2-[4-[2-methoxy-4-(trifluoromethyl)phenyl]-5-methyl-2-pyridyl]-7-methyl-1,7-diazaspiro[4.4]nonan-6-one;
(2R,5R)-2-[4-[2-methoxy-4-(trifluoromethyl)phenyl]-5-methyl-2-pyridyl]-7-methyl-1,7-diazaspiro[4.4]nonan-6-one;
(2R,5S)-2-[4-[2-methoxy-4-(trifluoromethyl)phenyl]-5-methyl-2-pyridyl]-7-methyl-1,7-diazaspiro[4.4]nonan-6-one;
(2S,5S)-2-[4-[2-methoxy-4-(trifluoromethyl)phenyl]-5-methyl-2-pyridyl]-7-methyl-1,7-diazaspiro[4.4]nonan-6-one;
(2S,5R)-2-[4-(5-ethoxy-2-fluoro-phenyl)-5-methyl-2-pyridyl]-7-methyl-1,7-diazaspiro[4.4]nonan-6-one;
(2R,5R)-2-[4-(5-ethoxy-2-fluoro-phenyl)-5-methyl-2-pyridyl]-7-methyl-1,7-diazaspiro[4.4]nonan-6-one;
(2R,5S)-2-[4-(5-ethoxy-2-fluoro-phenyl)-5-methyl-2-pyridyl]-7-methyl-1,7-diazaspiro[4.4]nonan-6-one;
(2S,5S)-2-[4-(5-ethoxy-2-fluoro-phenyl)-5-methyl-2-pyridyl]-7-methyl-1,7-diazaspiro[4.4]nonan-6-one;
(2R,5S)-2-[4-(5-ethoxy-2-fluoro-phenyl)-5-methyl-2-pyridyl]-7-methyl-1,7-diazaspiro[4.4]nonan-6-one;
(2S,5S)-2-[4-(5-ethoxy-2-fluoro-phenyl)-5-methyl-2-pyridyl]-7-methyl-1,7-diazaspiro[4.4]nonan-6-one;
(2S,5R)-2-[4-(5-ethoxy-2-fluoro-phenyl)-5-methyl-2-pyridyl]-7-methyl-1,7-diazaspiro[4.4]nonan-6-one;
(2R,5R)-2-[4-(5-ethoxy-2-fluoro-phenyl)-5-methyl-2-pyridyl]-7-methyl-1,7-diazaspiro[4.4]nonan-6-one;
(2R,5R)-2-[4-(5-ethoxy-2-fluoro)-phenyl]-5,6-dimethyl-2-pyridyl]-7-methyl-1,7-diazaspiro[4.4]nonan-6-one;
(2S,5S)-2-[4-(5-ethoxy-2-fluoro-phenyl)-5,6-dimethyl-2-pyridyl]-7-methyl-1,7-diazaspiro[4.4]nonan-6-one;
(2S,5R)-2-[4-(5-ethoxy-2-fluoro-phenyl)-5,6-dimethyl-2-pyridyl]-7-methyl-1,7-diazaspiro[4.4]nonan-6-one;
(2R,5S)-2-[4-(5-ethoxy-2-fluoro-phenyl)-5,6-dimethyl-2-pyridyl]-7-methyl-1,7-diazaspiro[4.4]nonan-6-one;
(2S,5R)-2-[4-(5-ethoxy-2-fluoro-phenyl)-2-pyridyl]-7-methyl-1,7-diazaspiro[4.4]nonan-6-one;
(2R,5R)-2-[4-(5-ethoxy-2-fluoro-phenyl)-2-pyridyl]-7-methyl-1,7-diazaspir-o[4.4]nonan-6-one;
(2S,5S)-2-[4-(5-ethoxy-2-fluoro-phenyl)-2-pyridyl]-7-methyl-1,7-diazaspiro[4.4]nonan-6-one;
(2S,5S)-2-[4-(5-ethoxy-2,4-difluoro-phenyl)-2-pyridyl]-7-methyl-1,7-diazaspiro[4.4]nonan-6-one;
(2R,5S)-2-[4-(5-ethoxy-2,4-difluor-o-phenyl)-2-pyridyl]-7-methyl-1,7-diazaspiro[4.4]nonan-6-one;
(2S,5S)-2-[4-(5-ethoxy-2-fluoro-4-methyl-phenyl)-2-pyridyl]-7-methyl-1,7-diazaspiro[4.4]nonan-6-one;
(2R,5S)-2-[4-(5-ethoxy-2-fluoro-4-methyl-phenyl)-2-pyridyl]-7-methyl-1,7-di azaspiro[4.4]nonan-6-one;
(2R,5R)-2-[5-methoxy-4-[4-(trifluoromethyl)phenyl]-2-pyridyl]-7-methyl-1,7-diazaspiro[4.4]nonan-6-one;
(2S,5R)-2-[5-methoxy-4-[4-(trifluoromethyl)phenyl]-2-pyridyl]-7-methyl-1,7-diazaspiro[4.4]nonan-6-one;
(2S,5S)-2-[5-methoxy-4-[4-(trifluoromethyl)phenyl]-2-pyridyl]-7-methyl-1,7-diazaspiro[4.4]nonan-6-one;
(2R,5S)-2-[5-methoxy-4-[4-(trifluoromethyl)phenyl]-2-pyridyl]-7-methyl-1,7-diazaspiro[4.4]nonan-6-one;
(2R,5S)-2-[4-(4-difluoromethoxy-2-fluoro-phenyl)-pyridin-2-yl]-7-methyl-1,7-diaza-spiro[4.4]nonan-6-one;
(2R,5S)-2-[4-(2-ethoxy-3-fluoro-phenyl)-2-pyridyl]-7-methyl-1,7-diazaspiro[4.4]nonan-6-one,
(2R,5S)-2-[4-(2-fluoro-5-isopropyl-phenyl)-2-pyridyl]-7-methyl-1,7-diazaspiro[4.4]nonan-6-one;
(2S,5S)-2-[4-(4-isopropoxyphenyl)-2-pyridyl]-7-methyl-1,7-diazaspiro[4.4]nonan-6-one;
(2R,5S)-2-[4-(4-isopropoxyphenyl)-2-pyridyl]-7-methyl-1,7-diazaspiro[4.4]nonan-6-one;
(2R,5S)-2-[4-(3,4-dimethoxyphenyl)-2-pyridyl]-7-methyl-1,7-diazaspiro[4.4]nonan-6-one;
2-Chloro-6-[2-[(2R,5S)-7-methyl-6-oxo-1,7-diazaspiro[4.4]nonan-2-yl]-4-pyridyl]benzonitrile;
(2R,5S)-2-[4-(4-ethoxy-3-methyl-phenyl)-2-pyridyl]-7-methyl-1,7-diazaspiro[4.4]nonan-6-one;
(2R,5S)-2-[4-[3-(methoxymethyl)phenyl]-2-pyridyl]-7-methy-1,7-diazaspiro[4.4]nonan-6-one;
(2R,5S)-2-[4-(2-ethoxy-4-fluoro-phenyl)-2-pyridyl]-7-methyl-1,7-diazaspiro[4.4]nonan-6-one;
1-[4-[2-[(2R,5S)-7-methyl-6-oxo-1,7-diazaspiro[4.4]nonan-2-yl]-4-pyridyl]phenyl]cylopropanecarbonitrile;

(2R,5S)-2-[4-(3,5-dimethylphenyl)-2-pyridyl]-7-methyl-1,7-diazaspiro[4.4]nonan-6-one;
(2R,5S)-2-[4-(5-ethoxy-2,3-difluoro-phenyl)-2-pyridyl]-7-methyl-1,7-diazaspiro[4.4]nonan-6-one;
(2R,5S)-2-[4-[2-fluoro-5-(trifluoromethoxy)phenyl]-2-pyridyl]-7-methyl-1,7-diazaspiro[4.4]nonan-6-one;
(2R,5S)-2-[4-(2-fluoro-5-propoxy-phenyl)-2-pyridyl]-7-methyl-1,7-diazaspiro[4.4]nonan-6-one;
(2R,5S)-2-[4-(5-ethoxy-2-methyl-phenyl)-2-pyridyl]-7-methyl-1,7-diazaspiro[4.4]nonan-6-one;
(2R,5S)-7-methyl-2-[4-(3-propoxyphenyl)-2-pyridyl]-1,7-diazaspiro[4.4]nonan-6-one;
2-isopropoxy-5-[2-[(2R,5S)-7-methyl-6-oxo-1,7-diazaspiro[4.4]nonan-2-yl]-4-pyridyl]benzonitrile;
(2R,5S)-2-[4-(2-Chloro-5-ethoxy-phenyl)-2-pyridyl]-7-methyl-1,7-diazaspiro[4.4]nonan-6-one;
(2R,5S)-2-[4-[5-(Cyclopropoxy)-2-fluoro-phenyl]-2-pyridyl]-7-methyl-1,7-diazaspiro[4.4]nonan-6-one;
(2R,5S)-2-[4-[2-fluoro-5-(methoxymethyl)phenyl]-2-pyridyl]-7-methyl-1,7-diazaspiro[4.4]nonan-6-one;
(2R,5S)-2-[4-[5-(ethoxymethyl)-2-fluoro-phenyl]-2-pyridyl]-7-methyl-1,7-diazaspiro[4.4]nonan-6-one;
(2R,5S)-2-[4-(3,4-diethoxyphenyl)-2-pyridyl]-7-methyl-1,7-diazaspiro[4.4]nonan-6-one;
(2R,5S)-2-[4-(4-fluoro-3-isobutoxy-phenyl)-2-pyridyl]-7-methyl-1,7-diazaspiro[4.4]nonan-6-one;
(2R,5S)-2-[4-(2-fluoro-5-methoxy-phenyl)-6-methyl-2-pyridyl]-7-methyl-1,7-diazaspiro[4.4]nonan-6-one;
(2R,5S)-2-[4-(2-fluoro-5-propoxy-phenyl)-6-methyl-2-pyridyl]-7-methyl-1,7-diazaspiro[4.4]nonan-6-one;
(2R,5S)-2-[4-(3-ethoxy-5-fluoro-phenyl)-6-methyl-2-pyridyl]-7-methyl-1,7-diazaspiro[4.4]nonan-6-one;
(2R,5S)-2-[4-(2-fluoro-5-isopropoxy-phenyl)-6-methyl-2-pyridyl]-7-methyl-1,7-diazaspiro[4.4]nonan-6-one;
(2R,5S)-2-[4-(3-ethoxy-2-fluoro-phenyl)-6-methyl-2-pyridyl]-7-methyl-1,7-diazaspiro[4.4]nonan-6-one;
(2R,5S)-2-[4-[2-fluoro-5-(trifluoromethoxy)phenyl]-6-methyl-2-pyridyl]-7-methyl-1,7-diazaspiro[4.4]nonan-6-one;
(2S,5R)-2-[4-(2-fluoro-5-propoxy-phenyl)-6-methyl-2-pyridyl]-7-methyl-1,7-diazaspiro[4.4]nonan-6-one;
(2R,5S)-2-[4-(5-ethoxy-2-fluoro-4-methyl-phenyl)-6-methyl-2-pyridyl]-7-methyl-1,7-diazaspiro[4.4]nonan-6-one;
(2R,5S)-2-[4-(5-ethyl-2-fluoro-phenyl)-6-methyl-2-pyridyl]-7-methyl-1,7-diazaspiro[4.4]nonan-6-one;
(2R,5S)-2-[4-(3-ethylphenyl)-6-methyl-2-pyridyl]-7-methyl-1,7-diazaspiro[4.4]nonan-6-one;
(2R,5S)-2-[4-(3-ethyl-2-fluoro-phenyl)-6-methyl-2-pyridyl]-7-methyl-1,7-diazaspiro[4.4]nonan-6-one;
(2R,5S)-2-[4-(3-ethoxyphenyl)-6-methyl-2-pyridyl]-7-methyl-1,7-diazaspiro[4.4]nonan-6-one;
(2S,5R)-2-[4-(4-ethylsulfonylphenyl)-6-methyl-2-pyridyl]-7-methyl-1,7-diazaspiro[4.4]nonan-6-one;
(2R,5S)-2-[4-(2,5-difluorophenyl)-6-methyl-2-pyridyl]-7-methyl-1,7-diazaspiro[4.4]nonan-6-one;
(2R,5R)-2-[4-(5-ethoxy-2-fluoro-phenyl)-3-methyl-2-pyridyl]-7-methyl-1,7-d-iazaspiro[4.4]nonan-6-one;
(2S,5R)-2-[4-(5-ethoxy-2-fluoro-phenyl)-3-methyl-2-pyridyl]-7-methyl-1,7-diazaspiro[4.4]nonan-6-one;
(2S,5S)-2-[4-(5-ethoxy-2-fluoro-phenyl)-3-methyl-2-pyridyl]-7-methyl-1,7-diazaspiro[4.4]nonan-6-one;
(2R,5S)-2-[4-(5-ethoxy-2-fluoro-phenyl)-3-methyl-2-pyridyl]-7-methyl-1,7-diazaspiro[4.4]nonan-6-one;
(2S,5S)-2-[4-(5-ethoxy-2-fluoro-phenyl)-2-pyridyl]-8,8-dimethyl-1,7-diazaspiro[4.4]nonan-6-one;
(2R,5S)-2-[4-(5-ethoxy-2-fluoro-phenyl)-2-pyridyl]-8,8-dimethyl-1,7-diazaspiro[4.4]nonan-6-one;
(2R,5R)-2-[4-(5-ethoxy-2-fluoro-phenyl)-2-pyridyl]-8,8-dimethyl-1,7-diazaspiro[4.4]nonan-6-one;
(2S,5R)-2-[4-(5-ethoxy-2-fluoro-phenyl)-2-pyridyl]-8,8-dimethyl-1,7-diazaspiro[4.4]nonan-6-one;
(2R,5R)-2-[4-(2-fluoro-5-hydroxy-phenyl)-2-pyridyl]-8,8-dimethyl-1,7-diaza-spiro[4.4]nonan-6-one;
(2S,5R)-2-[4-(5-ethoxy-2-fluoro-phenyl)-5-fluoro-2-pyridyl]-7-methyl-1,7-diazaspiro[4.4]nonan-6-one;
(2R,5R)-2-[4-(5-ethoxy-2-fluoro-phenyl)-5-fluoro-2-pyridyl]-7-methyl-1,7-diazaspiro[4.4]nonan-6-one;
(2R,5S)-2-[4-(5-ethoxy-2-fluoro-phenyl)-5-fluoro-2-pyridyl]-7-methyl-1,7-diazaspiro[4.4]nonan-6-one;
(2S,5S)-2-[4-(5-ethoxy-2-fluoro-phenyl)-5-fluoro-2-pyridyl]-7-methyl-1,7-diazaspiro[4.4]nonan-6-one;
(2R,5S)-1,7-dimethyl-2-[4-[4-(trifluoromethyl)phenyl]-2-pyridyl]-1,7-diaza-spiro[4.4]nonan-6-one;
(2S,5S)-1-methyl-2-[6-methyl-4-[4-(trifluoromethyl)phenyl]-2-pyridyl]-1,7-diazaspiro[4.4]nonan-6-one;
(2R,5R)-1-methyl-2-[6-methyl-4-[4-(trifluoromethyl)phenyl]-2-pyridyl]-1,7-diazaspiro[4.4]nonan-6-one;
(2S,5R)-1-methyl-2-[6-methyl-4-[4-(trifluoromethyl)phenyl]-2-pyridyl]-1,7-diazaspiro[4.4]nonan-6-one;
(2R,5S)-1-methyl-2-[6-methyl-4-[4-(trifluoromethyl)phenyl]-2-pyridyl]-1,7-diazaspiro[4.4]nonan-6-one;
(2S,5R)-2-[4-(5-ethoxy-2-fluoro-phenyl)-6-methy-2-pyridyl]-1,7-dimethyl-1,7-diazaspiro-[4.4]nonan-6-one;
(2R,5R)-2-[4-(5-ethoxy-2-fluoro-phenyl)-6-isopropyl-2-pyridyl]-7-methyl-1,7-diazaspiro[4.4]nonan-6-one;
(2S,5R)-2-[4-(5-ethoxy-2-fluoro-phenyl)-6-isopropyl-2-pyridyl]-7-methyl-1,7-diazaspiro[4.4]nonan-6-one;
(2S,5S)-2-[4-(5-ethoxy-2-fluoro-phenyl)-6-isopropyl-2-pyridyl]-7-methyl-1,7-diazaspiro[4.4]nonan-6-one;
(2R,5S)-2-[4-(5-ethoxy-2-fluoro-phenyl)-6-isopropyl-2-pyridyl]-7-methyl-1,7-diazaspiro[4.4]nonan-6-one;
(2S,3S,5R)-3-fluoro-7-methyl-2-[4-[4-(trifluoromethyl)phenyl]-2-pyridyl]-1,7-diazaspiro[4.4]nonan-6-one;
(2S,3R,5R)-3-fluoro-7-methyl-2-[4-[4-(trifluoromethyl)phenyl]-2-pyridyl]-1,7-diazaspiro[4.4]nonan-6-one;
(5R)-3,3-difluoro-7-methyl-2-[4-[4-(trifluoromethyl)phenyl]-2-pyridyl]-1,-7-diazaspiro[4.4]nonan-6-one;
(2R,5S)-2-[4-(5-ethoxy-2-fluoro-phenyl)-5-ethyl-2-pyridyl]-7-methyl-1,7-di-azaspiro[4.4]nonan-6-one;
(2S,5R)-2-[4-(5-ethoxy-2-fluoro-phenyl)-5-ethyl-2-pyridyl]-7-methyl-1,7-d-iazaspiro[4.4]nonan-6-one;
(2R,5R)-2-[4-(5-ethoxy-2-fluoro-phenyl)-6-methoxy-2-pyridyl]-7-methyl-1,7-diazaspiro[4.4]nonan-6-one;
(2S,5R)-2-[4-(5-ethoxy-2-fluoro-phenyl)-6-methoxy-2-pyridyl]-7-methyl-1,7-diazaspiro[4.4]nonan-6-one;
(2S,5S)-2-[4-(5-ethoxy-2-fluoro-phenyl)-6-methoxy-2-pyridyl]-7-methyl-1,7-diazaspiro[4.4]nonan-6-one;
(2R,5S)-2-[4-(5-ethoxy-2-fluoro-phenyl)-6-methoxy-2-pyridyl]-7-methyl-1,7-diazaspiro[4.4]nonan-6-one;
(2R,5S)-2-[4-[2-fluoro-5-(2-fluoroethoxyl)phenyl]-2-pyridyl]-7-methyl-1,7-diazaspiro[4.4]nonan-6-one;
(2R,5S)-2-[4-[5-(2,2-difluoroethoxy)-2-fluoro-phenyl]-2-pyridyl]-7-methyl-1,7-diazaspiro[4.4]nonan-6-one;
(2R,5S)-2-[4-(2-fluoro-5-isobutoxy-phenyl)-2-pyridyl]-7-methyl-1,7-diazaspiro[4.4]nonan-6-one;
(2R,5S)-2-[4-[5-(1,1-dideuterioethoxy)-2-fluoro-phenyl]-2-pyridyl]-7-methyl-1,7-diazaspiro[4.4]nonan-6-one;
(2R,5S)-2-[4-[5-(1-(Cyclopropyl)ethoxy)-2-fluoro-phenyl]-2-pyridyl]-7-methyl-1,7-diazaspiro[4.4]nonan-6-one;
2-[4-(5-ethoxy-2-fluoro-phenyl)-3,6-dimethyl-2-pyridyl]-7-methyl-1,7-diaza-spiro[4.4]nonan-6-one;

(2R,5S)-2-[4-(2-fluoro-5-propanoyl-phenyl)-2-pyridyl]-7-methyl-1,7-diazasp-iro[4.4]nonan-6-one;
or a pharmaceutically acceptable salt thereof.

* * * * *